United States Patent
Klopfer

(10) Patent No.: US 10,052,323 B2
(45) Date of Patent: *Aug. 21, 2018

(54) PHARMACEUTICAL COMPOSITIONS OF 7-(6-(2-HYDROXYPROPAN-2-YL)PYRIDIN-3-YL)-1-(TRANS)-4-METHOXYCYCLOHEXYL)-3,4-DIHYDROPYRAZINO [2,3-B]PYRAZIN-2(1H)-ONE, A SOLID FORM THEREOF AND METHODS OF THEIR USE

(71) Applicant: Signal Pharmaceuticals, LLC, San Diego, CA (US)

(72) Inventor: Kevin Klopfer, Flemington, NJ (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/918,544

(22) Filed: Mar. 12, 2018

(65) Prior Publication Data

US 2018/0200252 A1 Jul. 19, 2018

Related U.S. Application Data

(62) Division of application No. 15/708,222, filed on Sep. 19, 2017, which is a division of application No. 15/427,242, filed on Feb. 6, 2017, now Pat. No. 9,795,603, which is a division of application No. 14/288,521, filed on May 28, 2014, now Pat. No. 9,604,939.

(Continued)

(51) Int. Cl.
| | |
|---|---|
| *A61K 31/4985* | (2006.01) |
| *C07D 487/04* | (2006.01) |
| *A61K 9/20* | (2006.01) |
| *A61K 9/28* | (2006.01) |

(52) U.S. Cl.
CPC ........ *A61K 31/4985* (2013.01); *A61K 9/2013* (2013.01); *A61K 9/2018* (2013.01); *A61K 9/2054* (2013.01); *A61K 9/28* (2013.01); *C07D 487/04* (2013.01); *C07B 2200/13* (2013.01)

(58) Field of Classification Search
CPC .............. A61K 31/4985; A61K 9/2013; A61K 9/2018; A61K 9/2054; A61K 9/28; C07D 487/04

See application file for complete search history.

(56) References Cited

U.S. PATENT DOCUMENTS

| | | |
|---|---|---|
| 3,507,866 A | 4/1970 | Jones et al. |
| 3,567,725 A | 3/1971 | Grabowski et al. |

(Continued)

FOREIGN PATENT DOCUMENTS

| | | |
|---|---|---|
| CA | 2 458 699 | 3/2003 |
| DE | 262 026 | 11/1988 |

(Continued)

OTHER PUBLICATIONS

Barlin 1982, "Purine analogs as amplifiers of phleomycin. VII. Some 1H-inidazo[4,5-b]pyrazines and related compound," Australian Journal of Chemistry, vol. 35:2299-2306.

(Continued)

*Primary Examiner* — Trevor Love
(74) *Attorney, Agent, or Firm* — Jones Day

(57) ABSTRACT

Provided herein are compositions of 7-(6-(2-hydroxypropan-2-yl)pyridin-3-yl)-1-((trans)-4-methoxycyclohexyl)-3, 4-dihydropyrazino[2,3-b]pyrazin-2(1H)-one, solid forms, isotopologues and metabolites thereof, and methods of their use for the treatment of a disease, disorder, or condition.

7 Claims, 21 Drawing Sheets

Related U.S. Application Data

(60) Provisional application No. 61/828,506, filed on May 29, 2013.

(56) References Cited

U.S. PATENT DOCUMENTS

| | | | |
|---|---|---|---|
| 4,294,836 | A | 10/1981 | Lesher et al. |
| 4,294,837 | A | 10/1981 | Lesher et al. |
| 4,309,537 | A | 1/1982 | Lesher et al. |
| 4,317,909 | A | 3/1982 | Lesher et al. |
| 4,898,872 | A | 2/1990 | Campbell et al. |
| 4,963,561 | A | 10/1990 | Lesher et al. |
| 5,424,311 | A | 6/1995 | Billhardt-Troughton |
| 5,869,659 | A | 2/1999 | Stolle et al. |
| 6,031,105 | A | 2/2000 | Wright |
| 6,093,728 | A | 7/2000 | McMahon et al. |
| 6,372,740 | B1 | 4/2002 | Murata et al. |
| 6,566,367 | B2 | 5/2003 | Bakthavatchalam et al. |
| 6,791,006 | B2 | 9/2004 | Nezu et al. |
| 6,800,436 | B1 | 10/2004 | Jenne et al. |
| 6,825,184 | B2 | 11/2004 | Ciriillo et al. |
| 6,855,723 | B2 | 2/2005 | McMahon et al. |
| 7,199,119 | B2 | 4/2007 | Burkitt et al. |
| 7,247,621 | B2 | 7/2007 | Hong et al. |
| 7,429,572 | B2 | 9/2008 | Clark |
| 7,476,665 | B2 | 1/2009 | Burgey |
| 7,608,622 | B2 | 10/2009 | Liu et al. |
| 7,700,594 | B2 | 4/2010 | Chen et al. |
| 7,767,687 | B2 | 8/2010 | Oslob et al. |
| 7,902,187 | B2 | 3/2011 | Neagu et al. |
| 7,919,490 | B2 | 4/2011 | Neagu et al. |
| 7,968,556 | B2 | 6/2011 | Mortensen et al. |
| 7,981,893 | B2 | 7/2011 | Mortensen et al. |
| 8,110,578 | B2 | 2/2012 | Perrin-Ninkovic et al. |
| 8,268,809 | B2 | 9/2012 | Kalman |
| 8,372,976 | B2 | 2/2013 | Mortensen et al. |
| 8,383,634 | B2 | 2/2013 | Mortensen et al. |
| 8,492,381 | B2 | 7/2013 | Perrin-Ninkovic et al. |
| 8,569,494 | B2 | 10/2013 | Harris et al. |
| 8,642,660 | B2 | 2/2014 | Goldfard |
| 9,006,224 | B2 | 4/2015 | Wayne et al. |
| 9,155,736 | B2 | 10/2015 | Xu et al. |
| 9,358,232 | B2 | 6/2016 | Hege et al. |
| 9,359,364 | B2 | 6/2016 | Menon et al. |
| 9,375,443 | B2 | 6/2016 | Xu et al. |
| 9,403,829 | B2 | 8/2016 | Connolly et al. |
| 9,474,757 | B2 | 10/2016 | Hege et al. |
| 9,493,466 | B2 | 11/2016 | Xu et al. |
| 9,505,764 | B2 | 11/2016 | Raymon et al. |
| 9,555,033 | B2 | 1/2017 | Chopra et al. |
| 2004/0063658 | A1 | 4/2004 | Roberts et al. |
| 2006/0004014 | A1 | 1/2006 | Hoffmann et al. |
| 2006/0142269 | A1 | 6/2006 | Dykes |
| 2007/0036793 | A1 | 2/2007 | Hardie et al. |
| 2008/0194019 | A1 | 8/2008 | Cantley et al. |
| 2009/0181963 | A1 | 7/2009 | Wyeth |
| 2009/0281075 | A1 | 11/2009 | Roughton et al. |
| 2010/0144738 | A1 | 6/2010 | Bornmann et al. |
| 2011/0318336 | A1 | 12/2011 | Petricoin, III et al. |
| 2012/0028972 | A1 | 2/2012 | Wong et al. |
| 2013/0158023 | A1 | 6/2013 | Ning et al. |
| 2013/0245026 | A1 | 9/2013 | Xu et al. |
| 2013/0245027 | A1 | 9/2013 | Xu et al. |
| 2013/0245028 | A1 | 9/2013 | Xu et al. |
| 2013/0245029 | A1 | 9/2013 | Xu et al. |
| 2014/0314673 | A1 | 10/2014 | Raymon et al. |
| 2014/0314674 | A1 | 10/2014 | Raymon et al. |
| 2014/0314752 | A1 | 10/2014 | Lopez-Girona et al. |
| 2014/0315848 | A1 | 10/2014 | Raymon |
| 2014/0315900 | A1 | 10/2014 | Raymon et al. |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| JP | A-2004-503588 | 2/2004 |
| JP | 2009-516671 | 11/2006 |
| JP | A-2010-509400 | 3/2010 |
| JP | A-2012-523375 | 10/2012 |
| WO | WO 1999/16438 | 4/1999 |
| WO | WO 1999/28320 | 6/1999 |
| WO | WO 1999/28459 | 6/1999 |
| WO | WO 2000/73306 | 12/2000 |
| WO | WO 2002/005799 | 1/2002 |
| WO | WO 2002/048152 | 6/2002 |
| WO | WO 2002/076954 | 10/2002 |
| WO | WO 2003/032989 | 4/2003 |
| WO | WO 2003/072557 | 9/2003 |
| WO | WO 2003/093290 | 11/2003 |
| WO | WO 2004/042002 | 5/2004 |
| WO | WO 2004/048365 | 6/2004 |
| WO | WO 2004/065378 | 8/2004 |
| WO | WO 2004/076454 | 9/2004 |
| WO | WO 2004/078754 | 9/2004 |
| WO | WO 2004/085409 | 10/2004 |
| WO | WO 2004/096797 | 11/2004 |
| WO | WO 2005/003147 | 1/2005 |
| WO | WO 2005/021519 | 3/2005 |
| WO | WO 2005/120511 | 12/2005 |
| WO | WO 2006/001266 | 1/2006 |
| WO | WO 2006/018182 | 2/2006 |
| WO | WO 2006/030031 | 3/2006 |
| WO | WO 2006/036883 | 4/2006 |
| WO | WO 2006/045828 | 5/2006 |
| WO | WO 2006/046031 | 5/2006 |
| WO | WO 2006/050076 | 5/2006 |
| WO | WO 2006/065703 | 6/2006 |
| WO | WO 2006/087530 | 8/2006 |
| WO | WO 2006/090167 | 8/2006 |
| WO | WO 2006/090169 | 8/2006 |
| WO | WO 2006/091737 | 8/2006 |
| WO | WO 2006/108103 | 10/2006 |
| WO | WO 2007/044698 | 4/2007 |
| WO | WO 2007/044729 | 4/2007 |
| WO | WO 2007/044813 | 4/2007 |
| WO | WO 2007/047754 | 4/2007 |
| WO | WO 2007/060404 | 5/2007 |
| WO | WO 2007/066099 | 6/2007 |
| WO | WO 2007/066102 | 6/2007 |
| WO | WO 2007/080382 | 7/2007 |
| WO | WO 2007/125321 | 11/2007 |
| WO | WO 2007/129044 | 11/2007 |
| WO | WO 2007/129052 | 11/2007 |
| WO | WO 2007/129161 | 11/2007 |
| WO | WO 2007/135398 | 11/2007 |
| WO | WO 2008/016669 | 2/2008 |
| WO | WO 2008/023161 | 2/2008 |
| WO | WO 2008/032027 | 3/2008 |
| WO | WO 2008/032028 | 3/2008 |
| WO | WO 2008/032033 | 3/2008 |
| WO | WO 2008/032036 | 3/2008 |
| WO | WO 2008/032060 | 3/2008 |
| WO | WO 2008/032064 | 3/2008 |
| WO | WO 2008/032072 | 3/2008 |
| WO | WO 2008/032077 | 3/2008 |
| WO | WO 2008/032089 | 3/2008 |
| WO | WO 2008/032091 | 3/2008 |
| WO | WO 2008/051493 | 5/2008 |
| WO | WO 2008/060546 | 5/2008 |
| WO | WO 2008/064093 | 5/2008 |
| WO | WO 2008/115974 | 9/2008 |
| WO | WO 2008/140947 | 11/2008 |
| WO | WO 2009/007748 | 1/2009 |
| WO | WO 2009/007750 | 1/2009 |
| WO | WO 2009/007751 | 1/2009 |
| WO | WO 2009/052145 | 4/2009 |
| WO | WO 2009/102986 | 8/2009 |
| WO | WO 2010/006072 | 1/2010 |
| WO | WO 2010/062571 | 6/2010 |
| WO | WO 2010/068483 | 6/2010 |
| WO | WO 2010/092126 | 8/2010 |

(56) References Cited

FOREIGN PATENT DOCUMENTS

| WO | WO 2011/031965 | 3/2011 |
|---|---|---|
| WO | WO 2011/053518 | 5/2011 |
| WO | WO 2011/079114 | 6/2011 |
| WO | WO 2011/097333 | 8/2011 |
| WO | WO 2012/164060 | 12/2012 |

OTHER PUBLICATIONS

Beresnev et al., 2000, "Interaction of 5-methoxy-1,2,4-traizines with uras as a new route to 6-azapurines," Medeleev Commu., vol. 2:58-59.
Bergmann et al., 1963, "2-Phenylpurines, their chemical and enzumological reactivity," J. Chem Org., pp. 3729-3735.
Booth et al., 1992, "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. 2119-26.
Booth et al., 1995, "Synthesis of [1α, 2β,3α-2,3-bis(benzyloxymethyl)cyclobutl]imidazol-5-amines: important precursors to cyclobut-A derivatives," J. Chem Society, Perkin Tranactions 1: Organic and Bio-Organic Chemistry, vol. 6, pp. 669-675.
Booth et al., 2001, "The Reactions of Diaminomaleonitrile with Isocyanates and Either Aldehydes or Ketones Revisited," J. Org Chem, vol. 66:8436-8441.
Booth, et al., 1994, "Synthesis of 4- and 5-Disubstituted 1-Benzylimidazoles, Important Precursors of Purine Analogs," J. of Heterocyclic of Chemistry, vol. 31(2):345-50.
Carretero et al. 2010, "Integrative Genomic and Proteomic Analyses Indentity Targets for Lkb1-Deficient Metastatic Lung Tumors," Cancer Cell, vol. 17(6): 547-559.
Chupakhin et al., 2001, "A simple one pot synthesis of condensed 1,2,4-triazines by using the tandem $A_N$-$S_N$ipso and $S_N^H$—$S_N$ipso reactions," J. of Heterocyclic Chemistry, vol. 38(4):901-907.
Cohen, P. 2001, "The role of protein phosphorylation in human health and disease," Eur. J. Biochem,vol. 268:5001-5010.
Cohen, P. 2002, "Protein kinases—the major drug targets of the twenty-first century?" Nature Reviews/Drug Discovery, vol. 1:309-315.
Cohen, 2005, *Protein Kinase Inhibitors for the Treatment of Disease: The Promise and the Problems*, Handbook of Experimental Pharmacology, Springer Berlin Heidelberg, 167:1-7.
Coish, et al., 2006, "Small molecule inhibitors of IKK kinase activity," Expert Opin. Ther. Patents, vol. 16(1):1-12.
Crofts et al., 1997 "Metabolism of 2-amino-1-methyl-6-phenylimidazo [4,5-b]pyridine (PhIP) by human cytochrome P4501B1," Carcinogenesis, vol. 18(9):1793-1798.
Dang et al., 1999, "Efficient synthesis of purines and purine nucleosides via an inverse electron demand diels—alder reaction," J. Am Chem Soc., vol. 121(24):5833-5834.
Database Caplus Online Chemical Abstracts Service, Columbus, Ohio, Database Accession No. 1951:49974 (XP-002472261) (1951).
Database Caplus Online Chemical Abstracts Service, Columbus, Ohio, Database Accession No. 1978:433195 (XP-002472262) (1978).
Database Caplus Online Chemical Abstracts Service, Columbus, Ohio, Database Accession No. 1966:26849 (XP-002472263) (1965).
Dornow et al., 1957, "Synthese von2-Oxy-imidazolo-(5',4':2,3)-pyridinen)," Arch Pharm. vol. 290, pp. 20-31 (w/English language abstract).
Dzierba et al., 2004, "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47, pp. 5783-5790.
Fabbro et al., 2002, "Protein kinases as targets for anticancer agents: from inhibitors to useful drugs," Pharmacol Ther., 93(2-3):79-98.

Farhadi et al., 2006, "The role of protein kinase C isoforms in modulating injury and repair of the intestinal barrier," J. Pharm Exp. Ther., vol. 316(1):1-7.
Frandsen et al., 1992, "Reaction of the N2-acetoxy derivative of 2-amino-1-methyl-6-phenylimidazo[4,5,b] pyridine . . . ," Carcinogenesis, vol. 13(4):629-635.
Gao et al., 2010, "LKB1 inhibits lung cancer progression through lysyl oxidase and extracellular matrix remodeling," Proceedings of the National Academy of Sciences, vol. 107(44): 18892-18897.
Georgakis and Younes, 2006, "From rapi nui to rapamycin: targeting PI3K/Akt/mTOR for cancer therapy," Expert Rev. Anticancer Ther., vol. 6(1):131-140.
Grimmiger et al., 2010, "Targeting non-malignant disorders with tyrosine kinase inhibitors," Nat. Rev. Drug.Disc., 9(12):956-970.
Hamad, 2001, "A new synthesis of 4-cyano-1,3-dihydro-2-oxo-2H-imidazole-5-($N^1$-tosyl)carboxamide: Reactive precursor for thiopurine analogues," J of Heterocyclic Chemistry, vol. 38(4):939-944.
Hernan et al., "De novo germline mutation in the serine-threonine kinase STK11/LKB1 gene associated with Peutz-Jeghers syndrome," Clin Genet., 66(1):58-62.
Huang et al., 2010, "Genetic and epigenetic silencing of SCARA5 may contribute to human hepatocellular carcinoma by activating FAK signaling," Journal of Clinical Investigation, American Society for Clinical investigation, vol. 120(1): 223-241.
Inge et al., 2009, "Expression of LKB1 tumor suppressor in non-small cell lung cancer determines sensitivity to 2-deoxyglucose," Journal of Thoracic and Cardiovascular Surgery, vol. 137(3): 580-586.
Irie et al., 2005, "Toward the development of new medicinal leads with selectivity for protein kinase C isozymes," The Chemical Record, vol. 5:185-195.
Itoh et al., 2004, "A novel practical synthesis of C-2-aiylpurines," Advanced Synthesis & Catalysis, vol. 346:1859-1867.
Ji et al., 2007, "LKB1 modulates lung cancer differentiation and metastasis," Nature, 448(7155):807-810.
Jones et al., 1973, "6-Substituted-5-chloro-1,3-dihydro-2H-imidazo(4,5-b)pyrazin-2-ones with hypotensive activity," J. Med. Chem., vol. 16(5):537-542.
Kazaoka et al.; 2003, "Synthesis of 6-substituted 9-benzyl-8-hydroxypurines with potential interferon-indcuing activity," Chemical & Pharmaceutical Bulletin, vol. 51(5):608-611.
Killday et al., 2001, "Microxine, a new cdc2 kinase inhibitor from the Australian marine sponge *Microxina* species," J. of Natural Products, vol. 64(4):525-526.
Mahoney et al., 2009, "LKB1/KRAS mutant lung cancers constitute a genetic subset of NSCLC with increased sensitivity to MAPK and mTOR signalling inhibition," Br J Cancer, 100(2):370-375.
Minehan et al., 2000, "Molecular recognition of DNA by Hoechst Benzimidazoles: Exploring beyond theopyrrole-imidazole-hydroxypyrrole polyamide-pairing code," Helvitica Chima Acta, vol. 83(9):2197-2213.
Nagashima et al., 2004, "Solution-Phase parallel synthesis of an N-Alkylated dihydropteridinone library from fluorous amino acids," J of Comb. Chemistry, vol. 6(6):942-949.
Park et al., 2000, "A novel mechanism of TRAF signaling revealed by structural and functional analyses of the TRADD-TRAF2 interaction," Cell, vol. 101:777-787.
Patani et al., 1998, "Bioisosterim: A rational approach in drug design," Chemical Reviews, vol. 96:3147-3176.
PCT Annex to Form PCT/ISA?206 Communication Relating to the Results of the Partial International Search issued in connection with PCT/US2012/049281,filed Aug. 2, 2012.
PCT International Search Report issued in connection with PCT/US2012/049281, filed Aug. 2, 2012.
PCT Written Opinion of the International Searching Authority issued in connection with PCT/US2012/049281, filed Aug. 2, 2012.
Registry File Document for RN 863501-03-5, 863502-39-0 and others (Sep. 20, 2005).
Yuan et al., 2009, "Targeting tumorigenesis: development and use of mTOR inhibitors in cancer therapy," Journal of Hematology & Oncology, Biomed Central Ltd., London UK, vol. 2(1): 45.

(56) References Cited

OTHER PUBLICATIONS

Seela et al., 2004, "Product Class 17: Purines," Science of Synthesis, vol. 16, pp. 945-1108.
Shaw et al., 2004, "The LKB1 tumor suppressor negativiely regulates mTOR signaling," Cancer Cell, vol. 6(1): 91-99.
Shaw et al., 2009, "LKB1 and AMP-activated protein kinase control of mTOR signalling and growth," Acta. Physiol (Oxf.) 196(1):65-80.
Singh et al., 1994, "Novel cAMP PDE III Inhibitors: Imidazo[4,5-b]pyridin-2(3H)-ones and Thiazolo [4,5-b]pyridin-2(3h)-ones and Their Analogs," J. Med. Chem, vol. 37(2):248-54.
Sridhar et al., 2000, "Protein kinases as therapeutic targets," Pharm. Res., 17(11):1345-1353.
Wallace 2008, "Palladium-catalyzed synthesis of quinoxaline derivatives," Tetrahedron, vol. 64:9675-9684.
Wei et al., 2009, "Chemopreventive efficacy of rapamycin on Peutz-Jeghers syndrome in a mouse model," Cancer Lett., 277(2):149-154.
Westover et al., 1981, "Synthesis and antiviral activity of certain 9-β-D-Riofuranoaylpurine-6-carboxamides," J.Med. Chem., vol. 24(8):941-46.
Wingo et al., 2009, "Somatic LKB1 mutations promote cervical cancer progression," PloS One, 4(4):1-8.
Gao et al.: 2011, "LKB1 in lung cancerigenesis: a serine/threonine kinase as tumor suppressor," Protein & Cell, Gaodeng Jiaoyu Chubanshe, China, vol. 2(2): 99-107.
Yoneda et al., 1976, "A transformationof 7-azapteridines into 6-azapurines (Imidazo [4,5-e]-as-triazines)," Heterocycles, vol. 4(9):1503-1508.
Yoneda et al., 1978, "Synthesis of imadazo[4,5-e]-as-triazine (6-Azapurine) Deriviatives," Chem & Pharm Bulletin, vol. 26(10):3154-3160.
Zaki et al., 2007, "The synthesis of imidazol[4,5-d]pyridines from a substituted imidazole and acyl or sulfonyl acetonitrile," Tetrahedron, vol. 63(18):3745-3753.
Zhong et al., 2006, "LKB1 mutation in large cell carcinoma of the lung," Cancer Lung, vol. 53(3):285-294.
Shoji et al., 2012, "Genotype-dependent efficacy of a dual PI3K/mTOR inhibitor, NVP-BEZ235, and an mTOR inhibitor, RAD001, in endometrial carcinomas." *PloS one* 7.5, 2012, e37431.
Gini et al., 2013, "The mTOR Kinase Inhibitors, CC214-1 and CC214-2, Preferentially Block the Growth of EGFRvIII-Activated Glioblastomas," Clin Cancer Res, 19:5722-5732.
Berstein, 2004, "Crystal Structure Prediction and Polymorphism," ACA Transactions, 39: 14-23.
Braga et al., 2005, "Making crystals from crystals: a green route to crystal engineering and Polymorphism," Chem. Commun., 3635-3645.
Jones et al., 2006, "Pharmaceutical Cocrystals: An Emerging Approach to Physical Property Enhancement," MRS Bulletin 31: 875-879.
Price, 2004, "The computational prediction of pharmaceutical crystal structures and polymorphism," Advanced Drug Delivery Reviews 56 (2004) 301-319.
Caira et al., 1998, "Crystalline Polymorphism of Organic Compounds," Topics in Current Chemistry, Jan. 1, 1998, pp. 163-208, vol. 198, Springer, Berlin, DE.
Reier, Avicel PH Microcrystalline Cellulose, NF, Ph Eur., JP, BP, 2000, FMC Corporation, pp. 1-27.
Rudnic, Oral Solid Dosage Forms (Ch. 89), 1990, Remington's Pharmaceutical Sciences, Gennaro editor, pp. 1633-1665.
Öberg, Kjell E (2010), "Gastrointestinal neuroendocrine tumors," *Annals of Oncology* 21.suppl_7 (2010): vii72-vii80.
Gardner, Nancy (2009), "Targeting the mTOR pathway in neuroendocrine tumors," *Clinical journal of oncology nursing* 13.5 (2009).

Form E (wet solids)

A

Form E (dried solids)

B

Form E (wet solids after AAC)

C

Form E (dried solids after AAC)

D

Area Percent Report

Sorted By          :    Signal
Multiplier         :    1.0000
Dilution           :    1.0000
Use Multiplier & Dilution Factor with ISTDs Signal 1: DAD1 C, Sig=220, 4 Ref=off

| Peak # | RetTime [min] | Type | Width [min] | Area [mAU*s] | Height [mAU] | Area % |
|---|---|---|---|---|---|---|
| 1 | 6.061 | BB | 0.0670 | 16.89769 | 3.58125 | 0.3399 |
| 2 | 7.248 | BB | 0.0618 | 11.19821 | 2.56970 | 0.2252 |
| 3 | 7.981 | BV | 0.0526 | 25.55524 | 7.53806 | 0.5140 |
| 4 | 8.103 | VB | 0.0659 | 4918.12354 | 1045.03748 | 98.9209 |

PHARMACEUTICAL COMPOSITIONS OF 7-(6-(2-HYDROXYPROPAN-2-YL)PYRIDIN-3-YL)-1-(TRANS)-4-METHOXYCYCLOHEXYL)-3,4-DIHYDROPYRAZINO[2,3-B]PYRAZIN-2(1H)-ONE, A SOLID FORM THEREOF AND METHODS OF THEIR USE

This application is a divisional of U.S. application Ser. No. 15/708,222, filed Sep. 19, 2017, currently allowed, which is a divisional of U.S. application Ser. No. 15/427,242, filed Feb. 8, 2017, now U.S. Pat. No. 9,795,603, issued Oct. 24, 2017, which is a divisional of U.S. application Ser. No. 14/288,521, filed May 28, 2014, now U.S. Pat. No. 9,604,939, issued Mar. 28, 2017, which claims the benefit of U.S. Provisional Application No. 61/828,506, filed May 29, 2013, the entire contents of which are incorporated herein by reference.

1. FIELD

Provided herein are compositions of 7-(6-(2-hydroxypropan-2-yl)pyridin-3-yl)-1-((trans)-4-methoxycyclohexyl)-3,4-dihydropyrazino[2,3-b]pyrazin-2(1H)-one, a solid form thereof, isotopologues thereof, and methods of their use for the treatment of a disease, disorder, or condition.

2. BACKGROUND

The connection between abnormal protein phosphorylation and the cause or consequence of diseases has been known for over 20 years. Accordingly, protein kinases have become a very important group of drug targets. See Cohen, *Nature*, 1:309-315 (2002). Various protein kinase inhibitors have been used clinically in treating a wide variety of diseases, such as cancer, chronic inflammatory diseases, diabetes, and stroke. See Cohen, *Eur. J. Biochem.*, 268: 5001-5010 (2001), *Protein Kinase Inhibitors for the Treatment of Disease: The Promise and the Problems*, Handbook of Experimental Pharmacology, Springer Berlin Heidelberg, 167 (2005).

The elucidation of the intricacy of protein kinase pathways and the complexity of the relationship and interaction among and between the various protein kinases and kinase pathways highlights the importance of developing pharmaceutical agents capable of acting as protein kinase modulators, regulators, or inhibitors that have beneficial activity on multiple kinases or multiple kinase pathways. Accordingly, there remains a need for new kinase modulators.

The protein named mTOR (mammalian target of rapamycin), also known as FRAP, RAFT1 or RAPT1, is a Ser/Thr protein kinase related to the lipid kinases of the phosphoinositide 3-kinase (PI3K) family. It functions as a sensor of mitogen, energy, and nutrient levels; and is a central controller of cell growth. mTOR has been shown to be one of the most critical proteins in the mTOR/PI3K/Akt pathway that regulates cell growth and proliferation. Georgakis and Younes, *Expert Rev. Anticancer Ther.* 6(1): 131-140 (2006). mTOR exists in two complexes, mammalian target of rapamycin complex 1 (mTORC1) which complexes with raptor, and mammalian target of rapamycin complex 2 (mTORC2) which complexes with rictor. While mTORC1 is sensitive to rapamycin analogs (such as temsirolimus or everolimus), mTORC2 is largely rapamycin-insensitive (Kim et al., *Cell* 110(2): 163-175 (2002); Sarbassov et al., *Science* 307:1098-1101 (2005)).

Several mTOR inhibitors have been or are being evaluated in clinical trials for the treatment of cancer. For example, temsirolimus was approved for use in renal cell carcinoma in 2007 and sirolimus was approved in 1999 for the prophylaxis of renal transplant rejection. Everolimus was approved in 2009 for renal cell carcinoma patients that have progressed on vascular endothelial growth factor receptor inhibitors, in 2010 for subependymal giant cell astrocytoma (SEGA) associated with tuberous sclerosis (TS) in patients who require therapy but are not candidates for surgical resection, and in 2011 for progressive neuroendocrine tumors of pancreatic origin (PNET) in patients with unresectable, locally advanced or metastatic disease. The interesting but limited clinical success of these mTORC1 compounds demonstrates the usefulness of mTOR inhibitors in the treatment of cancer and transplant rejection, and the increased potential for compounds with both mTORC1 and mTORC2 inhibitory activity.

The preparation and selection of a solid form of a pharmaceutical compound are complex, given that a change in the solid form may affect a variety of physical and chemical properties of the compound, which may in turn provide benefits or drawbacks in processing, formulation, stability, and bioavailability of the compound. Potential pharmaceutical solids include crystalline solids and amorphous solids. An amorphous solid is characterized by a lack of long-range structural order, whereas a crystalline solid is characterized by structural periodicity. The desired class of pharmaceutical solids depends upon the specific application; an amorphous solid is sometimes selected on the basis of, e.g., an enhanced dissolution profile, while a crystalline solid may be desirable for properties, such as physical or chemical stability. See Vippagunta et al., *Adv. Drug. Deliv. Rev.*, 48:3-26 (2001); Yu, *Adv. Drug. Deliv. Rev.*, 48:27-42 (2001).

Whether crystalline or amorphous, potential solid forms of a pharmaceutical compound may include single-component solids. A single-component solid contains essentially the pharmaceutical compound in the absence of other compounds. Variety among single-component crystalline materials may potentially arise, e.g., from the phenomenon of polymorphism, wherein multiple three-dimensional arrangements exist for a single pharmaceutical compound. See Byrn et al., Solid State Chemistry of Drugs, SSCI, West Lafayette (1999). The importance of polymorphs in pharmaceuticals was underscored by the case of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed. See Chemburkar et al., *Org. Process Res. Dev.*, 4:413-417 (2000).

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*:3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)). The preparation of solid forms is of great importance in the development of a safe, effective, stable, and marketable pharmaceutical compound.

Citation or identification of any references in this disclosure is not to be construed as an admission that the references are prior art to this disclosure.

3. SUMMARY

Provided herein are compositions of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof. In one embodiment, the solid form is crystalline. In another embodiment, the solid form is a single-component crystalline form of 7-(6-(2-hydroxypropan-2-yl)pyridin-3-yl)-1-((trans)-4-methoxycyclohexyl)-3,4-dihydropyrazino[2,3-b]pyrazin-2(1H)-one. In yet another embodiment, the solid form is crystalline Form A of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In yet another embodiment, the solid form is a hydrate. In yet another embodiment, the solid form is hydrate Form B of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In yet another embodiment, the solid form is anhydrous. In yet another embodiment, the solid form is anhydrous Form C of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In yet another embodiment, the solid form is a solvate. In yet another embodiment, the solid form is methanol solvate Form D of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In yet another embodiment, the solid form is p-xylene solvate Form E of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In yet another embodiment, the solid form is a pinacol co-crystal of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In another embodiment, the isotopologue is enriched in $^{13}C$, $^{14}C$, $^{2}H$, $^{3}H$ and/or $^{15}N$. In another embodiment, the isotopologue is enriched in $^{13}C$, $^{14}C$, and/or $^{2}H$.

Without intending to be limited by any particular theory, a solid form provided herein has particular advantageous physical and/or chemical properties making them useful, e.g., for manufacturing, processing, formulation and/or storage, while also possessing particularly advantageous biological properties, such as, e.g., bioavailability and/or biological activity.

Also provided herein are pharmaceutical compositions comprising 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, and one or more pharmaceutically acceptable excipients.

In one embodiment, the pharmaceutical composition comprises a solid form of 7-(6-(2-hydroxypropan-2-yl)pyridin-3-yl)-1-((trans)-4-methoxycyclohexyl)-3,4-dihydropyrazino[2,3-b]pyrazin-2(1H)-one, and one or more pharmaceutically acceptable excipients.

In one embodiment, the pharmaceutical composition comprises Form A of 7-(6-(2-hydroxypropan-2-yl)pyridin-3-yl)-1-((trans)-4-methoxycyclohexyl)-3,4-dihydropyrazino[2,3-b]pyrazin-2(1H)-one, and one or more pharmaceutically acceptable excipients In one embodiment, the pharmaceutical composition comprises Form B of 7-(6-(2-hydroxypropan-2-yl)pyridin-3-yl)-1-((trans)-4-methoxycyclohexyl)-3,4-dihydropyrazino[2,3-b]pyrazin-2(1H)-one, and one or more pharmaceutically acceptable excipients.

In one embodiment, the pharmaceutical composition comprises Form C of 7-(6-(2-hydroxypropan-2-yl)pyridin-3-yl)-1-((trans)-4-methoxycyclohexyl)-3,4-dihydropyrazino[2,3-b]pyrazin-2(1H)-one, and one or more pharmaceutically acceptable excipients.

In one embodiment, the pharmaceutical composition comprises Form D of 7-(6-(2-hydroxypropan-2-yl)pyridin-3-yl)-1-((trans)-4-methoxycyclohexyl)-3,4-dihydropyrazino[2,3-b]pyrazin-2(1H)-one, and one or more pharmaceutically acceptable excipients.

In one embodiment, the pharmaceutical composition comprises Form E of 7-(6-(2-hydroxypropan-2-yl)pyridin-3-yl)-1-((trans)-4-methoxycyclohexyl)-3,4-dihydropyrazino[2,3-b]pyrazin-2(1H)-one, and one or more pharmaceutically acceptable excipients.

In one embodiment, the pharmaceutical composition comprises a pinacol co-crystal of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, and one or more pharmaceutically acceptable excipients.

In one embodiment, the pharmaceutical composition comprises amorphous 7-(6-(2-hydroxypropan-2-yl)pyridin-3-yl)-1-((trans)-4-methoxycyclohexyl)-3,4-dihydropyrazino[2,3-b]pyrazin-2(1H)-one, and one or more pharmaceutically acceptable excipients.

In another embodiment, the pharmaceutical composition comprises an isotopologue of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, and one ore more pharmaceutically acceptable excipients. In one embodiment, the isotopologue is enriched in $^{13}C$, $^{14}C$, $^{2}H$, $^{3}H$ and/or $^{15}N$. In another embodiment, the isotopologue is enriched in $^{13}C$, $^{14}C$, and/or $^{2}H$.

Additionally, provided herein are isotopologues of 7-(6-(2-hydroxypropan-2-yl)pyridin-3-yl)-1-((trans)-4-methoxycyclohexyl)-3,4-dihydropyrazino[2,3-b]pyrazin-2(1H)-one itself, including isotopologues enriched in $^{13}C$, $^{14}C$, $^{2}H$, $^{3}H$ and/or $^{15}N$, including those set forth herein.

Additionally, provided herein is are methods of treating or preventing a disease, disorder, or condition in a subject, which comprises administering to the subject a therapeutically effective amount of a composition of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof. In certain embodiments, the disease, disorder, or condition is cancer, inflammatory conditions, immunological conditions, neurodegenerative diseases, diabetes, obesity, neurological disorders, age-related diseases, and/or cardiovascular conditions, and/or conditions treatable or preventable by inhibition of a kinase pathway. In one embodiment, the kinase pathway is the mTOR/PI3K/Akt pathway.

Provided herein are methods of treating or preventing a disease, disorder, or condition in a subject, which comprise inhibiting a kinase pathway in said subject with a metabolite of 7-(6-(2-hydroxypropan-2-yl)pyridin-3-yl)-1-((trans)-4- methoxycyclohexyl)-3,4-dihydropyrazino[2,3-b]pyrazin-2(1H)-one. In certain embodiments, the metabolite is the O-desmethyl metabolite (having the name 1-((trans)-4-hydroxycyclohexyl)-7-(6-(2-hydroxypropan-2-yl)pyridin-3-yl)-3,4-dihydropyrazino[2,3-b]pyrazin-2(1H)-one). In certain embodiments, the disease, disorder, or condition is cancer, inflammatory conditions, immunological conditions, neurodegenerative diseases, diabetes, obesity, neurological disorders, age-related diseases, and/or cardiovascular conditions, and/or conditions treatable or preventable by inhibition of a kinase pathway. In one embodiment, the kinase pathway is the mTOR/PI3K/Akt pathway.

Provided herein are methods of treating or preventing a disease, disorder, or condition in a subject, which comprise administering an effective amount of a compound that provides a metabolite of 7-(6-(2-hydroxypropan-2-yl)pyridin-3-yl)-1-((trans)-4-methoxycyclohexyl)-3,4-dihydropyrazino[2,3-b]pyrazin-2(1H)-one upon administration to said patient. In certain embodiments, the metabolite is the O-desmethyl metabolite (having the name 1-((trans)-4-hydroxycyclohexyl)-7-(6-(2-hydroxypropan-2-yl)pyridin-3-yl)-3,4-dihydropyrazino[2,3-b]pyrazin-2(1H)-one). In certain embodiments, the disease, disorder, or condition is cancer, inflammatory conditions, immunological conditions, neurodegenerative diseases, diabetes, obesity, neurological disorders, age-related diseases, and/or cardiovascular conditions, and/or conditions treatable or preventable by inhibition of a kinase pathway. In one embodiment, the kinase pathway is the mTOR/PI3K/Akt pathway.

In one embodiment, the method comprises administering to the subject a therapeutically effective amount of Form A of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of Form B of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of Form C of 7-(6-(2-hydroxypropan-2-yl)pyridin-3-yl)-1-((trans)-4-methoxycyclohexyl)-3,4-dihydropyrazino[2,3-b]pyrazin-2(1H)-one.

1 In one embodiment, the method comprises administering to the subject a therapeutically effective amount of Form D of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of Form E of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of a pinacol co-crystal of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of amorphous 7-(6-(2-hydroxypropan-2-yl)pyridin-3-yl)-1-((trans)-4-methoxycyclohexyl)-3,4-dihydropyrazino[2,3-b]pyrazin-2(1H)-one.

In another embodiment, the method comprises administering to the subject a therapeutically effective amount of an isotopologue of 7-(6-(2-hydroxypropan-2-yl)pyridin-3-yl)-1-((trans)-4-methoxycyclohexyl)-3,4-dihydropyrazino[2,3-b]pyrazin-2(1H)-one. In one embodiment, the isotopologue is enriched in $^{13}C$, $^{14}C$, $^{2}H$, $^{3}H$ and/or $^{15}N$. In another embodiment, the isotopologue is enriched in $^{13}C$, $^{14}C$, and/or $^{2}H$.

Further provided herein is are methods of treating or preventing a proliferative disease in a subject, which comprises administering to the subject a therapeutically effective amount of a composition of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof.

In one embodiment, the method comprises administering to the subject a therapeutically effective amount of Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

In one embodiment, the method comprises administering to the subject a therapeutically effective amount of Form B of 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

In one embodiment, the method comprises administering to the subject a therapeutically effective amount of Form C of 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

In one embodiment, the method comprises administering to the subject a therapeutically effective amount of Form D of 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

In one embodiment, the method comprises administering to the subject a therapeutically effective amount of Form E of 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

In one embodiment, the method comprises administering to the subject a therapeutically effective amount of a pinacol co-crystal of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount amorphous 7-(6-(2-hydroxypropan-2-yl)pyridin-3-yl)-1-((trans)-4-methoxycyclohexyl)-3,4-dihydropyrazino[2,3-b]pyrazin-2(1H)-one.

In another embodiment, the method comprises administering to the subject a therapeutically effective amount of an isotopologue of 7-(6-(2-hydroxypropan-2-yl)pyridin-3-yl)-1-((trans)-4-methoxycyclohexyl)-3,4-dihydropyrazino[2,3-b]pyrazin-2(1H)-one. In one embodiment, the isotopologue is enriched in $^{13}C$, $^{14}C$, $^{2}H$, $^{3}H$ and/or $^{15}N$. In another embodiment, the isotopologue is enriched in $^{13}C$, $^{14}C$, and/or $^{2}H$.

Provided herein are methods of treating or preventing an mTOR-mediated disease in a subject, which comprises administering to the subject a therapeutically effective amount of a composition of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof.

In one embodiment, the method comprises administering to the subject a therapeutically effective amount of Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

In one embodiment, the method comprises administering to the subject a therapeutically effective amount of Form B of 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

In one embodiment, the method comprises administering to the subject a therapeutically effective amount of Form C of 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

In one embodiment, the method comprises administering to the subject a therapeutically effective amount of Form D of 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

In one embodiment, the method comprises administering to the subject a therapeutically effective amount of Form E of 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

1 In one embodiment, the method comprises administering to the subject a therapeutically effective amount of a pinacol co-crystal of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of amorphous 7-(6-(2-hydroxypropan-2-yl)pyridin-3-yl)-1-((trans)-4-methoxycyclohexyl)-3,4-dihydropyrazino[2,3-b]pyrazin-2(1H)-one.

In another embodiment, the method comprises administering to the subject a therapeutically effective amount of an isotopologue of 7-(6-(2-hydroxypropan-2-yl)pyridin-3-yl)-1-((trans)-4-methoxycyclohexyl)-3,4-dihydropyrazino[2,3-b]pyrazin-2(1H)-one. In one embodiment, the isotopologue is enriched in $^{13}C$, $^{14}C$, $^{2}H$, $^{3}H$ and/or $^{15}N$. In another embodiment, the isotopologue is enriched in $^{13}C$, $^{14}C$, and/or $^{2}H$.

Provided herein are methods of inhibiting the growth of a cell, comprising contacting the cell with a composition of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof.

In one embodiment, the method comprises contacting the cell with Form A of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises contacting the cell with Form B of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises contacting the cell with Form C of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises contacting the cell with Form D of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises contacting the cell with Form E of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises contacting the cell with a pinacol co-crystal of 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

In one embodiment, the method comprises contacting the cell with amorphous 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

In another embodiment, the method comprises contacting a cell with an isotopologue of 7-(6-(2-hydroxypropan-2-yl)pyridin-3-yl)-1-((trans)-4-methoxycyclohexyl)-3,4-dihydropyrazino[2,3-b]pyrazin-2(1H)-one. In one embodiment, the isotopologue is enriched in $^{13}C$, $^{14}C$, $^{2}H$, $^{3}H$ and/or $^{15}N$. In another embodiment, the isotopologue is enriched in $^{13}C$, $^{14}C$, and/or $^{2}H$.

Provided herein are methods of modulating the activity of TOR kinase, comprising contacting TOR kinase with a composition of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite, or solid form thereof.

In one embodiment, the method comprises contacting TOR kinase with Form A of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises contacting TOR kinase with Form B of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises contacting TOR kinase with Form C of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises contacting TOR kinase with Form D of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises contacting TOR kinase with Form E of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises contacting TOR kinase with a pinacol co-crystal of 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

In one embodiment, the method comprises contacting TOR kinase with amorphous 7-(6-(2-hydroxypropan-2-yl)pyridin-3-yl)-1-((trans)-4-methoxycyclohexyl)-3,4-dihydro-pyrazino[2,3-b]pyrazin-2(1H)-one.

In another embodiment, the method comprises the method comprises contacting TOR kinase with an isotopologue of 7-(6-(2-hydroxypropan-2-yl)pyridin-3-yl)-1-((trans)-4-methoxycyclohexyl)-3,4-dihydropyrazino[2,3-b]pyrazin-2(1H)-one. In one embodiment, the isotopologue is enriched in $^{13}C$, $^{14}C$, $^{2}H$, $^{3}H$ and/or $^{15}N$. In another embodiment, the isotopologue is enriched in $^{13}C$, $^{14}C$, and/or $^{2}H$.

Provided herein are methods for treating or preventing a solid tumor, non-Hodgkin lymphoma or multiple myeloma comprising administering an effective amount of a composition of 7-(6-(2-hydroxypropan-2-yl)pyridin-3-yl)-1-((trans)-4-methoxycyclohexyl)-3,4-dihydropyrazino[2,3-b]pyrazin-2(1H)-one, isotopologue, metabolite or a pharmaceutically acceptable salt or solid form thereof, to a subject having a solid tumor, non-Hodgkin lymphoma or multiple myeloma.

In one embodiment, the method comprises administering to the subject a therapeutically effective amount of Form A of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of Form B of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of Form C of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of Form D of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of Form E of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of a pinacol co-crystal of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of amorphous 7-(6-(2-hydroxypropan-2-yl)pyridin-3-yl)-1-((trans)-4-methoxycyclohexyl)-3,4-dihydropyrazino[2,3-b]pyrazin-2(1H)-one.

In another embodiment, the method comprises administering to the subject a therapeutically effective amount of an isotopologue of 7-(6-(2-hydroxypropan-2-yl)pyridin-3-yl)-1-((trans)-4-methoxycyclohexyl)-3,4-dihydropyrazino[2,3-b]pyrazin-2(1H)-one. In one embodiment, the isotopologue is enriched in $^{13}C$, $^{14}C$, $^{2}H$, $^{3}H$ and/or $^{15}N$. In another embodiment, the isotopologue is enriched in $^{13}C$, $^{14}C$, and/or $^{2}H$.

In certain embodiments, provided herein are methods for achieving a Response Evaluation Criteria in Solid Tumors (RECIST 1.1) of complete response, partial response or stable disease, improving the International Workshop Criteria (IWC) for NHL, International Uniform Response Criteria for Multiple Myeloma (IURC), Eastern Cooperative Oncology Group Performance Status (ECOG) or Response Assessment for Neuro-Oncology (RANO) Working Group for GBM comprising administering an effective amount of a composition of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, or a pharmaceutically acceptable salt, isotopologue, metabolite or solid form thereof to a subject having a solid tumor, non-Hodgkin lymphoma or multiple myeloma In one embodiment, the method comprises administering to the subject a therapeutically effective amount of Form A of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of Form B of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of Form C of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of Form D of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of Form E of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of a pinacol co-crystal of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, the method comprises administering to the subject a therapeutically effective amount of amorphous 7-(6-(2-hydroxypropan-2-yl)pyridin-3-yl)-1-((trans)-4-methoxycyclohexyl)-3,4-dihydropyrazino[2,3-b]pyrazin-2(1H)-one.

In another embodiment, the method comprises administering to the subject a therapeutically effective amount of an isotopologue of 7-(6-(2-hydroxypropan-2-yl)pyridin-3-yl)-1-((trans)-4-methoxycyclohexyl)-3,4-dihydropyrazino[2,3-b]pyrazin-2(1H)-one. In one embodiment, the isotopologue is enriched in $^{13}C$, $^{14}C$, $^{2}H$, $^{3}H$ and/or $^{15}N$. In another embodiment, the isotopologue is enriched in $^{13}C$, $^{14}C$, and/or $^{2}H$.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving amorphous 7-(6-(2-hydroxypropan-2-yl)pyridin-3-yl)-1-((trans)-4-methoxycyclohexyl)-3,4-dihydro-pyrazino[2,3-b]pyrazin-2(1H)-one in toluene, MTBE (methyl tert-butyl ether), DIPE (diisopropyl ether), THF (tetrahydrofuran), DME (dimethoxyethane), IPAc (isopropyl acetate), EtOAc (ethyl acetate), MIBK (methyl isobutyl ketone), acetone, IPA (isopropyl alcohol), ethanol, ACN (acetonitrile), nitromethane, or IPA:water (95:5) and allowing the resulting solution to evaporate at room temperature.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT (butylated hydroxytoluene), IPA and water, heating and then cooling to room temperature.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT and MeOAc (methyl acetate), heating, cooling to room temperature, distilling under vacuum and contacting with n-heptane.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino

[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT and MeOAc (methyl acetate), heating, filtering, cooling, distilling under vacuum and contacting with n-heptane.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one and 7-(6-(2-hydroxypropan-2-yl)pyridin-3-yl)-1-((trans)-4-methoxycyclohexyl)-3,4-dihydropyrazino[2,3-b]pyrazin-2(1H)-one pinacol cocrystal in IPA.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT, THF and water, contacting with IPAc, heating, distilling, cooling, contacting with IPAc, heating, distilling and then cooling to room temperature.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT, THF and water, contacting with IPAc, heating, distilling under reduced pressure, contacting with IPAc, and then cooling to room temperature. In one embodiment, the methods additionally comprise treating with activated carbon.

In certain embodiments, provided herein are methods for making Form B of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT, IPA and water, heating mixture and adding water, cooling the mixture, collecting by filtration, washing with IPA & water, and drying. In certain embodiments, this method further comprises adding a small amount of Form B in water to the mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one in BHT, IPA and water.

In certain embodiments, provided herein are methods for making Form C of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT, MeOH, distilling to remove MeOH, further distillation with IPA, cooling the mixture, collecting by filtration, washing with IPA and drying.

In certain embodiments, provided herein are methods for making Form D of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT in MeOH, heating, then cooling with stirring, collection by filtration, washing and drying.

In certain embodiments, provided herein are methods for making Form E of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising obtaining a slurry of 7-(6-(2-hydroxypropan-2-yl)pyridin-3-yl)-1-((trans)-4-methoxycyclohexyl)-3,4-dihydro-pyrazino[2,3-b]pyrazin-2(1H)-one in p-xylene/acetone (50/50), heating the slurry to about 60° C., filtering the slurry to yield a solution, cooling down the solution to about 25° C. to yield solids, and collecting the solids.

In certain embodiments, provided herein are methods for making a pinacol co-crystal of 7-(6-(2-hydroxypropan-2-yl)pyridin-3-yl)-1-((trans)-4-methoxycyclohexyl)-3,4-dihydropyrazino[2,3-b]pyrazin-2(1H)-one, comprising mixing 7-(6-(2-hydroxypropan-2-yl)pyridin-3-yl)-1-((trans)-4-methoxycyclohexyl)-3,4-dihydropyrazino[2,3-b]pyrazin-2(1H)-one with pinacol in solution, heating until solids are dissolved, distilling said solution and seeding with a pinacol co-crystal of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In certain embodiments, provided herein are methods for preparing a composition provided herein, comprising: (i) weighing out the desired amount of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, or a pharmaceutically acceptable salt, isotopologue, metabolite or solid form thereof and the desired amount of excipients; (ii) mixing or blending 7-(6-(2-hydroxypropan-2-yl)pyridin-3-yl)-1-((trans)-4-methoxycyclohexyl)-3,4-dihydro-pyrazino[2,3-b]pyrazin-2(1H)-one, or a pharmaceutically acceptable salt, isotopologue, metabolite or solid form thereof and the excipients; (iii) passing the mixture of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, or a pharmaceutically acceptable salt, isotopologue, metabolite or solid form thereof and excipients through a screen; (iv) mixing or blending 7-(6-(2-hydroxypropan-2-yl)pyridin-3-yl)-1-((trans)-4-methoxycyclohexyl)-3,4-dihydro-pyrazino[2,3-b]pyrazin-2(1H)-one, or a pharmaceutically acceptable salt, isotopologue, metabolite or solid form thereof and the excipients; (v) weighing out the desired amount of lubricating agents; (vi) passing the lubricating agents through a screen; (vii) mixing or blending 7-(6-(2-hydroxypropan-2-yl)pyridin-3-yl)-1-((trans)-4-methoxycyclohexyl)-3,4-dihydro-pyrazino[2,3-b]pyrazin-2(1H)-one, or a pharmaceutically acceptable salt, isotopologue, metabolite or solid form thereof, the excipients and the lubricating agents; (viii) compressing the mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents; and (ix) coating the compressed mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents.

In certain embodiments, provided herein are methods for preparing a composition provided herein, comprising: (i) weighing out the desired amount of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, or a pharmaceutically acceptable salt, isotopologue, metabolite or solid form thereof and the desired amount of excipients; (ii) passing the excipients through a screen; (iii) mixing or blending 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof and the excipients; (iv) passing the mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof and excipients through a screen; (v) mixing or blending 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof and the excipients; (vi) weighing out the desired amount of lubricating agents; (vii) passing the lubricating agents through a screen; (viii) mixing or blending 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents; (ix) compressing the mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents; and (x) coating the compressed mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents.

4. BRIEF DESCRIPTION OF THE DRAWINGS

Figure 17:
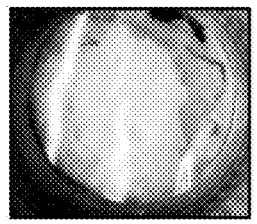
Figure 17:
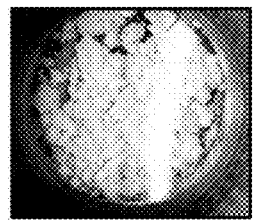
Figure 17:
Figure 17:
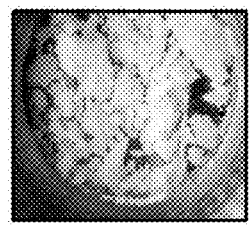

FIG. 17: (A) depicts a digital image of Form E as a wet solid of 7-(6-(2-hydroxypropan-2-yl)pyridin-3-yl)-1-((trans)-4-methoxycyclohexyl)-3,4-dihydropyrazino[2,3-b]pyrazin-2(11H)-one. (B) depicts a digital image of Form E as a dried solid of 7-(6-(2-hydroxypropan-2-yl)pyridin-3-yl)-1-((trans)-4-methoxycyclohexyl)-3,4-dihydropyrazino[2,3-b]pyrazin-2(11H)-one. (C) depicts a digital image of Form E as a wet solid after exposure to AAC of 7-(6-(2-hydroxypropan-2-yl)pyridin-3-yl)-1-((trans)-4-methoxycyclohexyl)-3,4-dihydropyrazino[2,3-b]pyrazin-2(1H)-one. (D) depicts a digital image of Form E as a dried solid after exposure to AAC of 7-(6-(2-hydroxypropan-2-yl)pyridin-3-yl)-1-((trans)-4-methoxycyclohexyl)-3,4-dihydropyrazino[2,3-b]pyrazin-2(1H)-one.

Figure 18:
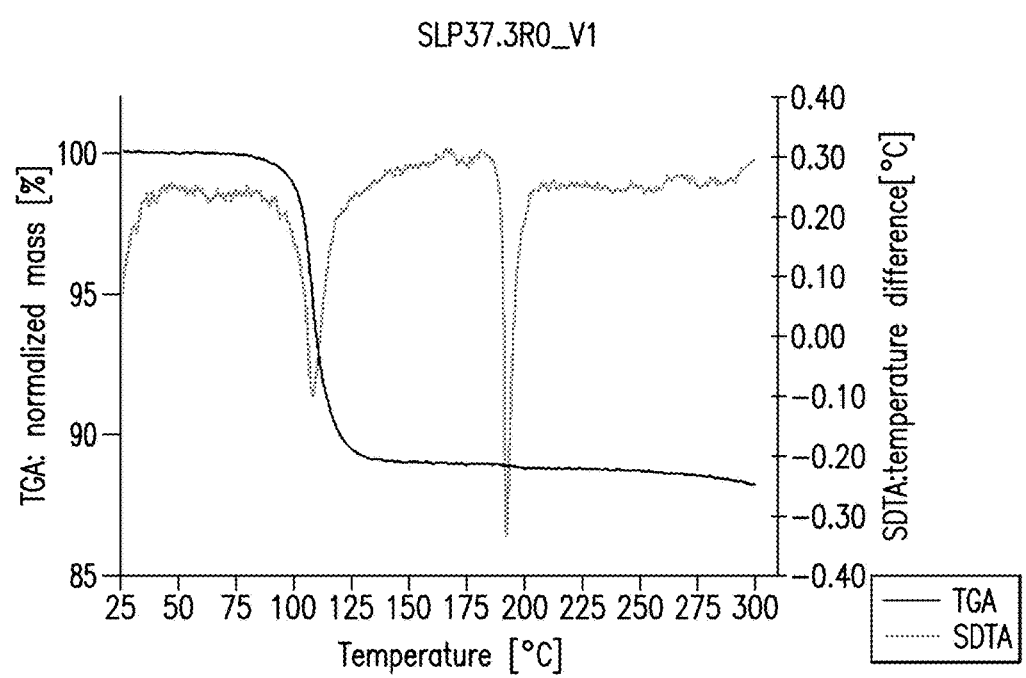

FIG. 18 depicts a thermogravimetrical analysis and single differential thermal analysis of Form E of 7-(6-(2-hydroxypropan-2-yl)pyridin-3-yl)-1-((trans)-4-methoxycyclohexyl)-3,4-dihydropyrazino[2,3-b]pyrazin-2(1H)-one.

Figure 19:
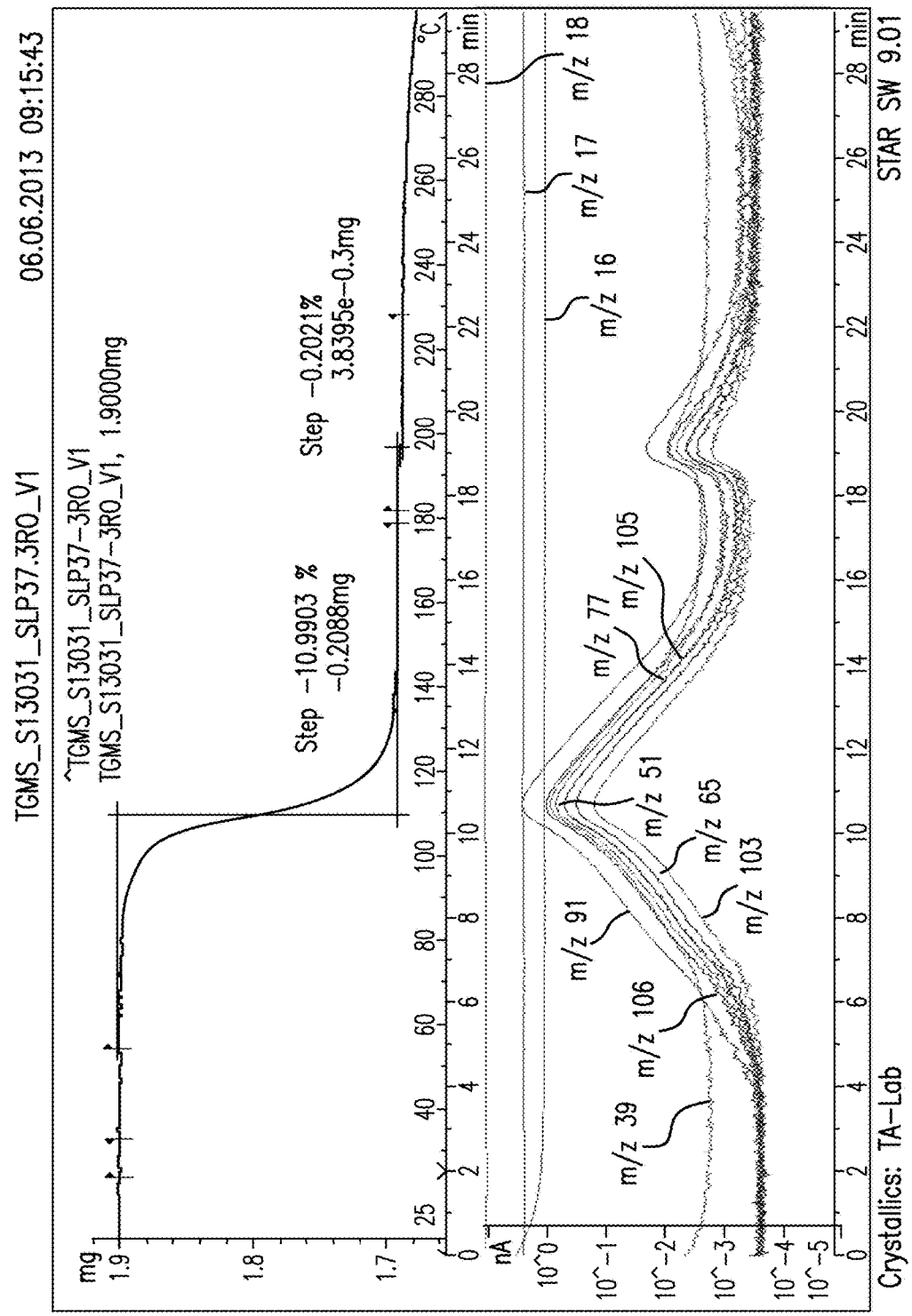

FIG. 19 depicts a thermogravimetric analysis coupled with mass spectroscopy of Form E of 7-(6-(2-hydroxypropan-2-yl)pyridin-3-yl)-1-((trans)-4-methoxycyclohexyl)-3,4-dihydropyrazino[2,3-b]pyrazin-2(1H)-one.

Figure 20:
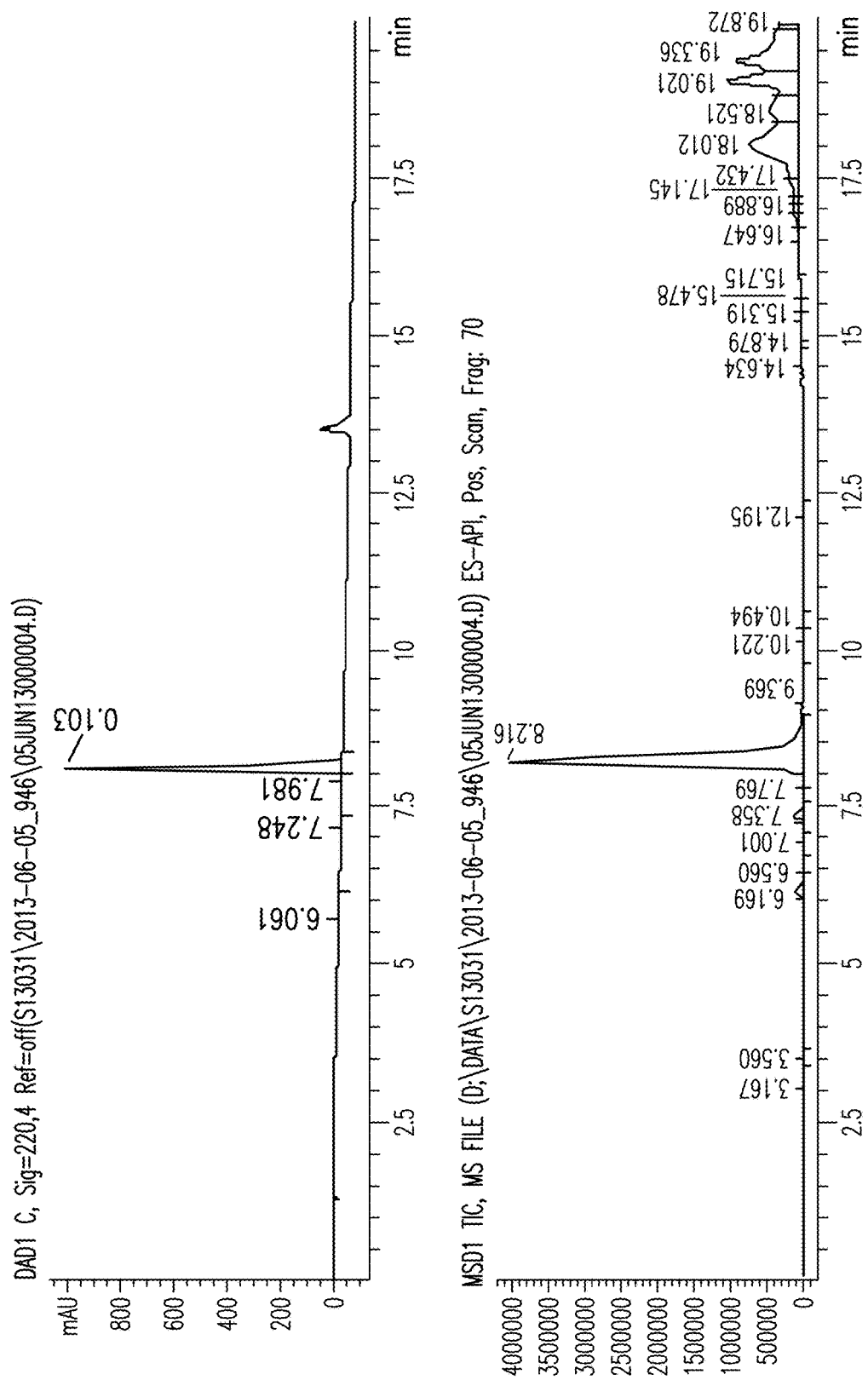

FIG. 20 depicts high performance liquid chromatography coupled with mass spectrometry of Form E of 7-(6-(2-hydroxypropan-2-yl)pyridin-3-yl)-1-((trans)-4-methoxycyclohexyl)-3,4-dihydropyrazino[2,3-b]pyrazin-2(1H)-one.

5. DETAILED DESCRIPTION

5.1 Definitions

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The term "Compound A" refers to 7-(6-(2-hydroxypropan-2-yl)pyridin-3-yl)-1-((trans)-4-methoxycyclohexyl)-3,4-dihydropyrazino[2,3-b]pyrazin-2(1H)-one, also having the chemical names 7-(6-(2-hydroxypropan-2-yl)pyridin-3-yl)-1-((1r,4r)-4-methoxycyclohexyl)-3,4-dihydropyrazino[2,3-b]pyrazin-2(1H)-one and 7-(6-(2-hydroxypropan-2-yl)pyridin-3-yl)-1-((1R*,4R*)-4-methoxycyclohexyl)-3,4-dihydropyrazino[2,3-b]pyrazin-2(1H)-one, which has the following structure:

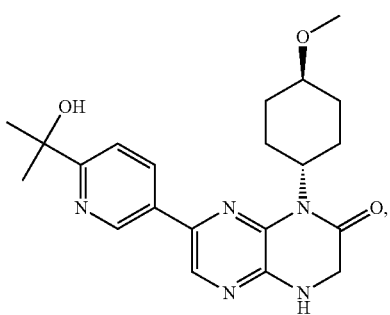 [SMILES: CO[C@H]1CC[C@H](N2C(=O)CNc3ncc(-c4ccc(C(C)(C)O)nc4)nc32)CC1]

including pharmaceutically acceptable salts, isotopologues, solid forms and metabolites thereof.

Compound A can be prepared according to the methods described in U.S. Pat. Appl. Publ. Nos. 2010/0216781 and 2011/0137028, the disclosure of each of which is incorporated herein by reference in its entirety. Compound A can also be synthesized according to other methods apparent to those of skill in the art based upon the teaching herein.

The term "subject" refers to an animal, including, but not limited to, a primate (e.g., human), cow, pig, sheep, goat, horse, dog, cat, rabbit, rat, or mouse. The terms "subject" and "patient" are used herein interchangeably in reference, for example, to a mammalian subject, such as a human subject, in one embodiment, a human. In one embodiment, the subject has or is susceptible to having a disease, disorder, or condition provided herein.

The term "treat," "treating," or "treatment" means an alleviation, in whole or in part, of a disease, disorder, or condition provided herein, or one or more symptoms associated with the disease, disorder, or condition, or slowing, or halting of further progression or worsening of the disease, disorder, or condition, or one or more symptoms associated with the disease, disorder, or condition.

The term "prevent," "preventing," or "prevention" means prevention of the onset, recurrence, or spread of a disease, disorder, or condition provided herein, or one or more symptoms associated with the disease, disorder, or condition, in a subject at risk for developing the disease, disorder, or condition.

The term "effective amount" or "therapeutically effective amount" refers to, in one embodiment, an amount of Compound A capable of alleviating, in whole or in part, one or more symptoms associated with a disease, disorder, or condition provided herein, or slowing or halting further progression or worsening of one or more of the symptoms of the disease, disorder, or condition; in another embodiment, an amount capable of preventing or providing prophylaxis for the disease, disorder, or condition in a subject at risk for developing the disease, disorder, or condition, such as cancer, inflammatory conditions, immunological conditions, neurodegenerative diseases, diabetes, obesity, neurological disorders, age-related diseases, and/or cardiovascular conditions, and/or diseases, disorders, and conditions treatable or preventable by inhibition of a kinase pathway, for example, the mTOR/PI3K/Akt pathway. In one embodiment, an effective amount of a compound is an amount that inhibits a kinase in a cell, such as, for example, in vitro or in vivo. In one embodiment the kinase is TOR kinase. In certain embodiments, the effective amount of a compound inhibits the kinase in a cell by about 10%, about 20%, about 30%, about 40%, about 50%, about 60%, about 70%, about 80%, about 90%, or about 99%, compared to the activity of the kinase in an untreated cell. In one embodiment, "effective amount" refers to the amount of Compound A capable of alleviating, in whole or in part, symptoms associated with a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma, including advanced solid tumors), non-Hodgkin lymphoma or multiple myeloma, or slowing or halting further progression or worsening of those symptoms, or treating or preventing a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma in a subject having or at risk for having a solid tumor, non-Hodgkin lymphoma or multiple myeloma. As will be apparent to those skilled in the art, it is to be expected that the effective amount of a compound disclosed herein may vary depending on the indication being treated, e.g., the effective amount of the compound would likely be different for treating patients suffering from, or at risk for, inflammatory conditions relative to the effective amount of the compound for treating patients suffering from, or at risk of, a different disorder, e.g., a disorder provided herein.

In the context of a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma, including advanced solid tumors), non-Hodgkin lymphoma or multiple myeloma, inhibition may be assessed by inhibition or retarding of disease progression, inhibition of tumor growth, reduction or regression of primary and/or secondary tumor (s), relief of tumor-related symptoms, improvement in quality of life, inhibition of tumor secreted factors (including tumor secreted hormones, such as those that contribute to carcinoid syndrome), reductions in endocrine hormone markers (for example, chromogranin, gastrin, serotonin, and/or glucagon), delayed appearance or recurrence of primary or secondary tumors, slowed development of primary and/or secondary tumors, decreased occurrence of primary and/or secondary tumors, slowed or decreased severity of secondary effects of disease, arrested tumor growth and/or regression of tumors, increased Time To Progression (TTP), increased Progression Free Survival (PFS), increased Overall Survival (OS), among others. OS as used herein means the time from randomization until death from any cause, and is measured in the intent-to-treat population. TTP as used herein means the time from randomization until objective tumor progression; TTP does not include deaths. As used herein, PFS means the time from randomization until objective tumor progression or death. In one embodiment, PFS rates will be computed using the Kaplan-Meier estimates. In the extreme, complete inhibition, is referred to herein as prevention or chemoprevention. In this context, the term "prevention" includes either preventing the onset of clinically evident solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma, including advanced solid tumors), non-Hodgkin lymphoma or multiple myeloma altogether or preventing the onset of a preclinically evident stage of a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma, including advanced solid tumors), non-Hodgkin lymphoma or multiple myeloma. Also intended to be encompassed by this definition is the prevention of transformation into malignant cells or to arrest or reverse the progression of premalignant cells to malignant cells. This includes prophylactic treatment of those at risk of developing a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma, including advanced solid tumors), non-Hodgkin lymphoma or multiple myeloma.

The term "cancer" refers to any of various malignant neoplasms characterized by the proliferation of cells that can invade surrounding tissue and metastasize to new body sites. Both benign and malignant tumors are classified according to the type of tissue in which they are found. For example, fibromas are neoplasms of fibrous connective tissue, and melanomas are abnormal growths of pigment (melanin) cells. Malignant tumors originating from epithelial tissue, e.g., in skin, bronchi, and stomach, are termed carcinomas. Malignancies of epithelial glandular tissue such as are found in the breast, prostate, and colon, are known as adenocarcinomas. Malignant growths of connective tissue, e.g., muscle, cartilage, lymph tissue, and bone, are called sarcomas. Lymphomas and leukemias are malignancies arising among white blood cells. Through the process of metastasis, tumor cell migration to other areas of the body establishes neoplasms in areas away from the site of initial appearance. Bone tissues are one of the most favored sites of metastases of malignant tumors, occurring in about 30% of all cancer cases. Among malignant tumors, cancers of the lung, breast, prostate or the like are particularly known to be likely to metastasize to bone.

An "advanced solid tumor" as used herein, means a solid tumor that has spread locally, or metastasized or spread to another part of the body.

In certain embodiments, the treatment may be assessed by Response Evaluation Criteria in Solid Tumors (RECIST 1.1) (see Thereasse P., et al. New Guidelines to Evaluate the Response to Treatment in Solid Tumors. J. of the National Cancer Institute; 2000; (92) 205-216 and Eisenhauer E. A., Therasse P., Bogaerts J., et al. New response evaluation criteria in solid tumours: Revised RECIST guideline (version 1.1). European J. Cancer; 2009; (45) 228-247). Overall responses for all possible combinations of tumor responses in target and non-target lesions with our without the appearance of new lesions are as follows:

| Target lesions | Non-target lesions | New lesions | Overall response |
| --- | --- | --- | --- |
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response;
PR = partial response;
SD = stable disease; and
PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions and stable disease (SD) is neither sufficient shrinkage to qualify for partial response nor sufficient increase to qualify for progressive disease, taking as reference the smallest sum longest diameter since the treatment started.

With respect to the evaluation of non-target lesions, complete response (CR) is the disappearance of all non-target lesions and normalization of tumor marker level; incomplete response/stable disease (SD) is the persistence of one or more non-target lesion(s) and/or the maintenance of tumor marker level above the normal limits, and progressive disease (PD) is the appearance of one or more new lesions and/or unequivocal progression of existing non-target lesions.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
| --- | --- | --- | --- | --- |
| CR | Disappearance of all evidence of disease | (a) FDG-avid or PET positive prior to therapy; mass of any size permitted if PET negative<br>(b) Variably FDG-avid or PET negative; regression to normal size on CT | Not palpable, nodules disappeared | Infiltrate cleared on repeat biopsy; if indeterminate by morphology, immunohisto-chemistry should be negative |
| PR | Regression of measurable disease and no new sites | ≥50% decrease in SPD of up to 6 largest dominant masses; no increase in size of other nodes<br>(a) FDG-avid or PET positive prior to therapy; one or more PET positive at previously involved site<br>(b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or PD | (a) FDG-avid or PET positive prior to therapy; PET positive at prior sites of disease and no new sites on CT or PET<br>(b) Variably FDG-avid or PET negative; no change in size of previous lesions on CT | | |
| PD or relapsed disease | Any new lesion or increase by ≥ 50% of previously involved sites from nadir | Appearance of a new lesion(s) ≥1.5 cm in any axis, ≥50% increase in SPD of more than one node, or ≥ 50% increase in longest diameter of a previously identifed node ≥ 1 cm in short axis Lesions PET positive if FDG-avid lymphoma or PET positive prior to therapy | ≥50% increase from nadir in the SPD of any previous lesions | New or recurrent involvement |

Abbreviations:
CR, complete remission;
FDG, [$^{18}$F]fluorodeoxyglucose;
PET, positron emission tomography;
CT, computed tomography;
PR, partial remission;
SPD, sum of the product of the diameters;
SD, stable disease;
PD, progressive disease.

| End point | Patients | Definition | Measured from |
| --- | --- | --- | --- |
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations:
CR: complete remission;
PR: partial remission.

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of lymphoma-related symptoms can also be used in this end point.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7), using the response and endpoint definitions shown below:

| Response Subcategory | Response Criteria[a] |
| --- | --- |
| sCR | CR as defined below plus<br>Normal FLC ratio and<br>Absence of clonal cells in bone marrow[b] by<br>immunohistochemistry or immunofluorescence[c] |
| CR | Negative immunofixation on the serum and urine and<br>Disappearance of any soft tissue plasmacytomas and <<br>5% plasma cells in bone marrow[b] |
| VGPR | Serum and urine M-protein detectable by<br>immunofixation but not on electrophoresis or 90% or<br>greater reduction in serum M-protein plus urine M-<br>protein level < 100 mg per 24 h |
| PR | ≥50% reduction of serum M-protein and reduction in<br>24-h urinary M-protein by ≥ 90% or to < 200 mg per<br>24 h<br>If the serum and urine M-protein are unmeasurable,[d] a ≥<br>50% decrease in the difference between involved and<br>uninvolved FLC levels is required in place of the M-<br>protein criteria<br>If serum and urine M-protein are unmeasurable, and<br>serum free light assay is also unmeasurable, ≥50%<br>reduction in plasma cells is required in place of M-<br>protein, provided baseline bone marrow plasma cell<br>percentage was ≥ 30%<br>In addition to the above listed criteria, if present at<br>baseline, a ≥ 50% reduction in the size of soft tissue<br>plasmacytomas is also required |
| SD (not recommended for use as an indicator of response; stability of disease is best described by providing the time to progression estimates) | Not meeting criteria for CR, VGPR, PR or progressive disease |

Abbreviations:
CR, complete response;
FLC, free light chain;
PR, partial response;
SD, stable disease;
sCR, stringent complete response;
VGPR, very good partial response;
[a]All response categories require two consecutive assessments made at anytime before the institution of any new therapy; all categories also require no known evidence of progressive or new bone lesions if radiographic studies were performed. Radiographic studies are not required to satisfy these response requirements;
[b]Confirmation with repeat bone marrow biopsy not needed;
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of > 4:1 or < 1:2.
[d]Measurable disease defined by at least one of the following measurements: Bone marrow plasma cells ≥ 30%; Serum M-protein ≥ 1 g/dl (≥10 gm/l)[10 g/l]; Urine M-protein ≥ 200 mg/24 h; Serum FLC assay: Involved FLC level ≥ 10 mg/dl (≥100 mg/l); provided serum FLC ratio is abnormal.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for highgrade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MRI scan is defined as the assessment performed at the end of the post-surgery rest period, prior to re-initiating compound treatment. The baseline MRI is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined MRI scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bidimensionally. A measurement is made of the maximal enhancing tumor diameter (also known as the longest diameter, LD). The greatest perpendicular diameter is measured on the same image. The cross hairs of bidimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bidimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all nonenhancing and other truly nonmeasurable lesions. Nonmeasurable lesions include foci of enhancement that are less than the specified smallest diameter (ie., less than 5 mm by 5 mm), nonenhancing lesions (eg., as seen on T1-weighted post-contrast, T2-weighted, or fluid-attenuated inversion recovery (FLAIR) images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (eg., recorded in the same order on source documents and eCRFs). All measurable and nonmeasurable lesions must be assessed using the same technique as at baseline (e.g., subjects should be imaged on the same MRI scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "solid form" refers to a physical form which is not predominantly in a liquid or a gaseous state. As used herein and unless otherwise specified, the term "solid form," when used herein to refer to Compound A, refers to a physical form comprising Compound A which is not predominantly in a liquid or a gaseous state. A solid form may be a crystalline form, an amorphous form, or a mixture thereof. In certain embodiments, a solid form may be a liquid crystal. In certain embodiments, the term "solid forms comprising Compound A" includes crystal forms comprising Compound A, amorphous forms comprising Compound A, and mixtures thereof.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23' ed., 1843-1844 (1995).

The term "crystal form" or "crystalline form" refers to a solid form that is crystalline. In certain embodiments, crystal forms include salts. In certain embodiments, a crystal form of a substance may be substantially free of amorphous forms and/or other crystal forms. In certain embodiments, a crystal form of a substance may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous forms and/or other crystal forms. In certain embodiments, a crystal form of a substance may be physically and/or chemically pure. In certain embodiments, a crystal form of a substance may be about 99%, about 98%, about 97%, about 96%, about 95%, about 94%, about 93%, about 92%, about 91%, or about 90% physically and/or chemically pure.

The term "amorphous" or "amorphous form" means that the substance, component, or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In certain embodiments, an amorphous form of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous forms and/or crystal forms on a weight basis. In certain embodiments, an amorphous form of a substance may be physically and/or chemically pure. In certain embodiments, an amorphous form of a substance be about 99%, about 98%, about 97%, about 96%, about 95%, about 94%, about 93%, about 92%, about 91%, or about 90% physically and/or chemically pure.

The term "solvate" means a crystalline structure comprised of either stoichiometric or nonstoichiometric amounts of a solvent incorporated within the crystalline structure.

The term "hydrate" means a crystalline structure comprised of either stoichiometric or nonstoichiometric amounts of water incorporated within the crystalline structure.

Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis, and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder.

The term "pharmaceutically acceptable salt(s)" means a salt prepared from a pharmaceutically acceptable non-toxic acid or base including an inorganic acid and base and an organic acid and base. Suitable pharmaceutically acceptable base addition salts of Compound A include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, Remington's Pharmaceutical Sciences, 18th eds., Mack Publishing, Easton Pa. (1990) or Remington: The Science and Practice of Pharmacy, 19th eds., Mack Publishing, Easton Pa. (1995).

The term "isotopologue" means any form of Compound A, including metabolites thereof, in which at least one atom of natural isotopic abundance is replaced with an isotopically enriched form that differs from natural abundance. An isotopologue can be based on replacement of hydrogen for deuterium and/or tritium. Similarly, naturally abundant $^{12}C$ can be replaced with $^{13}C$ or $^{14}C$, naturally abundant $^{14}N$ can be replaced with $^{15}N$, and naturally abundant $^{16}O$ with $^{17}O$ or $^{18}O$, and so on in any combination. Other isotopologues can be based on isotopic enrichment of fluorine, sulfur, phosphorus, boron, and the like. Isotopologues can include replacing any number atoms within the compound with isotopically enriched forms. The isotopic enrichment can be effected to any degree, including, 1, 5, 10, 15, 20, 25, 30, 35, 40, 45, 50, 60, 70, 80, 90, 95, and 99, and 100% enrichment, including any value in between and fractions thereof.

The term "metabolite" means any compound produced upon administration of Compound A to a subject. In one embodiment, the metabolite of Compound A is the O-desmethyl metabolite (having the name 1-((trans)-4-hydroxycyclohexyl)-7-(6-(2-hydroxypropan-2-yl)pyridin-3-yl)-3,4-dihydropyrazino[2,3-b]pyrazin-2(1H)-one), alternatively named 1-((1 r,4r)-4-hydroxycyclohexyl)-7-(6-(2-hydroxypropan-2-yl)pyridin-3-yl)-3,4-dihydropyrazino[2,3-b]pyrazin-2(1H)-one, having the structure:

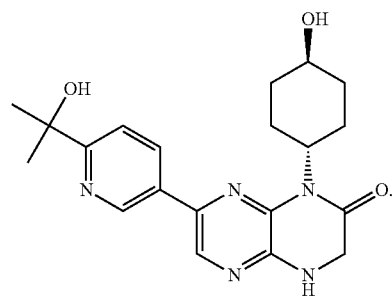 [SMILES: CC(C)(O)c1ccc(-c2cnc3c(n2)N([C@H]2CC[C@H](O)CC2)C(=O)CN3)cn1]

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%/a, 20%, 15%, 10%, 9%, 8%, 7%, 6%, 5%, 4%, 3%, 2%, 1%, 0.5%, or 0.05% of a given value or range.

As used herein and unless otherwise specified, a sample comprising a particular crystal form or amorphous form that is "substantially pure," e.g., substantially free of other solid forms and/or of other chemical compounds, contains, in particular embodiments, less than about 25%, less than about 20%, less than about 15%, less than about 10%, less than about 9%, less than about 8%, less than about 7%, less than about 6%, less than about 5%, less than about 4%, less than about 3%, less than about 2%, less than about 1%, less than about 0.75%, less than about 0.5%, less than about 0.25%, or less than about 0.1% by weight of one or more other solid forms and/or of other chemical compounds.

As used herein and unless otherwise specified, a sample or composition that is "substantially free" of one or more other solid forms and/or other chemical compounds means that the composition contains, in particular embodiments, less than about 25%, less than about 20%/a, less than about 15%, less than about 10%, less than about 9%, less than about 8%, less than about 7%, less than about 6%, less than about 5%, less than about 4%, less than about 3%, less than about 2%, less than about 1%, less than about 0.75%, less than about 0.5%, less than about 0.25%, or less than about 0.1% by weight of one or more other solid forms and/or other chemical compounds.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of Compound A include, but are not limited to metallic salts made from aluminum, calcium, lithium, magnesium, potassium, sodium and zinc or organic salts made from lysine, N,N'- dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, Remington's Pharmaceutical Sciences, 18th eds., Mack Publishing, Easton Pa. (1990) or Remington: The Science and Practice of Pharmacy, 19th eds., Mack Publishing, Easton Pa. (1995).

The term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In certain embodiments, a stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

5.2 Solid Forms of Compound A

In one embodiment, provided herein is a solid form of Compound A or a pharmaceutically acceptable salt thereof. In certain embodiments, the solid form is crystalline. In certain embodiments, the solid form is a single-component solid form. In certain embodiments, the solid form is anhydrous.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

The solid forms provided herein (for example, Form A of Compound A) may be characterized using a number of methods known to a person skilled in the art, including, but not limited to, single crystal X-ray diffraction, X-ray powder diffraction (XRPD), microscopy (e.g., scanning electron microscopy (SEM)), thermal analysis (e.g., differential scanning calorimetry (DSC), thermal gravimetric analysis (TGA), and hot-stage microscopy), and spectroscopy (e.g., infrared, Raman, and solid-state nuclear magnetic resonance). The particle size and size distribution of the solid form provided herein may be determined by conventional methods, such as laser light scattering technique.

The purity of the solid forms provided herein may be determined by standard analytical methods, such as thin layer chromatography (TLC), gel electrophoresis, gas chromatography, high performance liquid chromatography (HPLC), and mass spectrometry (MS).

It should be understood that the numerical values of the peaks of an X-ray powder diffraction pattern may vary slightly from one machine to another or from one sample to another, and so the values quoted are not to be construed as absolute, but with an allowable variability, such as ±0.2 degrees two-theta (degrees two-theta also noted as degrees $2\theta$, or $2\Theta$) (see United States Pharmacopoeia, page 2228 (2003)).

Figure 1:
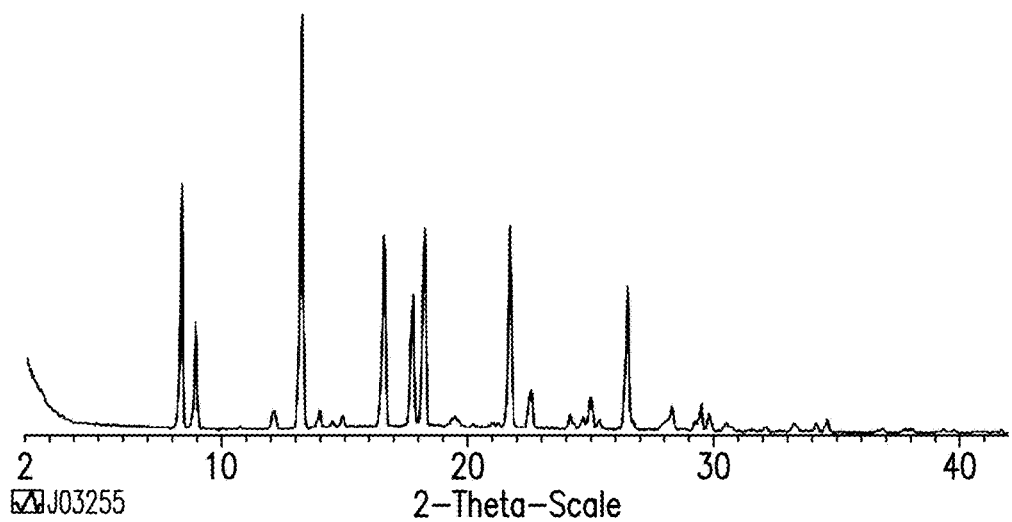
FIG. 1 depicts an X-ray powder diffractogram of Form A of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, provided herein is Form A of Compound A. In one embodiment, Form A of Compound A has an X-ray powder diffraction pattern substantially as shown in FIG. 1. In one embodiment, Form A of Compound A has an X-ray powder diffraction pattern comprised of one or more of the peaks set forth in Table 2. In another embodiment, Form A of Compound A has one or more characteristic X-ray powder diffraction peaks at a two-theta angle of approximately 8.3, 8.8, 12.0, 13.2, 13.9, 14.4, 14.8, 16.5, 17.7, 18.2, 19.3, 19.5, 19.6, 21.0, 21.2, 21.7, 22.5, 24.1, 24.7, 25.0, 25.3, 26.5, 26.7, 28.3, 29.3, 29.5, 29.8, 30.5, 32.1, 33.3, 34.2 or 34.6 degrees. In a specific embodiment, Form A of Compound A has one, two, three, four, five, six, seven or eight characteristic X-ray powder diffraction peaks at a two-theta angle of approximately 8.3, 8.8, 13.2, 16.5, 17.7, 18.2, 21.7 or 26.5 degrees. In another embodiment, Form A of Compound A has one, two, three or four characteristic X-ray powder diffraction peaks at a two-theta angle of approximately 8.3, 13.2, 18.2 or 21.7 degrees. In a particular embodiment, Form A of Compound A has one or more characteristic X-ray powder diffraction peaks at a two-theta angle of approximately 8.0, 9.0, 12.0, 13.0, 16.5, 17.5, 18.2, 21.5, 22.5, 25.0 or 26.5 degrees. In a specific embodiment, Form A of Compound A has one, two, three, four, five, six, seven or eight characteristic X-ray powder diffraction peaks at a two-theta angle of approximately 8.0, 9.0, 13.0, 16.5, 17.5, 18.2, 21.5 or 26.5 degrees. In another embodiment, Form A of Compound A has one, two, three or four characteristic X-ray powder diffraction peaks at a two-theta angle of approximately 8.0, 13.0, 18.2 or 21.5 degrees. In another embodiment, Form A of Compound A has one, two, three or four characteristic X-ray powder diffraction peaks at a two-theta angle of approximately 13.0, 16.5, 18.2 or 21.5 degrees.

Figure 3:
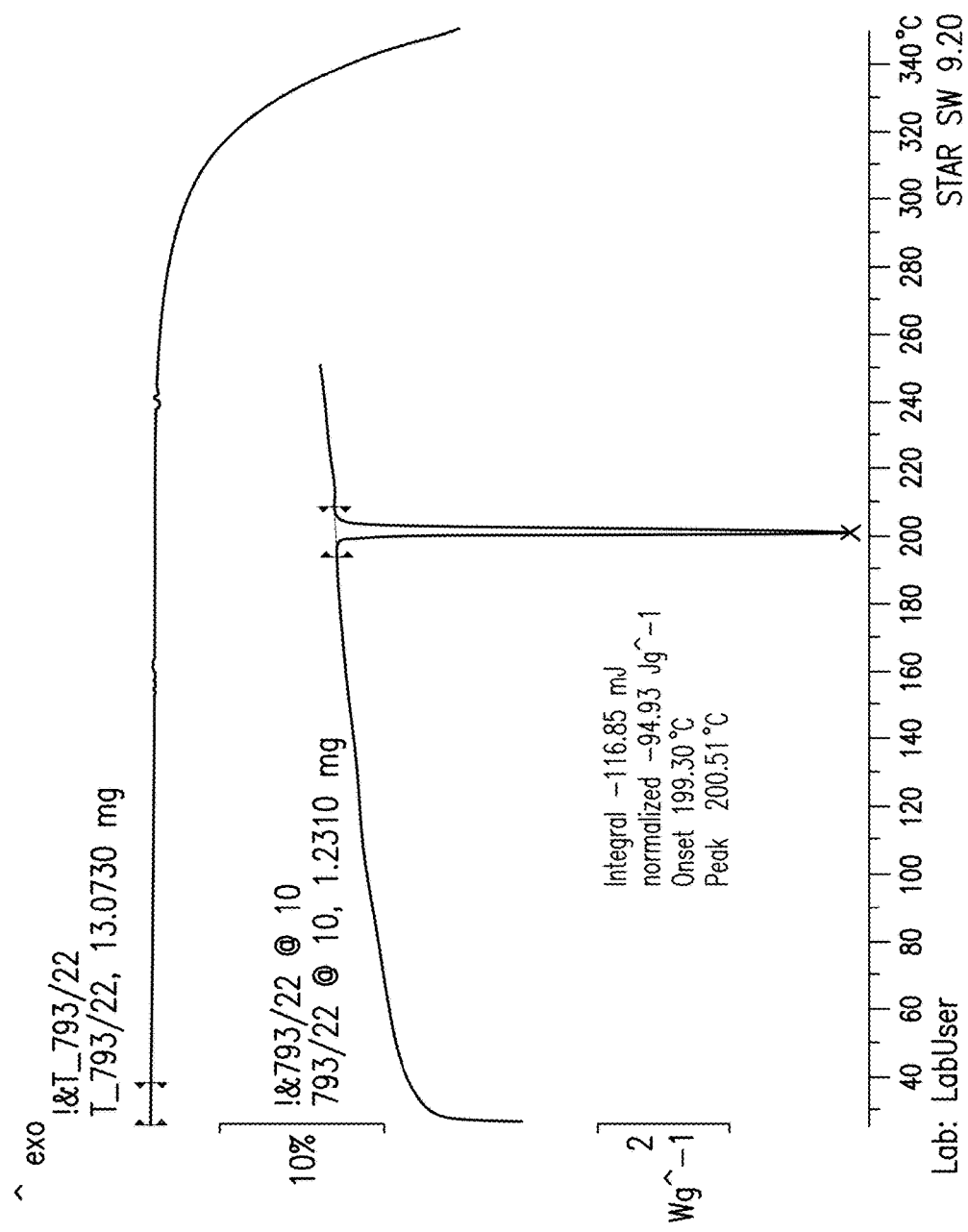
FIG. 3 depicts a thermogravimetric thermogram (top) and a differential scanning calorimetric thermogram (bottom) of Form A of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In another embodiment, Form A of Compound A has a thermogravimetric thermogram substantially as shown in FIG. 3. In certain embodiments, Form A of Compound A shows less than about 10%, less than about 5%, less than about 3%, less than about 2%, less than about 1%, less than about 0.5%, less than about 0.2%, less than about 0.1%, less than about 0.05%, or less than about 0.03%, e.g., about 0.024%, weight loss between about 25° C. to about 100° C. in a thermogravimetric thermogram. In certain embodiments, Form A of Compound A shows less than about 0.1% weight loss between about 25° C. to about 100° C. in a thermogravimetric thermogram. In certain embodiments, Form A of Compound A shows about 0.025% weight loss between about 25° C. to about 100° C. in a thermogravimetric thermogram. In certain embodiments, Form A of Compound A shows no weight loss until degradation at about 260° C. in a thermogravimetric thermogram. In certain embodiments, Form A of Compound A is anhydrous. In certain embodiments, Form A of Compound A is unsolvated.

Figure 4:
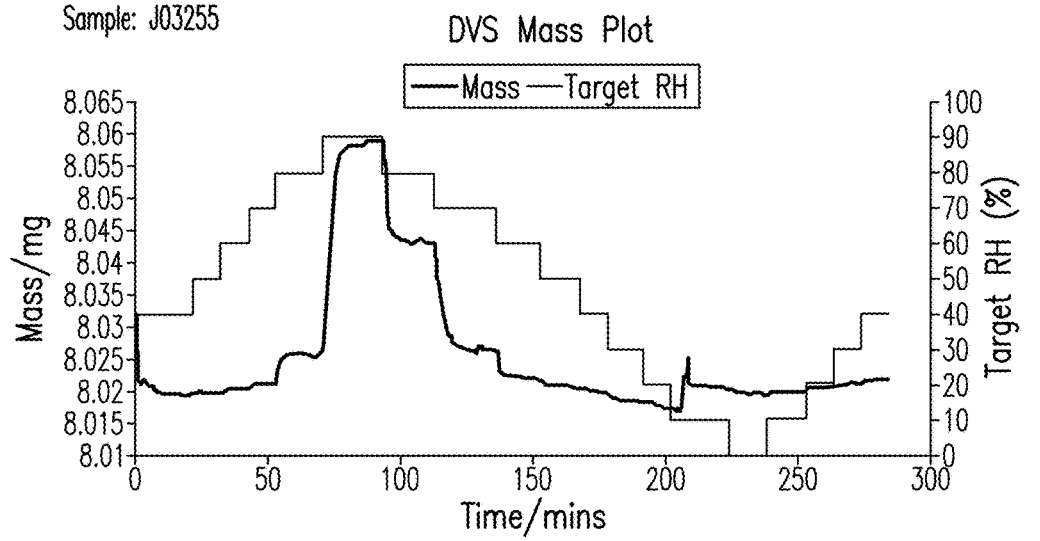
FIG. 4 depicts kinetic (top) and isotherm (bottom) DVS curves of Form A of 7-(6-(2-hydroxypropan-2-yl)pyridin-3-yl)-1-((trans)-4-methoxycyclohexyl)-3,4-dihydropyrazino[2,3-b]pyrazin-2(1H)-one.
Figure 4:
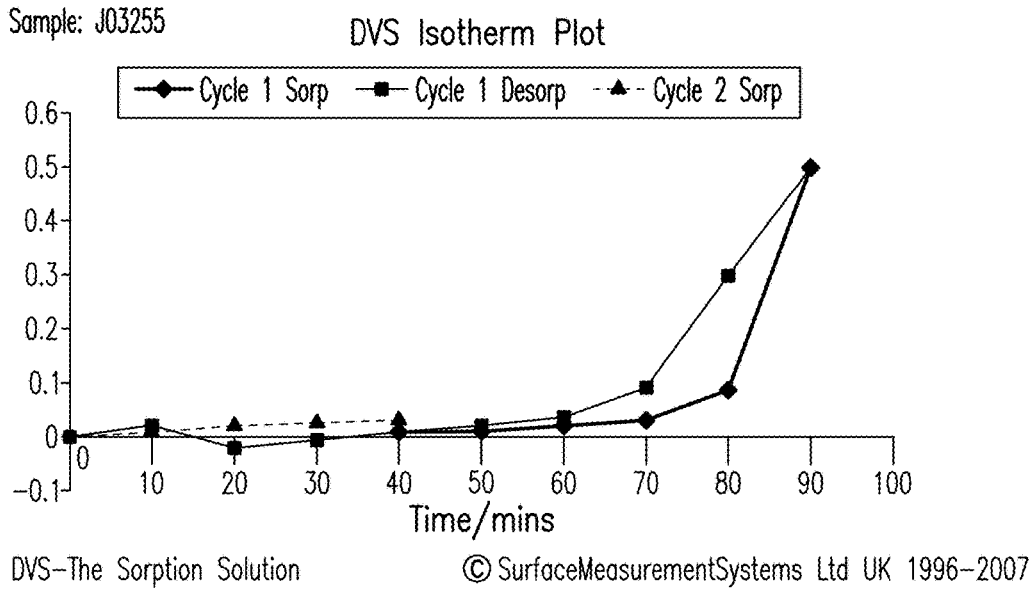

In yet another embodiment, Form A of Compound A has a differential scanning calorimetric (DSC) thermogram substantially as shown in FIG. 4. In certain embodiments, Form A of Compound A has an endotherm with a peak temperature of about 201° C. in a DSC thermogram. In certain embodiments, Form A of Compound A has an endotherm with an onset temperature of about 197° C. in a DSC thermogram. In certain embodiments, Form A of Compound A has an endotherm with a peak temperature of about 199° C. and an onset temperature of about 197° C. in a DSC thermogram. In one embodiment, Form A of Compound A has a melting temperature of about 197-199° C. In certain embodiment, Form A of Compound A has a melting temperature of about 199° C. In one embodiment, Form A of Compound A has an endotherm of about 195° C. in a DSC thermogram.

In yet another embodiment, Form A of Compound A is non-hygroscopic, e.g., exhibits a mass gain of less than about 0.1% w/w of when subjected to an increase in humidity from about 0% to about 80% relative humidity (RH). In another embodiment, Form A of Compound A exhibits a mass gain of about 0.5% w/w of when subjected to an increase in humidity from about 80% to about 90% relative humidity. In certain embodiments, Form A of Compound A exhibits no greater than about 2% w/w, no greater than about 1% w/w, no greater than about 0.6% w/w, no greater than about 0.4% w/w, no greater than about 0.2% w/w, or no greater than about 0.1% w/w weight gain in response to an increase in humidity from about 0% to about 95% relative humidity at about 25° C. In certain embodiments, Form A of Compound A exhibits about 0.3% w/w weight gain in response to an increase in humidity from about 0% to about 95% relative humidity at about 25° C. In certain embodiments, Form A of Compound A exhibits no greater than about 2% w/w, no greater than about 1% w/w, no greater than about 0.6% w/w, no greater than about 0.4% w/w, no greater than about 0.2% w/w, or no greater than about 0.1% w/w weight gain in response to an increase in humidity from about 0% to about 50% relative humidity at about 25° C. In certain embodiments, Form A of Compound A exhibits about 0.1% w/w weight gain in response to an increase in humidity from about 0% to about 50% relative humidity at about 25° C.

Figure 9:
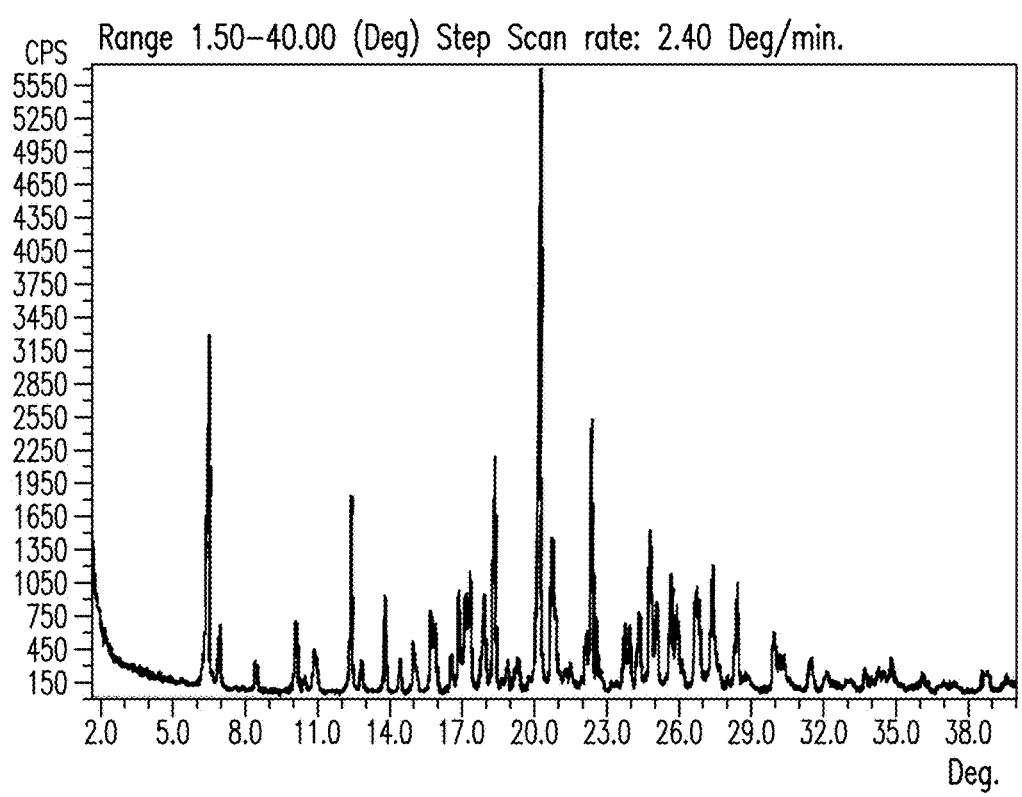
FIG. 9 depicts an X-ray powder diffractogram of Form B of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, provided herein is Form B of Compound A. In one embodiment, Form B of Compound A has an X-ray powder diffraction pattern substantially as shown in FIG. 9. In another embodiment, Form B of Compound A has one or more characteristic X-ray powder diffraction peaks at a two-theta angle of approximately 6.0, 7.0, 8.0, 10.0, 12.0, 14.0, 17.0, 18.0, 20.0, 20.5, 22.5, or 24.5 degrees. In a specific embodiment, Form B of Compound A has one, two, three, four, five, six, or seven characteristic X-ray powder diffraction peaks at a two-theta angle of approximately 6.0, 7.0, 8.0, 10.0, 12.0, 14.0, 17.0, 18.0, 20.0, 20.5, 22.5, or 24.5 degrees. In another embodiment, Form B of Compound A has one, two, three or four characteristic X-ray powder diffraction peaks at a two-theta angle of approximately 6.0, 7.0, 8.0, 10.0, 12.0, 14.0, 17.0, 18.0, 20.0, 20.5, 22.5, or 24.5 degrees.

In certain embodiments, Form B of Compound A shows less than about 10% or less than about 7%, e.g., about 6.4%, weight loss and an onset temperature of about 50° C. in a thermogravimetric thermogram. In certain embodiments, Form B of Compound A is a hydrate.

Figure 10:
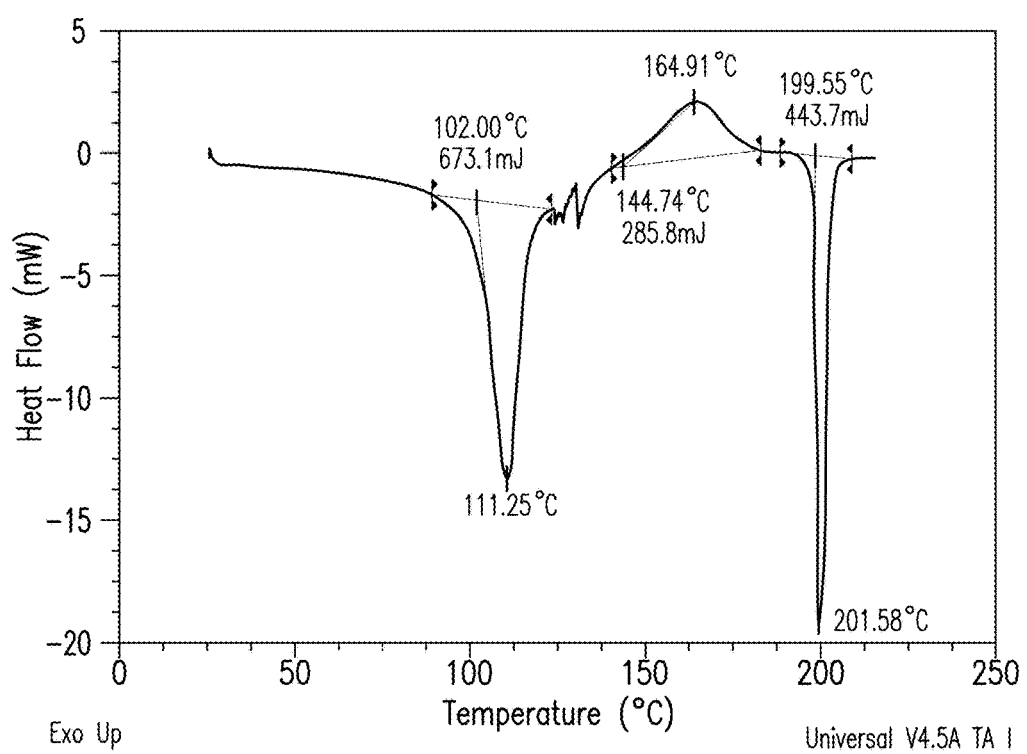
FIG. 10 depicts a differential scanning calorimetric (DSC) thermogram of Form B of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In yet another embodiment, Form B of Compound A has a differential scanning calorimetric (DSC) thermogram substantially as shown in FIG. 10. In certain embodiments, Form B of Compound A has an endotherm with a peak temperature of about 111.3° C., and an exotherm with a peak temperature of about 164.9° C. in a DSC thermogram. In certain embodiments, Form B of Compound A has an endotherm with a peak temperature of about 202° C.

Figure 11:
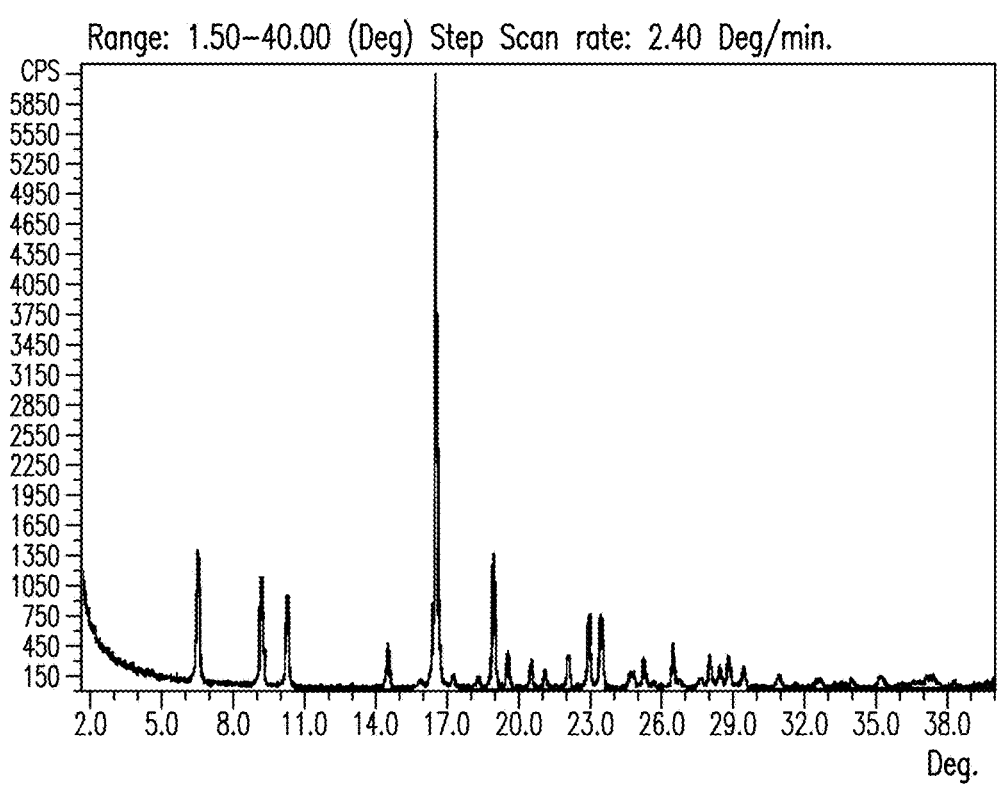
FIG. 11 depicts an X-ray powder diffractogram of Form C of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, provided herein is Form C of Compound A. In one embodiment, Form C of Compound A has an X-ray powder diffraction pattern substantially as shown in FIG. 11. In another embodiment, Form C of Compound A has one or more characteristic X-ray powder diffraction peaks at a two-theta angle of approximately 6.5, 9.0, 10.0, 14.5, 16.5, 19.0, 23.0, or 23.5 degrees. In a specific embodiment, Form C of Compound A has one, two, three, four, five, six, or seven characteristic X-ray powder diffraction peaks at a two-theta angle of approximately 6.5, 9.0, 10.0, 14.5, 16.5, 19.0, 23.0, or 23.5 degrees. In another embodiment, Form C of Compound A has one, two, three or four characteristic X-ray powder diffraction peaks at a two-theta angle of approximately 6.5, 9.0, 10.0, 14.5, 16.5, 19.0, 23.0, or 23.5 degrees. In a particular embodiment, Form C of Compound A has one or more characteristic X-ray powder diffraction peaks at a two-theta angle of approximately 6.5, 9.0, 10.0, 14.5, 16.5, 19.0, 23.0, or 23.5 degrees.

In certain embodiments, Form C of Compound A is anhydrous.

Figure 12:
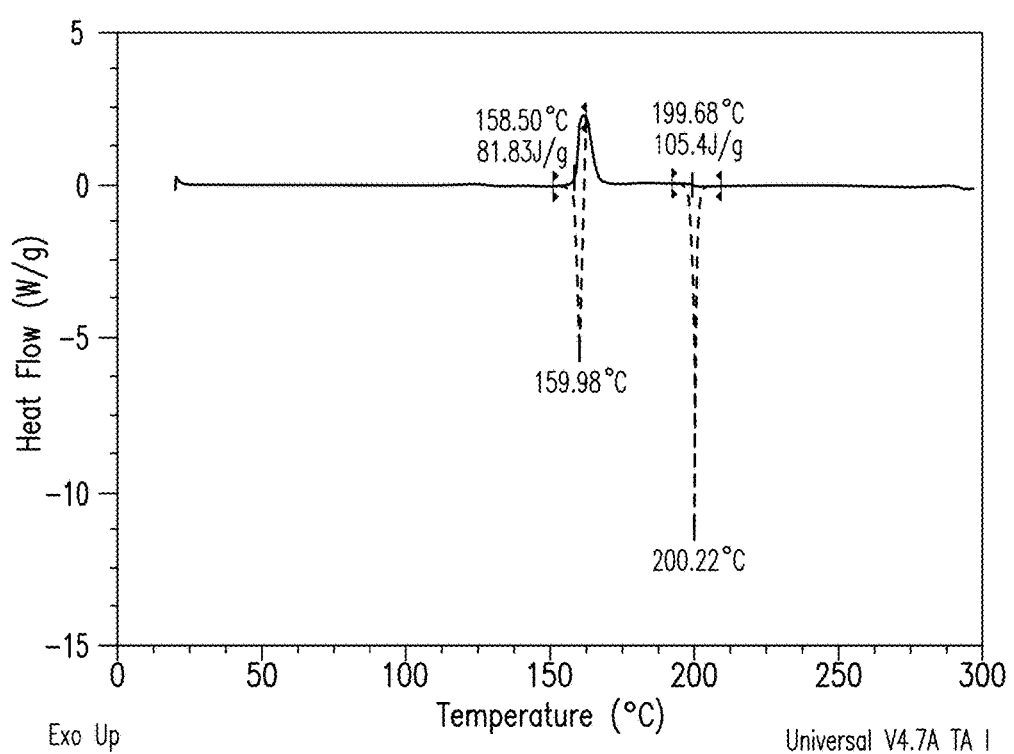
FIG. 12 depicts a differential scanning calorimetric (DSC) thermogram of Form C of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In yet another embodiment, Form C of Compound A has a differential scanning calorimetric (DSC) thermogram substantially as shown in FIG. 12. In certain embodiments, Form C of Compound A has an endotherm and exotherm of about 160° C. and an endotherm of about 200° C. in a DSC thermogram. In certain embodiments, Form C of Compound A has an endotherm of about 162° C. and an endotherm of about 200° C. in a DSC thermogram.

Figure 14:
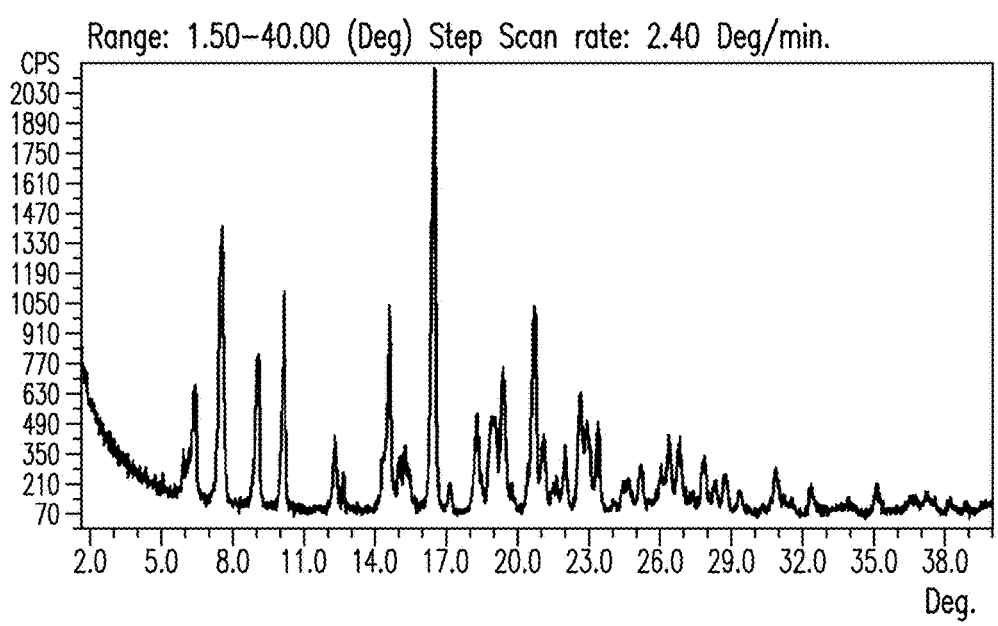
FIG. 14 depicts an X-ray powder diffractogram of Form D of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, provided herein is Form D of Compound A. In one embodiment, Form D of Compound A has an X-ray powder diffraction pattern substantially as shown in FIG. 14. In another embodiment, Form D of Compound A has one or more characteristic X-ray powder diffraction peaks at a two-theta angle of approximately 6.0, 8.0, 9.0, 10.0, 12.5, 14.5, 16.5, 18.0, 19.0, 19.5, 20.5, 22.5, 23.5, or 27.5 degrees. In a specific embodiment, Form D of Compound A has one, two, three, four, five, six, seven, eight, nine, ten, eleven, or twelve characteristic X-ray powder diffraction peaks at a two-theta angle of approximately 6.0, 7.5, 8.0, 9.0, 10.0, 12.5, 14.5, 16.5, 19.0, 19.5, 20.5, or 23.0 degrees. In another embodiment, Form D of Compound A has one, two, three or four characteristic X-ray powder diffraction peaks at a two-theta angle of approximately 6.0, 7.5, 8.0, 9.0, 10.0, 12.5, 14.5, 16.5, 19.0, 19.5, 20.5, or 23.0 degrees. In a particular embodiment, Form D of Compound A has one or more characteristic X-ray powder diffraction peaks at a two-theta angle of approximately 6.0, 7.5, 8.0, 9.0, 10.0, 12.5, 14.5, 16.5, 19.0, 19.5, 20.5, or 23.0 degrees.

In certain embodiments, Form D of Compound A shows less than about 10% or less than about 8%, e.g., about 7.4%, weight loss and an onset temperature of about 80° C. in a thermogravimetric thermogram. In certain embodiments, Form D of Compound A is a solvate.

Figure 13:
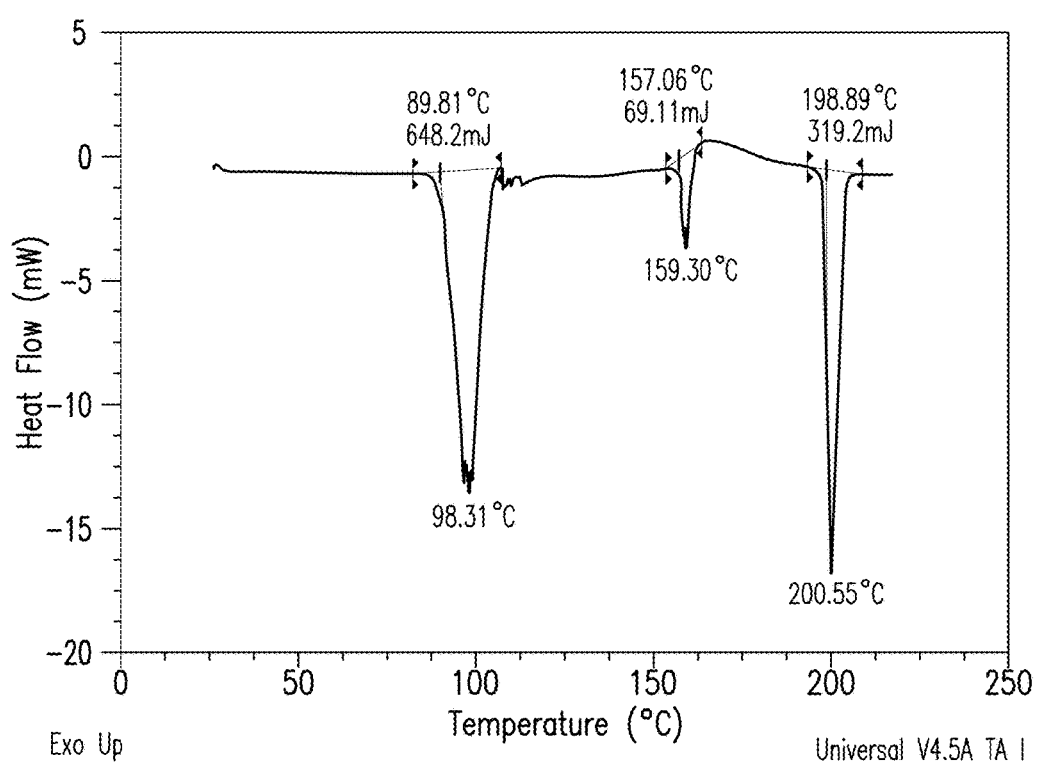
FIG. 13 depicts a differential scanning calorimetric (DSC) thermogram of Form D of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In yet another embodiment, Form D of Compound A has a differential scanning calorimetric (DSC) thermogram substantially as shown in FIG. 13. In certain embodiments, Form D of Compound A has an endotherm with a peak temperature of about 98.3° C., and an endotherm with a peak temperature of about 159.3° C. in a DSC thermogram. In certain embodiments, Form D of Compound A has an endotherm with a peak temperature of about 200.6° C.

In one embodiment, Form E is a p-xylene solvated form of Compound A. In one embodiment, Form E is a p-xylene hemi-solvated form of Compound A. In another embodiment, Form E of Compound A is crystalline.

Figure 16:
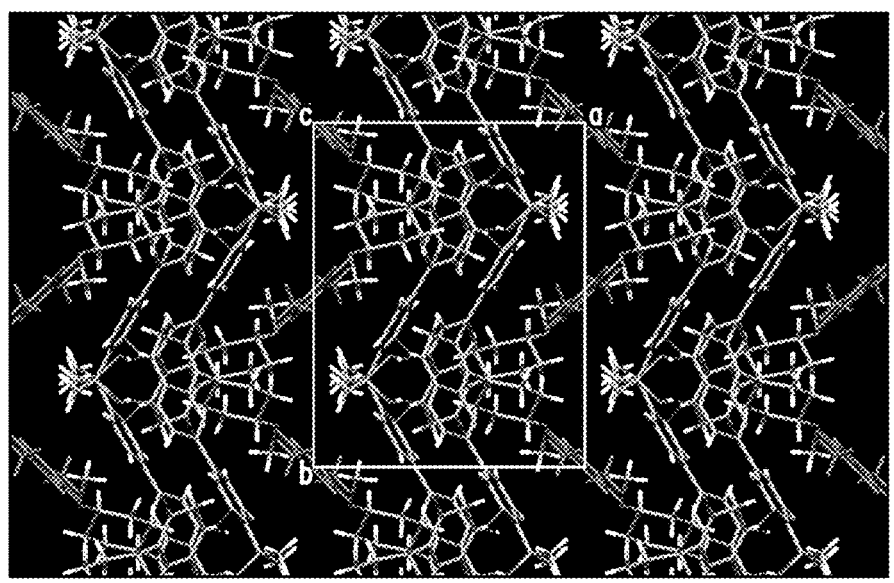
FIG. 16 depicts a crystal packing pattern of Form E of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, a single-crystal X-ray diffraction analysis is employed to determine the crystal structure of Form E of Compound A. Table 4 and Table 5 present a summary of the crystallographic data from the crystal-structure determination. In one embodiment, Form E of Compound A has a crystal packing pattern substantially as shown in FIG. 16. In one embodiment, Form E is a p-xylene hemi-solvated form crystallizing in a monoclinic crystal system. In one embodiment, Form E is a p-xylene hemi-solvated form crystallizing in a monoclinic crystal system with a $P2_1/c$ space group.

Figure 15:
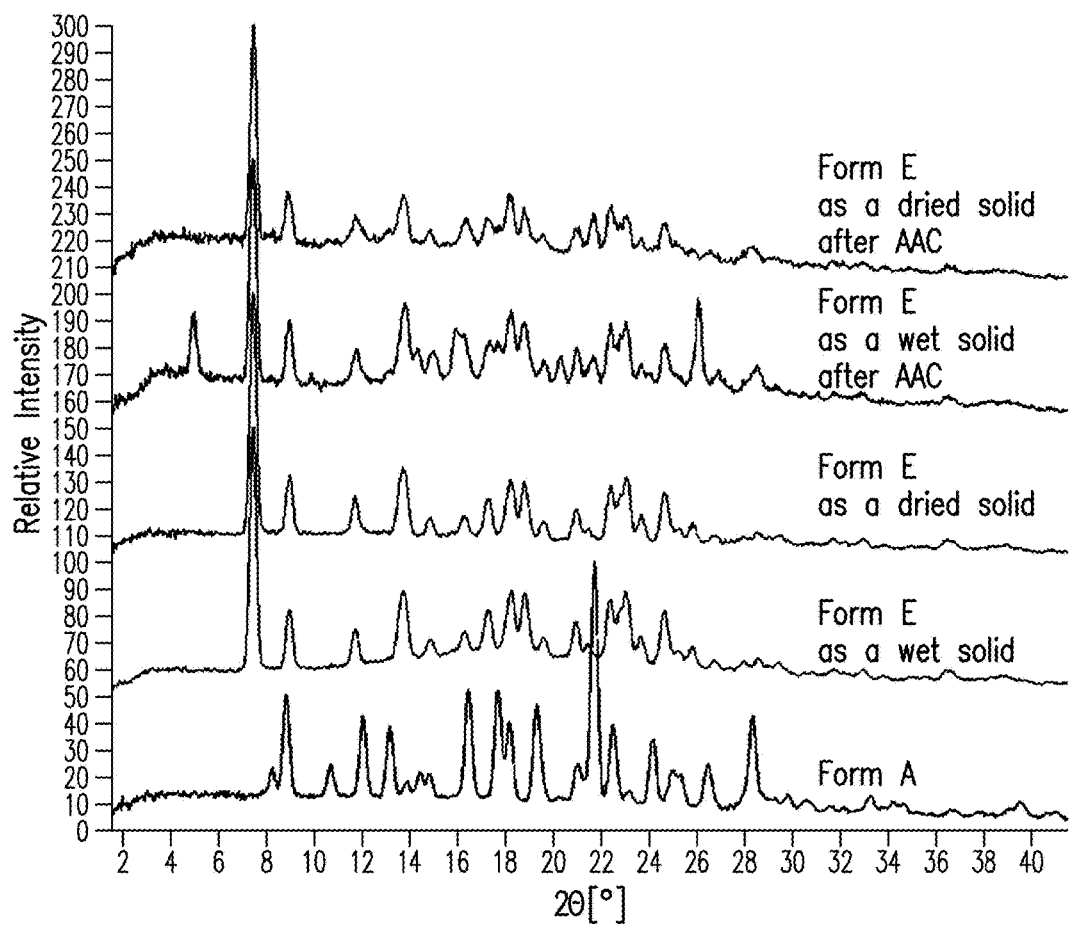
FIG. 15 depicts an X-ray powder diffractogram stack plot of Form A, Form E as a wet solid, Form E as a dried solid, Form E as a wet solid after exposure to accelerated aging conditions (AAC) and Form E as a dried solid after exposure to AAC of 7-(6-(2-hydroxypropan-2-yl)pyridin-3-yl)-1-((trans)-4-methoxycyclohexyl)-3,4-dihydropyrazino[2,3-b]pyrazin-2(1H)-one (from bottom to top).

In certain embodiments, a solid form provided herein (e.g., Form E) is substantially crystalline, as indicated by, e.g., X-ray powder diffraction measurements. In one embodiment, Form E of Compound A has an X-ray powder diffraction pattern substantially as shown in FIG. 15 (the second pattern from the bottom). In one embodiment, Form E of Compound A has one or more characteristic X-ray powder diffraction peaks at a two-theta angle of approximately 7.46, 8.94, 11.7, 13.7, 17.26, 18.22, 18.78, 20.94, 22.38, 23.06 or 24.62 degrees as depicted in FIG. 15 (the second pattern from the bottom). In another embodiment, Form E of Compound A has one, two, three, four five, six, seven or eight characteristic X-ray powder diffraction peaks at a two-theta angle of approximately 7.46, 8.94, 13.7, 18.22, 18.78, 22.38, 23.06 or 24.62 degrees. In another embodiment, Form E of Compound A has one, two, three or four characteristic X-ray powder diffraction peaks at a two-theta angle of approximately 7.46, 13.7, 18.22 or 23.06 degrees. In another embodiment, Form E of Compound A has one, two, three, four, five, six, seven, eight, nine, ten or eleven characteristic X-ray powder diffraction peaks as set forth in Table 3.

In certain embodiments, Form E of Compound A has digital images substantially as shown in FIG. 17A and FIG. 17B.

In one embodiment, provided herein is a crystalline form of Compound A having a thermogravimetric (TGA) thermograph corresponding substantially to the representative TGA thermogram as depicted in FIG. 19. In certain embodiments, the crystalline form exhibits a TGA thermogram comprising a total mass loss of approximately 11.0%-11.5% (e.g., 11.0% or 11.2%) of the total mass of the sample between approximately 50° C. and approximately 200° C. when heated from approximately 25° C. to approximately 300° C. Thus, in certain embodiments, the crystalline form loses about 11.0% of its total mass when heated from about ambient temperature to about 300° C. In certain embodiments, the crystalline form contains 0.5 molar equivalents of solvent in the crystal lattice corresponding to approximately 0.5 mole of p-xylene per mole of Compound A. The theoretical p-xylene content of a p-xylene hemi-solvate of Compound A is 10.5% by weight, matching the TGA weight loss observed. In certain embodiments, the crystalline form is a p-xylene hemi-solvate of Compound A.

In one embodiment, provided herein is a crystalline form of Compound A having a single differential thermal analysis (SDTA) thermogram as depicted in FIG. 18 comprising an endothermic event between about 90° C. and about 125° C. with a maximum at about 106-110° C., when heated from approximately 25° C. to approximately 300° C.

In one embodiment, provided herein is a crystalline form of Compound A having a SDTA thermogram comprising an endothermic event as depicted in FIG. 17 with a maximum at about 193° C. when heated from approximately 25° C. to approximately 300° C.

In still another embodiment, Form A of Compound A is substantially pure. In certain embodiments, the substantially pure Form A of Compound A is substantially free of other solid forms, e.g., amorphous form. In certain embodiments, the purity of the substantially pure Form A of Compound A is no less than about 95% pure, no less than about 96% pure, no less than about 97% pure, no less than about 98% pure, no less than about 98.5% pure, no less than about 99% pure, no less than about 99.5% pure, or no less than about 99.8% pure.

In still another embodiment, Form B of Compound A is substantially pure. In certain embodiments, the substantially pure Form B of Compound A is substantially free of other solid forms, e.g., amorphous form. In certain embodiments, the purity of the substantially pure Form B of Compound A is no less than about 95% pure, no less than about 96% pure, no less than about 97% pure, no less than about 98% pure, no less than about 98.5% pure, no less than about 99% pure, no less than about 99.5% pure, or no less than about 99.8% pure.

In still another embodiment, Form C of Compound A is substantially pure. In certain embodiments, the substantially pure Form C of Compound A is substantially free of other solid forms, e.g., amorphous form. In certain embodiments, the purity of the substantially pure Form C of Compound A is no less than about 95% pure, no less than about 96% pure, no less than about 97% pure, no less than about 98% pure, no less than about 98.5% pure, no less than about 99% pure, no less than about 99.5% pure, or no less than about 99.8% pure.

In still another embodiment, Form D of Compound A is substantially pure. In certain embodiments, the substantially pure Form D of Compound A is substantially free of other solid forms, e.g., amorphous form. In certain embodiments, the purity of the substantially pure Form D of Compound A is no less than about 95% pure, no less than about 96% pure, no less than about 97% pure, no less than about 98% pure, no less than about 98.5% pure, no less than about 99% pure, no less than about 99.5% pure, or no less than about 99.8% pure.

In still another embodiment, Form E of Compound A is substantially pure. In certain embodiments, the substantially pure Form E of Compound A is substantially free of other solid forms, e.g., amorphous form. In certain embodiments, the purity of the substantially pure Form E of Compound A is no less than about 95% pure, no less than about 96% pure, no less than about 97% pure, no less than about 98% pure, no less than about 98.5% pure, no less than about 99% pure, no less than about 99.5% pure, or no less than about 99.8% pure.

Figure 7:
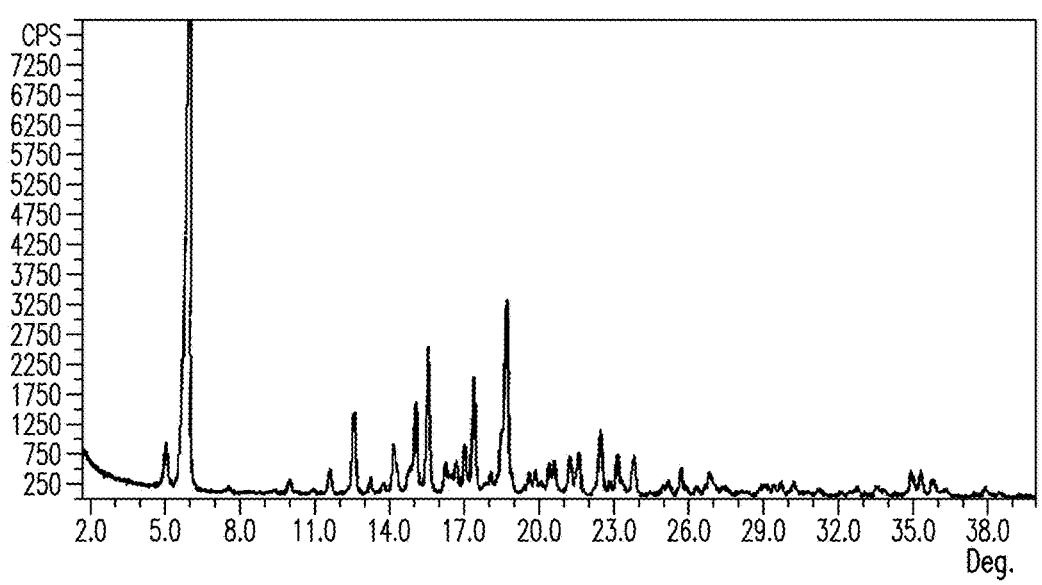
FIG. 7 depicts an X-ray powder diffractogram of a pinacol co-crystal of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In one embodiment, provided herein is a pinacol co-crystal of Compound A. In one embodiment, the pinacol co-crystal of Compound A has an X-ray powder diffraction pattern substantially as shown in FIG. 7. In another embodiment, the pinacol co-crystal of Compound A has one or more characteristic X-ray powder diffraction peaks at a two-theta angle of approximately 5.0, 6.0, 12.5, 14.0, 15.0, 15.5, 17.5, 18.5, and 22.5 degrees. In a specific embodiment, the pinacol co-crystal of Compound A has one, two, three, four, or five characteristic X-ray powder diffraction peaks at a two-theta angle of approximately 5.0, 6.0, 12.5, 14.0, 15.0, 15.5, 17.5, 18.5, and 22.5 degrees. In another embodiment, the pinacol co-crystal of Compound A has one, two, three or four characteristic X-ray powder diffraction peaks at a two-theta angle of approximately 5.0, 6.0, 12.5, 14.0, 15.0, 15.5, 17.5, 18.5, and 22.5 degrees.

Figure 6:
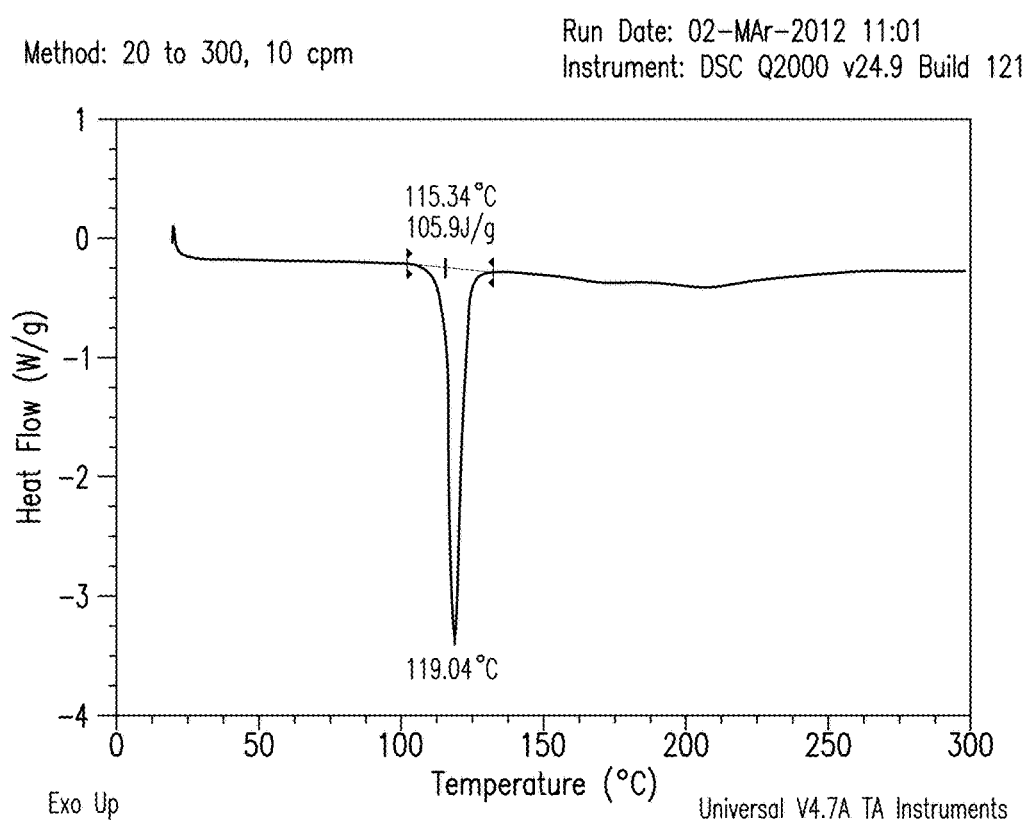
FIG. 6 depicts a differential scanning calorimetric (DSC) thermogram of a pinacol co-crystal of 7-(6-(2-hydroxypropan-2-yl)pyridin-3-yl)-1-((trans)-4-methoxycyclohexyl)-3,4-dihydropyrazino[2,3-b]pyrazin-2(1H)-one.

In yet another embodiment, the pinacol co-crystal of Compound A has a differential scanning calorimetric (DSC) thermogram substantially as shown in FIG. 6. In certain embodiments, the pinacol co-crystal of Compound A has an endotherm with a peak temperature of about 119° C. in a DSC thermogram. In certain embodiments, the pinacol co-crystal of Compound A has an endotherm with an onset temperature of about 115° C. in a DSC thermogram. In certain embodiments, the pinacol co-crystal of Compound A has an endotherm with a peak temperature of about 119° C. and an onset temperature of about 115° C. in a DSC thermogram. In another embodiment, the pinacol co-crystal of Compound A is comprised of about 20% by weight of pinacol.

In still another embodiment, the pinacol co-crystal of Compound A is substantially pure. In certain embodiments, the substantially pure pinacol co-crystal of Compound A is substantially free of other solid forms, e.g., amorphous form. In certain embodiments, the purity of the substantially pure pinacol co-crystal of Compound A is no less than about 95% pure, no less than about 96% pure, no less than about 97% pure, no less than about 98% pure, no less than about 98.5% pure, no less than about 99% pure, no less than about 99.5% pure, or no less than about 99.8% pure.

The solid forms of Compound A provided herein (for example, Forms A, B, C, D or E) can be prepared by the methods described herein.

In certain embodiments, Form A of Compound A can be prepared by solvent evaporation of a solution or slurry of Compound A in toluene, MTBE (methyl tert-butyl ether), DIPE (diisopropyl ether), THF (tetrahydrofuran), DME (dimethoxyethane), IPAc (isopropyl acetate), EtOAc (ethyl acetate), MIBK (methyl isobutyl ketone), acetone, IPA (isopropyl alcohol), ethanol, ACN (acetonitrile), nitromethane or IPA:water (for example, 95:5).

In certain embodiments, Form A of Compound A can be prepared by subjecting a solution or slurry of Compound A in toluene, MTBE (methyl tert-butyl ether), DIPE (diisopropyl ether), THF (tetrahydrofuran), DME (dimethoxyethane), IPAc (isopropyl acetate), EtOAc (ethyl acetate), MIBK (methyl isobutyl ketone), acetone, IPA (isopropyl alcohol), ethanol, ACN (acetonitrile), nitromethane or IPA:water (95:5) to cycles of heating to about 50° C. and cooling to room temperature, followed by solvent evaporation.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving amorphous 7-(6-(2-hydroxypropan-2-yl)pyridin-3-yl)-1-((trans)-4-methoxycyclohexyl)-3,4-dihydro-pyrazino[2,3-b]pyrazin-2(1H)-one in toluene, MTBE (methyl tert-butyl ether), DIPE (diisopropyl ether), THF (tetrahydrofuran), DME (dimethoxyethane), IPAc (isopropyl acetate), EtOAc (ethyl acetate), MIBK (methyl isobutyl ketone), acetone, IPA (isopropyl alcohol), ethanol, ACN (acetonitrile), nitromethane, or IPA:water (95:5) and allowing the resulting solution to evaporate at room temperature.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT (butylated hydroxytoluene), IPA and water, heating and then cooling to room temperature. In some embodiments, the methods further comprise collection by filtration, washing with IPA and water and drying.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT and MeOAc (methyl acetate), heating, cooling to room temperature, distilling under vacuum and contacting with n-heptane. In certain embodiments, the methods further comprise collection by filtration and washing with MeOAc and n-heptane and drying. In certain embodiments, this method further comprises adding a small amount of Form A in MeOAc to the mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one in BHT and MeOAc. In some embodiments, the methods further comprise filtration of the hot BHT and MeOAc solution.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT and MeOAc (methyl acetate), heating, filtering, cooling, distilling under vacuum and contacting with n-heptane. In certain embodiments, the methods further comprise collection by filtration and washing with MeOAc and n-heptane and drying. In certain embodiments, this method further comprises adding a small amount of Form A in MeOAc to the mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one in BHT and MeOAc. In some embodiments, the methods further comprise filtration of the hot BHT and MeOAc solution.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one and 7-(6-(2-hydroxypropan-2-yl)pyridin-3-yl)-1-((trans)-4-methoxycyclohexyl)-3,4-dihydropyrazino[2,3-b]pyrazin-2(1H)-one pinacol cocrystal in IPA. In some embodiments, the methods further comprise collection by filtration and drying, such as under reduced pressure.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT, THF and water, contacting with IPAc, heating, distilling, cooling, contacting with IPAc, heating, distilling, and then cooling to room temperature. In some embodiments, the methods further comprise collection by filtration, washing with IPAc, and drying. In some embodiment, the method additionally comprises treating the BHT, THF and water solution with activated carbon. In certain embodiments, the method further comprises filtration of the BHT, THF and water solution. In some embodiments, the methods comprise a first distillation step at atmospheric pressure at constant volume (by addition of IPAc) and then cooling. In certain embodiments, this method further comprises adding a small amount of Form A in IPAc after the first distillation. In some embodiments, the method further comprises a second distillation at atmospheric pressure at constant volume ((by addition of IPAc) and then cooling.

In certain embodiments, provided herein are methods for making Form A of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT, THF and water, contacting with IPAc, heating, distilling under reduced pressure, contacting with IPAc, and then cooling to room temperature. In some embodiments, the methods further comprise collection by filtration, washing with IPAc, and drying. In some embodiment, the method additionally comprises treating the BHT, THF and water solution with activated carbon. In certain embodiments, the method further comprises filtration of the BHT, THF and water solution. In some embodiments, the methods comprise a first distillation step at reduced pressure at constant temperature, with addition of IPAc. In certain embodiments, this method further comprises adding a small amount of Form A in IPAc after the first distillation. In some embodiments, the method further comprises a second distillation under vacuum, with addition of IPAc, and then cooling to room temperature.

In certain embodiments, provided herein are methods for making Form B of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT, IPA and water, heating the mixture and adding water, cooling the mixture, collection by filtration, washing with IPA and water, and drying. In certain embodiments, this method further comprises adding a small amount of Form B in water to the mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one in BHT, IPA and water.

In certain embodiments, provided herein are methods for making Form C of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT, MeOH, distilling to remove MeOH, further distillation with IPA, cooling the mixture, collection by filtration, washing with IPA and drying.

In certain embodiments, provided herein are methods for making Form D of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising dissolving 7-(6-(2-hydroxypropan-2-yl)pyridin-3-yl)-1-((trans)-4-methoxycyclohexyl)-3,4-dihydropyrazino[2,3-b]pyrazin-2(1H)-one in a mixture of BHT in MeOH, heating, then cooling with stirring, collection by filtration, washing and drying.

In certain embodiments, Form E is obtained by crystallization from certain solvent systems, for example, solvent systems comprising one or more of the following solvents or solvent combinations: p-xylene/acetone (e.g., 50/50), p-xylene/MTBE (e.g., 50/50) and p-xylene.

In certain embodiments, provided herein are methods for making Form E of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising obtaining a slurry of 7-(6-(2-hydroxypropan-2-yl)pyridin-3-yl)-1((trans)-4-methoxycyclohexyl)-3,4-dihydro-pyrazino[2,3-b]pyrazin-2(1H)-one in a solvent, heating the slurry to a first temperature (e.g., about 50° C. to about 70° C.), filtering the slurry to yield a solution, cooling down the solution to a second temperature (e.g., about 15° C. to about 35° C.) to yield solids, and collecting the solids. In certain embodiments, provided herein are methods for making Form E of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising obtaining a slurry of 7-(6-(2-hydroxypropan-2-yl)pyridin-3-yl)-1-((trans)-4-methoxycyclohexyl)-3,4-dihydro-pyrazino[2,3-b]pyrazin-2(1H)-one in p-xylene/acetone (50/50), heating the slurry to about 60° C., filtering the slurry to yield a solution, cooling down the solution to about 25° C. to yield solids, and collecting the solids.

In certain embodiments, provided herein are methods for making Form E of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising mixing 7-(6-(2-hydroxypropan-2-yl)pyridin-3-yl)-1-((trans)-4-methoxycyclohexyl)-3,4-dihydro-pyrazino[2,3-b]pyrazin-2(1H)-one with a solvent, filtering the mixture to yield a solution if 7-(6-(2-hydroxypropan-2-yl)pyridin-3-yl)-1-((trans)-4-methoxycyclohexyl)-3,4-dihydro-pyrazino[2,3-b]pyrazin-2(1H)-one does not dissolve completely, and evaporating the solution under certain air pressure to yield a solid. In certain embodiments, provided herein are methods for making Form E of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising mixing 7-(6-(2-hydroxypropan-2-yl)pyridin-3-yl)-1-((trans)-4-methoxycyclohexyl)-3,4-dihydro-pyrazino[2,3-b]pyrazin-2(1H)-one with p-xylene/MTBE (50/50), filtering the mixture to yield a solution if 7-(6-(2-hydroxypropan-2-yl)pyridin-3-yl)-1-((trans)-4-methoxycyclohexyl)-3,4-dihydro-pyrazino[2,3-b]pyrazin-2(1H)-one does not dissolve completely, and evaporating the solution under 200 mbar air pressure to yield a solid.

In certain embodiments, provided herein are methods for making Form E of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising obtaining a slurry of 7-(6-(2-hydroxypropan-2-yl)pyridin-3-yl)-1-((trans)-4-methoxycyclohexyl)-3,4-dihydro-pyrazino[2,3-b]pyrazin-2(1H)-one in a solvent, stirring the slurry, collecting solids from the slurry by filtration (e.g., centrifuge filtration) and optionally washing (e.g., washing with the solvent) and drying. In certain embodiments, provided herein are methods for making Form E of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, comprising obtaining a slurry of 7-(6-(2-hydroxypropan-2-yl)pyridin-3-yl)-1-((trans)-4-methoxycyclohexyl)-3,4-dihydro-pyrazino[2,3-b]pyrazin-2(1H)-one in p-xylene, stirring the slurry, collecting solids from the slurry by centrifuge filtration and optionally washing with p-xylene and drying.

In certain embodiments, provided herein are methods for making a pinacol co-crystal of 7-(6-(2-hydroxypropan-2-yl)pyridin-3-yl)-1-((trans)-4-methoxycyclohexyl)-3,4-dihydropyrazino[2,3-b]pyrazin-2(1H)-one, comprising mixing 7-(6-(2-hydroxypropan-2-yl)pyridin-3-yl)-1-((trans)-4-methoxycyclohexyl)-3,4-dihydropyrazino[2,3-b]pyrazin-2(1H)-one with pinacol in solution (for example THF and toluene), heating until solids are dissolved, distilling said solution and seeding with a pinacol co-crystal of 7-(6-(2-hydroxypropan-2-yl)pyridin-3-yl)-1-((trans)-4-methoxycyclohexyl)-3,4-dihydropyrazino[2,3-b]pyrazin-2(1H)-one.

IN some embodiments, the methods further comprise collection by filtration, washing with THF/toluene and drying.

5.3 Process of Preparation of Compound A

In certain embodiments, provided herein are methods for preparing Compound A, comprising: (1) contacting ethyl-2-(3,5-dibromopyrazin-2-ylamino)acetate with trans-4-methoxycyclohexylamine hydrochloride and 1-methyl-2-pyrrolidine and adding DIPEA to produce ethyl 2-((5-bromo-3-(((trans)-4-methoxycyclohexyl)amino)pyrazin-2-yl)amino)acetate; (2) contacting ethyl 2-((5-bromo-3-(((trans)-4-methoxycyclohexyl)amino)pyrazin-2-yl)amino)acetate with an acid (such as a phosphoric acid solution) to produce 7-bromo-1-((trans)-4-methoxycyclohexyl)-3,4-dihydropyrazino[2,3-b]pyrazin-2(1H)-one; and (3) contacting 7-bromo-1-((trans)-4-methoxycyclohexyl)-3,4-dihydropyrazino[2,3-b]pyrazin-2(1H)-one with 2-(5-(4,4,5,5-tetramethyl-1,3,2-dioxaborolan-2-yl)pyridin-2-yl)propan-2-ol and PdCl$_2$(Amphos)$_2$.

Provided herein are methods of preparing Compound A

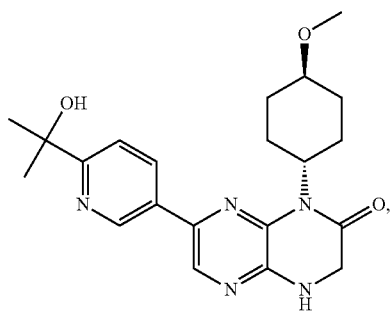

Compound A the method comprising contacting a compound of Formula b

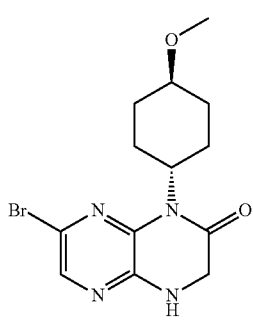

b with a compound of formula c

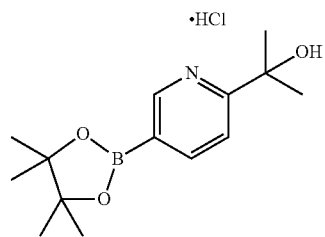

c in a solvent (e.g., THF), in the presence of a base (e.g., K$_2$CO$_3$) and a palladium catalyst (e.g., PdCl$_2$(Amphos)$_2$), wherein said contacting occurs under conditions suitable to provide Compound A. In some embodiments, the contacting occurs at elevated temperature (e.g., reflux). In certain embodiments, the palladium catalyst is chloro(2-dicyclohexylphosphino-2',6'-di-i-propoxy-1,1'-biphenyl)[2-(2-aminoethylphenyl)]palladium(II), chloro(2-dicyclohexylphosphino-2',6'-di-i-propoxy-1,1'-biphenyl)(2-amino-1,1'-biphenyl-2-yl)palladium(II), chloro(2-dicyclohexylphosphino-2',6'-dimethoxy-1,1'-biphenyl)[2-(2-aminoethylphenyl)]palladium(II) dichloromethane adduct, chloro(2-dicyclohexylphosphino-2',6'-dimethoxy-1,1'-biphenyl)(2'-amino-1,1'-biphenyl-2-yl) palladium(II), chloro(2-dicyclohexylphosphino-2',4',6'-tri-i-propyl-1,1'-biphenyl)[2-(2-aminoethyl)phenyl]palladium(II), chloro(2-dicyclohexylphosphino-2',4',6'-triisopropyl-1,1'-biphenyl)[2-(2'-amino-1,1'-biphenyl)]palladium(II), chloro[2-(dicyclohexylphosphino)-3,6-dimethoxy-2'-4'-6'-tri-i-propyl-1,1'-biphenyl][2-(2-aminoethyl)phenyl]palladium (II), [1,1'-bis(di-tert-butylphosphino)ferrocene] dichloropalladium, [1,1'-bis(diphenylphosphino)ferrocene] dichloropalladium, bis(triphenylphosphine)palladium(II) chloride complex, tetrakis(triphenylphosphine)palladium (0), dichlorobis(tricyclohexylphoshine)palladium(II), palladium(II) chloride with 2'-(dicyclohexylphosphino)acetophenone ethylene ketal ligand, palladium (II) chloride with 1,2,3,4,5-pentaphenyl-1'-(di-tert-butylphosphino)ferrocene ligand, palladium (II) chloride with 2-dicyclohexylphosphino-2'-(N,N-dimethylamino)biphenyl ligand, palladium (II) chloride with 4,5-bis(diphenylphosphino)-9,9-dimethylxanthene ligand or palladium (II) chloride with 2-dicyclohexylphosphino-2'-methylbiphenyl ligand.

In some such embodiments, the methods further comprise preparing a compound of formula b

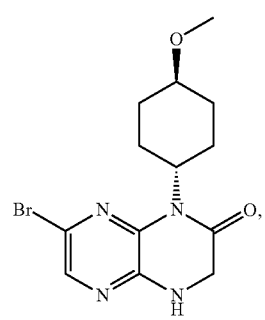

b the method comprising contacting a compound of formula d

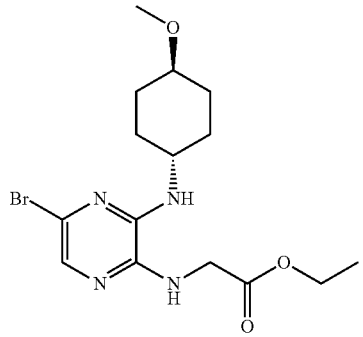

d with an acid (e.g., phosphoric acid), wherein said contacting occurs under conditions suitable to provide a compound of formula b. In some embodiments, the contacting occurs at elevated temperature (e.g., 80° C.).

In some such embodiments, the methods further comprise preparing a compound of formula d

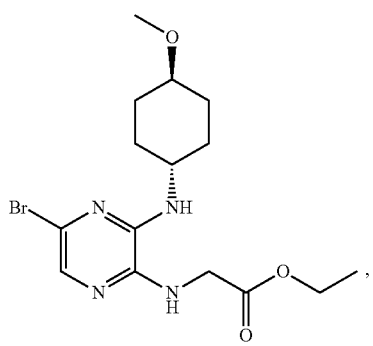

d the method comprising contacting a compound of formula e

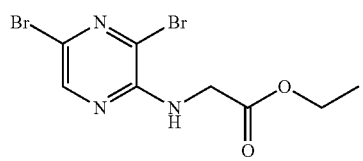

e with trans-4-methoxycyclohexylamine hydrochloride, in the presence of a base (e.g., DIPEA), in a solvent (e.g., NMP), wherein said contacting occurs under conditions suitable to provide a compound of formula b.

In some embodiments, the contacting occurs at elevated temperature (e.g., 125-130° C.).

Isotopologues of Compound A and metabolites thereof can be prepared by the methods provided herein.

In one embodiment, provided herein are processes for preparing a compound having the formula:

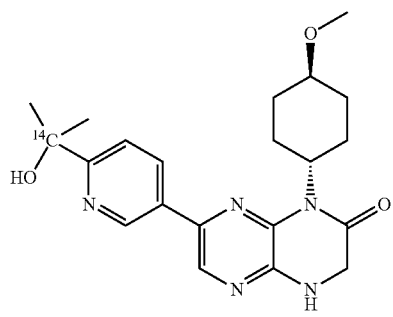

$^{14}$C-Compound A the method comprising contacting

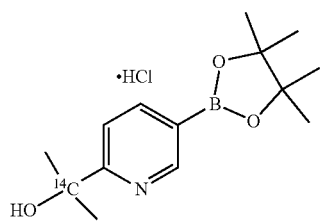 [SMILES: CC1(C)OB(c2ccc([14C](C)(C)O)nc2)OC1(C)C ; Cl]

with

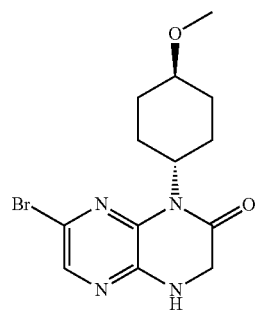 [SMILES: CO[C@H]1CC[C@H](N2C(=O)CNc3ncc(Br)nc32)CC1]

in the presence of a palladium catalyst (e.g., PdCl$_2$(Amphos)$_2$) and a base (e.g., K$_2$CO$_3$) in a solvent (e.g., THF, optionally with water), wherein said contacting occurs under conditions suitable to produce

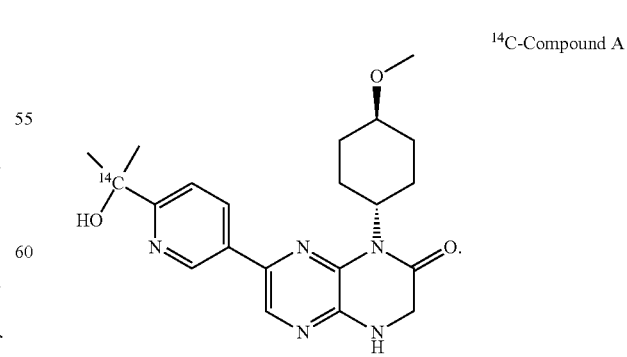

$^{14}$C-Compound A

In some embodiments, the contacting occurs at elevated temperature (e.g., 73° C.).

In one embodiment, provided herein are processes for preparing a compound having the formula:

14C-Compound A

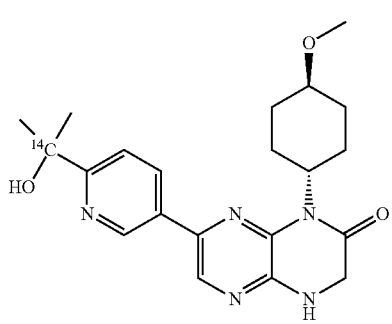

the method comprising contacting

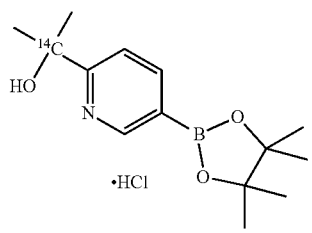 [SMILES: CC1(C)OB(c2ccc([14C](C)(C)O)nc2)OC1(C)C ; Cl]

with

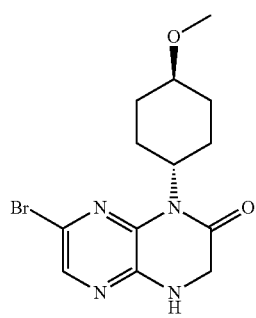

in the presence of a palladium catalyst (e.g., PdCl$_2$(Amphos)$_2$) and a base (e.g., K$_2$CO$_3$) in a solvent (e.g., THF, optionally with water), wherein said contacting occurs under conditions suitable to produce 14C-Compound A

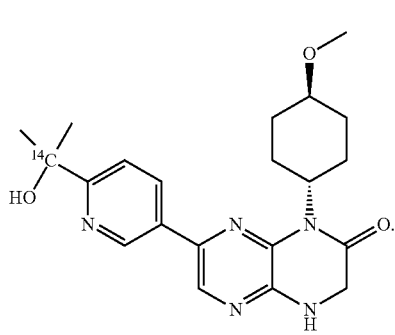

In some such embodiments, the contacting occurs at elevated temperature (e.g., 73° C.). In some such embodiments, the method further comprises addition of EtOAc, and isolation of crude 14C-compound A using EtOAc, DCM, methanol, and silica gel and drying. In some such embodiments, crude 14C-compound A is dissolved in BHT and ACN and isolated using EtOAc.

In some embodiments, the methods further comprise contacting

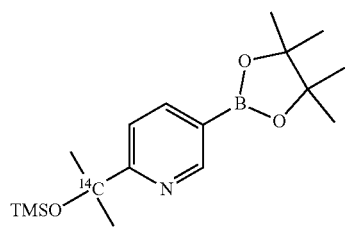

with an acid (e.g., HCl) in a solvent (e.g., 1,4-dioxane), wherein said contacting occurs under conditions suitable to produce

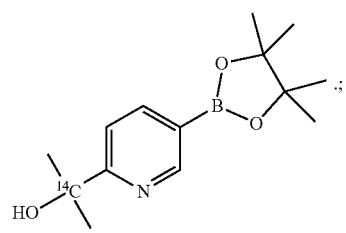 [SMILES: CC1(C)OB(c2ccc([14C](C)(C)O)nc2)OC1(C)C]

In some embodiments, the methods further comprise contacting

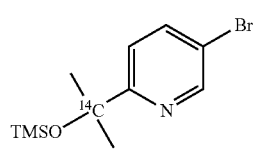

with

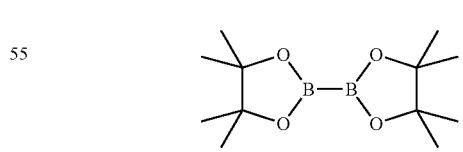

in the presence of a palladium catalyst (e.g., PdCl$_2$(dppf)-DCM complex) and a base (e.g., KOAc) in a solvent (e.g., 1,4-dioxane), wherein said contacting occurs under conditions suitable to produce

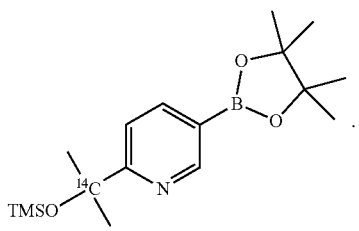

In some embodiments, the methods further comprise contacting

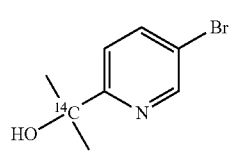

with TMSCl in the presence of a base (e.g., TEA) in a solvent (e.g., DCM), wherein said contacting occurs under conditions suitable to produce

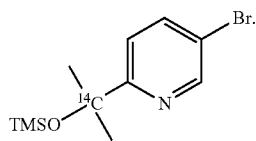

In some embodiments, the methods further comprise contacting

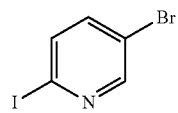

with

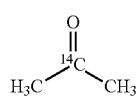

in the presence of a base (e.g., butyl lithium) in a solvent (e.g., DCM) wherein said contacting occurs under conditions suitable to produce

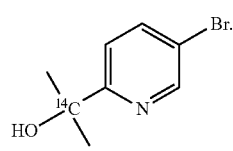

Further provided herein are processes for preparing a compound having the formula:

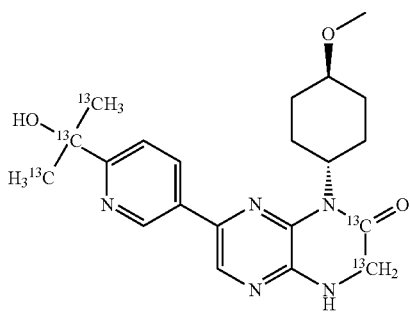 [SMILES: CO[C@H]1CC[C@H](N2c3nc(-c4ccc([13C]([13CH3])([13CH3])O)nc4)cnc3N[13CH2][13C]2=O)CC1]

the method comprising contacting

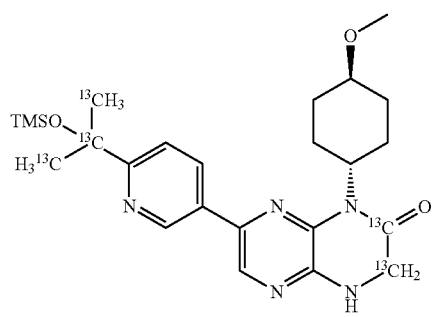

with an acid (aqueous HCl) in a solvent (e.g., ACN) wherein said contacting occurs under conditions suitable to produce

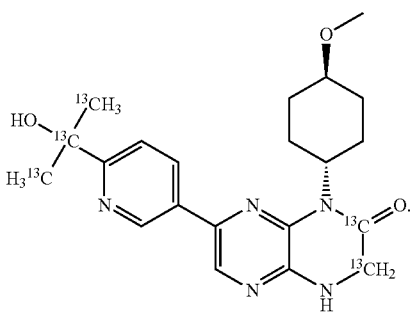 [SMILES: CO[C@H]1CC[C@H](N2c3nc(-c4ccc([13C]([13CH3])([13CH3])O)nc4)cnc3N[13CH2][13C]2=O)CC1]

In some embodiments, the methods further comprise contacting

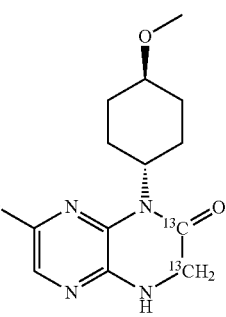

with

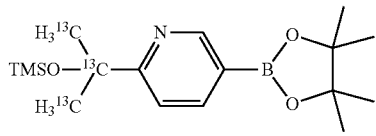

in the presence of a palladium catalyst (e.g., PdCl$_2$(Amphos)$_2$) and a base (e.g., K$_2$CO$_3$) in a solvent (e.g., IPA, optionally in the presence of water), wherein said contacting occurs under conditions suitable to produce

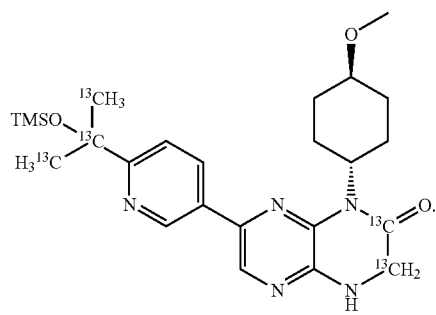

In some such embodiments, the contacting occurs at elevated temperatures (e.g., 69-71° C.).

In some embodiments, the methods further comprise contacting

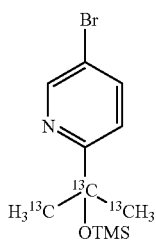

with

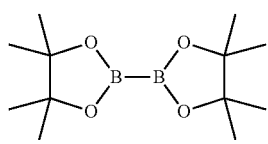

in the presence of a palladium catalyst (e.g., PdCl$_2$(dppf)-DCM complex) and a base (e.g., K$_2$CO$_3$) in a solvent (e.g. 1,4-dioxane), wherein said contacting occurs under conditions suitable to produce

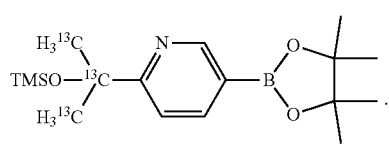

In some such embodiments, the contacting occurs at elevated temperature (e.g., 90-95° C.).

In some embodiments, the methods further comprise contacting

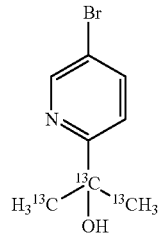

with TMSCl in the presence of a base (e.g., TEA, optionally in the presence of DMAP) in a solvent (e.g., in DCM), wherein said contacting occurs under conditions suitable to produce

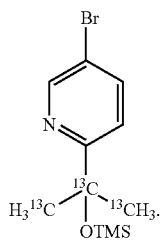

In some such embodiments, the contacting occurs at low temperature (e.g., 0-5° C.).

In some embodiments, the methods further comprise contacting

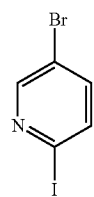

with

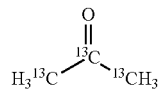

in the presence of a base (e.g., n-butyllithium) in a solvent (e.g., DCM), wherein said contacting occurs under conditions suitable to produce

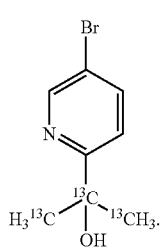

In some such embodiments, the contacting occurs at low temperature (e.g., −78° C.).

In some embodiments, the methods further comprise contacting

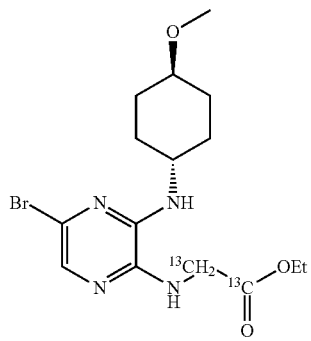 [SMILES: CCO[13C](=O)[13CH2]Nc1ncc(Br)nc1N[C@H]1CC[C@H](OC)CC1]

with a base (e.g., potassium tert-butoxide) in a solvent (e.g THF), wherein said contacting occurs under conditions suitable to produce

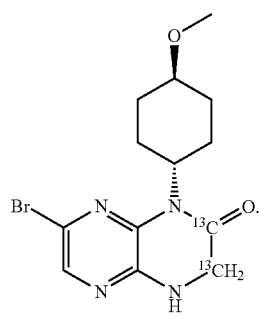 [SMILES: CO[C@H]1CC[C@H](N2c3nc(Br)cnc3N[13CH2][13C]2=O)CC1]

In some other embodiments, the methods further comprise contacting

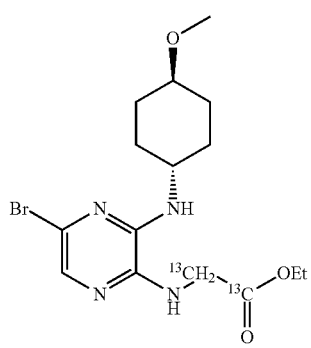 [SMILES: CCO[13C](=O)[13CH2]Nc1ncc(Br)nc1N[C@H]1CC[C@H](OC)CC1]

with and acid (e.g. phosphoric acid) in a solvent (e.g water), wherein said contacting occurs under conditions suitable to produce

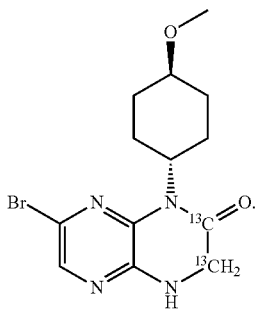 [SMILES: CO[C@H]1CC[C@H](N2c3nc(Br)cnc3N[13CH2][13C]2=O)CC1]

In some such embodiments, the contacting occurs at elevated temperature (e.g., 80° C.).

In some embodiments, the methods further comprise contacting

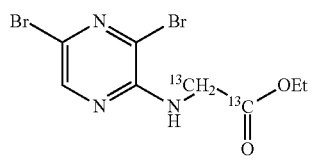 [SMILES: CCO[13C](=O)[13CH2]Nc1ncc(Br)nc1Br]

with

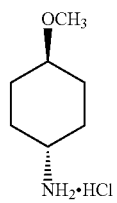

in the presence of a base (e.g., DIPEA) in a solvent (e.g., NMP), wherein said contacting occurs under conditions suitable to produce

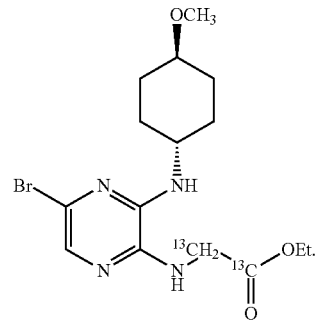 [SMILES: CCO[13C](=O)[13CH2]Nc1ncc(Br)nc1N[C@H]1CC[C@H](OC)CC1]

In some such embodiments, the contacting occurs at elevated temperature (e.g., 124-129° C.).

In some embodiments, the methods further comprise contacting

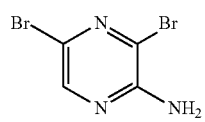

with

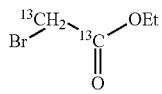

in the presence of a base (e.g., K₂CO₃) in a solvent e.g acetone), optionally in the presence of tetrabutylammonium hydrogensulfate, wherein said contacting occurs under conditions suitable to produce

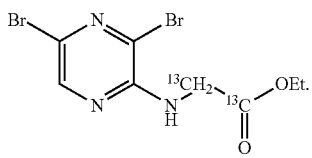 [SMILES: CCO[13C](=O)[13CH2]Nc1ncc(Br)nc1Br]

In one embodiment, provided herein are methods of preparing a compound having the formula:

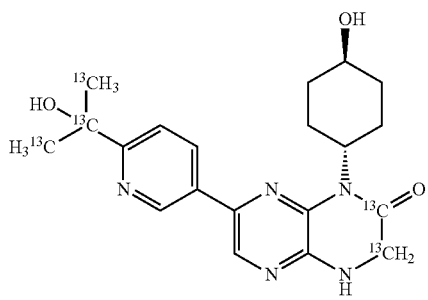 [SMILES: [13CH3][13C]([13CH3])(O)c1ccc(-c2cnc3c(n2)N([C@H]2CC[C@H](O)CC2)[13C](=O)[13CH2]N3)cn1]

the methods comprising contacting

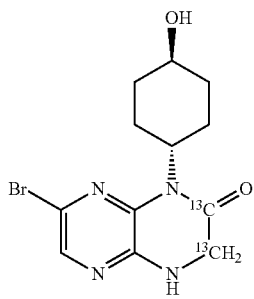

with

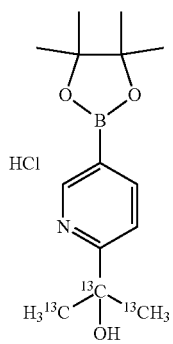

in the presence of a palladium catalyst (e.g., PdCl₂(Amphos)₂) and a base (e.g., K₂CO₃) in a solvent (e.g., THF, optionally with water), wherein said contacting occurs under conditions suitable to produce

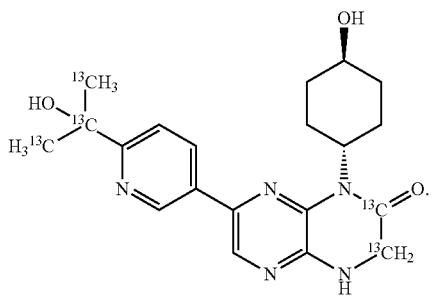 [SMILES: [13CH3][13C]([13CH3])(O)c1ccc(-c2cnc3c(n2)N([C@H]2CC[C@H](O)CC2)[13C](=O)[13CH2]N3)cn1]

In some such embodiments, the contacting occurs at elevated temperatures (e.g., reflux).

In some embodiments, the methods further comprise contacting

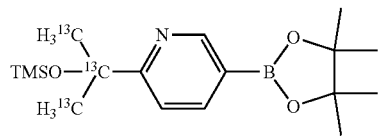

with an acid (e.g., HCl) in a solvent (e.g., 1,4-dioxane), wherein said contacting occurs under conditions suitable to produce

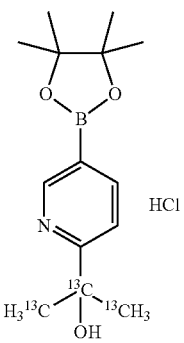

In some embodiments, the methods further comprise contacting

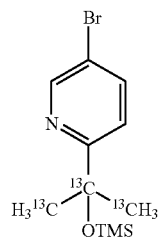

with

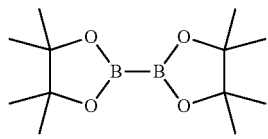

in the presence of a palladium catalyst (e.g., PdCl₂(dppf)-DCM complex) and a base (e.g., K₂CO₃) in a solvent (e.g. 1,4-dioxane), wherein said contacting occurs under conditions suitable to produce

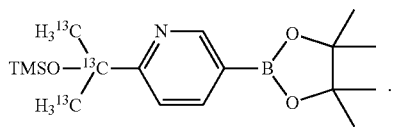

In some embodiments, the contacting occurs at elevated temperature (e.g. reflux).

In some embodiments, the methods further comprise contacting

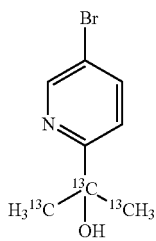

with TMSCl in the presence of a base (e.g., TEA, optionally in the presence of DMAP) in a solvent (e.g., DCM), wherein said contacting occurs under conditions suitable to produce

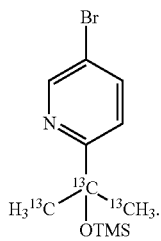

In some embodiments, the methods further comprise contacting

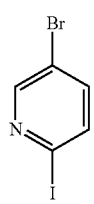

with

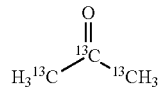

in the presence of a base (e.g n-butyllithium) in a solvent (e.g., DCM), wherein said contacting occurs under conditions suitable to produce

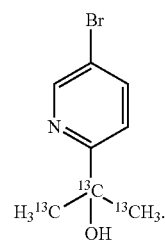

In some embodiments, the the contacting occurs at low temperature (e.g., −78° to −72° C.).

In some embodiments, the methods further comprise contacting

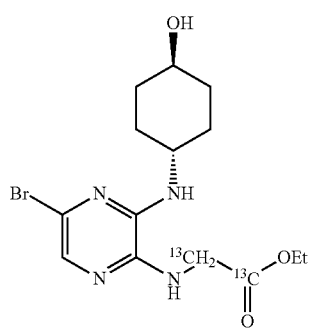 [SMILES: CCO[13C](=O)[13CH2]Nc1ncc(Br)nc1N[C@H]1CC[C@H](O)CC1]

with an acid (e.g., aqueous phosphoric acid), wherein said contacting occurs under conditions suitable to produce

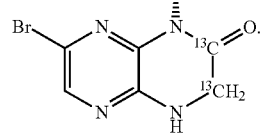

In some embodiments, the the contacting occurs at elevated temperature (e.g., 75-80° C.).

In some embodiments, the methods further comprise contacting

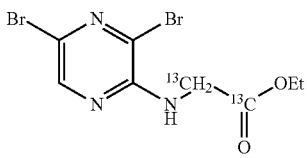 [SMILES: CCO[13C](=O)[13CH2]Nc1ncc(Br)nc1Br]

with

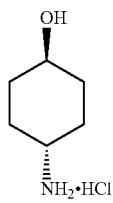

in the presence of a base (e.g., DIPEA) in a solvent (e.g., NMP), wherein said contacting occurs under conditions suitable to produce

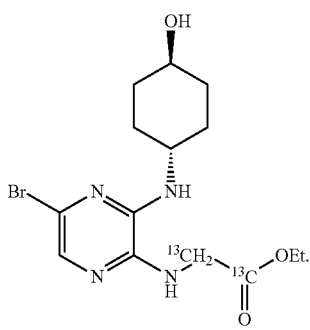 [SMILES: CCO[13C](=O)[13CH2]Nc1ncc(Br)nc1N[C@H]1CC[C@H](O)CC1]

In some embodiments, the the contacting occurs at elevated temperature (e.g., reflux).

In some embodiments, the methods further comprise contacting

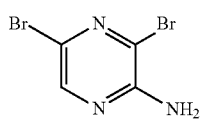

with

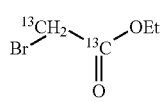

in the presence of a base (e.g., K₂CO₃) in a solvent (e.g., acetone), optionally in the presence of tetrabutylammonium hydrogensulfate, wherein said contacting occurs under conditions suitable to produce

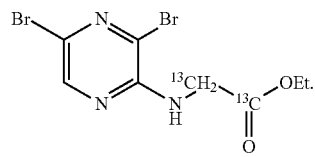 [SMILES: CCO[13C](=O)[13CH2]Nc1ncc(Br)nc1Br]

In some embodiments, the the contacting occurs at elevated temperature (e.g., reflux).

In one embodiment, the compound having the formula:

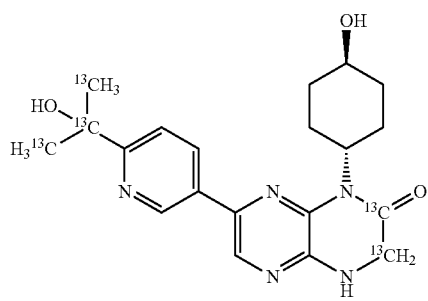 [SMILES: [13CH3][13C]([13CH3])(O)c1ccc(-c2cnc3c(n2)N([C@H]2CC[C@H](O)CC2)[13C](=O)[13CH2]N3)cn1]

is recrystallized from a mixture of 2-propanol and water in the presence of 2,6-di-tert-butyl-4-methylphenol.

In one embodiment, provided herein are methods of preparing a compound having the formula:

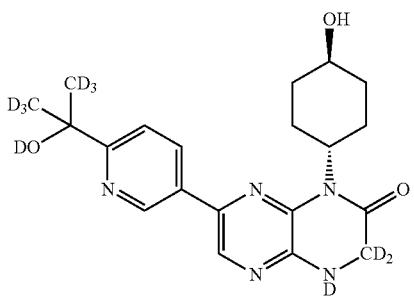

the methods comprising contacting

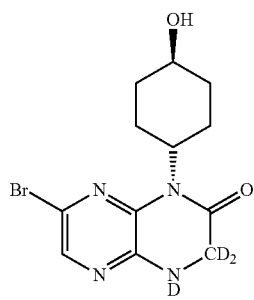

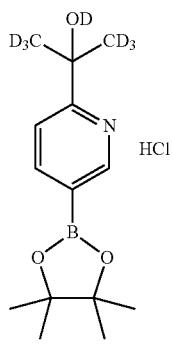

in the presence of a palladium catalyst (e.g., PdCl₂(Amphos)₂) and a base (e.g., K₂CO₃) in a solvent (e.g., THF, optionally with water), wherein said contacting occurs under conditions suitable to produce

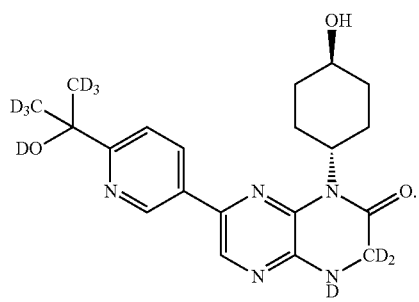

In some such embodiments, the contacting occurs at elevated temperatures (e.g., reflux).

In some embodiments, the methods further comprise contacting

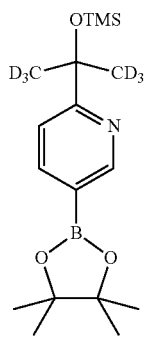

with an acid (e.g., HCl) in a solvent (e.g., 1,4-dioxane), wherein said contacting occurs under conditions suitable to produce

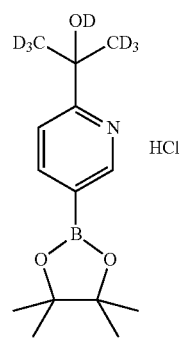

In some embodiments, the methods further comprise contacting

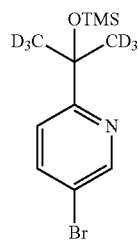

with

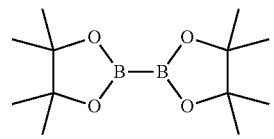

in the presence of a palladium catalyst (e.g., PdCl₂(dppf)-DCM complex) and a base (e.g., K₂CO₃) in a solvent (e.g. 1,4-dioxane), wherein said contacting occurs under conditions suitable to produce

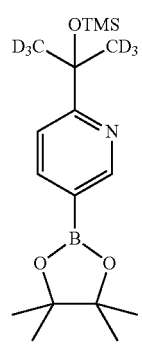

In some embodiments, the contacting occurs at elevated temperature (e.g. reflux).

In some embodiments, the methods further comprise contacting

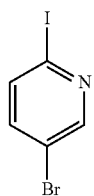

with TMSCl in the presence of a base (e.g., n-butyl-lithium) in a solvent (e.g., d6-acetone), wherein said contacting occurs under conditions suitable to produce

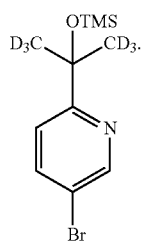

In some embodiments, the methods further comprise contacting

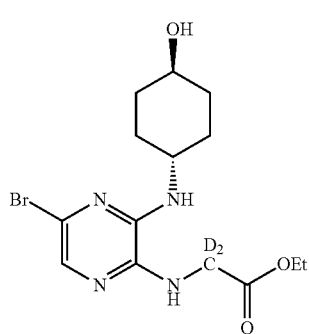

with an acid (e.g., aqueous phosphoric acid), wherein said contacting occurs under conditions suitable to produce

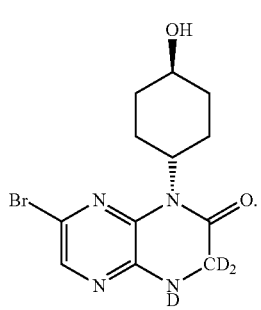

In some embodiments, the the contacting occurs at elevated temperature (e.g., 75-80° C.).

In some embodiments, the methods further comprise contacting

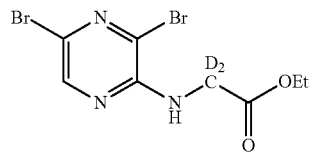

with

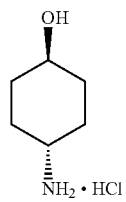

in the presence of a base (e.g., DIPEA) in a solvent (e.g., NMP), wherein said contacting occurs under conditions suitable to produce

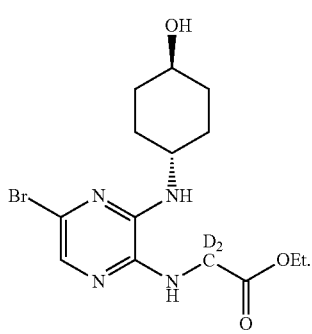

In some embodiments, the the contacting occurs at elevated temperature (e.g., reflux).

In some embodiments, the methods further comprise contacting

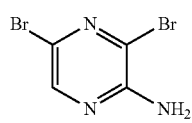

with

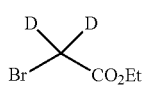

in the presence of a base (e.g., K₂CO₃) in a solvent (e.g., acetone), optionally in the presence of tetrabutylammonium hydrogensulfate, wherein said contacting occurs under conditions suitable to produce

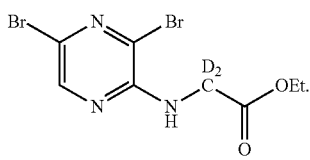

In some embodiments, the the contacting occurs at elevated temperature (e.g., reflux).

In one embodiment, provided herein are methods of preparing a compound having the formula:

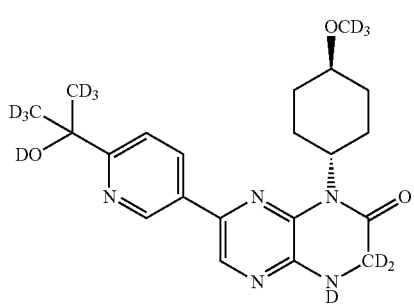

the methods comprising contacting

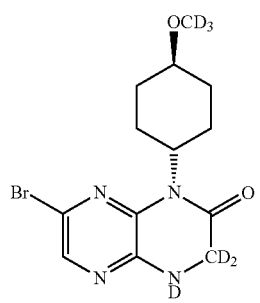

with

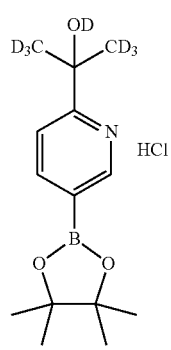

in the presence of a palladium catalyst (e.g., PdCl$_2$(Amphos)$_2$) and a base (e.g., K$_2$CO$_3$) in a solvent (e.g., THF, optionally with water), wherein said contacting occurs under conditions suitable to produce

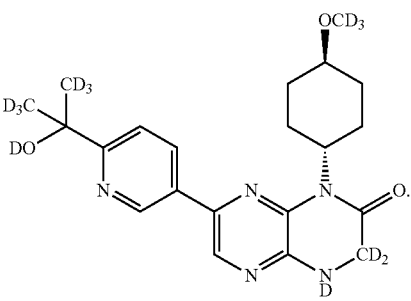

In some such embodiments, the contacting occurs at elevated temperatures (e.g., reflux).

In some embodiments, the methods further comprise contacting

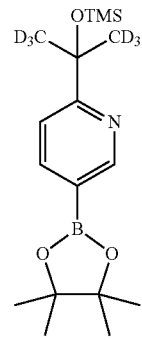

with an acid (e.g., HCl) in a solvent (e.g., 1,4-dioxane), wherein said contacting occurs under conditions suitable to produce

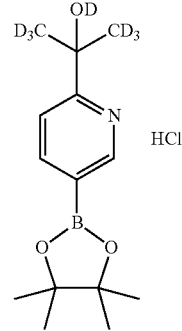

In some embodiments, the methods further comprise contacting

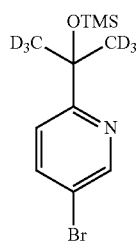

with

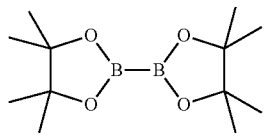

in the presence of a palladium catalyst (e.g., PdCl$_2$(dppf)-DCM complex) and a base (e.g., K$_2$CO$_3$) in a solvent (e,g. 1,4-dioxane), wherein said contacting occurs under conditions suitable to produce

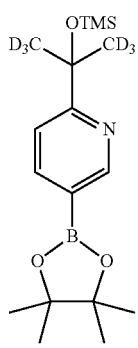

In some embodiments, the contacting occurs at elevated temperature (e.g., reflux).

In some embodiments, the methods further comprise contacting

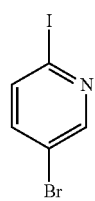

with TMSCl in the presence of a base (e.g., n-butyl-lithium) in a solvent (e.g., d$^6$-acetone), wherein said contacting occurs under conditions suitable to produce

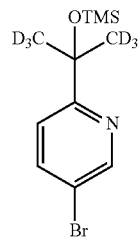

In some embodiments, the methods further comprise contacting

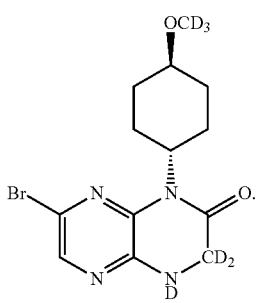

with an acid (e.g., aqueous phosphoric acid), wherein said contacting occurs under conditions suitable to produce

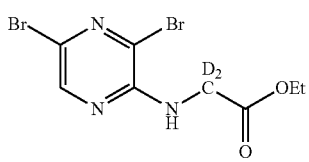

In some embodiments, the the contacting occurs at elevated temperature (e.g., 75-80° C.).

In some embodiments, the methods further comprise contacting

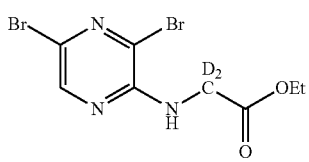

with

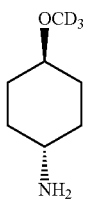

in the presence of a base (e.g., DIPEA) in a solvent (e.g., NMP), wherein said contacting occurs under conditions suitable to produce

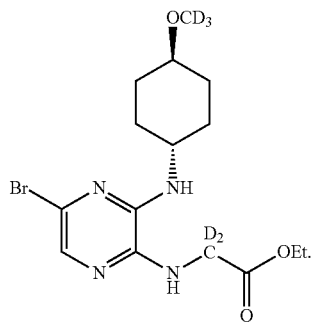

In some embodiments, the the contacting occurs at elevated temperature (e.g., reflux).

In some embodiments, the methods further comprise contacting

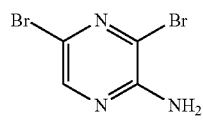

with

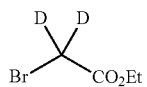

in the presence of a base (e.g., K₂CO₃) in a solvent (e.g., acetone), optionally in the presence of tetrabutylammonium hydrogensulfate, wherein said contacting occurs under conditions suitable to produce

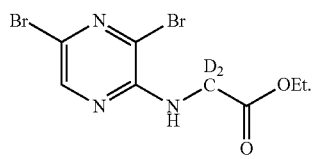

In some embodiments, the the contacting occurs at elevated temperature (e.g., reflux).

In one embodiment, the compound having the formula:

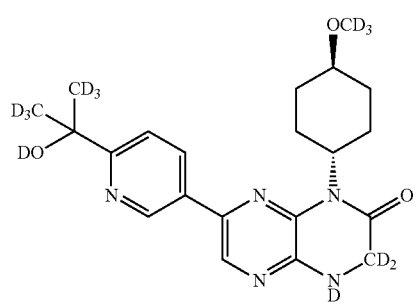

In one embodiment, provided herein are methods of preparing a compound having the formula:

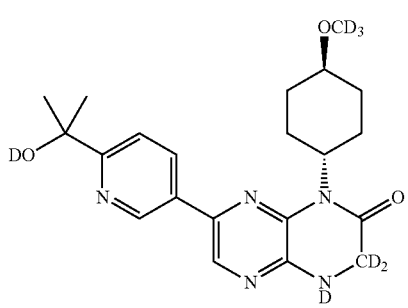

the methods comprising contacting

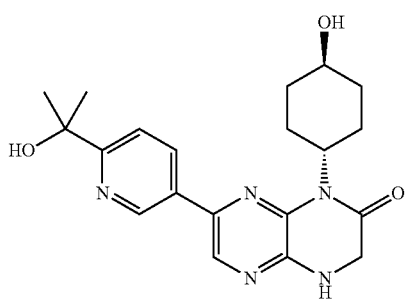 [SMILES: CC(C)(O)c1ccc(-c2cnc3c(n2)N([C@H]2CC[C@H](O)CC2)C(=O)CN3)cn1]

with a base and CD₃I to produce

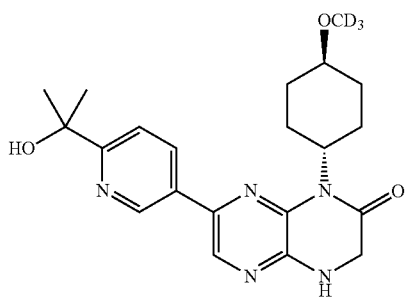

further contacting with a base and ROD/D₂O, wherein said contacting occurs under conditions suitable to produce

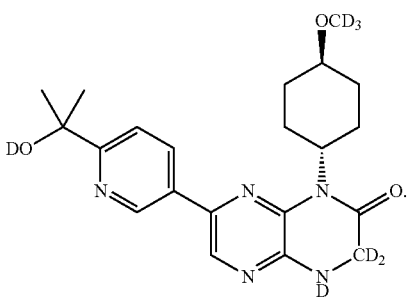

In one embodiment, provided herein are methods of preparing a compound having the formula:

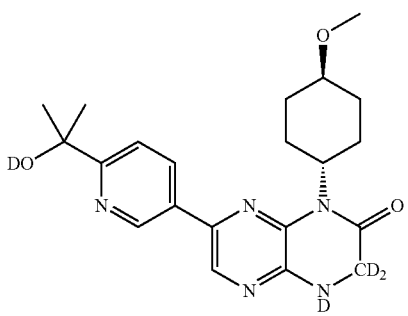

the methods comprising contacting

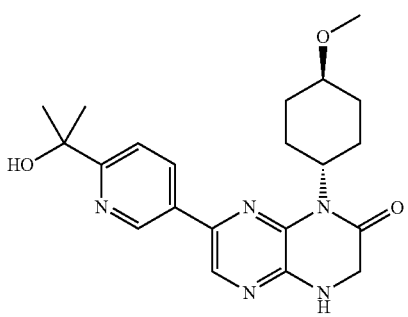

with a base and ROD/D₂O, wherein said contacting occurs under conditions suitable to produce

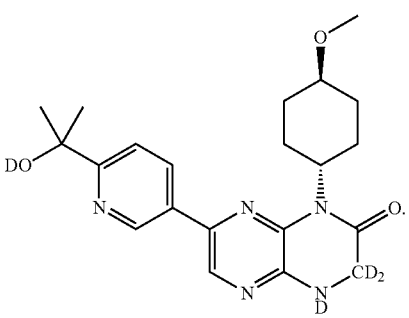

5.4 Pharmaceutical Compositions

In one embodiment, provided herein are pharmaceutical compositions comprising Compound A and one or more pharmaceutically acceptable excipients or carriers. In one embodiment, the pharmaceutical compositions provided herein comprise Form A of Compound A and one or more pharmaceutically acceptable excipients or carriers. In one embodiment, the pharmaceutical compositions provided herein comprise Form B (a hydrate) of Compound A and one or more pharmaceutically acceptable excipients or carriers. In one embodiment, the pharmaceutical compositions provided herein comprise Form C (anhydrous) of Compound A and one or more pharmaceutically acceptable excipients or carriers. In one embodiment, the pharmaceutical compositions provided herein comprise Form D (a methanol solvate) of Compound A and one or more pharmaceutically acceptable excipients or carriers. In one embodiment, the pharmaceutical compositions provided herein comprise Form E (a p-xylene solvate) of Compound A and one or more pharmaceutically acceptable excipients or carriers. In one embodiment, the pharmaceutical compositions provided herein comprise amorphous Compound A and one or more pharmaceutically acceptable excipients or carriers.

In one embodiment, the pharmaceutical compositions provided herein comprise an isotopologue of Compound A and one or more pharmaceutically acceptable excipients or carriers. In one embodiment, the pharmaceutical compositions provided herein comprise a metabolite of Compound A and one or more pharmaceutically acceptable excipients or carriers. With respect to the pharmaceutical compositions provided herein, each reference to "Compound A" is contemplated as including pharmaceutically acceptable salts, solid forms (including Form A, Form B, Form C, Form D, Form E, and/or amorphous Compound A), isotopologues and metabolites of Compound A.

In one embodiment, the pharmaceutically acceptable excipients and carriers are selected from binders, diluents, disintegrants and lubricants.

In certain embodiments, the binders include, but are not limited to, cellulose (e.g., microcrystalline cellulose, such as AVICEL® PH 101, AVICEL® PH 102 and AVICEL® PH 112) and starch (e.g., pregelatinized starch (STARCH 1500®)). In one embodiment, the binder is cellulose. In another embodiment, the binder is microcrystalline cellulose. In yet another embodiment, the binder is AVICEL® PH 101. In yet another embodiment, the binder is AVICEL® PH 102. In yet another embodiment, the binder is AVICEL® PH 112. In yet another embodiment, the binder is starch. In yet another embodiment, the binder is pregelatinized starch. In still another embodiment, the binder is STARCH 1500®.

In certain embodiments, the diluents include, but are not limited to, lactose (e.g., lactose monohydrate (FAST FLO® 316) and lactose anhydrous), cellulose (e.g., microcrystalline cellulose, such as AVICEL® PH 101, AVICEL® PH 102 and AVICEL® PH 112). In one embodiment, the diluent is lactose. In another embodiment, the diluent is lactose monohydrate. In yet another embodiment, the diluent is FAST FLO® 316. In yet another embodiment, the diluent is lactose anhydrous. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102. In still another embodiment, the diluent is AVICEL® PH 112.

In certain embodiments, the disintegrants include, but are not limited to, starch (e.g., corn starch) and carboxymethyl cellulose (e.g., croscarmellose sodium, such as AC-DI-SOL®). In one embodiment, the disintegrant is starch. In another embodiment, the disintegrant is corn starch. In yet another embodiment, the disintegrant is carboxymethyl cellulose. In yet another embodiment, the disintegrant is croscarmellose sodium. In still another embodiment, the disintegrant is AC-DI-SOL®.

In certain embodiments, the lubricants include, but are not limited to, starch (e.g., corn starch), magnesium stearate, and stearic acid. In one embodiment, the lubricant is starch. In another embodiment, the lubricant is corn starch. In yet another embodiment, the lubricant is magnesium stearate. In still another embodiment, the lubricant is stearic acid.

In another embodiment, the pharmaceutical compositions provided herein comprise Compound A and one or more pharmaceutically acceptable excipients or carriers, each independently selected from carboxymethyl cellulose, cellulose, lactose, magnesium stearate, starch, and stearic acid.

In another embodiment, the pharmaceutical compositions provided herein comprise Compound A and one or more pharmaceutically acceptable excipients or carriers, each independently selected from carboxymethyl cellulose, cellulose, lactose, magnesium stearate and starch.

In yet another embodiment, the pharmaceutical compositions provided herein comprise Compound A and one or more pharmaceutically acceptable excipients or carriers, each independently selected from croscarmellose sodium, microcrystalline cellolose, lactose anhydrous, lactose monohydrate, magnesium stearate, corn starch, pregelatinized starch, and stearic acid.

In yet another embodiment, the pharmaceutical compositions provided herein comprise Compound A and one or more pharmaceutically acceptable excipients or carriers, each independently selected from croscarmellose sodium, microcrystalline cellolose, lactose anhydrous, lactose monohydrate, magnesium stearate, corn starch and pregelatinized starch.

In certain embodiments, the pharmaceutical compositions provided herein do not comprise stearic acid.

In yet another embodiment, the pharmaceutical compositions provided herein comprise Compound A and one or more pharmaceutically acceptable excipients or carriers, each independently selected from AC-DI-SOL®, AVICEL PH 101®, AVICEL PH 102®, lactose anhydrous, FAST FLO 316®, magnesium stearate, corn starch, STARCH 1500®, and stearic acid.

In yet another embodiment, the pharmaceutical compositions provided herein comprise Compound A and one or more pharmaceutically acceptable excipients or carriers, each independently selected from AC-DI-SOL®, AVICEL PH 101®, AVICEL PH 102®, lactose anhydrous, FAST FLO 316®, magnesium stearate, corn starch and STARCH 1500®.

In one embodiment, the pharmaceutical compositions provided herein comprise Compound A, a diluent(s)/binder(s), a disintegrant(s), and a lubricant(s).

In one embodiment, the pharmaceutical compositions provided herein comprise Compound A, stearic acid and lactose monohydrate.

In one embodiment, the pharmaceutical compositions provided herein comprise Compound A and lactose monohydrate.

In one embodiment, the pharmaceutical compositions provided herein comprise Compound A, stearic acid, lactose monohydrate and microcyrstalline cellulose.

In one embodiment, the pharmaceutical compositions provided herein comprise Compound A, lactose monohydrate and microcyrstalline cellulose.

In another embodiment, the pharmaceutical compositions provided herein comprise Compound A, lactose monohydrate, microcrystalline cellulose, carboxymethyl cellulose, and magnesium stearate.

In another embodiment, the pharmaceutical compositions provided herein comprise Compound A, lactose monohydrate, microcrystalline cellulose, croscarmellose sodium, stearic acid and magnesium stearate.

In another embodiment, the pharmaceutical compositions provided herein comprise Compound A, lactose monohydrate, microcrystalline cellulose, croscarmellose sodium and magnesium stearate.

In still another embodiment, the pharmaceutical compositions provided herein comprise Compound A, FAST FLO 316®, AVICEL PH 102®, AC-DI-SOL®, stearic acid and magnesium stearate.

In still another embodiment, the pharmaceutical compositions provided herein comprise Compound A, FAST FLO 316®, AVICEL PH 112®, AC-DI-SOL® and magnesium stearate.

In one embodiment, the pharmaceutical compositions provided herein comprise about 10-20% by weight of Compound A, about 70-90% by weight of diluent(s)/binder(s), about 1-5% by weight of disintegrant(s), and about 0.1-2% by weight of lubricant(s).

In one embodiment, the pharmaceutical compositions provided herein comprise about 15% by weight of Compound A, about 80% by weight of diluent(s)/binder(s), about 3% by weight of disintegrant(s), and about 1.4% by weight of lubricant(s).

In another embodiment, the pharmaceutical compositions provided herein comprise about 10-20% by weight of Form A of Compound A, about 30-60% by weight of lactose, about 20-40% by weight of microcrystalline cellulose, about 1-5% by weight of carboxymethyl cellulose, about 0.1-2% by weight of stearic acid and about 0.5-3% by weight of magnesium stearate.

In another embodiment, the pharmaceutical compositions provided herein comprise about 10-20% by weight of Form A of Compound A, about 30-60% by weight of lactose, about 20-40% by weight of microcrystalline cellulose, about 1-5% by weight of carboxymethyl cellulose and about 0.5-3% by weight of magnesium stearate.

In another embodiment, the pharmaceutical compositions provided herein comprise about 15% by weight of Form A of Compound A, about 49% by weight of lactose, about 31% by weight of microcrystalline cellulose, about 3% by weight of carboxymethyl cellulose, about 0.4% by weight of stearic acid and about 1% by weight of magnesium stearate.

In another embodiment, the pharmaceutical compositions provided herein comprise about 15% by weight of Form A of Compound A, about 49% by weight of lactose, about 31% by weight of microcrystalline cellulose, about 3% by weight of carboxymethyl cellulose and about 1% by weight of magnesium stearate.

In yet another embodiment, the pharmaceutical compositions provided herein comprise about 10-20% by weight of Form A of Compound A, about 30-60% by weight of lactose monohydrate, about 20-40% by weight of microcrystalline cellulose, about 1-5% by weight of croscarmellose sodium, about 0.1-2% by weight stearic acid and about 0.5-3% by weight of magnesium stearate.

In yet another embodiment, the pharmaceutical compositions provided herein comprise about 10-20% by weight of Form A of Compound A, about 30-60% by weight of lactose monohydrate, about 20-40% by weight of microcrystalline cellulose, about 1-5% by weight of croscarmellose sodium and about 0.5-3% by weight of magnesium stearate.

In yet another embodiment, the pharmaceutical compositions provided herein comprise about 15% by weight of Form A of Compound A, about 49% by weight of lactose monohydrate, about 31% by weight of microcrystalline cellulose, about 3% by weight of croscarmellose sodium, about 0.4% by weight of stearic acid and about 1% by weight of magnesium stearate.

In yet another embodiment, the pharmaceutical compositions provided herein comprise about 15% by weight of Form A of Compound A, about 49% by weight of lactose monohydrate, about 31% by weight of microcrystalline cellulose, about 3% by weight of croscarmellose sodium and about 1% by weight of magnesium stearate.

In still another embodiment, the pharmaceutical compositions provided herein comprise about 10-20% by weight of Form A of Compound A, about 30-60% by weight of FAST FLO 316®, about 20-40% by weight of AVICEL PH 102®, about 1-5% by weight of AC-DI-SOL®, about 0.1-2% by weight of stearic acid and about 0.5-3% by weight of magnesium stearate.

In still another embodiment, the pharmaceutical compositions provided herein comprise about 10-20% by weight of Form A of Compound A, about 30-60% by weight of FAST FLO 316®, about 20-40% by weight of AVICEL PH 112®, about 1-5% by weight of AC-DI-SOL® and about 0.5-3% by weight of magnesium stearate.

In still another embodiment, the pharmaceutical compositions provided herein comprise about 15% by weight of Form A of Compound A, about 49% by weight of FAST FLO 316®, about 31% by weight of AVICEL PH 102®, about 3% by weight of AC-DI-SOL®, about 0.4% by weight of stearic acid and about 1% by weight of magnesium stearate.

In still another embodiment, the pharmaceutical compositions provided herein comprise about 15% by weight of Form A of Compound A, about 49% by weight of FAST FLO 316®, about 31% by weight of AVICEL PH 112®, about 3% by weight of AC-DI-SOL® and about 1% by weight of magnesium stearate.

In one embodiment, the pharmaceutical compositions provided herein comprise Form A of Compound A, lactose, starch, carboxymethyl cellulose, stearic acid and magnesium stearate.

In one embodiment, the pharmaceutical compositions provided herein comprise Form A of Compound A, lactose, starch, carboxymethyl cellulose and magnesium stearate.

In another embodiment, the pharmaceutical compositions provided herein comprise Form A of Compound A, lactose monohydrate, pregelatinized starch, croscarmellose sodium, stearic acid and magnesium stearate.

In another embodiment, the pharmaceutical compositions provided herein comprise Form A of Compound A, lactose monohydrate, pregelatinized starch, croscarmellose sodium and magnesium stearate.

In still another embodiment, the pharmaceutical compositions provided herein comprise Compound A, FAST FLO 316®, STARCH 1500®, AC-DI-SOL®, stearic acid and magnesium stearate.

In still another embodiment, the pharmaceutical compositions provided herein comprise Compound A, FAST FLO 316®, STARCH 1500®, AC-DI-SOL® and magnesium stearate.

In one embodiment, the pharmaceutical compositions provided herein comprise about 15% by weight of Compound A, from about 55% to about 80% by weight of diluent(s)/binder(s), from about 20% to about 30% by weight of disintegrant(s), and about 1% by weight of lubricant(s).

In another embodiment, the pharmaceutical compositions provided herein comprise about 15% by weight of Compound A, about 55% by weight of lactose, about 25% by weight of starch, about 3% by weight of carboxymethyl cellulose, about 0.4% by weight of stearic acid and about 1% by weight of magnesium stearate.

In another embodiment, the pharmaceutical compositions provided herein comprise about 15% by weight of Compound A, about 55% by weight of lactose, about 25% by weight of starch, about 3% by weight of carboxymethyl cellulose and about 1% by weight of magnesium stearate.

In yet another embodiment, the pharmaceutical compositions provided herein comprise about 15% by weight of Compound A, about 55% by weight of lactose monohydrate, about 25% by weight of pregelatinized starch, about 3% by weight of croscarmellose sodium, about 0.4% by weight of stearic acid and about 1% by weight of magnesium stearate.

In yet another embodiment, the pharmaceutical compositions provided herein comprise about 15% by weight of Compound A, about 55% by weight of lactose monohydrate, about 25% by weight of pregelatinized starch, about 3% by weight of croscarmellose sodium and about 1% by weight of magnesium stearate.

In still another embodiment, the pharmaceutical compositions provided herein comprise about 15% by weight of Compound A, about 55% by weight of FAST FLO 316®, about 25% by weight of STARCH 1500®, about 3% by weight of AC-DI-SOL®, about 0.4% by weight of stearic acid and about 1% by weight of magnesium stearate.

In still another embodiment, the pharmaceutical compositions provided herein comprise about 15% by weight of Compound A, about 55% by weight of FAST FLO 316®, about 25% by weight of STARCH 1500®, about 3% by weight of AC-DI-SOL® and about 1% by weight of magnesium stearate.

In one embodiment, the pharmaceutical compositions provided herein comprise Compound A, lactose, microcrystalline cellulose, carboxymethyl cellulose, stearic acid and magnesium stearate.

In one embodiment, the pharmaceutical compositions provided herein comprise Compound A, lactose, microcrystalline cellulose, carboxymethyl cellulose and magnesium stearate.

In another embodiment, the pharmaceutical compositions provided herein comprise Compound A, lactose monohydrate, microcrystalline cellulose, croscarmellose sodium, stearic acid and magnesium stearate.

In another embodiment, the pharmaceutical compositions provided herein comprise Compound A, lactose monohydrate, microcrystalline cellulose, croscarmellose sodium and magnesium stearate.

In still another embodiment, the pharmaceutical compositions provided herein comprise Compound A, FAST FLO 316®, AVICEL PH 102®, AC-DI-SOL®, about 0.4% by weight of stearic acid and magnesium stearate.

In still another embodiment, the pharmaceutical compositions provided herein comprise Compound A, FAST FLO 316®, AVICEL PH 112®, AC-DI-SOL® and magnesium stearate.

In one embodiment, the pharmaceutical compositions provided herein comprise about 15% by weight of Compound A, about 80% by weight of diluent(s)/binder(s), about 3% by weight of disintegrant(s), and about 1% by weight of lubricant(s).

In another embodiment, the pharmaceutical compositions provided herein comprise about 15% by weight of Compound A, about 50% by weight of lactose, about 30% by weight of microcrystalline cellulose, about 3% by weight of carboxymethyl cellulose, about 0.4% by weight of stearic acid and about 1% by weight of magnesium stearate.

In another embodiment, the pharmaceutical compositions provided herein comprise about 15% by weight of Compound A, about 50% by weight of lactose, about 30% by weight of microcrystalline cellulose, about 3% by weight of carboxymethyl cellulose and about 1% by weight of magnesium stearate.

In yet another embodiment, the pharmaceutical compositions provided herein comprise about 15% by weight of Compound A, about 50% by weight of lactose monohydrate, about 30% by weight of microcrystalline cellulose, about 3% by weight of croscarmellose sodium, about 0.4% by weight of stearic acid and about 1% by weight of magnesium stearate.

In yet another embodiment, the pharmaceutical compositions provided herein comprise about 15% by weight of Compound A, about 50% by weight of lactose monohydrate, about 30% by weight of microcrystalline cellulose, about 3% by weight of croscarmellose sodium and about 1% by weight of magnesium stearate.

In still another embodiment, the pharmaceutical compositions provided herein comprise about 15% by weight of Compound A, about 50% by weight of FAST FLO 316®, about 30% by weight of AVICEL PH 102®, about 3% by weight of AC-DI-SOL®, about 0.4% by weight of stearic acid and about 1% by weight of magnesium stearate.

In still another embodiment, the pharmaceutical compositions provided herein comprise about 15% by weight of Compound A, about 50% by weight of FAST FLO 316®, about 30% by weight of AVICEL PH 112®, about 3% by weight of AC-DI-SOL® and about 1% by weight of magnesium stearate.

In one embodiment, the pharmaceutical compositions provided herein comprise Compound A, lactose, microcrystalline cellulose, corn starch, carboxymethyl cellulose, stearic acid and magnesium stearate.

In one embodiment, the pharmaceutical compositions provided herein comprise Compound A, lactose, microcrystalline cellulose, corn starch, carboxymethyl cellulose and magnesium stearate.

In another embodiment, the pharmaceutical compositions provided herein comprise Compound A, lactose monohydrate, microcrystalline cellulose, corn starch, croscarmellose sodium, stearic acid and magnesium stearate.

In another embodiment, the pharmaceutical compositions provided herein comprise Compound A, lactose monohydrate, microcrystalline cellulose, corn starch, croscarmellose sodium and magnesium stearate.

In still another embodiment, the pharmaceutical compositions provided herein comprise Compound A, FAST FLO 316®, AVICEL PH 102®, corn starch, AC-DI-SOL®, stearic acid and magnesium stearate.

In still another embodiment, the pharmaceutical compositions provided herein comprise Compound A, FAST FLO 316®, AVICEL PH 102®, corn starch, AC-DI-SOL® and magnesium stearate.

In one embodiment, the pharmaceutical compositions provided herein comprise about 15% by weight of Compound A, from about 85% to about 90% by weight of diluent(s)/binder(s), from about 1% to about 10% by weight of disintegrant(s), and from about 1% to about 6% by weight of lubricants.

In another embodiment, the pharmaceutical compositions provided herein comprise about 15% by weight of Compound A, about 45% by weight of lactose, about 30% by weight of microcrystalline cellulose, about 3% by weight of corn starch, about 3% by weight of carboxymethyl cellulose, about 0.4% by weight of stearic acid and about 1% by weight of magnesium stearate.

In another embodiment, the pharmaceutical compositions provided herein comprise about 15% by weight of Compound A, about 45% by weight of lactose, about 30% by weight of microcrystalline cellulose, about 3% by weight of corn starch, about 3% by weight of carboxymethyl cellulose and about 1% by weight of magnesium stearate.

In yet another embodiment, the pharmaceutical compositions provided herein comprise about 15% by weight of Compound A, about 88% by weight of lactose, about 25% by weight of microcrystalline cellulose, about 4% by weight of corn starch, about 4% by weight of carboxymethyl cellulose, about 0.4% by weight of stearic acid and about 1.5% by weight of magnesium stearate.

In yet another embodiment, the pharmaceutical compositions provided herein comprise about 15% by weight of Compound A, about 88% by weight of lactose, about 25% by weight of microcrystalline cellulose, about 4% by weight of corn starch, about 4% by weight of carboxymethyl cellulose and about 1.5% by weight of magnesium stearate.

In yet another embodiment, the pharmaceutical compositions provided herein comprise about 15% by weight of Compound A, about 45% by weight of lactose monohydrate, about 30% by weight of microcrystalline cellulose, about 3% by weight of corn starch, about 3% by weight of croscarmellose sodium, about 0.4% by weight of stearic acid and about 1% by weight of magnesium stearate.

In yet another embodiment, the pharmaceutical compositions provided herein comprise about 15% by weight of Compound A, about 45% by weight of lactose monohydrate, about 30% by weight of microcrystalline cellulose, about 3% by weight of corn starch, about 3% by weight of croscarmellose sodium and about 1% by weight of magnesium stearate.

In yet another embodiment, the pharmaceutical compositions provided herein comprise about 15% by weight of Compound A, about 88% by weight of lactose monohydrate, about 25% by weight of microcrystalline cellulose, about 4% by weight of corn starch, about 4% by weight of croscarmellose sodium, about 0.4% by weight of stearic acid and about 1.5% by weight of magnesium stearate.

In yet another embodiment, the pharmaceutical compositions provided herein comprise about 15% by weight of Compound A, about 88% by weight of lactose monohydrate, about 25% by weight of microcrystalline cellulose, about 4% by weight of corn starch, about 4% by weight of croscarmellose sodium and about 1.5% by weight of magnesium stearate.

In yet another embodiment, the pharmaceutical compositions provided herein comprise about 15% by weight of Compound A, about 45% by weight of FAST FLO 316®, about 30% by weight of AVICEL PH 102®, about 3% by weight of corn starch, about 3% by weight of AC-DI-SOL®, about 0.4% by weight of stearic acid and about 1% by weight of magnesium stearate.

In yet another embodiment, the pharmaceutical compositions provided herein comprise about 15% by weight of Compound A, about 45% by weight of FAST FLO 316®, about 30% by weight of AVICEL PH 102®, about 3% by weight of corn starch, about 3% by weight of AC-DI-SOL® and about 1% by weight of magnesium stearate.

In still another embodiment, the pharmaceutical compositions provided herein comprise about 15% by weight of Compound A, about 88% by weight of FAST FLO 316®, about 25% by weight of AVICEL PH 102®, about 4% by weight of corn starch, about 4% by weight of AC-DI-SOL®, about 0.4% by weight of stearic acid and about 1.5% by weight of magnesium stearate.

In still another embodiment, the pharmaceutical compositions provided herein comprise about 15% by weight of Compound A, about 88% by weight of FAST FLO 316®, about 25% by weight of AVICEL PH 102®, about 4% by weight of corn starch, about 4% by weight of AC-DI-SOL® and about 1.5% by weight of magnesium stearate.

In one embodiment, the pharmaceutical compositions provided herein comprise Compound A, lactose, microcrystalline cellulose, corn starch, carboxymethyl cellulose, stearic acid, and magnesium stearate.

In one embodiment, the pharmaceutical compositions provided herein comprise Compound A, lactose, microcrystalline cellulose, corn starch, carboxymethyl cellulose and magnesium stearate.

In one embodiment, the pharmaceutical compositions provided herein comprise about 5% by weight of Compound A, about 90% by weight of diluent(s)/binder(s), from about 3% to about 6% by weight of disintegrant(s), and from about 1.5% to about 5% by weight of lubricants.

In another embodiment, the pharmaceutical compositions provided herein comprise about 5% by weight of Compound A, about 60% by weight of lactose, about 30% by weight of microcrystalline cellulose, about 3% by weight of corn starch, about 3% by weight of carboxymethyl cellulose, about 0.5% by weight of stearic acid, and about 1% by weight of magnesium stearate.

In another embodiment, the pharmaceutical compositions provided herein comprise about 5% by weight of Compound A, about 60% by weight of lactose, about 30% by weight of microcrystalline cellulose, about 3% by weight of corn starch, about 3% by weight of carboxymethyl cellulose and about 1% by weight of magnesium stearate.

In yet another embodiment, the pharmaceutical compositions provided herein comprise about 5% by weight of Compound A, about 60% by weight of lactose monohydrate, about 30% by weight of microcrystalline cellulose, about 3% by weight of corn starch, about 3% by weight of croscarmellose sodium, about 0.5% by weight of stearic acid, and about 1% by weight of magnesium stearate.

In yet another embodiment, the pharmaceutical compositions provided herein comprise about 5% by weight of Compound A, about 60% by weight of lactose monohydrate, about 30% by weight of microcrystalline cellulose, about 3% by weight of corn starch, about 3% by weight of croscarmellose sodium and about 1% by weight of magnesium stearate.

In still another embodiment, the pharmaceutical compositions provided herein comprise about 5% by weight of Compound A, about 60% by weight of FAST FLO 316®, about 30% by weight of AVICEL PH 102®, about 3% by weight of corn starch, about 3% by weight of AC-DI-SOL®, about 0.5% by weight of stearic acid, and about 1% by weight of magnesium stearate.

In still another embodiment, the pharmaceutical compositions provided herein comprise about 5% by weight of Compound A, about 60% by weight of FAST FLO 316®, about 30% by weight of AVICEL PH 102®, about 3% by weight of corn starch, about 3% by weight of AC-DI-SOL® and about 1% by weight of magnesium stearate.

In one embodiment, the pharmaceutical compositions provided herein comprise Compound A, lactose, microcrystalline cellulose, carboxymethyl cellulose, stearic acid, and magnesium stearate.

In one embodiment, the pharmaceutical compositions provided herein comprise Compound A, lactose, microcrystalline cellulose, carboxymethyl cellulose and magnesium stearate.

In another embodiment, the pharmaceutical compositions provided herein comprise Compound A, lactose monohydrate, microcrystalline cellulose, croscarmellose sodium, stearic acid, and magnesium stearate.

In another embodiment, the pharmaceutical compositions provided herein comprise Compound A, lactose monohydrate, microcrystalline cellulose, croscarmellose sodium and magnesium stearate.

In still another embodiment, the pharmaceutical compositions provided herein comprise Compound A, FAST FLO 316®, AVICEL PH 102®, AC-DI-SOL®, stearic acid, and magnesium stearate.

In still another embodiment, the pharmaceutical compositions provided herein comprise Compound A, FAST FLO 316®, AVICEL PH 102®, AC-DI-SOL® and magnesium stearate.

In one embodiment, the pharmaceutical compositions provided herein comprise about 12% by weight of Compound A, from about 80% to about 85% by weight of diluent(s)/binder(s), about 3% by weight of disintegrant(s), and about 1.5% by weight of lubricant(s).

In another embodiment, the pharmaceutical compositions provided herein comprise about 12% by weight of Compound A, about 52.5% by weight of lactose, about 30% by weight of microcrystalline cellulose, about 3% by weight of carboxymethyl cellulose, about 0.5% by weight of stearic acid, and about 1% by weight of magnesium stearate.

In another embodiment, the pharmaceutical compositions provided herein comprise about 12% by weight of Compound A, about 52.5% by weight of lactose, about 30% by weight of microcrystalline cellulose, about 3% by weight of carboxymethyl cellulose and about 1% by weight of magnesium stearate.

In yet another embodiment, the pharmaceutical compositions provided herein comprise about 12% by weight of Compound A, about 52.5% by weight of lactose monohydrate, about 30% by weight of microcrystalline cellulose, about 3% by weight of croscarmellose sodium, about 0.5% by weight of stearic acid, and about 1% by weight of magnesium stearate.

In yet another embodiment, the pharmaceutical compositions provided herein comprise about 12% by weight of Compound A, about 52.5% by weight of lactose monohydrate, about 30% by weight of microcrystalline cellulose, about 3% by weight of croscarmellose sodium and about 1% by weight of magnesium stearate.

In still another embodiment, the pharmaceutical compositions provided herein comprise about 12% by weight of Compound A, about 52.5% by weight of FAST FLO 316®, about 30% by weight of AVICEL PH 102®, about 3% by weight of AC-DI-SOL®, about 0.5% by weight of stearic acid, and about 1% by weight of magnesium stearate.

In still another embodiment, the pharmaceutical compositions provided herein comprise about 12% by weight of Compound A, about 52.5% by weight of FAST FLO 316®, about 30% by weight of AVICEL PH 102®, about 3% by weight of AC-DI-SOL® and about 1% by weight of magnesium stearate.

In one embodiment, the pharmaceutical compositions provided herein comprise about 12% by weight of Compound A, about 80% by weight of diluent(s)/binder(s), about 3% by weight of disintegrant(s), and about 4% by weight of lubricant(s).

In another embodiment, the pharmaceutical compositions provided herein comprise about 12% by weight of Compound A, about 63% by weight of lactose, about 18% by weight of microcrystalline cellulose, about 3% by weight of carboxymethyl cellulose, about 3% by weight of stearic acid, and about 1% by weight of magnesium stearate.

In another embodiment, the pharmaceutical compositions provided herein comprise about 12% by weight of Compound A, about 63% by weight of lactose, about 18% by weight of microcrystalline cellulose, about 3% by weight of carboxymethyl cellulose and about 1% by weight of magnesium stearate.

In yet another embodiment, the pharmaceutical compositions provided herein comprise about 12% by weight of Compound A, about 63% by weight of lactose monohydrate, about 18% by weight of microcrystalline cellulose, about 3% by weight of croscarmellose sodium, about 3% by weight of stearic acid, and about 1% by weight of magnesium stearate.

In yet another embodiment, the pharmaceutical compositions provided herein comprise about 12% by weight of Compound A, about 63% by weight of lactose monohydrate, about 18% by weight of microcrystalline cellulose, about 3% by weight of croscarmellose sodium and about 1% by weight of magnesium stearate.

In still another embodiment, the pharmaceutical compositions provided herein comprise about 12% by weight of Compound A, about 63% by weight of FAST FLO 316®, about 18% by weight of AVICEL PH 102®, about 3% by weight of AC-DI-SOL®, about 3% by weight of stearic acid, and about 1% by weight of magnesium stearate.

In still another embodiment, the pharmaceutical compositions provided herein comprise about 12% by weight of Compound A, about 63% by weight of FAST FLO 316®, about 18% by weight of AVICEL PH 102®, about 3% by weight of AC-DI-SOL® and about 1% by weight of magnesium stearate.

In one embodiment, the pharmaceutical compositions provided herein comprise about 15% by weight of Compound A, about 80% by weight of a diluent/binder, about 3% by weight of a disintegrant, and about 1.5% by weight of lubricants.

In another embodiment, the pharmaceutical compositions provided herein comprise about 15% by weight of Compound A, about 50% by weight of lactose, about 30% by weight of microcrystalline cellulose, about 3% by weight of carboxymethyl cellulose, about 0.5% by weight of stearic acid, and about 1% by weight of magnesium stearate.

In another embodiment, the pharmaceutical compositions provided herein comprise about 15% by weight of Compound A, about 50% by weight of lactose, about 30% by weight of microcrystalline cellulose, about 3% by weight of carboxymethyl cellulose and about 1% by weight of magnesium stearate.

In yet another embodiment, the pharmaceutical compositions provided herein comprise about 15% by weight of Compound A, about 50% by weight of lactose monohydrate, about 30% by weight of microcrystalline cellulose, about 3% by weight of croscarmellose sodium, about 0.5% by weight of stearic acid, and about 1% by weight of magnesium stearate.

In yet another embodiment, the pharmaceutical compositions provided herein comprise about 15% by weight of Compound A, about 50% by weight of lactose monohydrate, about 30% by weight of microcrystalline cellulose, about 3% by weight of croscarmellose sodium and about 1% by weight of magnesium stearate.

In still another embodiment, the pharmaceutical compositions provided herein comprise about 15% by weight of Compound A, about 50% by weight of FAST FLO 316®, about 30% by weight of AVICEL PH 102®, about 3% by weight of AC-DI-SOL®, about 0.5% by weight of stearic acid, and about 1% by weight of magnesium stearate.

In still another embodiment, the pharmaceutical compositions provided herein comprise about 15% by weight of Compound A, about 50% by weight of FAST FLO 316®, about 30% by weight of AVICEL PH 102®, about 3% by weight of AC-DI-SOL® and about 1% by weight of magnesium stearate.

In one embodiment, the pharmaceutical compositions provided herein comprise about 17% by weight of Form A of Compound A, about 80% by weight of dilent(s)/binder(s), about 3% by weight of disintegrant(s), and about 1% by weight of lubricant(s).

In another embodiment, the pharmaceutical compositions provided herein comprise about 17% by weight of Form A of Compound A, about 50% by weight of lactose, about 30% by weight of microcrystalline cellulose, about 3% by weight of carboxymethyl cellulose, and about 1% by weight of magnesium stearate.

In yet another embodiment, the pharmaceutical compositions provided herein comprise about 17% by weight of Form A of Compound A, about 50% by weight of lactose monohydrate, about 30% by weight of microcrystalline cellulose, about 3% by weight of croscarmellose sodium, and about 1% by weight of magnesium stearate.

In still another embodiment, the pharmaceutical compositions provided herein comprise about 17% by weight of Form A of Compound A, about 50% by weight of FAST FLO 316®, about 30% by weight of AVICEL PH 101®, about 3% by weight of AC-DI-SOL®, and about 1% by weight of magnesium stearate.

In one embodiment, the pharmaceutical compositions provided herein comprise about 17% by weight of Form A of Compound A, from about 55% to about 80% by weight of dilent(s)/binder(s), from about 20% to about 30% by weight of disintegrant(s), and about 1% by weight of lubricant(s).

In another embodiment, the pharmaceutical compositions provided herein comprise about 17% by weight of Form A of Compound A, about 55% by weight of lactose, about 25% by weight of starch, about 3% by weight of carboxymethyl cellulose, and about 1% by weight of magnesium stearate.

In yet another embodiment, the pharmaceutical compositions provided herein comprise about 17% by weight of Form A of Compound A, about 55% by weight of lactose monohydrate, about 25% by weight of pregelatinized starch, about 3% by weight of croscarmellose sodium, and about 1% by weight of magnesium stearate.

In still another embodiment, the pharmaceutical compositions provided herein comprise about 17% by weight of Form A of Compound A, about 55% by weight of FAST FLO 316®, about 25% by weight of STARCH 1500®, about 3% by weight of AC-DI-SOL®, and about 1% by weight of magnesium stearate.

In one embodiment, the pharmaceutical compositions provided herein comprise about 17% by weight of Form A of Compound A, about 80% by weight of dilent(s)/binder(s), about 3% by weight of disintegrant(s), and about 1% by weight of lubricant(s).

In another embodiment, the pharmaceutical compositions provided herein comprise about 17% by weight of Form A of Compound A, about 50% by weight of lactose, about 30% by weight of microcrystalline cellulose, about 3% by weight of carboxymethyl cellulose, and about 1% by weight of magnesium stearate.

In yet another embodiment, the pharmaceutical compositions provided herein comprise about 17% by weight of Form A of Compound A, about 50% by weight of lactose monohydrate, about 30% by weight of microcrystalline cellulose, about 3% by weight of croscarmellose sodium, and about 1% by weight of magnesium stearate.

In still another embodiment, the pharmaceutical compositions provided herein comprise about 17% by weight of Form A of Compound A, about 50% by weight of FAST FLO 316®, about 30% by weight of AVICEL PH 102®, about 3% by weight of AC-DI-SOL®, and about 1% by weight of magnesium stearate.

In one embodiment, the pharmaceutical compositions provided herein comprise about 17% by weight of Form A of Compound A, from about 85% to about 90% by weight of dilent(s)/binder(s), from about 3% to about 9% by weight of disintegrant(s), and from about 1% to about 6% by weight of lubricants.

In another embodiment, the pharmaceutical compositions provided herein comprise about 17% by weight of Form A of Compound A, about 45% by weight of lactose, about 30% by weight of microcrystalline cellulose, about 3% by weight of corn starch, about 3% by weight of carboxymethyl cellulose, and about 1% by weight of magnesium stearate.

In yet another embodiment, the pharmaceutical compositions provided herein comprise about 17% by weight of Form A of Compound A, about 88% by weight of lactose, about 25% by weight of microcrystalline cellulose, about 4% by weight of corn starch, about 4% by weight of carboxymethyl cellulose, and about 1.5% by weight of magnesium stearate.

In yet another embodiment, the pharmaceutical compositions provided herein comprise about 17% by weight of Form A of Compound A, about 45% by weight of lactose monohydrate, about 30% by weight of microcrystalline cellulose, about 3% by weight of corn starch, about 3% by weight of croscarmellose sodium, and about 1% by weight of magnesium stearate.

In yet another embodiment, the pharmaceutical compositions provided herein comprise about 17% by weight of Form A of Compound A, about 88% by weight of lactose monohydrate, about 25% by weight of microcrystalline cellulose, about 4% by weight of corn starch, about 4% by weight of croscarmellose sodium, and about 1.5% by weight of magnesium stearate.

In yet another embodiment, the pharmaceutical compositions provided herein comprise about 17% by weight of Form A of Compound A, about 45% by weight of FAST FLO 316®, about 30% by weight of AVICEL PH 102®, about 3% by weight of corn starch, about 3% by weight of AC-DI-SOL®, and about 1% by weight of magnesium stearate.

In still another embodiment, the pharmaceutical compositions provided herein comprise about 17% by weight of Form A of Compound A, about 88% by weight of FAST FLO 316®, about 25% by weight of AVICEL PH 102®, about 4% by weight of corn starch, about 4% by weight of AC-DI-SOL®, and about 1.5% by weight of magnesium stearate.

In certain embodiments, provided herein are pharmaceutical compositions comprising Compound A and stearic acid. In certain embodiments, stearic acid is present in an amount of about 0.1-5%, 0.1 to 1%, or 0.4% by weight. Without being limited by theory, it was found that the addition of stearic acid improved lubrication (reduced sticking) without impacting disintegration and compressability.

In certain embodiments, provided herein are pharmaceutical compositions comprising Compound A and lactose monohydrate. In certain embodiments, lactose monohydrate is present in an amount of about 40-60%, 45-55%, 49.2% or 49.6% by weight. Without being limited by theory, it was found that lactose monohydrate provided better flowability than lactose anhydrous.

In certain embodiments, provided herein are pharmaceutical compositions comprising Compound A and AVICEL PH 102®. In certain embodiments, AVICEL PH 102® is present in an amount of about 20-40%, 25-35%, or 31% by weight. Without being limited by theory, it was found that AVICEL PH 102® provided better flowability than AVICEL PH 101®.

In certain embodiments, provided herein are pharmaceutical compositions comprising Compound A and AVICEL PH 112®. In certain embodiments, AVICEL PH 112® is present in an amount of about 20-40%, about 25-35%, or about 31% by weight. It was unexpectedly found that Compound A is susceptible to hydrolysis. Without being limited by theory, it is thought that AVICEL PH 112®, being a low-moisture grade microcrystalline cellulose, can reduce hydrolysis of Compound A.

In certain embodiments, provided herein are pharmaceutical compositions comprising Compound A, stearic acid, lactose monohydrate and AVICEL PH 102®. In certain embodiments, provided herein are pharmaceutical compositions comprising Compound A, stearic acid (in an amount of about 0.1-5%, 0.1 to 1%, or 0.4% by weight), lactose monohydrate (in an amount of about 40-60%, 45-55%, or 49.2% by weight) and AVICEL PH 102® (in an amount of about 20-40%, 25-35%, or 31% by weight).

In certain embodiments, provided herein are pharmaceutical compositions comprising Compound A, lactose monohydrate and AVICEL PH 102®. In certain embodiments, provided herein are pharmaceutical compositions comprising Compound A, lactose monohydrate (in an amount of about 40-60%, 45-55%, or 49.2% by weight) and AVICEL PH 102® (in an amount of about 20-40%, 25-35%, or 31% by weight).

In certain embodiments, provided herein are pharmaceutical compositions comprising an opaque coating. Without being limited by theory, it was found that a more opaque coating protected the drug product from degradation. In some embodiments, the pharmaceutical composition is formulated as a tablet. In some such embodiments, the tablet is film coated. In some embodiments, the tablet is film coated to a weight gain of 1-8%. In others, the film coating is about 4% by weight of the tablet.

In certain embodiments, provided herein are pharmaceutical compositions comprising Compound A that do not comprise stearic acid. Without being limited by theory, a lack of picking or sticking of certain tablet formulations by visual observation indicated that acceptable tablet formulations could be produced without the use of stearic acid.

In certain embodiments, provided herein are pharmaceutical compositions as set forth in Table 6-Table 14, Table 17-Table 19, Table 26-Table 28 and Table 31-Table 34, wherein the amounts of the recited components can independently be varied by 1%, 2%, 3%, 4%, 5%, 6%, 7%, 8%, 9%, 10%, 15%, 20% or 25%.

In certain embodiments, provided herein are liquid formulations comprising Compound A, an alcohol and polyethylene glycol. In certain embodiments, the alcohol and polyethylene glycol are present in a ratio of about 80:20 to about 20:80. In certain embodiments, the alcohol and polyethylene glycol are present in a ratio of about 50:50. In certain embodiments, the alcohol is ethanol. In certain embodiments, the polyethylene glycol is PEG 400. In one embodiment, provided herein are capsules filled with a liquid formulation comprising Compound A, an alcohol and polyethylene glycol. In one embodiment, Compound A is an isotopologue of 7-(6-(2-hydroxypropan-2-yl)pyridin-3-yl)-1-((trans)-4-methoxycyclohexyl)-3,4-dihydropyrazino[2,3-b]pyrazin-2(1H)-one. In some embodiments, the isotopologue is enriched in $^{14}C$.

The pharmaceutical compositions provided herein can be provided in a unit-dosage form or multiple-dosage form. A unit-dosage form, as used herein, refers to physically discrete unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an individually packaged tablet or capsule. A unit-dosage form may be administered in fractions or multiples thereof. A multiple-dosage form is a plurality of identical unit-dosage forms packaged in a single container to be administered in segregated unit-dosage form. In certain embodiments, the unit dosage forms provided herein comprise about 1 mg to about 100 mg of Compound A. In other embodiments, the unit dosage forms provided herein comprise about 5 mg to about 50 mg of Compound A. In other embodiments, the unit dosage forms provided herein comprise about 1 mg, about 5 mg, about 20 mg, about 45 mg, about 50 mg, about 75 mg or about 100 mg of Compound A. In other embodiments, the unit dosage forms provided herein comprise about 5 mg, about 15 mg, about 20 mg, about 30 mg, about 45 mg, and about 50 mg of Compound A.

In certain embodiments, provided herein are methods for preparing a composition provided herein, comprising: (i) weighing out the desired amount of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form (such as Form A, Form B, Form C, Form D, or Form E) thereof and the desired amount of excipients (such as lactose monohydrate, croscarmellose sodium and microcrystalline cellulose); (ii) mixing or blending 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof and the excipients; (iii) passing the mixture of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, or a pharmaceutically acceptable salt, isotopologue, metabolite or solid form thereof and excipients through a screen (such as an 18 mesh or 1000 m screen); (iv) mixing or blending 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof and the excipients after passage through the screen; (v) weighing out the desired amount of lubricating agents (such as stearic acid and/or magnesium stearate); (vi) passing the lubricating agents through a screen (such as a 30 mesh or 600 μm screen); (vii) mixing or blending 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents; (viii) compressing the mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents (such as into a tablet form); and (ix) coating the compressed mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents with a coating agent (such as Opadry pink, yellow or beige).

In certain embodiments, provided herein are methods for preparing a composition provided herein, comprising: (i) weighing out the desired amount of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form (such as Form A, Form B, Form C, Form D, or Form E) thereof and the desired amount of excipients (such as lactose monohydrate, croscarmellose sodium and microcrystalline cellulose); (ii) mixing or blending 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof and the excipients; (iii) passing the mixture of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, or a pharmaceutically acceptable salt, isotopologue, metabolite or solid form thereof and excipients through a screen (such as an 18 mesh or 1000 μm screen); (iv) mixing or blending 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof and the excipients after passage through the screen; (v) weighing out the desired amount of lubricating agents (such as stearic acid and/or magnesium stearate); (vi) passing the lubricating agents through a screen (such as a 60 mesh or 250 μm screen); (vii) mixing or blending 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents; (viii) compressing the mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents (such as into a tablet form); and (ix) coating the compressed mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents with a coating agent (such as Opadry pink, yellow or beige).

In certain embodiments, provided herein are methods for preparing a composition provided herein, comprising: (i) weighing out the desired amount of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, or a pharmaceutically acceptable salt, isotopologue, metabolite or solid form thereof and the desired amount of excipients (such as lactose monohydrate, croscarmellose sodium and microcrystalline cellulose); (ii) passing the excipients through a screen (such as an 18 mesh or 1000 μm screen); (iii) mixing or blending (such as at 26 revolutions per minute for 20 minutes) 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form (such as Form A, Form B, Form C, Form D, or Form E) thereof and the excipients; (iv) passing the mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof and excipients through a screen (such as an 18 mesh or 1000 μm screen); (v) mixing or blending (such as at 26 revolutions per minute for 10 minutes) 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof and the excipients; (vi) weighing out the desired amount of lubricating agents (such as stearic acid and/or magnesium stearate); (vii) passing the lubricating agents through a screen (such as a 30 mesh or 600 μm screen); (viii) mixing or blending (such as at 26 revolutions per minute for 3 minutes) 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents; (ix) compressing the mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents (such as into a tablet form); and (x) coating the compressed mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents with a coating agent (such as Opadry pink, yellow or beige).

In certain embodiments, provided herein are methods for preparing a composition provided herein, comprising: (i) weighing out the desired amount of 7-(6-(2-hydroxypropan-2-yl)pyridin-3-yl)-1-((trans)-4-methoxycyclohexyl)-3,4-dihydro-pyrazino[2,3-b]pyrazin-2(1H)-one, or a pharmaceutically acceptable salt, isotopologue, metabolite or solid form thereof and the desired amount of excipients (such as lactose monohydrate, croscarmellose sodium and microcrystalline cellulose); (ii) passing the excipients through a screen (such as an 18 mesh or 1000 μm screen); (iii) mixing or blending (such as at 26 revolutions per minute for 20 minutes) 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form (such as Form A, Form B, Form C, Form D, or Form E) thereof and the excipients; (iv) passing the mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof and excipients through a screen (such as an 18 mesh or 1000 μm screen); (v) mixing or blending (such as at 26 revolutions per minute for 10 minutes) 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof and the excipients; (vi) weighing out the desired amount of lubricating agents (such as stearic acid and/or magnesium stearate); (vii) passing the lubricating agents through a screen (such as a 60 mesh or 250 μm screen); (viii) mixing or blending (such as at 26 revolutions per minute for 3 minutes) 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents; (ix) compressing the mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents (such as into a tablet form); and (x) coating the compressed mixture of 7-(6-(2-hydroxypropan-2-yl)pyridin-3-yl)-1-((trans)-4-methoxycyclohexyl)-3,4-dihydropyrazino[2,3-b]pyrazin-2(1H)-one, or a pharmaceutically acceptable salt, isotopologue, metabolite or solid form thereof, the excipients and the lubricating agents with a coating agent (such as Opadry pink, yellow or beige).

In certain embodiments, the pharmaceutical compositions provided herein comprise Form A of Compound A, including substantially pure Form A.

In certain embodiments, the pharmaceutical compositions provided herein comprise Form B of Compound A, including substantially pure Form B.

In certain embodiments, the pharmaceutical compositions provided herein comprise Form C of Compound A, including substantially pure Form C.

In certain embodiments, the pharmaceutical compositions provided herein comprise Form D of Compound A, including substantially pure Form D.

In certain embodiments, the pharmaceutical compositions provided herein comprise Form E of Compound A, including substantially pure Form E.

Further provided herein are kits comprising a pharmaceutical composition of Compound A provided herein. In particular embodiments, provided herein are kits comprising a unit dosage form of Compound A provided herein. In certain embodiments of the kits provided herein, Compound A is provided as Form A. In certain embodiments of the kits provided herein, Compound A is provided as Form B. In certain embodiments of the kits provided herein, Compound A is provided as Form C. In certain embodiments of the kits provided herein, Compound A is provided as Form D. In certain embodiments of the kits provided herein, Compound A is provided as Form E. In certain embodiments of the kits provided herein, Compound A is provided as a pinacol co-crystal. In certain embodiments of the kits provided herein, Compound A is provided as an amorphous form. In some embodiments, of the kits provided herein Compound A is provided as an isotopologue of 7-(6-(2-hydroxypropan-2-yl)pyridin-3-yl)-1-((trans)-4-methoxycyclohexyl)-3,4-dihydropyrazino[2,3-b]pyrazin-2(1H)-one. In some such embodiments, the isotopologue is enriched in is enriched in $^{13}C$, $^{14}C$, $^{2}H$, $^{3}H$ and/or $^{15}N$.

5.5 Methods of Use

The solid forms of Compound A (e.g., Form A, Form B, Form C, Form D, Form E or amorphous), isotopologues of Compound A, metabolites of Compound A (e.g, O-desmethyl Compound A) and the pharmaceutical compositions provided herein have utility as pharmaceuticals to treat or prevent a disease in a subject, e.g., a proliferative disease. Further, the solid forms of Compound A (e.g., Form A, Form B, Form C, Form D, Form E or amorphous), isotopologues of Compound A, metabolites of Compound A (e.g, O-desmethyl Compound A) and the pharmaceutical compositions provided herein provided herein are active against kinases (e.g., protein kinases), including those involved in cancer, inflammatory conditions, immunological conditions, neurodegenerative diseases, diabetes, obesity, neurological disorders, age-related diseases, and/or cardiovascular conditions. Without being limited by theory, it is thought the solid forms of Compound A (e.g., Form A, Form B, Form C, Form D, Form E or amorphous), isotopologues of Compound A, metabolites of Compound A (e.g, O-desmethyl Compound A) and the pharmaceutical compositions provided herein are effective for treating and preventing diseases and conditions due to its ability to modulate (e.g., inhibit) kinases that are involved in the etiology of the diseases and conditions. Accordingly, provided herein are uses of the solid forms of Compound A (e.g., Form A, Form B, Form C, Form D, Form E or amorphous), isotopologues of Compound A, metabolites of Compound A (e.g, O-desmethyl Compound A) and the pharmaceutical compositions provided herein, including the treatment or prevention of those diseases set forth herein. In certain embodiments, the methods provided herein comprise administering a solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, wherein the solid form of Compound A (e.g., Form A, Form B, Form C, Form D, Form E or amorphous), isotopologue of Compound A, metabolite of Compound A (e.g, O-desmethyl Compound A) or the pharmaceutical composition provided herein is part of a kit provided herein.

In one embodiment, provided herein is a method of treating and preventing a disease or condition in a subject, comprising the administration of an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein to the subject.

Representative immunological conditions that the solid forms of Compound A (e.g., Form A, Form B, Form C, Form D, Form E or amorphous), isotopologues of Compound A, metabolites of Compound A (e.g, O-desmethyl Compound A) and the pharmaceutical compositions provided herein are useful for treating or preventing include, but are not limited to, rheumatoid arthritis, rheumatoid spondylitis, osteoarthritis, multiple sclerosis, lupus, inflammatory bowel disease, ulcerative colitis, Crohn's disease, myasthenia gravis, Graves disease, encephalomyelitis, Type II diabetes, dermatomyositis, and transplant rejection (e.g., in the treatment of recipients of heart, lung, combined heart-lung, liver, kidney, pancreatic, skin, or corneal transplants; or graft-versus-host disease, such as following bone marrow transplantation).

Representative inflammatory conditions that the solid forms of Compound A (e.g., Form A, Form B, Form C, Form D, Form E or amorphous), isotopologues of Compound A, metabolites of Compound A (e.g, O-desmethyl Compound A) and the pharmaceutical compositions provided herein are useful for treating or preventing include, but are not limited to, psoriasis, asthma and allergic rhinitis, bronchitis, chronic obstructive pulmonary disease, cystic fibrosis, inflammatory bowel disease, irritable bowel syndrome, Crohn's disease, mucous colitis, ulcerative colitis, and obesity.

Representative cardiovascular diseases that the solids form of Compound A (e.g., Form A, Form B, Form C, Form D, Form E or amorphous), isotopologues of Compound A, metabolites of Compound A (e.g, O-desmethyl Compound A) and the pharmaceutical compositions provided herein are useful for treating or preventing include, but are not limited to, restenosis, Wolf-Parkinson-White Syndrome, stroke, myocardial infarction or ischemic damage to the heart, lung, gut, kidney, liver, pancreas, spleen or brain.

Representative neurodegenerative diseases that the solid forms of Compound A (e.g., Form A, Form B, Form C, Form D, Form E or amorphous), isotopologues of Compound A, metabolites of Compound A (e.g, O-desmethyl Compound A) and the pharmaceutical compositions provided herein are useful for treating or preventing include, but are not limited to, Huntington's disease, Alzheimer's disease, Parkinson's disease, dementias caused by tau mutations, spinocerebellar ataxia type 3, motor neuron disease caused by SODI mutations, neuronal ceroid lipofucinoses/Batten disease (pediatric neurodegene ration) and HIV-associated encephalitis.

Representative age-related diseases that the solid forms of Compound A (e.g., Form A, Form B, Form C, Form D, Form E or amorphous), isotopologues of Compound A, metabolites of Compound A (e.g, O-desmethyl Compound A) and the pharmaceutical compositions provided herein are useful for treating or preventing include, but are not limited to, cancer, obesity, type II diabetes mellitus, autoimmune disease, cardiovascular diseases and neuronal degeneration.

In certain embodiments, the disease or condition is a fibrotic disease or disorder. Thus, in one embodiment, provided herein is a method for treating or preventing a fibrotic disease or disorder in a subject, comprising the administration of an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein to the subject. In another embodiment, provided herein is a method of treating or preventing scleroderma, idiopathic pulmonary fibrosis, renal fibrosis, cystic fibrosis, myelofibrosis, hepatic fibrosis, steatofibrosis or steatohepatitis in a subject, comprising the administration of an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein to the subject.

Representative cancers that the solid forms of Compound A (e.g., Form A, Form B, Form C, Form D, Form E or amorphous), isotopologues of Compound A, metabolites of Compound A (e.g, O-desmethyl Compound A) and the pharmaceutical compositions provided herein are useful for treating or preventing include, but are not limited to, cancers of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system. The solid forms of Compound A (e.g., Form A, Form B, Form C, Form D, Form E or amorphous), isotopologues of Compound A, metabolites of Compound A (e.g, O-desmethyl Compound A) and the pharmaceutical compositions provided herein are also useful for treating or preventing solid tumors and bloodborne tumors.

In some embodiments, the cancers within the scope of the methods provided herein include those associated with the pathways involving mTOR, PI3K, or Akt kinases and mutants or isoforms thereof. In some embodiments, the cancers within the scope of the methods provided herein include those associated with the pathways of the following kinases: PI3Kα, PI3Kβ, PI3Kδ, KDR, GSK3α, GSK3δ, ATM, ATX, ATR, cFMS, and/or DNA-PK kinases and mutants or isoforms thereof. In some embodiments, the cancers associated with mTOR/PI3K/Akt pathways include solid and blood-borne tumors, for example, multiple myeloma, mantle cell lymphoma, diffused large B-cell lymphoma, acute myeloid lymphoma, follicular lymphoma, chronic lymphocytic leukemia; breast, lung, endometrial, ovarian, gastric, cervical, and prostate cancer; glioblastoma; renal carcinoma; hepatocellular carcinoma; colon carcinoma; neuroendocrine tumors; head and neck tumors; and sarcomas.

In one embodiment, provided herein is a method for treating or preventing a disease or disorder associated with activation of mTOR signaling, comprising the administration of an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein to a subject in need thereof. Examples of diseases or disorders associated with activation of mTOR signaling include, but are not limited to, tumor syndromes resulting directly or indirectly from genetic defects in PTEN (Phosphatase and tensin homologue deleted on chromosome 10), TSC1 (Tuberous sclerosis 1), TSC2 (Tuberous sclerosis 2), NF1 (Neurofibromin 1), AMPK (AMP-dependent protein kinase STK11, serine/threonine kinase 11), LKB1, VHL (von Hippel-Lindau disease) and PKD1 (polycystin-1). Without being limited by theory, it is thought that genetic defects associated with these proteins results in hyperactivation of the mTOR/PI3K/Akt pathway. In certain embodiments, the diseases which are treatable or preventable through inhibition of the mTOR/PI3K/Akt pathway include, but are not limited to, Cowden's disease, Cowden syndrome, Cowden-like syndrome, Bannayan-Zonana syndrome, Bannayan-Riley-Ruvalcaba syndrome, Lhermitte-Duclos disease, endometrial carcinoma, tuberous sclerosis complex, lymphangioleiomyomatosis, neurofibromatosis 1, Peutz-Jeghers syndrome, renal cell carcinoma, von Hippel-Lindau disease, Proteus syndrome, and polycystic kidney disease.

In another embodiment, provided herein is a method for treating or preventing a disease or disorder associated with mTOR, PI3K, Akt, and/or DNA-PK signaling, comprising the administration of an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided hereinto a subject in need thereof. Examples of diseases which are treatable or preventable by inhibiting mTOR, PI3K, Akt and/or DNA-PK signaling, include, but are not limited to, rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nephritis; multiple sclerosis; lupus erythematosus; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases (including retinitis pigmentosa), solid tumors, and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

In yet another embodiment, provided herein is a method of inhibiting a kinase in a cell expressing the kinase, comprising contacting the cell with an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein provided herein. In one embodiment, the kinase is TOR kinase. In certain embodiments, the cell is in a subject. In certain embodiments, the cell is from a subject.

In yet another embodiment, provided herein is a method of treating or preventing a condition treatable or preventable by the inhibition of a kinase pathway, in one embodiment, the mTOR/PI3K/Akt and/or DNA-PK pathway, comprising administering to a subject in need thereof an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein. Conditions treatable or preventable by the inhibition of the mTOR/PI3K/Akt pathway include, but are not limited to, solid and blood-borne tumors, for example, multiple myeloma, mantle cell lymphoma, diffused large B-cell lymphoma, acute myeloid lymphoma, follicular lymphoma, chronic lymphocytic leukemia; breast, lung, endometrial, ovarian, gastric, cervical, and prostate cancer; glioblastoma; renal carcinoma; hepatocellular carcinoma; colon carcinoma; neuroendocrine tumors; head and neck tumors; sarcomas; tumor syndromes resulting directly or indirectly from genetic defects in PTEN (Phosphatase and tensin homologue deleted on chromosome 10), TSC1 (Tuberous sclerosis 1), TSC2 (Tuberous sclerosis 2), NF1 (Neurofibromin 1), AMPK (AMP-dependent protein kinase STK11, serine/threonine kinase 11), and LKB1, VHL (von Hippel-Lindau disease) and PKD1 (polycystin-1); Cowden's disease, Cowden syndrome, Cowden-like syndrome, Bannayan-Zonana syndrome, Bannayan-Riley-Ruvalcaba syndrome, Lhermitte-Duclos disease, endometrial carcinoma, tuberous sclerosis complex, lymphangioleiomyomatosis, neurofibromatosis 1, Peutz-Jeghers syndrome, renal cell carcinoma, von Hippel-Lindau disease, Proteus syndrome, and polycystic kidney disease; rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nephritis; multiple sclerosis; lupus erythematosus; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases, including retinitis pigmentosa, solid tumors, and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

Provided herein are methods for treating or preventing a solid tumor, non-Hodgkin lymphoma or multiple myeloma, comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having a solid tumor, non-Hodgkin lymphoma or multiple myeloma. In one embodiment, the solid tumor, non-Hodgkin lymphoma or multiple myeloma, is rapamycin resistant.

In one embodiment, the non-Hodgkin lymphoma is diffuse large B-cell lymphoma (DLBCL), follicular lymphoma (FL), acute myeloid leukemia (AML), mantle cell lymphoma (MCL), or ALK+ anaplastic large cell lymphoma. In one embodiment, the non-Hodgkin lymphoma is advanced solid non-Hodgkin lymphoma.

In one embodiment, the solid tumor is a neuroendocrine tumor. In certain embodiments, the neuroendocrine tumor is a neuroendocrine tumor of gut origin. In certain embodiments, the neuroendocrine tumor is of non-pancreatic origin. In certain embodiments, the neuroendocrine tumor is non-pancreatic of gut origin. In certain embodiments, the neuroendocrine tumor is of unknown primary origin. In some embodiments, the neuroendocrine tumor is of non-gut origin, for example a bronchial neuroendocrine tumor, or a neuroendocrine tumor with origin in an organ above the diaphragm, for example, a laryngeal neuroendocrine tumor, a pharyngeal neuroendocrine tumor, or a thyroid neuroendocrine tumor. In certain embodiments, the neuroendocrine tumor is a symptomatic endocrine producing tumor or a nonfunctional tumor. In certain embodiments, the neuroendocrine tumor is locally unresectable, metastatic moderate, well differentiated, low (grade 1) or intermediate (grade 2).

In one embodiment, the solid tumor is non-small cell lung cancer (NSCLC).

In another embodiments the solid tumor is glioblastoma multiforme (GBM).

In another embodiment, the solid tumor is hepatocellular carcinoma (HCC).

In another embodiment, the solid tumor is breast cancer. In one embodiment, the breast cancer is estrogen receptor positive (ER+, ER+/Her2− or ER+/Her2+). In one embodiment, the breast cancer is estrogen receptor negative (ER−/Her2+). In one embodiment, the breast cancer is triple negative (TN) (breast cancer that does not express the genes and/or protein corresponding to the estrogen receptor (ER), progesterone receptor (PR), and that does not overexpress the Her2/neu protein).

In another embodiment, the solid tumor is colorectal cancer.

In another embodiment, the solid tumor is salivary cancer.

In another embodiment, the solid tumor is pancreatic cancer.

In another embodiment, the solid tumor is adenocystic cancer.

In another embodiment, the solid tumor is adrenal cancer.

In another embodiment, the solid tumor is esophageal cancer.

In another embodiment, the solid tumor is renal cancer.

In another embodiment, the solid tumor is leiomyosarcoma.

In another embodiment, the solid tumor is paraganglioma.

In one embodiment, the solid tumor is an advanced solid tumor.

In one embodiment, the advanced solid tumor is a neuroendocrine tumor. In certain embodiments, the neuroendocrine tumor is a neuroendocrine tumor of gut origin. In certain embodiments, the neuroendocrine tumor is of non-pancreatic origin. In certain embodiments, the neuroendocrine tumor is non-pancreatic of gut origin. In certain embodiments, the neuroendocrine tumor is of unknown primary origin. In some embodiments, the neuroendocrine tumor is of non-gut origin, for example a bronchial neuroendocrine tumor, or a neuroendocrine tumor with origin in an organ above the diaphragm, for example, a laryngeal neuroendocrine tumor, a pharyngeal neuroendocrine tumor, or a thyroid neuroendocrine tumor. In certain embodiments, the neuroendocrine tumor is a symptomatic endocrine producing tumor or a nonfunctional tumor. In certain embodiments, the neuroendocrine tumor is locally unresectable, metastatic moderate, well differentiated, low (grade 1) or intermediate (grade 2).

In one embodiment, the advanced solid tumor is non-small cell lung cancer (NSCLC).

In another embodiments the advanced solid tumor is glioblastoma multiforme (GBM).

In another embodiment, the advanced solid tumor is hepatocellular carcinoma (HCC).

In another embodiment, the advanced solid tumor is breast cancer. In one embodiment, the advanced solid tumor is estrogen receptor positive (ER+, ER+/Her2− or ER+/Her2+) breast cancer. In one embodiment, the advanced solid tumor is ER+/Her2− breast cancer. In one embodiment, the advanced solid tumor is ER+/Her2+ breast cancer. In one embodiment, the advanced solid tumor is ER−/Her2+ breast cancer. In one embodiment, the advanced solid tumor is triple negative (TN) breast cancer.

In another embodiment, the advanced solid tumor is colorectal cancer.

In another embodiment, the advanced solid tumor is salivary cancer.

In another embodiment, the advanced solid tumor is pancreatic cancer.

In another embodiment, the advanced solid tumor is adenocystic cancer.

In another embodiment, the advanced solid tumor is adrenal cancer.

In another embodiment, the advanced solid tumor is esophageal cancer.

In another embodiment, the advanced solid tumor is renal cancer.

In another embodiment, the advanced solid tumor is leiomyosarcoma.

In another embodiment, the advanced solid tumor is or paraganglioma.

In one embodiment, the non-Hodgkin lymphoma is diffuse large B-cell lymphoma (DLBCL).

In one embodiment, provided herein are methods for achieving a Response Evaluation Criteria in Solid Tumors (RECIST 1.1) (see Eisenhauer E. A., Therasse P., Bogaerts J., et al. New response evaluation criteria in solid tumours: Revised RECIST guideline (version 1.1). European J. Cancer; 2009; (45) 228-247) of complete response, partial response or stable disease in a patient comprising administering an effective amount of the solid form of Compound A (e.g., Form A, Form B, Form C, Form D, or Form E) or a pharmaceutical composition comprising the solid form of Compound A (e.g., Form A, Form B, Form C, Form D, or Form E) provided herein, to a subject having a solid tumor, such as an advanced solid tumor.

In one embodiment, provided herein are methods for preventing or delaying a Response Evaluation Criteria in Solid Tumors (RECIST 1.1) of progressive disease in a subject, comprising administering an effective amount of the solid form of Compound A (e.g., Form A, Form B, Form C, Form D, Form E or amorphous) or a pharmaceutical composition comprising the solid form of Compound A (e.g., Form A, Form B, Form C, Form D, Form E or amorphous) provided herein, to a subject having a solid tumor, such as an advanced solid tumor. In one embodiment the prevention or delaying of progressive disease is characterized or achieved by a change in overall size of the target lesions, of for example, between −30% and +20% compared to pre-treatment. In another embodiment, the change in size of the target lesions is a reduction in overall size of more than 30%, for example, more than 50% reduction in target lesion size compared to pre-treatment. In another, the prevention is characterized or achieved by a reduction in size or a delay in progression of non-target lesions compared to pre-treatment. In one embodiment, the prevention is achieved or characterized by a reduction in the number of target lesions compared to pre-treatment. In another, the prevention is achieved or characterized by a reduction in the number or quality of non-target lesions compared to pre-treatment. In one embodiment, the prevention is achieved or characterized by the absence or the disappearance of target lesions compared to pre-treatment. In another, the prevention is achieved or characterized by the absence or the disappearance of non-target lesions compared to pre-treatment. In another embodiment, the prevention is achieved or characterized by the prevention of new lesions compared to pre-treatment. In yet another embodiment, the prevention is achieved or characterized by the prevention of clinical signs or symptoms of disease progression compared to pre-treatment, such as cancer-related cachexia or increased pain.

In certain embodiments, provided herein are methods for decreasing the size of target lesions in a subject compared to pre-treatment, comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having a solid tumor, such as an advanced solid tumor.

In certain embodiments, provided herein are methods for decreasing the size of a non-target lesion in a subject compared to pre-treatment, comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having a solid tumor, such as an advanced solid tumor.

In certain embodiments, provided herein are methods for achieving a reduction in the number of target lesions in a subject compared to pre-treatment, comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having a solid tumor, such as an advanced solid tumor.

In certain embodiments, provided herein are methods for achieving a reduction in the number of non-target lesions in a subject compared to pre-treatment, comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having a solid tumor, such as an advanced solid tumor.

In certain embodiments, provided herein are methods for achieving an absence of all target lesions in a subject, comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having a solid tumor, such as an advanced solid tumor.

In certain embodiments, provided herein are methods for achieving an absence of all non-target lesions in a subject, comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having a solid tumor, such as an advanced solid tumor.

A method of treating a solid tumor, such as an advanced solid tumor, the method comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having a solid tumor, such as an advanced solid tumor, wherein the treatment results in a complete response, partial response or stable disease, as determined by Response Evaluation Criteria in Solid Tumors (RECIST 1.1).

A method of treating a solid tumor, such as an advanced solid tumor, the method comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having a solid tumor, such as an advanced solid tumor, wherein the treatment results in a reduction in target lesion size, a reduction in non-target lesion size and/or the absence of new target and/or non-target lesions, compared to pre-treatment.

A method of treating a solid tumor, such as an advanced solid tumor, the method comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having a solid tumor, such as an advanced solid tumor, wherein the treatment results in prevention or retarding of clinical progression, such as cancer-related cachexia or increased pain.

In another embodiment, provided herein are methods for improving the International Workshop Criteria (IWC) for NHL (see Cheson B D, Pfistner B, Juweid, M E, et. al. Revised Response Criteria for Malignant Lymphoma. J. Clin. Oncol: 2007: (25) 579-586.) of a subject comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having non-Hodgkin lymphoma. In another embodiment, provided herein are methods to increase Progression Free Survival rates, as determined by Kaplan-Meier estimates. In one embodiment, the treatment results in a complete remission, partial remission or stable disease, as determined by the International Workshop Criteria (IWC) for NHL. In another embodiment, the treatment results in an increase in overall survival, progression-free survival, event-free survival, time to progression, disease-free survival or lymphoma-free survival.

In another embodiment, provided herein are methods for inducing a therapeutic response characterized with the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7) of a subject comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having multiple myeloma. In one embodiment, the treatment results in a stringent complete response, complete response, or very good partial response, as determined by the the International Uniform Response Criteria for Multiple Myeloma (IURC). In another embodiment, the treatment results in an increase in overall survival, progression-free survival, event-free survival, time to progression, or disease-free survival.

In another embodiment, provided herein are methods for inducing a therapeutic response assessed with Response Assessment for Neuro-Oncology (RANO) Working Group for GBM (see Wen P., Macdonald, D R., Reardon, D A., et al. Updated response assessment criteria for highgrade gliomas: Response assessment in neuro-oncology working group. J. Clin. Oncol. 2010; 28: 1963-1972) of a subject comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having gliobastoma multiforme.

In another embodiment, provided herein are methods for improving the Eastern Cooperative Oncology Group Performance Status (ECOG) of a subject comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having a tumor, such as an advanced solid tumor.

In another embodiment, provided herein are methods for inducing a therapeutic response assessed by Positron Emission Tomography (PET) outcome of a subject comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein, to a subject having a tumor, such as an advanced solid tumor. In certain embodiments, provided herein are methods for treating a solid tumor, such as an advanced solid tumor, the methods comprising administering an effective amount of a TOR kinase inhibitor to a patient having a solid tumor, such as an advanced solid tumor, wherein the treatment results in a reduction in tumor metabolic activity, for example, as measured by PET imaging.

In another embodiment, provided herein are methods for inducing a therapeutic response assessed by a reduction in carcinoid syndrome-related symptoms, such as diarrhea and/or flushing, and/or a reduction in endocrine hormone markers, such as chromogranin, gastrin, serotonin, and/or glucagon.

In one embodiment, provided herein are methods for inhibiting phosphorylation of S6RP, 4E-BP1 and/or AKT in a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein to said subject. In some such embodiments, the inhibition of phosphorylation is assessed in a biological sample of the subject, such as in circulating blood and/or tumor cells, skin biopsies and/or tumor biopsies or aspirate. In such embodiments, the amount of inhibition of phosphorylation is assessed by comparison of the amount of phospho-S6RP, 4E-BP1 and/or AKT before and after administration of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein. In certain embodiments, provided herein are methods for measuring inhibition of phosphorylation of S6RP, 4E-BP1 or AKT in a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein to said subject, measuring the amount of phosphorylated S6RP, 4E-BP1 and/or AKT in said subject, and comparing said amount of phosphorylated S6RP, 4E-BP1 and/or AKT to that of said subject prior to administration of an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein. In some embodiments, the inhibition of phosphorylation of S6RP, 4E-BP1 and/or AKT is assessed in B-cells, T-cells and/or monocytes.

In certain embodiments, provided herein are methods for inhibiting phosphorylation of S6RP, 4E-BP1 and/or AKT in a biological sample of a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein to said subject and comparing the amount of phosphorylated S6RP, 4E-BP1 and/or AKT in a biological sample of a subject obtained prior to and after administration of said solid form of Compound A (e.g., Form A, Form B, Form C, Form D, Form E or amorphous), isotopologue of Compound A, metabolite of Compound A (e.g, O-desmethyl Compound A) or pharmaceutical composition provided herein, wherein less phosphorylated S6RP, 4E-BP1 and/or AKT in said biological sample obtained after administration of said solid form of Compound A (e.g., Form A, Form B, Form C, Form D, Form E or amorphous), isotopologue of Compound A, metabolite of Compound A (e.g, O-desmethyl Compound A) or a pharmaceutical composition provided herein relative to the amount of phosphorylated S6RP, 4E-BP1 and/or AKT in said biological sample obtained prior to administration of said solid form of Compound A (e.g., Form A, Form B, Form C, Form D, Form E or amorphous), isotopologue of Compound A, metabolite of Compound A (e.g, O-desmethyl Compound A) or pharmaceutical composition provided herein indicates inhibition. In some embodiments, the inhibition of phosphorylation of S6RP, 4E-BP1 and/or AKT is assessed in B-cells, T-cells and/or monocytes.

In one embodiment, provided herein are methods for inhibiting DNA-dependent protein kinase (DNA-PK) activity in a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein to said subject. In some embodiments, DNA-PK inhibition is assessed in the skin of the subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, in one example in a UV light-irradiated skin sample of said subject. In another embodiment, DNA-PK inhibition is assessed in a tumor biopsy or aspirate of a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma. In one embodiment, inhibition is assessed by measuring the amount of phosphorylated DNA-PK S2056 (also known as pDNA-PK S2056) before and after administration of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein. In certain embodiments, provided herein are methods for measuring inhibition of phosphorylation of DNA-PK S2056 in a skin sample of a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein to said subject, measuring the amount of phosphorylated DNA-PK S2056 present in the skin sample and comparing said amount of phosphorylated DNA-PK S2056 to that in a skin sample from said subject prior to administration of an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided herein. In one embodiment, the skin sample is irradiated with UV light.

In certain embodiments, provided herein are methods for inhibiting DNA-dependent protein kinase (DNA-PK) activity in a skin sample of a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, comprising administering an effective amount of the solid form of Compound A (e.g., Form A, Form B, Form C, Form D, Form E or amorphous), an isotopologue of Compound A, a metabolite of Compound A (e.g, O-desmethyl Compound A) or a pharmaceutical composition provided hereinto said subject and comparing the amount of phosphorylated DNA-PK in a biological sample of a subject obtained prior to and after administration of said solid form of Compound A (e.g., Form A, Form B, Form C, Form D, Form E or amorphous), isotopologue of Compound A, metabolite of Compound A (e.g, O-desmethyl Compound A) or pharmaceutical composition provided herein, wherein less phosphorylated DNA-PK in said biological sample obtained after administration of said solid form of Compound A (e.g., Form A, Form B, Form C, Form D, Form E or amorphous), isotopologue of Compound A, metabolite of Compound A (e.g, O-desmethyl Compound A) or pharmaceutical composition provided herein relative to the amount of phosphorylated DNA-PK in said biological sample obtained prior to administration of said solid form of Compound A (e.g., Form A, Form B, Form C, Form D, Form E or amorphous), isotopologue of Compound A, metabolite of Compound A (e.g, O-desmethyl Compound A) or pharmaceutical composition provided herein indicates inhibition.

The solid form of Compound A (e.g., Form A, Form B, Form C, Form D, Form E or amorphous), isotopologues of Compound A, metabolites of Compound A (e.g, O-desmethyl Compound A) and pharmaceutical compositions provided herein can be combined with radiation therapy or surgery. In certain embodiments, the solid form of Compound A (e.g., Form A, Form B, Form C, Form D, Form E or amorphous), isotopologues of Compound A, metabolites of Compound A (e.g, O-desmethyl Compound A) and pharmaceutical compositions provided herein are administered to subject who is undergoing radiation therapy, has previously undergone radiation therapy or will be undergoing radiation therapy. In certain embodiments, the solid form of Compound A (e.g., Form A, Form B, Form C, Form D, Form E or amorphous), isotopologues of Compound A, metabolites of Compound A (e.g, O-desmethyl Compound A) and pharmaceutical compositions provided herein are administered to a subject who has undergone tumor removal surgery (e.g., surgery to remove a GBM tumor).

Further provided herein are methods for treating subjects who have been previously treated for a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, but are non-responsive to standard therapies, as well as those who have not previously been treated. Further provided herein are methods for treating subjects who have undergone surgery in an attempt to treat the condition at issue, as well as those who have not. Because subjects with a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma have heterogenous clinical manifestations and varying clinical outcomes, the treatment given to a subject may vary, depending on his/her prognosis.

In certain embodiments, the pharmaceutical compositions provided herein comprising Compound A can be used for the treatment or prevention of a disease disclosed in U.S. Pat. Appl. Publ. No. 2010/0216781 (see, e.g., paragraphs [0415]-[0437]), the disclosure of which is incorporated herein by reference in its entirety.

Further provided herein are methods for achieving certain pharmacokinetic (PK) parameters with respect to Compound A in a subject, comprising administering a pharmaceutical composition provided herein to said subject. In certain embodiments, provided herein are methods for achieving a PK parameter set forth in the examples provided herein with respect to Compound A in a subject, comprising administering a pharmaceutical composition provided herein to said subject. In certain embodiments, the methods for achieving a PK parameter described herein further comprise measuring the amount of Compound A in a biological sample (e.g., urine, blood, serum or plasma) of a subject after administration of Compound A.

In certain embodiments, provided herein are methods for achieving a $T_{max}$ of about 0.5 to about 2 hours of Compound A in a subject, comprising administering a pharmaceutical composition provided herein to said subject. In specific embodiments, provided herein are methods for achieving a $T_{max}$ of about 1 hour, about 1.5 hours or about 2 hours of Compound A in a subject, comprising administering a pharmaceutical composition provided herein to said subject.

In certain embodiments, provided herein are methods for achieving a $t_{1/2}$ of about 4 to about 8 hours of Compound A in a subject, comprising administering a pharmaceutical composition provided herein to said subject. In specific embodiments, provided herein are methods for achieving a tin of about 4 hours, about 4.5 hours, about 5 hours, about 5.5 hours, about 6 hours, about 6.5 hours, about 7 hours, about 7.5 hours or about 8 hours of Compound A in a subject, comprising administering a pharmaceutical composition provided herein to said subject.

In certain embodiments, provided herein are methods for achieving a $C_{max}$ of about 150 to about 500 ng/mL of Compound A in a subject, comprising administering a pharmaceutical composition provided herein to said subject. In specific embodiments, provided herein are methods for achieving a $C_{max}$ of about 150 ng/mL, about 175 ng/mL, about 200 ng/mL, about 225 ng/mL, about 250 ng/mL, about 275 ng/mL, about 300 ng/mL, about 325 ng/mL, about 350 ng/mL, about 375 ng/mL, about 400 ng/mL, about 425 ng/mL, about 450 ng/mL, about 475 ng/mL or about 500 ng/mL of Compound A in a subject, comprising administering a pharmaceutical composition provided herein to said subject. In one embodiment, provided herein are methods for achieving a steady state Cm of about 485 ng/mL of Compound A in a subject, comprising administering a pharmaceutical composition provided herein to said subject.

In certain embodiments, provided herein are methods for achieving an $AUC_{0-24}$ of about 900 to about 2500 ng*h/mL of Compound A in a subject, comprising administering a pharmaceutical composition provided herein to said subject. In specific embodiments, provided herein are methods for achieving an $AUC_{0-24}$ of about 900 ng*hr/mL, about 950 ng*hr/mL, about 1000 ng*hr/mL, about 1050 ng*hr/mL, about 1100 ng*hr/mL, about 1150 ng*hr/mL, about 1200 ng*hr/mL, about 1250 ng*hr/mL, about 1300 ng*hr/mL, about 1350 ng*hr/mL, about 1400 ng*hr/mL, about 1450 ng*hr/mL, about 1500 ng*hr/mL, about 1550 ng*hr/mL, about 1600 ng*hr/mL, about 1650 ng*hr/mL, about 1700 ng*hr/mL, about 1750 ng*hr/mL, about 1800 ng*hr/mL, about 1850 ng*hr/mL, about 1900 ng*hr/mL, about 1950 ng*hr/mL, about 2000 ng*hr/mL, about 2050 ng*hr/mL, about 2100 ng*hr/mL, about 2150 ng*hr/mL, about 2200 ng*hr/mL, about 2250 ng*hr/mL, about 2300 ng*hr/mL, about 2350 ng*hr/mL, about 2400 ng*hr/mL, about 2450 ng*hr/mL or about 2500 ng*hr/mL of Compound A in a subject, comprising administering a pharmaceutical composition provided herein to said subject.

In certain embodiments, provided herein are methods for achieving an $AUC_\infty$ of about 900 to about 1100 ng*hr/mL of Compound A in a subject, comprising administering a pharmaceutical composition provided herein to said subject. In specific embodiments, provided herein are methods for achieving an $AUC_\infty$ of about 900 ng*hr/mL, about 950 ng*hr/mL, about 1000 ng*hr/mL, about 1050 ng*hr/mL or about 1000 ng*hr/mL of Compound A in a subject, comprising administering a pharmaceutical composition provided herein to said subject.

In certain embodiments, provided herein are methods for achieving a CL/F of about 19 to about 22 L/hr of Compound A in a subject, comprising administering a pharmaceutical composition provided herein to said subject. In specific embodiments, provided herein are methods for achieving a CL/F of about 19 L/hr, about 19.5 L/hr, about 20 L/hr, about 20.5 L/hr, about 21 L/hr, about 21.5 L/hr or about 22 L/hr of Compound A in a subject, comprising administering a pharmaceutical composition provided herein to said subject.

In certain embodiments, provided herein are methods for achieving a Vz/F of about 150 to about 180 L of Compound A in a subject, comprising administering a pharmaceutical composition provided herein to said subject. In specific embodiments, provided herein are methods for achieving a Vz/F of about 150 L, about 155 L, about 160 L, about 165 L, about 170 L, about 175 L or about 180 L of Compound A in a subject, comprising administering a pharmaceutical composition provided herein to said subject.

In certain embodiments, the methods of use and pharmaceutical compositions provided herein comprise in vivo production of a metabolite of Compound A.

In certain embodiments, the methods of use and pharmaceutical compositions provided herein comprise in vivo production of a metabolite of Compound A in a subject, wherein the metabolite has one or more of the pharmacokinetic parameters selected from a $C_{max}$ of about 100 to about 200 ng/mL (e.g., 143 ng/mL), a $T_{max}$ of about 7 to about 9 hours (e.g., 8 hours), an $AUC_{0-24}$ of about 2500 to about 3000 ng*h/mL (e.g., 2744 ng*h/mL), an $AUC_{0-\infty}$ of about 7750 to about 8250 ng*h/mL (e.g., 7948 ng*h/mL) and a $t_{1/2}$ of about 30 to about 40 hours (e.g., 35 hours) on day 1 of administration of about 7.5 mg of Compound A or a pharmaceutical composition thereof to said subject or wherein the metabolite has one or more of the pharmacokinetic parameters selected from a $C_{max}$ of about 300 to about 400 ng/mL (e.g., 363 ng/mL), a $T_{max}$ of about 1 to about 3 hours (e.g., 2 hours), an $AUC_{0-24}$ of about 6250 to about 6750 ng*h/mL (e.g., 6404 ng*h/mL), an $AUC_{0-\infty}$ of about 42500 to about 47500 ng*h/mL (e.g., 45602 ng*h/mL) and a $C_{trough}$ of about 200 to about 300 ng/mL (e.g., 267 ng/mL) on day 15 of once a day administration of about 7.5 mg of Compound A or a pharmaceutical composition thereof to said subject.

In certain embodiments, the methods of use and pharmaceutical compositions provided herein comprise in vivo production of a metabolite of Compound A in a subject, wherein the metabolite has one or more of the pharmacokinetic parameters selected from a $C_{max}$ of about 250 to about 350 ng/mL (e.g., 309 ng/mL), a $T_{max}$ of about 1 to about 3 hours (e.g., 2 hours), an $AUC_{0-24}$ of about 3500 to about 4000 ng*h/mL (e.g., 3828 ng*h/mL), an $AUC_{0-\infty}$ of about 5500 to about 6000 ng*h/mL (e.g., 5821 ng*h/mL) and a $t_{1/2}$ of about 10 to about 14 hours (e.g., 12 hours) on day 1 of administration of about 15 mg of Compound A or a pharmaceutical composition thereof to said subject or wherein the metabolite has one or more of the pharmacokinetic parameters selected from a $C_{max}$ of about 400 to about 500 ng/mL (e.g., 458 ng/mL), a $T_{max}$ of about 2 to about 4 hours (e.g., 3 hours), an $AUC_{0-24}$ of about 5500 to about 6000 ng*h/mL (e.g., 5677 ng*h/mL), an $AUC_{0-\infty}$ of about 9500 to about 10000 ng*h/mL (e.g., 9753 ng*h/mL) and a $C_{trough}$ of about 100 to about 200 ng/mL (e.g., 145 ng/mL) on day 15 of once a day administration of about 15 mg of Compound A or a pharmaceutical composition thereof to said subject.

In certain embodiments, the methods of use and pharmaceutical compositions provided herein comprise in vivo production of a metabolite of Compound A in a subject, wherein the metabolite has one or more of the pharmacokinetic parameters selected from a $C_{max}$ of about 700 to about 800 ng/mL (e.g., 776 ng/mL), a $T_{max}$ of about 6 to about 8 hours (e.g., 7 hours), an $AUC_{0-24}$ of about 13000 to about 13500 ng*h/mL (e.g., 13288 ng*h/mL), an $AUC_{0-\infty}$ of about 25000 to about 30000 ng*h/mL (e.g., 27672 ng*h/mL) and a tin of about 18 to about 24 hours (e.g., 21 hours) on day 1 of administration of about 30 mg of Compound A or a pharmaceutical composition thereof to said subject or wherein the metabolite has one or more of the pharmacokinetic parameters selected from a $C_{max}$ of about 1600 to about 2000 ng/mL (e.g., 1768 ng/mL), a Tax of about 1 to about 3 hours (e.g., 2 hours), an $AUC_{0-24}$ of about 27500 to about 32500 ng*h/mL (e.g., 29423 ng*h/mL), an $AUC_{0-\infty}$ of about 110000 to about 130000 ng*h/mL (e.g., 117697 ng*h/mL) and a $C_{trough}$ of about 1000 to about 1200 ng/mL (e.g., 1102 ng/mL) on day 15 of once a day administration of about 30 mg of Compound A or a pharmaceutical composition thereof to said subject.

In certain embodiments, the methods of use and pharmaceutical compositions provided herein comprise in vivo production of a metabolite of Compound A in a subject, wherein the metabolite has one or more of the pharmacokinetic parameters selected from a $C_{max}$ of about 1100 to about 1200 ng/mL (e.g., 1153 ng/mL), a Tax of about 2 to about 4 hours (e.g., 3 hours), an $AUC_{0-24}$ of about 15500 to about 16000 ng*h/mL (e.g., 15854 ng*h/mL), an $AUC_{0-\infty}$ of about 25000 to about 30000 ng*h/mL (e.g., 27274 ng*h/mL) and a tin of about 14 to about 20 hours (e.g., 17 hours) on day 1 of administration of about 45 mg of Compound A or a pharmaceutical composition thereof to said subject or wherein the metabolite has one or more of the pharmacokinetic parameters selected from a $C_{max}$ of about 2000 to about 2500 ng/mL (e.g., 2243 ng/mL), a Tax of about 1 to about 3 hours (e.g., 2 hours), an $AUC_{0-24}$ of about 30000 to about 35000 ng*h/mL (e.g., 32705 ng*h/mL), an $AUC_{0-\infty}$ of about 75000 to about 80000 ng*h/mL (e.g., 77722 ng*h/mL) and a $C_{trough}$ of about 1100 to about 1200 ng/mL (e.g., 1181 ng/mL) on day 15 of once a day administration of about 45 mg of Compound A or a pharmaceutical composition thereof to said subject.

In certain embodiments, the methods of use and pharmaceutical compositions provided herein comprise in vivo production of a metabolite of Compound A in a subject, wherein the metabolite has one or more of the pharmacokinetic parameters selected from a $C_{max}$ of about 1400 to about 1500 ng/mL (e.g., 1438 ng/mL), a Tax of about 4 to about 6 hours (e.g., 5 hours), an $AUC_{0-24}$ of about 21000 to about 22000 ng*h/mL (e.g., 21454 ng*h/mL), an $AUC_{0-\infty}$ of about 35000 to about 40000 ng*h/mL (e.g., 37490 ng*h/mL) and a tin of about 12 to about 20 hours (e.g., 16 hours) on day 1 of administration of about 60 mg of Compound A or a pharmaceutical composition thereof to said subject or wherein the metabolite has one or more of the pharmacokinetic parameters selected from a $C_{max}$ of about 2250 to about 2750 ng/mL (e.g., 2521 ng/mL), a Tax of about 2 to about 4 hours (e.g., 3 hours), an $AUC_{0-24}$ of about 45000 to about 50000 ng*h/mL (e.g., 46852 ng*h/mL), an $AUC_{0-\infty}$ m of about 135000 to about 145000 ng*h/mL (e.g., 138418 ng*h/mL) and a $C_{trough}$ of about 1400 to about 1500 ng/mL (e.g., 1467 ng/mL) on day 15 of once a day administration of about 60 mg of Compound A or a pharmaceutical composition thereof to said subject.

In certain embodiments, the methods of use and pharmaceutical compositions provided herein comprise in vivo production of a metabolite of Compound A in a subject, wherein the metabolite has a Tax of about 2 to about 4 hours (e.g., 3 hours) upon administration of about 20 mg of Compound A or a pharmaceutical composition thereof or about 45 mg of Compound A or a pharmaceutical composition thereof to said subject.

In certain embodiments, the methods of use and pharmaceutical compositions provided herein comprise in vivo production of a metabolite of Compound A in a subject, wherein the metabolite has a $C_{max}$ of about 450 to about 550 ng/mL (e.g., 503 ng/mL) upon administration of about 20 mg of Compound A or a pharmaceutical composition thereof or a $C_{max}$ of about 1100 to about 1200 ng/mL (e.g., 1153 ng/mL) upon administration of about 45 mg of Compound A or a pharmaceutical composition thereof to said subject.

In certain embodiments, the methods of use and pharmaceutical compositions provided herein comprise in vivo production of a metabolite of Compound A in a subject, wherein the metabolite has an $AUC_\infty$ of about 10000 to about 15000 ng/mL (e.g., 11928 ng*h/mL) upon administration of about 20 mg of Compound A or a pharmaceutical composition thereof or an $AUC_\infty$ of about 25000 to about 30000 ng/mL (e.g., 27274 ng*h/mL) upon administration of about 45 mg of Compound A or a pharmaceutical composition thereof to said subject.

In certain embodiments, the methods of use and pharmaceutical compositions provided herein comprise in vivo production of a metabolite of Compound A in a subject, wherein the metabolite has an $AUC_{0-24}$ of about 7000 to about 8000 ng/mL (e.g., 7484 ng*h/mL) upon administration of about 20 mg of Compound A or a pharmaceutical composition thereof or an $AUC_{0-24}$ of about 12500 to about 17500 ng/mL (e.g., 15854 ng*h/mL) upon administration of about 45 mg of Compound A or a pharmaceutical composition thereof to said subject.

In certain embodiments, the methods of use and pharmaceutical compositions provided herein comprise in vivo production of a metabolite of Compound A in a subject, wherein the metabolite has a $t_{1/2}$ of about 12 to about 16 hours (e.g., 14.3 hours) upon administration of about 20 mg of Compound A or a pharmaceutical composition thereof or a $t_{1/2}$ of about 12 to about 16 hours (e.g., 14.7 hours) upon administration of about 45 mg of Compound A or a pharmaceutical composition thereof to said subject.

In certain embodiments, the pharmacokinetic parameters in connection with the metabolite of Compound A produced via administration of 7.5 mg, 15 mg, 30 mg, 45 mg and 60 mg of Compound A are obtained using the protocol set forth in Section 5.2.1 (paragraphs [00497]-[00520]) of U.S. provisional application No. 61/653,436, filed May 31, 2012, which is incorporated by reference herein in its entirety.

In certain embodiments, the pharmacokinetic parameters in connection with the metabolite of Compound A produced via administration of 20 mg of Compound A were obtained using the protocol set forth in Section 6.5.1, below.

In certain embodiments, the pharmacokinetic parameters set forth herein are mean values obtained from multiple subjects.

In certain embodiments, the metabolite of Compound A is the O-desmethyl metabolite.

6. EXAMPLES

Chem-4D Draw (ChemInnovation Software, Inc., San Diego, Calif.), ChemDraw Ultra (Cambridgesoft, Cambridge, Mass.) or ACD/Name (Advanced Chemistry Development, Inc. Toronto, Ontario) was used to generate names for chemical structures.

The following abbreviations were used in descriptions and examples:
ACN Acetonitrile
Amphos Di-tert-butyl(4-dimethylaminophenyl)phosphine
BHT Butylated hydroxytoluene
Boc tert-Butoxycarbonyl
dba Dibenzylideneacetone
DCM Dichloromethane
DIBE Diisobutyl hexahydrophthalate
DIPEA N,N-Diisopropylethylamine
DIPE Diisopropyl ether
DME Dimethoxyethane
DMAP 4-Dimethylaminopyridine
DMSO Dimethylsulfoxide
dppf 1,1'-Bis(diphenylphosphino)ferrocene
DSC Differential scanning calorimetry
ESI Electrospray ionization
EtOAc Ethyl acetate
DVS Dynamic vapor sorption
HPLC High performance liquid chromatography
IPA Isopropyl alcohol
IPAc Isopropyl acetate
MeOAc Methyl acetate
MIBK Methyl isobutyl ketone
mp Melting point
MS Mass spectrometry
MTBE Methyl tert-butyl ether
NBS N-Bromosuccinimide
NMR Nuclear magnetic resonance
NMP N-methyl-2-pyrrolidinone
PEG Polyethylene glycol
PFL Protect from light
REF Refrigerated
RTmp or RT Room temperature
TEA Triethylamine
TFA Trifluoroacetic acid
TGA Thermogravimetric analysis
THF Tetrahydrofuran
TLC Thin layer chromatography
TMS Trimethylsilyl
XRPD X-ray powder diffraction The following Examples are presented by way of illustration, not limitation.

6.1 Solid Form Screen

6.1.1 Characterization Methodology 6.1.1.1 X-ray Powder Diffraction (XRPD)

All of solid samples generated in the solid form screen were analyzed by XRPD. XRPD analysis was conducted on a Bruker AXS C2 GADDS or Bruker AXS D8 Advance X-ray powder diffractometer.

Certain X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. A weekly performance check is carried out using a certified standard NIST 1976 Corundum (flat plate). The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds. The software used for data collection was GADDS for WNT 4.1.16 and the data were analyzed and presented using Diffrac Plus EVA v11.0.0.2 or v13.0.0.2. Ambient conditions: Samples run under ambient conditions were prepared as flat plate specimens using powder as received without grinding. Approximately 1-2 mg of the sample was lightly pressed on a glass slide to obtain a flat surface. Non-ambient conditions: Samples run under non-ambient conditions were mounted on a silicon wafer with heatconducting compound. The sample was then heated to the appropriate temperature at 20° C./min and subsequently held isothermally for 1 minute before data collection was initiated.

Certain X-Ray Powder Diffraction patterns were collected on a Bruker D8 diffractometer using CuKα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analyzed and presented using Diffrac Plus EVA v 1.0.0.2 or v13.0.0.2. Samples were run under ambient conditions as flat plate specimens using powder as received. The sample was gently packed into a cavity cut into polished, zero-background (510) silicon wafer. The sample was rotated in its own plane during analysis. The details of the data collection are: Angular range: 2 to 42 °2θ; Step size: 0.05 °2 θ; Collection time: 0.5 s/step.

6.1.1.2 Differential Scanning Calorimetry (DSC)

Modulated DSC data were collected on a TA Instruments Q2000 equipped with a 50 position auto-sampler. The calibration for thermal capacity was carried out using sapphire and the calibration for energy and temperature was carried out using certified indium. Typically 3-1.5 mg of each sample, in a pin-holed aluminum pan, was heated at 2° C./min from −80° C. to 300° C. A purge of dry nitrogen at 50 mL/min was maintained over the sample. Modulated temperature DSC was carried out using an underlying heating rate of 2° C./min and temperature modulation parameters of +1.272° C. (amplitude) every 60 seconds (period). The instrument control software was Advantage for Q Series v2.8.0.392 and Thermal Advantage v4.8.3 and the data were analyzed using Universal Analysis v4.4A.

Non-modulated DSC data were collected on a TA Instruments Q2000 equipped with a 50 position auto-sampler. The calibration for thermal capacity was carried out using sapphire and the calibration for energy and temperature was carried out using certified indium. Typically 1 to 5 mg of each sample, in an aluminum pan, was heated at 10° C./min from 20° C. to 300° C. A purge of dry nitrogen at 50 mL/min was maintained over the sample. The instrument control software was Advantage for Q Series v2.8.0.392 and Thermal Advantage v4.8.3 and the data were analyzed using Universal Analysis v4.4A.

6.1.1.3 Thermogravimetric Analysis (TGA)

TGA data were collected on a Mettler TGA/SDTA 851e equipped with a 34 position autosampler. The instrument was temperature calibrated using certified indium. Typically 5-15 mg of each sample was loaded onto a pre-weighed aluminum crucible and was heated at 10° C./min from ambient temperature to 350° C. A nitrogen purge at 50 ml/min was maintained over the sample. The instrument control and data analysis software was STARe v9.20.

6.1.1.4 Polar Light Microscopy

Samples were studied on a Leica LM/DM polarized light microscope with a digital video camera for image capture. A small amount of each sample was placed on a glass slide, mounted in immersion oil and covered with a glass slip, the individual particles being separated as well as possible. The sample was viewed with appropriate magnification and partially polarised light, coupled to a λ false-colour filter.

6.1.1.5 Gravimetric Vapour Sorption (GVS)

Sorption isotherms were obtained using a SMS DVS Intrinsic moisture sorption analyser, controlled by DVS Intrinsic Control software v1.0.0.30. The sample temperature was maintained at 25° C. by the instrument controls. The humidity was controlled by mixing streams of dry and wet nitrogen, with a total flow rate of 200 mL/min. The relative humidity was measured by a calibrated Rotronic probe (dynamic range of 1.0-100% RH), located near the sample. The weight change, (mass relaxation) of the sample as a function of % RH was constantly monitored by the microbalance (accuracy±0.005 mg). Typically 5-20 mg of sample was placed in a tared mesh stainless steel basket under ambient conditions. The sample was loaded and unloaded at 40% RH and 25° C. (typical room conditions). The standard isotherm was performed at 25° C. at 10% RH intervals over a 0-90% RH range. Data analysis was undertaken in Microsoft Excel using DVS Analysis Suite v6.0.0.7.

6.1.2 Solid Form Screen Experiments

The solvents used in the polymorph screen were either HPLC or reagent grade, including toluene, MTBE (methyl tert-butyl ether), DIPE (diisopropyl ether), THF (tetrahydrofuran), DME (dimethoxyethane), IPAc (isopropyl acetate), EtOAc (ethyl acetate), MIBK (methyl isobutyl ketone), acetone, IPA (isopropyl alcohol), ethanol, ACN (acetonitrile), nitromethane, p-xylene, p-xylene/acetone (e.g., 50:50), p-xylene/MTBE (e.g., 50:50), or IPA:water (e.g., 95:5).

The solid form generated from the screen was characterized by X-ray powder diffraction (XRPD), differential scanning calorimetry (DSC), thermogravimetric analysis (TGA), optical microscopy, and gravimetric vapor sorption (GVS).

6.1.2.1 Equilibration/Slurry and Evaporation

Amorphous Compound A (~10 mg per experiment) was treated with the stated solvent. Solutions were allowed to slowly evaporate at room temperature and the residual solids were analyzed by XRPD. Suspensions were subjected to heat/cool cycles (50° C./room temperature, 8 hour cycle) for 16 hours; the solvent was then allowed to evaporate and the residual solids were analyzed by XRPD.

The results of slurry experiments are summarized in Table 1. All of the solids obtained from filtration of the slurries were confirmed to be Form A by XRPD.

TABLE 1

Slurry Experiments of Form A of Compound A at Room Temperature

| Solvent | XRPD Result |
|---|---|
| Toluene | Form A |
| MTBE | Form A |
| DIPE | Form A |
| THF | Form A |
| DME | Form A |
| IPAc | Form A |
| EtOAc | Form A |
| MIBK | Form A |
| Acetone | Form A |
| IPA | Form A |
| Ethanol | Form A |
| ACN | Form A |
| Nitromethane | Form A |
| IPA:water (95:5) | Form A |

6.1.3 Characterization of Form A of Compound A

6.1.3.1 XRPD, TGA, and DSC Characterization

Figure 2:
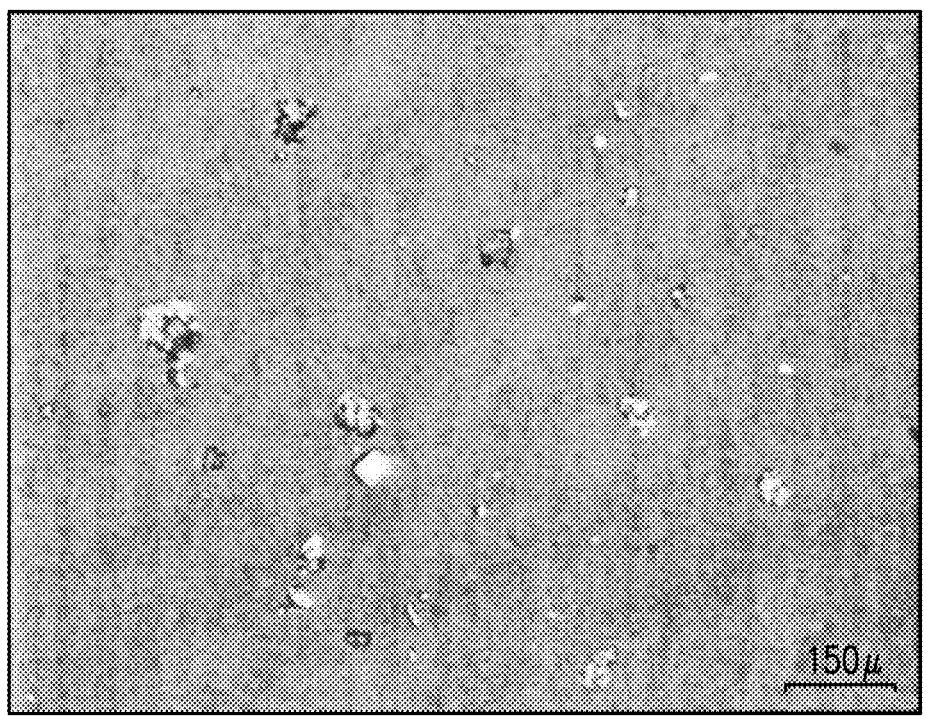
FIG. 2 depicts polar light microscopy photographs of Form A of 7-(6-(2-hydroxypropan-2-yl)pyridin-3-yl)-1-((trans)-4-methoxycyclohexyl)-3,4-dihydropyrazino[2,3-b]pyrazin-2(1H)-one.

Form A has a crystalline XRPD pattern as shown in FIG. 1 and an irregular plate crystal habit as shown in FIG. 2. The XRPD pattern of Form A of Compound A shows that Form A is crystalline. Some XRPD peaks of crystalline Form A are summarized in Table 2.

TABLE 2

X-Ray Diffraction Peaks for Form A of Compound A

| Two-theta angle (°) | d Space (Å) | Intensity (%) |
|---:|---:|---:|
| 8.3 | 10.648 | 58.3 |
| 8.8 | 9.984 | 26.8 |
| 12.0 | 7.342 | 8.1 |
| 13.2 | 6.708 | 100.0 |
| 13.9 | 6.357 | 8.0 |
| 14.4 | 6.125 | 3.3 |
| 14.8 | 5.961 | 8.7 |
| 16.5 | 5.352 | 50.2 |
| 17.7 | 4.996 | 35.4 |
| 18.2 | 4.872 | 50.7 |
| 19.3 | 4.586 | 8.2 |
| 19.5 | 4.560 | 7.7 |
| 19.6 | 4.526 | 7.3 |

TABLE 2-continued

X-Ray Diffraction Peaks for Form A of Compound A

| Two-theta angle (°) | d Space (Å) | Intensity (%) |
|---|---|---|
| 21.0 | 4.230 | 4.4 |
| 21.2 | 4.185 | 3.9 |
| 21.7 | 4.094 | 50.9 |
| 22.5 | 3.942 | 13.6 |
| 24.1 | 3.684 | 8.4 |
| 24.7 | 3.603 | 7.1 |
| 25.0 | 3.560 | 12.8 |
| 25.3 | 3.512 | 5.6 |
| 26.5 | 3.363 | 35.7 |
| 26.7 | 3.332 | 5.7 |
| 28.3 | 3.147 | 11.4 |
| 29.3 | 3.051 | 5.5 |
| 29.5 | 3.022 | 9.9 |
| 29.8 | 2.992 | 7.9 |
| 30.5 | 2.924 | 3.2 |
| 32.1 | 2.782 | 2.9 |
| 33.3 | 2.690 | 3.4 |
| 34.2 | 2.621 | 3.5 |
| 34.6 | 2.587 | 4.4 |

TGA and DSC thermograms of Form A are shown in FIG. 3. Form A was found to lose up to 0.02% volatiles during TGA analysis upon 100° C., which indicates that Form A is unsolvated and anhydrous. Form A exhibited a single melting peak at 199.3° C. (onset).

6.1.3.2 Hygroscopicity

Hygroscopicity of Form A was determined by moisture adsorption and desorption. The moisture sorption/desorption behavior of Form A was determined by DVS and the results are summarized in FIG. 4. Form A showed no significant water uptake (<0.1% w/w) between 0 and 80% relative humidity, which indicates that Form A is not hygroscopic. After undergoing the full adsorption/desorption cycle, the XRPD diffractogram of the sample showed that the material was unchanged from the initial Form A. Based on the characterization results, Form A was found to be an anhydrous and non-hygroscopic crystalline material.

6.1.4 Alternative Methods for the Preparation of Form A of Compound A

Preparation 1:

Compound A was combined with BHT (0.001 equiv) in IPA and water (3×:5× vol). The mixture was heated 65° C. and while maintaining this temperature, water (5× vol) heated to 65° C. was added. A small amount of the title compound (0.02 equiv) in water heated to 65° C. was added. The mixture was held for 2 h, cooled to room temperature over 4 h, and stirred for an additional 2 h. The resulting solids were collected by filtration, washed with 20% IPA in water and dried to give Compound A as a white to yellow solid. $^1$H NMR (400 MHz, DMSO-d$_6$) δ (ppm) 9.03 (d, J=1.56 Hz, 1H), 8.28 (s, 1H), 8.24 (dd, J=2.34, 8.20 Hz, 1H), 7.74 (d, J=7.81 Hz, 1H), 7.61 (s, 1H), 5.26 (s, 1H), 4.90 (tt, J=3.71, 12.10 Hz, 1H), 4.13 (s, 2H), 3.28 (s, 3H), 3.20 (tt, J=4.00, 10.84 Hz, 1H), 2.58 (qd, J=2.93, 12.82 Hz, 2H), 2.14 (d, J=10.15 Hz, 2H), 1.68 (d, J=10.93 Hz, 2H), 1.47 (s, 6H), 1.17-1.35 (m, 2H); MS (ESI) m/z 398.3 [M+1]$^+$. DSC endotherm at 201.9° C. XRPD diffractogram (top peaks±0.5°) two-theta angle (°): 8.0, 9.0, 12.0, 13.0, 16.5, 17.5, 18.2, 21.5, 22.5, 25.0, 26.5.

Preparation 2:

Compound A was combined with BHT (0.02 equiv) in MeOAc (25× vol) and heated to 55° C. The solution was cooled to 25° C. and a small amount of the title compound (0.02 equiv) in MeOAc was added. The slurry was held for 1 h, distilled under vacuum to a reduced volume and treated with n-heptane (10× vol). The slurry was held for 2 h, and the resulting solids were collected by filtration, washed with 50% MeOAc in n-heptane and dried to give Compound A as a white to yellow solid. $^1$H NMR (400 MHz, DMSO-d$_6$) δ (ppm) 9.03 (d, J=1.56 Hz, 1H), 8.28 (s, 1H), 8.24 (dd, J=2.34, 8.20 Hz, 1H), 7.74 (d, J=7.81 Hz, 1H), 7.61 (s, 1H), 5.26 (s, 1H), 4.90 (tt, J=3.71, 12.10 Hz, 1H), 4.13 (s, 2H), 3.28 (s, 3H), 3.20 (tt, J=4.00, 10.84 Hz, 1H), 2.58 (qd, J=2.93, 12.82 Hz, 2H), 2.14 (d, J=10.15 Hz, 2H), 1.68 (d, J=10.93 Hz, 2H), 1.47 (s, 6H), 1.17-1.35 (m, 2H); MS (ESI) m/z 398.3 [M+1]$^+$. DSC endotherm at 201.9° C. XRPD diffractogram (top peaks, ±0.5°) two-theta angle (°): 8.0, 9.0, 12.0, 13.0, 16.5, 17.5, 18.2, 21.5, 22.5, 25.0, 26.5

Preparation 3:

Compound A was combined with BHT (0.02 equiv), and MeOAc, and heated to 55° C., forming a clear solution. The solution was filtered while hot, cooled to 30° C. and a small amount of the title compound (0.02 equiv) in MeOAc was added. The slurry was agitated for at least 1 h, distilled under vacuum to a reduced volume and treated with n-heptane. The resulting solid was collected through filtration, washed with a 1:1 mixture of MeOAc in n-heptane and dried to give Compound A as a white to yellow solid $^1$H NMR (400 MHz, DMSO-d$_6$) δ (ppm) 9.03 (d, J=1.56 Hz, 1H), 8.28 (s, 1H), 8.24 (dd, J=2.34, 8.20 Hz, 1H), 7.74 (d, J=7.81 Hz, 1H), 7.61 (s, 1H), 5.26 (s, 1H), 4.90 (tt, J=3.71, 12.10 Hz, 1H), 4.13 (s, 2H), 3.28 (s, 3H), 3.20 (tt, J=4.00, 10.84 Hz, 1H), 2.58 (qd, J=2.93, 12.82 Hz, 2H), 2.14 (d, J=10.15 Hz, 2H), 1.68 (d, J=10.93 Hz, 2H), 1.47 (s, 6H), 1.17-1.35 (m, 2H); MS (ESI) m/z 398.3 [M+1]$^+$. DSC endotherm at 201.9° C. XRPD diffractogram (top peaks, +0.5°) two-theta angle (°): 8.0, 9.0, 12.0, 13.0, 16.5, 17.5, 18.2, 21.5, 22.5, 25.0, 26.5.

Preparation 4:

A 1:1 wt/wt mixture of Compound A (Form A) and Compound A (pinacol co-crystal) was treated with IPA (6× vol) with agitation for 4 days at ambient temperature. The solids were collected by filtration and dried under reduced pressure at 40-50° C. to give Compound A (Form A) as a yellow solid. DSC endotherm of 195° C. XRPD diffractogram (top peaks, ±0.5°) two-theta angle (°): 8.0, 9.0, 12.0, 13.0, 16.5, 17.5, 18.2, 21.5, 22.5, 25.0, 26.5.

Preparation 5:

Compound A was combined with BHT (0.02 equiv) and 5% aqueous THF (5× vol) to form a clear solution. The solution was optionally treated with activated carbon for 4 h. The solution was filtered, treated with isopropyl acetate (3× vol), and distilled at atmospheric pressure at constant volume with addition of isopropyl acetate until the solution temperature reached 80° C. The solution was cooled to 75° C. and treated with a small amount of the title compound (0.02 equiv) in isopropyl acetate, and the slurry was held for 2 h. The slurry was distilled at atmospheric pressure at constant volume with addition of isopropyl acetate until the slurry temperature reached 88° C. The slurry was cooled to 80-85° C., held for 2 h, cooled to 25° C. over 4 h, and held for at least 8 h. The resulting solid was collected through filtration, washed with isopropyl acetate, and dried to give Form A as a white to yellow solid. Alternatively, after filtration and addition of isopropyl acetate, the distillation at constant volume can be carried out under reduced pressure keeping the reaction mixture at 40° C. until isopropyl acetate (3.5× vol) has been added. The solution at 40° C. is then treated with a small amount of the title compound (0.02 equiv) in isopropyl acetate, held for 2 h, and distilled at constant volume under vacuum at 40° C. with addition of an additional portion of isopropyl acetate (10× vol). The slurry is aged at 40° C. for 2 h, cooled to 25° C. over 2 h, held for at least 8 h, and the solid collected through filtration, washed with isopropyl acetate, and dried to give Form A as a white to yellow solid. $^1$H NMR (400 MHz, DMSO-$d_6$) δ (ppm) 9.03 (d, J=1.56 Hz, 1H), 8.28 (s, 1H), 8.24 (dd, J=2.34, 8.20 Hz, 1H), 7.74 (d, J=7.81 Hz, 1H), 7.61 (s, 1H), 5.26 (s, 1H), 4.90 (tt, J=3.71, 12.10 Hz, 1H), 4.13 (s, 2H), 3.28 (s, 3H), 3.20 (tt, J=4.00, 10.84 Hz, 1H), 2.58 (qd, J=2.93, 12.82 Hz, 2H), 2.14 (d, J=10.15 Hz, 2H), 1.68 (d, J=10.93 Hz, 2H), 1.47 (s, 6H), 1.17-1.35 (m, 2H); MS (ESI) m/z 398.3 [M+1]$^+$. DSC endotherm at 201.9° C. XRPD diffractogram (top peaks, ±0.5°) two-theta angle (°): 8.0, 9.0, 12.0, 13.0, 16.5, 17.5, 18.2, 21.5, 22.5, 25.0, 26.5.

6.1.5 Preparation of Pinacol Co-Crystal of Compound A

Compound A, pinacol (2.4 equiv), and THF (5× vol) were combined and heated to 45-50° C., and toluene (1× vol) was added. The solution was distilled under reduced pressure (300-350 Torr) keeping the temperature between 40-45° C. to 4× vol. The solution was cooled, and toluene (5× vol) was added while continuously removing solvent under reduced pressure (300-350 Torr), until 15% THF in toluene composition was achieved. The batch was seeded with pinacol co-crystal (0.02 equiv) at 25° C., and the batch was held for 72 h. The solids were filtered, rinsed with THF/toluene and dried at 45-50° C. under vacuum to afford Compound A pinacol co-crystal (71% yield, 20 wt % pinacol by $^1$H NMR). DSC melt at 119.0° C. XRPD diffractogram (top peaks, +0.5°) two-theta angle (°): 5.0, 6.0, 12.5, 14.0, 15.0, 15.5, 17.5, 18.5, 22.5.

6.1.6 Preparation of Hydrate of Compound A (Form B)

Compound A was combined with BHT (0.001 equiv) in IPA and water (3×:5× vol). The mixture was heated to 55° C., and water (5× vol) was added. A small amount of the title compound (0.02 equiv) in water was added. The mixture was cooled to room temperature over 1 h and stirred for an additional 48 h at room temperature. The resulting solids were collected by filtration, washed with 20% IPA in water and dried to give Compound A hydrate as a pink solid. The solid had a DSC endotherm of 111.3° C., exotherm of 164.9° C., and endotherm of 201.6° C. TGA analysis showed 6.4% weight loss and an onset temperature of 50° C. XRPD diffractogram (top peaks, +0.5°) two-theta angle (°): 6.0, 7.0, 8.0, 10.0, 12.0, 14.0, 17.0, 18.0, 20.0, 20.5, 22.5, 24.5.

6.1.7 Preparation of Anhydrous Form of Compound A (Form C)

Preparation 1:
Compound A was combined with BHT (0.001 equiv) in MeOH (10× vol). The mixture was distilled to a reduced volume (5×) and further distilled with the addition of IPA until an additional 50 mL of distillate was collected, and the solution was cooled to room temperature. The resulting solids were collected by filtration, washed with IPA, (2× vol) and dried to give Compound A as an off-white solid. DSC analysis of the solid showed an endotherm of 161° C. and an endotherm of 200° C. XRPD diffractogram (top peaks, +0.5°) two-theta angle (°): 6.5, 9.0, 10.0, 14.5, 16.5, 19.0, 23.0, 23.5.

Preparation 2:
Compound A (pinacol co-crystal) and BHT (0.01× wt) were treated with IPA (8× vol) with agitation for 4 days at ambient temperature. The solids were collected by filtration, washed with IPA, and dried under reduced pressure at 40-50° C. to give Compound A (Form C) as a solid. DSC analysis of the solid showed an endotherm and exotherm at 160° C. and an endotherm at 200° C. XRPD diffractogram (top peaks, ±0.5°) two-theta angle (°): 6.5, 9.0, 10.0, 14.5, 16.5, 19.0, 23.0, 23.5.

6.1.8 Preparation of Methanol Solvate of Compound A (Form D)

Compound A was combined with BHT (0.001 equiv) in MeOH (20× vol) and heated to 65° C. The solution was cooled to room temperature and stirred for an additional 18 h. The resulting solids were collected by filtration, washed and dried at 40-45° C. to give Compound A as a pink solid. The solid had a DSC endotherm of 98.3° C., an exotherm of 159.3° C., and an endotherm of 200.6° C. TGA analysis showed 7.4% weight loss and an onset temperature of 80° C. XRPD diffractogram (top peaks, ±0.5°) two-theta angle (°): 6.0, 7.5, 8.0, 9.0, 10.0, 12.5, 14.5, 16.5, 19.0, 19.5, 20.5, 23.0.

6.1.9 Preparation of p-Xylene Solvate of Compound A (Form E)

The XRPD pattern, crystal habit, TGA, SDTA, TGA-MS, HPLC and MS of Form E of Compound A are shown in FIGS. 15-20. Form E was prepared in at least three experiments, including: a slurry conversion experiment in p-xylene, a hot-filtration experiment in acetone/p-xylene (50/50), and an evaporative experiment in MTBE/p-xylene (50/50). The samples used for further analyses were prepared in the slurry conversion experiment in p-xylene.

FIG. 15 provides an overlay of XRPD patterns (from bottom to top) of: starting material (Form A of Compound A), Form E as a wet solid obtained from a slurry conversion experiment in p-xylene, Form E as a dried solid, Form E as a wet solid obtained from a slurry conversion experiment in p-xylene after exposure to accelerated aging conditions (AAC) and Form E as a dried solid after exposure to AAC. A list of X-Ray Diffraction Peaks for Form E of Compound A is provided below in Table 3.

TABLE 3

X-Ray Diffraction Peaks for Form E of Compound A

| Two-theta angle (°) | d Space (Å) | Relative Intensity (%) |
|---|---|---|
| 7.46 | 11.84 | 86.65 |
| 8.94 | 9.88 | 20.92 |
| 11.7 | 7.55 | 13.33 |
| 13.7 | 6.46 | 24.65 |
| 17.26 | 5.13 | 14.44 |
| 18.22 | 4.86 | 21.32 |
| 18.78 | 4.72 | 20.1 |
| 20.94 | 4.24 | 11.48 |
| 22.38 | 3.97 | 19.83 |
| 23.06 | 3.85 | 23.69 |
| 24.62 | 3.61 | 18.4 |

A single-crystal X-ray diffraction analysis is employed to determine the crystal structure of Form E of Compound A. Table 4 and Table 5 present a summary of the crystallographic data from the crystal-structure determination. Form E of Compound A has a crystal packing pattern as shown in FIG. 16. From the crystal structure results, it is confirmed that Form E is a p-xylene hemi-solvated form crystallizing in a monoclinic crystal system.

TABLE 4

Crystal data and structure refinement of Form E

| | |
|---|---|
| Empirical formula | $C_{21}H_{27}N_5O_3 \cdot 0.5\ C_8H_{10}$ |
| Fw | 450.56 |
| T [K] | 296(2) |
| λ [Å] | 0.71073 |
| Crystal system | Monoclinic |
| Space group | $P\ 2_1/c$ |
| Unit cell dimensions | |
| a [Å] | 12.3583(6) |
| b [Å] | 15.1360(9) |
| c [Å] | 13.4604(6) |
| β [°] | 105.272(4) |
| V [Å$^3$] | 2428.9(2) |
| Z | 4 |
| $D_c$ [g/cm$^3$] | 1.232 |
| μ [mm$^{-1}$] | 0.083 |
| F(000) | 964 |
| Crystal size [mm$^3$] | 0.35 x 0.26 x 0.12 |
| θ range for data collection [°] | 2.5 → 32.6 |
| Reflections collected | 26665 |
| Independent reflections | 8818 [$R_{int}$ is 0.0361] |
| Completeness to θ = 32.6° [%] | 99.3 |
| Max. and min. transmission | 0.9901 and 0.9716 |
| Data/restraints/parameters | 8818/0/406 |
| Goodness-of-fit on F$^2$ | 1.043 |
| Final R indices [I > 2σ(I)] | R1 = 0.0531, wR2 = 0.1342 |
| R indices (all data) | R1 = 0.0785, wR2 = 0.1528 |

TABLE 5

Hydrogen bonds of Form E

| D-H . . . A | D-H [Å] | H . . . A [Å] | D . . . A [Å] | D-H . . . A [°] |
|---|---|---|---|---|
| O(1)—H(1) . . . N(13)$^i$ | 0.89(2) | 2.01(2) | 2.865(2) | 162(2) |
| N(15)—H(15) . . . N(6)$^{ii}$ | 0.86(2) | 2.14(2) | 2.976(2) | 164(2) |

FIG. 17A is a digital image of Form E as a wet solid obtained from slurry conversion experiment in p-xylene. FIG. 17B is a digital image of Form E as a dried solid. FIG. 17C is a digital image of Form E as a wet solid obtained from slurry conversion experiment in p-xylene after exposure to AAC. FIG. 17D is a digital image of Form E as a dried solid after exposure to AAC.

FIG. 18 and FIG. 19 provide TGA/SDTA signal and TGA-MS data, respectively, of Form E.

The TGA thermogram of Form E in FIG. 18 shows a mass loss corresponding to a broad endothermic event observed in the SDTA signal between 90° C. and 125° C. with a maximum at about 106-110° C., which may be the desolvation of Form E. After the desolvation, the SDTA data of Form E in FIG. 18 shows a melting event at 193° C., corresponding to the melting of the starting material, Form A of Compound A.

The TGA thermogram of Form E in FIG. 19 comprises a total mass loss of approximately 11.0% of the total mass of the sample between approximately 50° C. and approximately 180° C. when heated from approximately 25° C. to approximately 300° C. Thus, Form E loses about 11.0% of its total mass when heated from about ambient temperature to about 300° C. The thermal data indicates that Form E contains 0.5 molar equivalents of solvent in the crystal lattice corresponding to approximately 0.5 mole of p-xylene per mole of Compound A. The theoretical p-xylene content of a p-xylene hemi-solvate of Compound A is 10.5% by weight, matching the TGA weight loss observed. These observations suggest that Form E is a p-xylene hemi-solvate of Compound A.

FIG. 20 provides HPLC and MS data of Form E. The peak retention time is 8.1 minutes with a sample purity of 98.9% (area %).

6.2 Synthesis

6.2.1 Large Scale Synthesis of Compound A

6.2.1.1 Synthesis 1

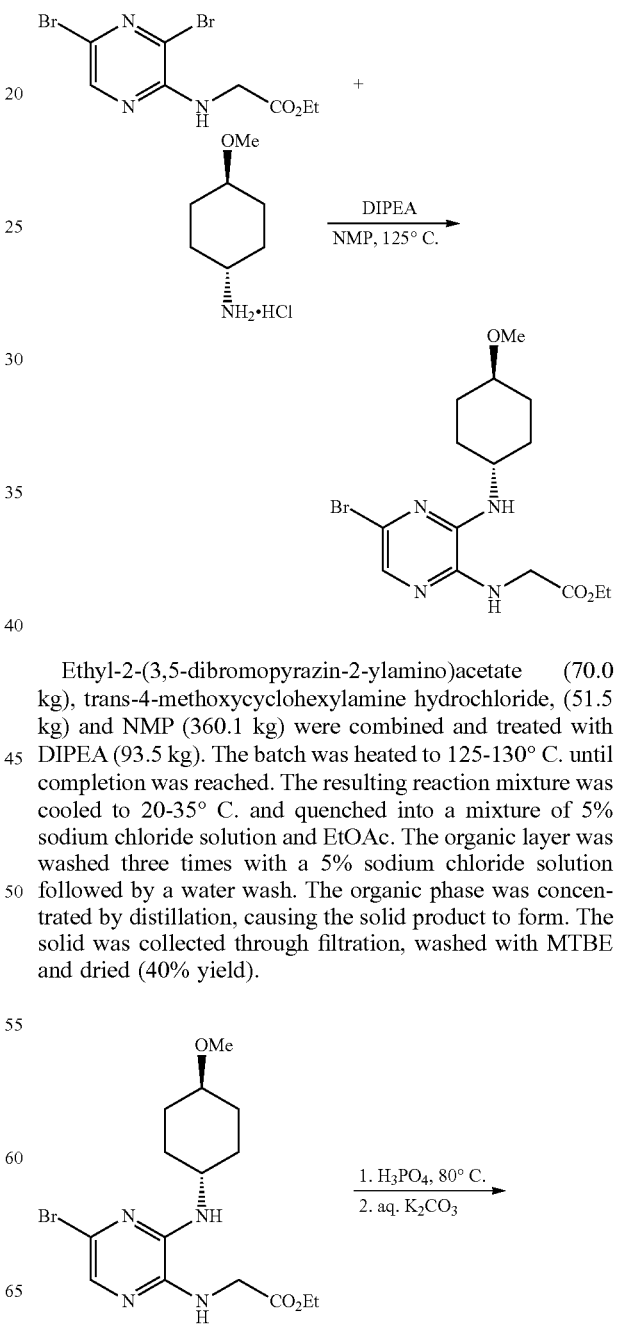

Ethyl-2-(3,5-dibromopyrazin-2-ylamino)acetate (70.0 kg), trans-4-methoxycyclohexylamine hydrochloride, (51.5 kg) and NMP (360.1 kg) were combined and treated with DIPEA (93.5 kg). The batch was heated to 125-130° C. until completion was reached. The resulting reaction mixture was cooled to 20-35° C. and quenched into a mixture of 5% sodium chloride solution and EtOAc. The organic layer was washed three times with a 5% sodium chloride solution followed by a water wash. The organic phase was concentrated by distillation, causing the solid product to form. The solid was collected through filtration, washed with MTBE and dried (40% yield).

-continued

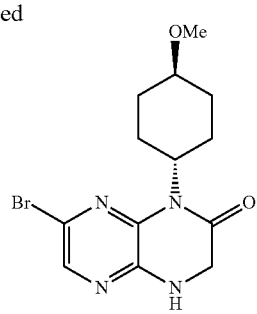

Ethyl 2-((5-bromo-3-(((trans)-4-methoxycyclohexyl)amino)pyrazin-2-yl)amino)acetate (35.0 kg) was treated with a 21% phosphoric acid solution (147.4 kg) at 80° C. for at least 12 h. The resulting suspension was cooled to room temperature an d the solid was collected through filtration and washed with water. The solid was slurried in water and treated with a 1 M potassium carbonate solution (1 equiv, 12.6 kg). The resulting solid was collected through filtration, washed with water, and dried (85% yield).

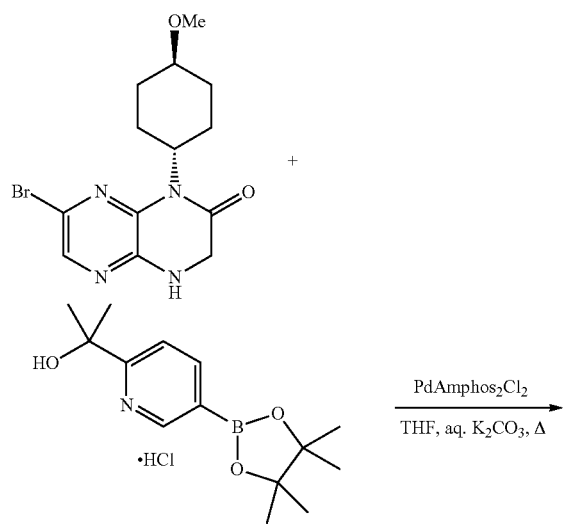

7-Bromo-1-((trans)-4-methoxycyclohexyl)-3,4-dihydropyrazino[2,3-b]pyrazin-2(1H)-one (27.5 kg), 2-(5-(4,4,5,5-tetramethyl-1,3,2-dioxaborolan-2-yl)pyridin-2-yl)propan-2-ol hydrochloride (26.2 kg), and PdCl₂(Amphos)₂ (137.5 g) in THF (219.8 kg) were combined with a potassium carbonate solution (27.5 kg), and heated to reflux until reaction completion was reached. The mixture was cooled, treated with toluene, and the aqueous layer was removed. The organic solution was washed with an aqueous potassium dihydrogen phosphate solution, and the aqueous layer was removed. The organic layer was treated with SiliaBond® Thiol (4.2 kg) and twice with activated carbon (2×2.8 kg). The organic solution was distilled to a reduced volume followed by continuous distillation with the addition of toluene until a 15% THF in toluene solution was reached, at which time the batch was cooled and the product was left to precipitate. The resulting solid was collected through filtration, washed with toluene, and dried (70% yield).

6.2.1.2 Synthesis 2

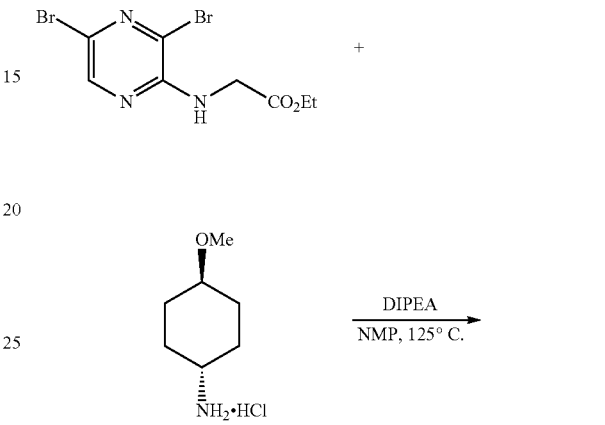

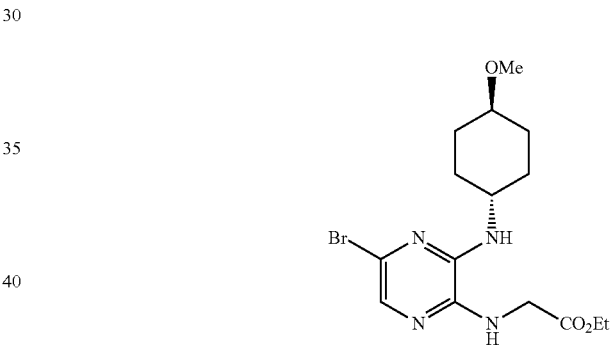

A mixture of ethyl-2-(3,5-dibromopyrazin-2-ylamino)acetate (69.1 kg), trans-4-methoxycyclohexylamine hydrochloride, (50.8 kg) and NMP (360 kg) was heated to 125-130° C. until completion was achieved. The mixture was cooled to 20-30° C., and treated with 5% sodium chloride solution (5 vol) and EtOAc (8 vol). The aqueous layer was removed, and the organic layer was washed three times with 5% sodium chloride (3×5 vol) and once with water (5 vol). The organic layer was concentrated by vacuum distillation to a reduced volume, cooled to 25° C., and agitated at this temperature for 19 h. The slurry was filtered and the wet cake was washed with MTBE. The product was dried in a vacuum oven at to obtain ethyl 2-((5-bromo-3-(((trans)-4-methoxycyclohexyl)amino)pyrazin-2-yl)amino)acetate (44% yield). Alternatively, the reaction can be carried out using NMP (3× vol) and after workup and distillation to a reduced volume, the reaction mixture can be held at 50° C., seeded with a small amount of the target compound (0.02 equiv), treated with n-heptane (3× vol), cooled to 25° C. over 2 h, and aged at least 12 h. The solids can be collected by filtration, washing with a EtOAc/n-heptane mixture, and drying (75% yield).

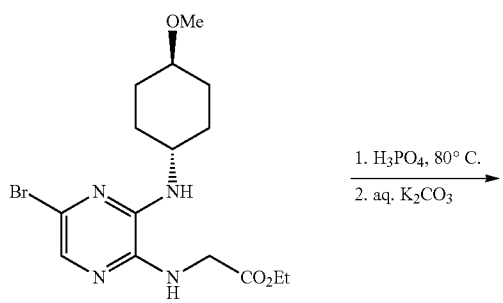
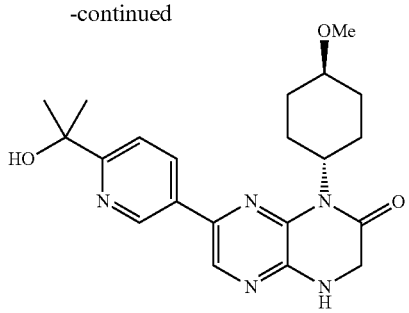

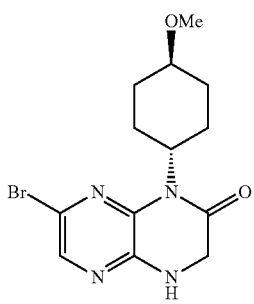

Ethyl 2-((5-bromo-3-(((trans)-4-methoxycyclohexyl)amino)pyrazin-2-yl)amino)acetate (35 kg) was treated with a 21% phosphoric acid solution (410 kg) at 80° C. until completion was achieved. The suspension was cooled to 30-35° C. and filtered, and the wet cake was washed with water (5× vol), charged to a reactor, and suspended in water (3× vol). The slurry was treated with 1M potassium carbonate solution (1 equiv), filtered and washed with water (2×5× vol). The product was dried at 50-55° C. in a vacuum oven to deliver 7-bromo-1-((trans)-4-methoxycyclohexyl)-3,4-dihydropyrazino[2,3-b]pyrazin-2(1H)-one (91% yield).

A mixture of 7-bromo-1-((trans)-4-methoxycyclohexyl)-3,4-dihydropyrazino[2,3-b]pyrazin-2(1H)-one (also having the chemical name 7-bromo-1-((trans)-4-methoxycyclohexyl)-3,4-dihydropyrazino[2,3-b]pyrazin-2(1H)-one) (27.7 kg), 2-(5-(4,4,5,5-tetramethyl-1,3,2-dioxaborolan-2-yl)pyridin-2-yl)propan-2-ol hydrochloride (26.3 kg) and PdCl$_2$(Amphos)$_2$ (137.6 g) in THF (122.7 kg) was combined with a solution of potassium carbonate (27.5 kg) in water (220 kg). The mixture was heated to reflux and held until reaction completion. The batch was cooled to 45° C., toluene (71.4 kg) was added, and the aqueous phase was removed. The organic solution was treated with aqueous potassium dihydrogen phosphate solution, SiliaBond® Thiol, and twice with activated carbon. The resulting organic solution was distilled under atmospheric pressure to a reduced volume and continuously distilled with toluene addition until a composition of ~15 wt % THF in toluene was reached. The batch was cooled to 25° C., filtered, and the solids were washed with toluene, and dried under vacuum to deliver Compound A as a light yellow solid (87% yield).

Alternatively, after reaction completion the batch can be treated with tert-butyl ether (MTBE), washed with aqueous potassium dihydrogen phosphate solution, treated with SiliaBond® Thiol, and activated carbon, followed by distillative solvent exchange to isopropanol under either atmospheric or reduced pressure to afford crystallization, followed by the addition of n-heptane, filtration and drying under vacuum to afford Compound A (90% yield). Without being limited by theory, it is thought that the distillative solvent exchange to isopropanol can avoid or reduce formation of a pinacol co-crystal, thus providing Compound A of higher purity.

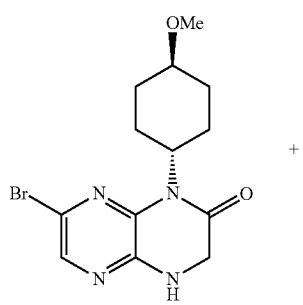

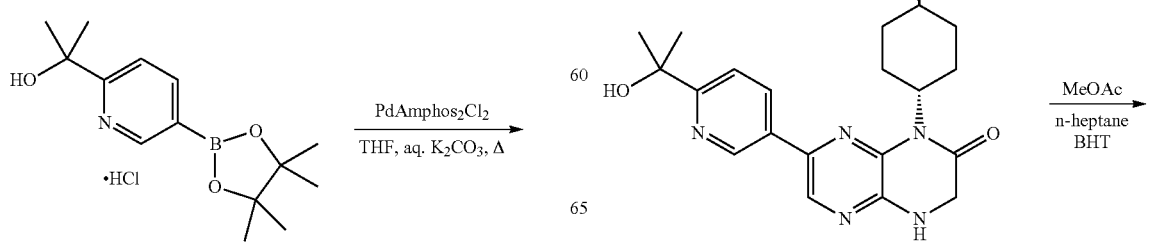

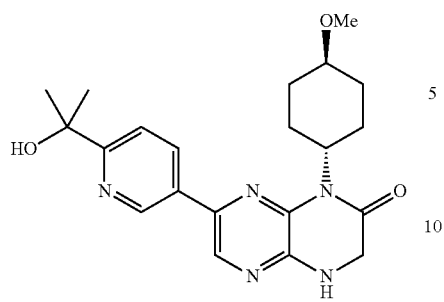

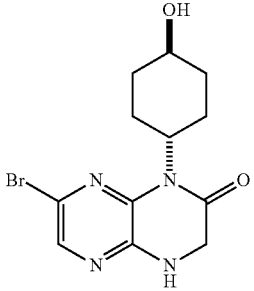

Compound A (27.1 kg), BHT, (270 g) and MeOAc (604 kg) were combined, heated to 50-55° C., and filtered. A slurry of small amount of Compound A (540 g) in MeOAc (2.6 kg) was added, and the batch was held for 1 h. The batch was distilled under vacuum to 10× vol, and treated with heptane while maintaining the batch temperature at 25-30° C. until the composition is 1:1 (v/v/) MeOAc/heptane. The batch was held at 20-25° C. for 14 h, filtered, and the wet cake was washed twice with 1:1 MeOAc/heptane and dried at 50-55° C. under vacuum to deliver Compound A (78% yield) as an off-white to light yellow solid. DSC confirmed the crystal Form A. $^1$H NMR (DMSO-$d_6$) was consistent with the assigned structure.

6.2.2 Large Scale Synthesis of Metabolite of Compound A

A metabolite of Compound A was prepared as follows:

A vessel was charged with 1 (2.15 kg), 2 (1.44 kg), and NMP (6.5 L), and the resulting slurry was agitated at 20-30° C. and treated with DIPEA (3.87 L). The batch was heated to 125-130° C., held for 20 hours until completion was achieved, cooled to 20-35° C., and transferred to a vessel containing a mixture of EtOAc (17.2 L) and 5% aq. NaCl (10.7 L). The batch was agitated for 10-15 minutes, allowed to settle for 10-15 minutes, and the aqueous layer was removed. The batch was washed an additional three times with 5% aq. NaCl (10.7 L) and once with water (10.7 L). The batch was distilled under reduced pressure (50-60° C.; 250-300 Torr) until reaching 2× volume. The resulting slurry was treated with n-heptane (6.3 L) while maintaining a batch temperature of 50-60° C. The batch was cooled to 20-30° C., held for 17 hours, and filtered. The filter cake was washed with n-heptane and dried at 50-60° C. under vacuum to afford 3 (66% yield) as a solid.

The solid 3 (1.56 kg) and a 10% aq. $H_3PO_4$ solution (16 L) were heated to 75-85° C., held for 15 hours, cooled to 20-30° C., and filtered. The filter cake was washed with water (5 L) and dried on the filter for 1 hour. The filter cake was charged to a vessel, treated with water (15 L), and agitated at 20-30° C. for 2 hours. The batch was filtered, washed with water (2×4.7 L), dried in a vacuum oven at 50-60° C. to obtain 4 (54% for two steps) as solid. MS: Calc: 327.0 [M+H]; Obsd: 309.0 [M-OH], 329.0 [M+3].

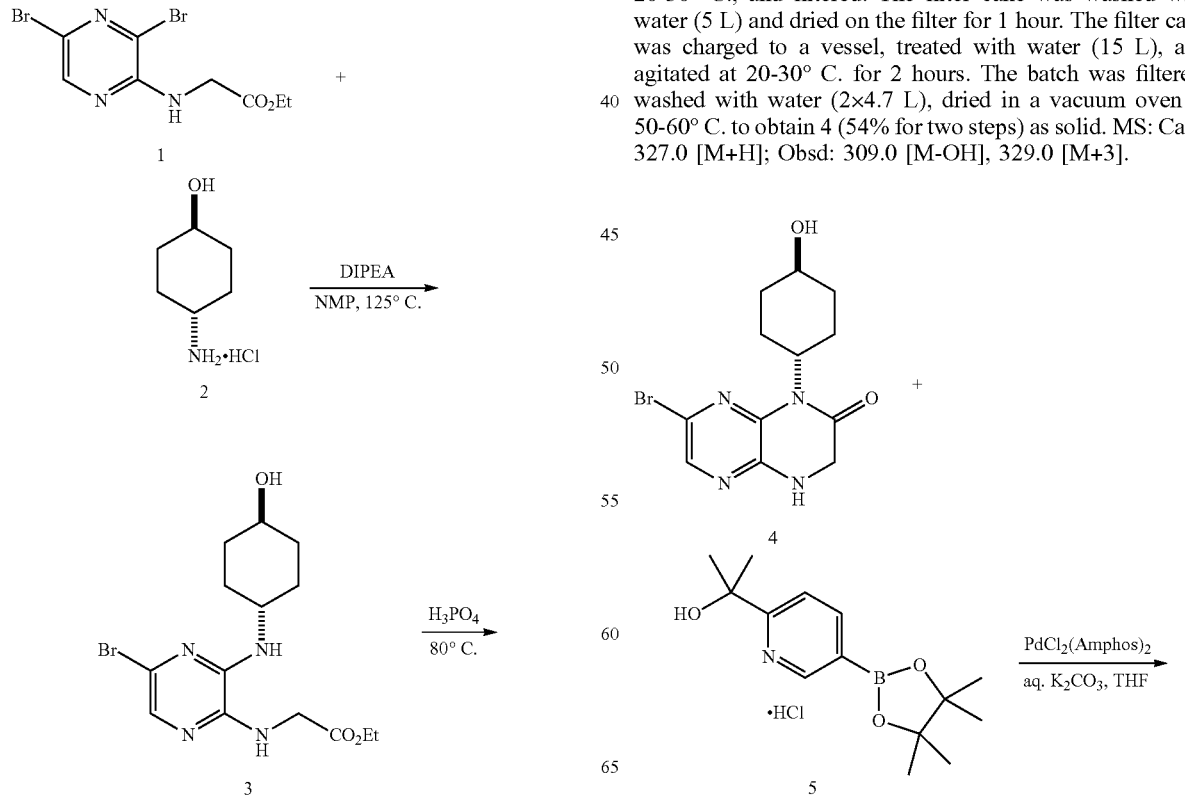

-continued

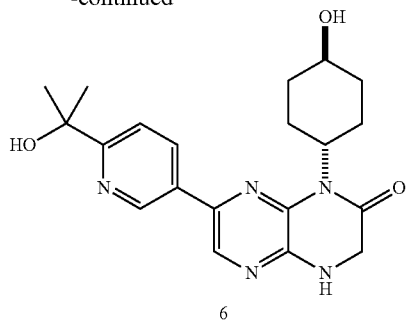

6

A vessel was charged with 4 (447 g), 5 (425 g), PdAmphos₂Cl₂ (0.00023 eq.), and THF (2.2 L) that had been sparged with N₂ for 30 min. The slurry was agitated and treated with a solution of K₂CO₃ (2.4 eq.) in water (3.6 L), that had been sparged with N₂ for 30 min. The batch was heated to reflux, held for 15 h, cooled to just below the reflux point, and an additional charge of PdAmphos₂Cl₂ (0.00046 eq.) was added. The mixture was heated to reflux, held for 20 h, cooled to 40-50° C., treated with toluene (447 mL), and the aqueous layer was removed. The batch was treated with toluene (447 mL) at which time precipitation of solids began. The batch was distilled under atmospheric pressure to 6× vol and distilled at constant volume with addition of toluene until the composition reached ~30% THF in toluene.

The supernatant was removed, and the remaining solids were treated with THF (447 mL), heated to 60-65° C., and treated with THF (447 mL). The batch was held at 60-65° C. for 30 minutes, cooled to 20-30° C. over 45 minutes, and aged for 15 hours at 20-30° C. The batch was treated with THF (447 mL) and filtered. The filter cake was dried under vacuum at 40-50° C. to obtain crude 6 (59% yield) as a solid. MS: Calcd: 384.2 [M+H]; Obsd: 384.2.

The THF filtrate was concentrated under reduced pressure, slurried in IPA (500 mL) for 4 hours and filtered. The filtered solids were dried under vacuum at 40-50° C. to obtain crude 6 (23% yield) as a solid. MS: Calcd: 384.2 [M+H]; Obsd: 384.2.

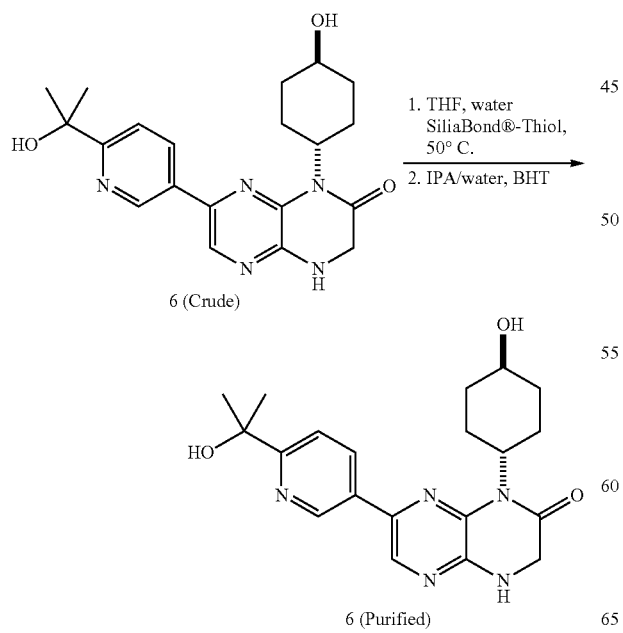

A vessel was charged with crude 6 (310 g), BHT (155 mg), SiliaBond® Thiol (47 g), THF (11.8 L), and water (620 mL) and agitated to form a slurry. The batch was heated to 50-55° C., held for 4 hours, cooled to 30-40° C., and filtered. The filtrate was charged to a vessel distilled under reduced pressure (27-30° C., 200 mmHg) until reaching 5-6× vol. The batch was cooled to 20-30° C., agitated for 2 hours, and filtered. The filter cake was washed with THF (300 mL) and dried under vacuum at 45-50° C. The resulting solid (153 g), BHT (75 mg), IPA (1.1 L), and water (380 mL), were combined and agitated to form a slurry. The slurry was heated at elevated temperature (reflux) for 18 h, cooled to 20-30° C., held for 3-4 hours, and filtered. The filter cake was dried at 50° C. under vacuum to deliver purified 6 (66% yield) as a solid. MS: Calcd: 384.2 [M+H]; Obsd: 384.2.

6.3 Synthesis of Isotopologues of Compound A 6.3.1 Synthesis of $^{14}C$ Enriched Compound A $^{14}C$-radiolabeled Compound A was prepared as follows.

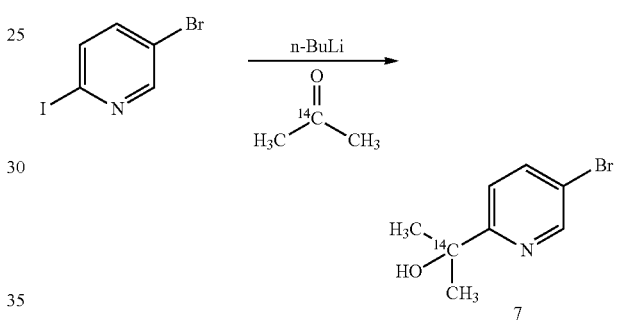

5-Bromo-2-iodopyridine (1 equiv) in DCM was cooled to −78° C. and treated sequentially with n-BuLi (1.05 equiv of 2.5M in hexane) and $^{14}C$-labeled acetone (3 equiv). The mixture was slowly warmed to ambient temperature, stirred for 30 min, and treated with water (10 mL). The organic layer was dried with Na₂SO₄, filtered, and concentrated under reduced pressure. The crude product was taken to the next step with no additional purification.

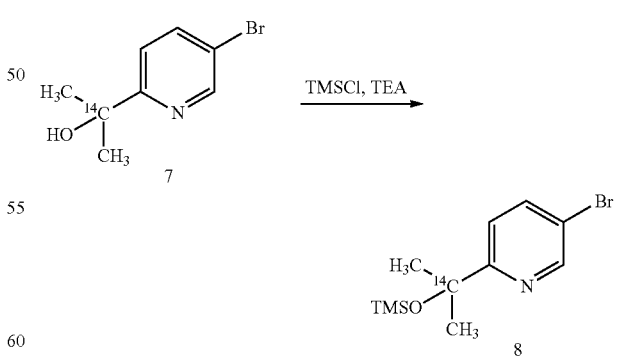

Crude 7 in DCM at ambient temperature was sequentially treated with TEA (3 equiv) and TMSCl (2 equiv) and stirred for 18 h. The reaction mixture was treated with saturated NaHCO₃ (15 mL), and extracted with DCM. The organic layer was dried with Na₂SO₄, filtered, and concentrated under reduce pressure. The oil was purified by column chromatography (5% EtOAc/hexane) to deliver 8 as an oil (52% over 2 steps).

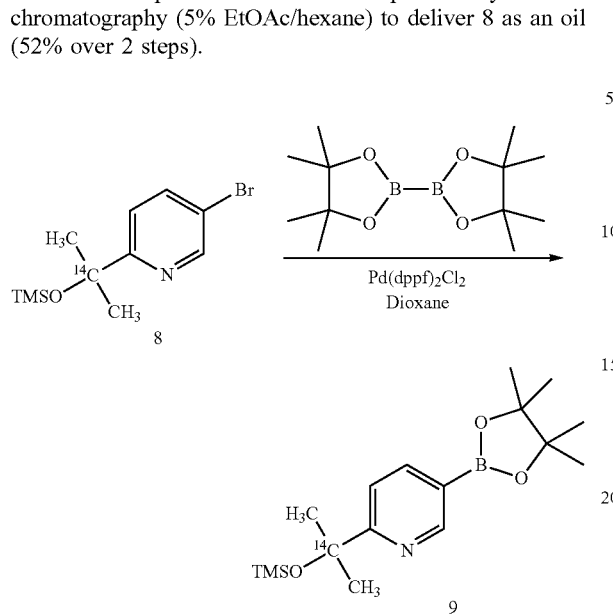

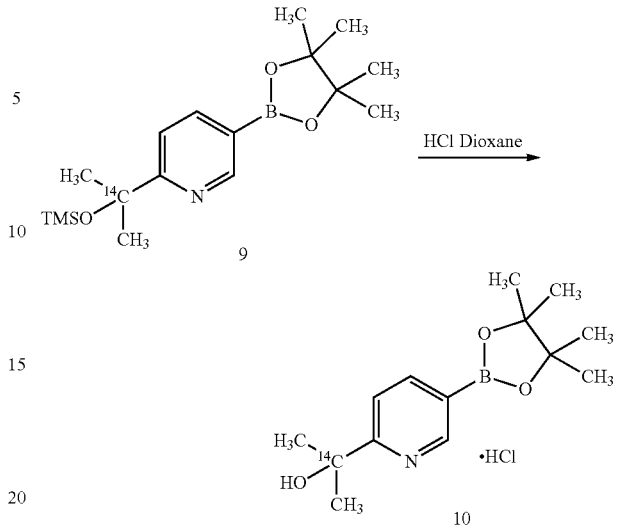

Compound 9 in 1,4-dioxane was treated with 4 M HCl in 1,4-dioxane (2 equiv) at ambient temperature and stirred for 2 h. The mixture was concentrated under a flow of $N_2$ to give an off white solid, which was treated with MTBE for 1 h and filtered to obtain Compound 10 as a solid (98% yield).

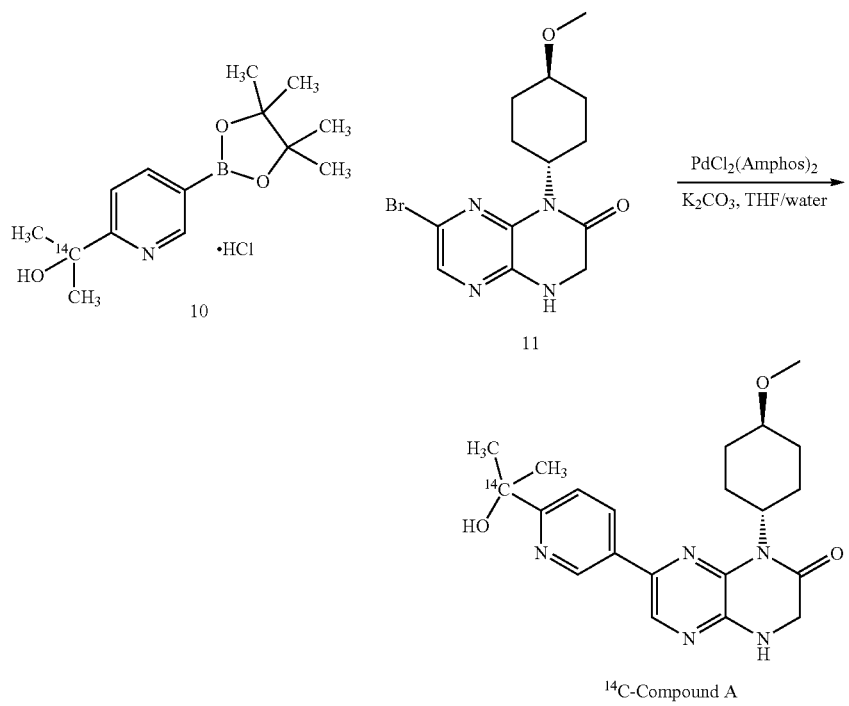

Compound 8, bis(pinacolato)diborane (1.1 equiv), KOAc (3 equiv), and PdCl$_2$(dppf)-DCM complex (0.03 equiv) were combined in 1,4-dioxane, heated to 90° C., and held for ~18 h. The mixture was cooled to ambient temperature, diluted with MTBE, filtered, and concentrated under reduced pressure. The crude material was purified by column chromatography (1:1 EtOAc:hexane) to obtain Compound 9 as a solid (27% yield).

Compound 10, Compound 11 (1.08 equiv), PdCl$_2$(Amphos)$_2$ (0.02 equiv), THF, and an aqueous K$_2$CO$_3$ solution (2.5 equiv K$_2$CO$_3$) were heated in a sealed tube at 70-75° C. for 16 h. The tube was cooled to 25° C., and the mixture was extracted with toluene and concentrated under reduced pressure. The crude oil was purified by column chromatography (1:1 THF/DCM) and isocratic semi-preparative HPLC. The isolated fractions were concentrated under reduced pressure, dissolved in EtOAc, dried with Na$_2$SO$_4$, filtered, and concentrated under reduced pressure. The material was dissolved in THF and concentrated under a flow of nitrogen followed by high vacuum. The isolated oil was treated with ACN and concentrated with a stream of $N_2$ to induce crystallization. The contents of were concentrated under high vacuum to obtain $^{14}$C-labeled Compound A as a solid.

Alternatively, 14C-Compound A can be prepared from 10 and 11 as follows:

Compound 10 and 11 (1.1 equiv), THF, and aqueous $K_2CO_3$ (2.5 equiv $K_2CO_3$), were combined with PdAmphos$_2$Cl$_2$ (0.02 equiv) and heated to 70-75° C. until reaction completion (about 18 h). The mixture was cooled, treated with EtOAc and brine and the layers separated. The organic layer was dried over $Na_2SO_4$, filtered, and concentrated to a residue. The residue was purified by column chromatography on silica gel (CH$_2$Cl$_2$:EtOAc 1:3; followed by MeOH:EtOAc 2:98) and concentrated to a residue. The residue was then purified by preparative HPLC using 0.015 M KH$_2$PO$_4$ and MeCN. The collected fractions were extracted with EtOAc, dried over $Na_2SO_4$, filtered, and concentrated to obtain $^{14}$C-labeled Compound A as a solid.

6.3.2 Synthesis of $^{13}$C Enriched Compound A $^{13}$C-labeled Compound A was prepared as follows.

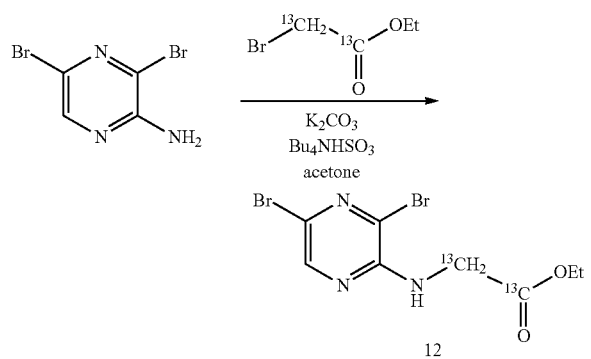

$K_2CO_3$ (1.5 eq) and ethyl bromoacetate-$^{13}C_2$ (1.3 eq) were added to a solution of 3,5-dibromopyrazin-2-amine (1.0 eq) in acetone (10× vol). The slurry was heated to 30° C., Bu$_4$NHSO$_4$ (0.074 eq) was added, and the mixture was stirred for 2 d at reflux. The reaction slurry was cooled to ambient temperature, filtered through celite, and the cake was washed with acetone (10 vol). The filtrate was concentrated under reduced pressure, dissolved in EtOAc (11.4 vol), and the organic phase was washed with water (2×3.2 vol) and saturated aqueous NaCl (2×3.2 vol). The combined aqueous phase was extracted with EtOAc, and the combined organic phase was dried over MgSO$_4$, filtered, and washed with EtOAc. Ecosorb-906 (0.11 wt) was added, and the mixture was stirred 13 h. The slurry was filtered washed with EtOAc, and the filtrate was concentrated under reduced pressure to a slurry to which was added a 2% EtOAc in heptane solution (7.9 vol). The slurry was filtered after stirring for 3 h at ambient temperature. The collected solid was washed with heptane (3 vol) and dried in a vacuum oven at 35° C. to provide (12) as a solid (57% yield). $^1$H NMR (CDCl$_3$, 300 MHz): δ=8.05 (s, 1H), 5.77 (br. s., 1H), 4.41 (t, J=5.7 Hz, 1H), 4.26 (qd, J=7.1, 3.0 Hz, 2H), 3.94 (t, 1H), 1.31 (t, J=7.1 Hz, 3H) ppm. LC/MS: Calculated: 340.9, Found: ES+ (M+1) 341.9.

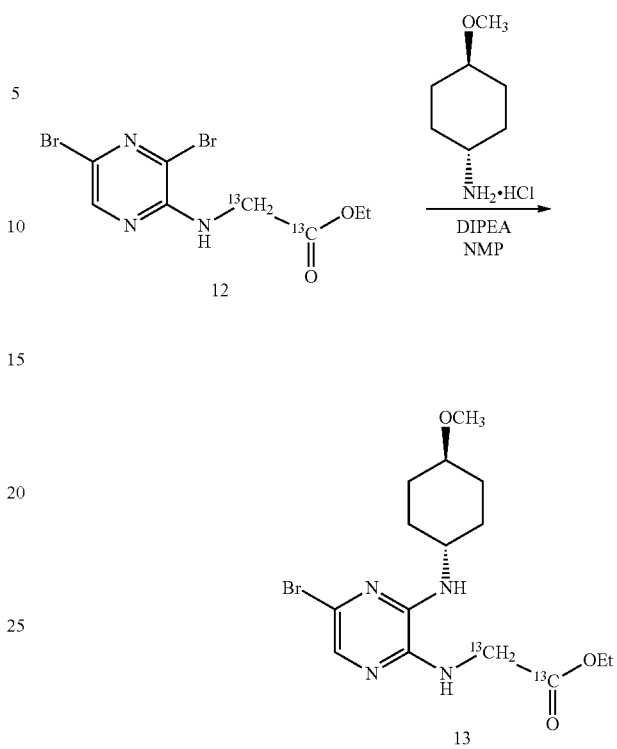

A reaction flask was sequentially charged with trans-4-methoxycyclohexanamine hydrochloride (1.5 eq), compound (12) (1.0 eq), NMP (5.0 vol) and DIPEA (3.5 eq). The solution was heated to 125° C. for 24 h and then cooled to 25° C. EtOAc (10 vol) and 5% aqueous NaCl (15 vol) were added, and the layers were separated. The organic layer was washed with a 5% aqueous NaCl (2×15 vol) and concentrated under reduced pressure. The residue was treated with MTBE (4.0 vol), stirred 1 hour at ambient temperature and filtered. The solid was washed with MTBE and dried in a vacuum oven at 20-30° C. to provide (13) as a solid (61% yield). $^1$H NMR (DMSO-d$_6$, 300 MHz): δ=7.21 (s, 1H), 6.98 (t, J=4.8 Hz, 1H), 6.48 (d, J=6.8 Hz, 1H), 4.26 (t, J=5.5 Hz, 1H), 4.09 (qd, J=7.1, 3.1 Hz, 2H), 3.79 (t, J=5.6 Hz, 1H), 3.73 (br. s., 1H), 3.25 (s, 3H), 3.05-3.22 (m, 1H), 1.89-2.14 (m, 4H), 1.21-1.37 (m, 4H), 1.18 (t, J=7.1 Hz, 3H) ppm. LC/MS: Calculated: 388.1; Found ES+ 389.1 (M+1) 391.1 (M+1+2).

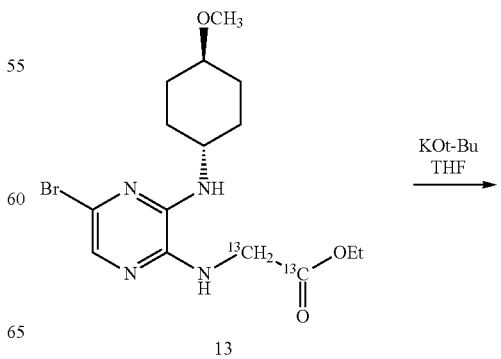

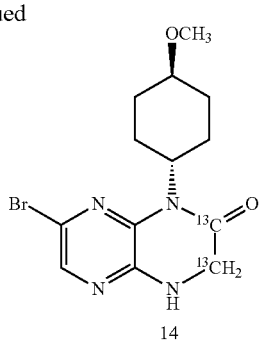

14

A 1 M solution of KOt-Bu in THF (0.20 eq) was added to a stirred mixture of (13) (1.0 eq) in THF (8.0 vol) over 4 min at ambient temperature. The mixture was stirred for 2 h and quenched into a 9% aqueous $KH_2PO_4$ solution (4.0 vol). IPAc (5 vol) was added, and the layers were separated. The organic layer was washed with 5% aqueous NaCl (4 vol) and concentrated under reduced pressure with azeotropic removal of THF with IPAc. The solid was dissolved in IPAc (10 vol), passed through silica gel, eluted with IPAc, and concentrated under reduced pressure. The solids were dried at 20-25° C. under vacuum to afford (14) as a solid (70% yield). $^1$H NMR (DMSO-$d_6$, 300 MHz): δ=7.70 (s, 1H), 7.57 (d, J=7.6 Hz, 1H), 4.55-4.77 (m, 1H), 4.22-4.36 (m, 1H), 3.76-3.86 (m, 1H), 3.25 (s, 3H), 3.04-3.19 (m, 1H), 2.33-2.47 (m, 2H), 1.98-2.20 (m, 2H), 1.61 (d, J=11.1 Hz, 2H), 1.07-1.33 (m, 3H). LC/MS: Calculated:342.1; found: ES+ (M+1) 343.0; (M+2+1) 345.1.

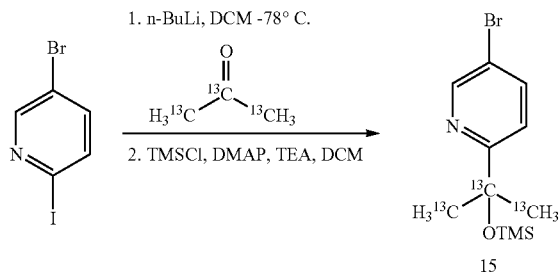

A mixture of 5-bromo-2-iodopyridine (1.0 eq) in DCM (12 vol) was cooled to −78° C. and treated with n-BuLi (2.5 M solution in hexanes, 1.0 eq). The mixture was treated with acetone-$^{13}C_3$ (10 eq) while maintaining the temperature below −55° C., cooled to −78° C., and held for 30 min. The reaction mixture was warmed to −40° C. over 1 h, warmed to −15° C., quenched with water (10 vol), warmed to 10° C. over 10 minutes, and the layers were separated. The aqueous phase was extracted with DCM, and the organic layers were washed with water, saturated aqueous NaCl, dried over $Na_2SO_4$, and filtered. The cake was washed with DCM, and the filtrate was concentrated under reduced pressure to obtain an oil. The oil was dissolved in DCM (12.0 vol), and DMAP (0.05 eq) and TEA (3.0 eq) were added. The solution was cooled to 0-5° C. and treated with TMSCl (2.5 eq) over 15 minutes keeping the temperature below 5° C. The mixture was stirred for 1.5 h, quenched with 5% aqueous $NaHCO_3$ (6.5 vol) maintaining the temperature at 10-15° C.

The layers were separated, and the organic layer was washed with water and saturated aqueous NaCl. The organic layer was dried over $Na_2SO_4$, filtered, and concentrated under reduced pressure. Hexanes (2×9 vol) were charged and the mixture was concentrated under reduced pressure to afford an oil. The oil was purified by column chromatography on silica gel (5% EtOAc in hexanes) to afford (15) (63% yield). $^1$H NMR (MeOD, 300 MHz): δ=8.38 (d, J=2.1 Hz, 1H), 7.78 (dd, J=8.6, 2.4 Hz, 1H), 7.48 (d, J=8.5 Hz, 1H), 1.61-1.70 (m, 3H), 1.18-1.27 (m, 3H), 0.00 (s, 9H).

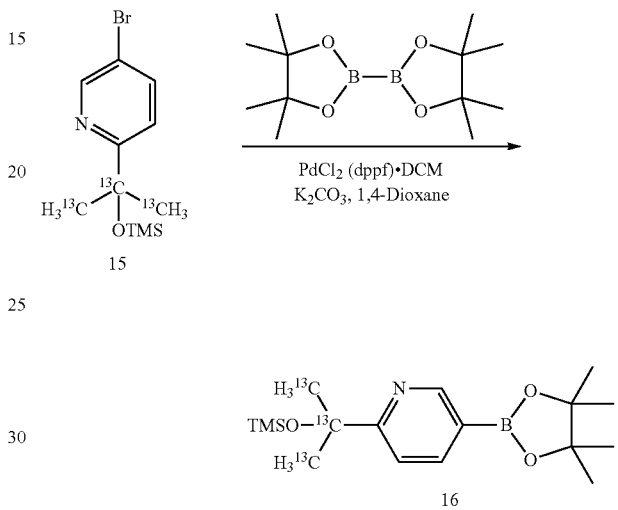

Compound (15) (1.0 eq), bis(pinacolato)diboron (1.0 eq) and KOAc (3.0 eq) were stirred in 1,4-dioxane (8 vol) and treated with $PdCl_2$(dppf)*DCM complex (0.015 eq). The mixture was heated to 90-95° C. and stirred for 4.5 h. The reaction mixture was cooled to 20-25° C. over 1 h, diluted with MTBE (5 vol), filtered on a celite plug, and the cake was washed with MTBE. The filtrate was washed with water, and the aqueous layer was extracted with MTBE. The organic layers were washed with saturated aqueous NaCl, dried over $Na_2SO_4$, and filtered. The filtrate was concentrated under reduced pressure to an oil, treated with MTBE and concentrated to an oil three times. The oil was dried under high vacuum at 20-25° C. to afford a solid. This solid was dissolved in THF (7.5 vol), treated with SiliaBond® Thiol (1× wt), stirred for 20 min, filtered, and the cake washed with THF. The filtrate was concentrated under reduced pressure to afford a solid, which was dried under high vacuum. The solid was dissolved in MTBE, treated with silica gel (1× wt), and concentrated under reduced pressure. The silica gel containing the crude product was purified by column chromatography on silica gel (eluent: MTBE) and concentrated under reduced pressure to obtain the product (16) as a solid (72% yield). $^1$H NMR (CDCl$_3$, 300 MHz): δ=8.71 (s, 1H), 7.90 (d, J=7.6 Hz, 1H), 7.45-7.55 (m, 1H), 1.64-1.72 (m, 3H), 1.25 (d, J=4.0 Hz, 3H), 1.20 (s, 12H), 1.13 (s, 1H), 1.10 (s, 1H), 0.00 (s, 9H) ppm. MS Calculated: 410.2, found ES+ 257 (as boric acid).

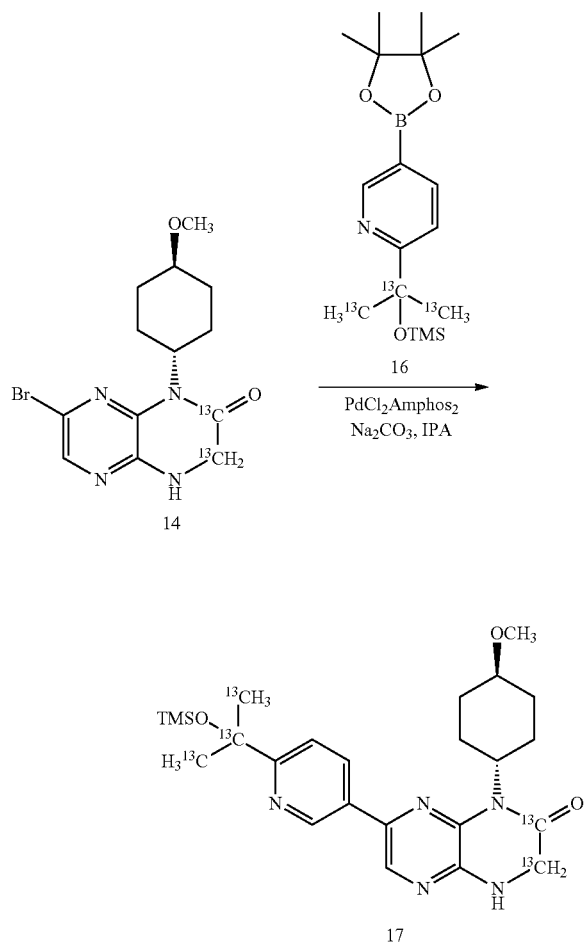

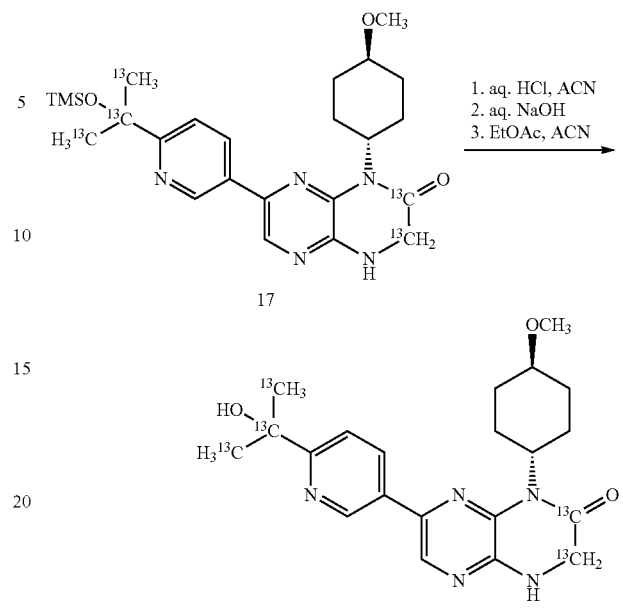

A slurry of compound (14) (1.0 eq) and compound (16) (1.20 eq) in IPA (10 vol) was treated with 2 M aqueous Na$_2$CO$_3$ (2.5 eq) and PdCl$_2$Amphos$_2$ (0.0135 eq). The reaction mixture was heated to 70° C., stirred for 2 h, cooled to ambient temperature, and treated with EtOAc (38 vol) and water (13 vol). The organic layer was washed with 2% aqueous NaCl to reach pH 6 and concentrated under reduced pressure. EtOAc (13 vol) was added to the concentrate, the aqueous layer was extracted with EtOAc, and the combined organic phases were concentrated under reduced pressure. The residue was dissolved in EtOAc and purified by column chromatography on silica gel (EtOAc/hexanes), concentrated under reduced pressure and cooled to 0° C. The solids were dissolved in IPA, concentrated under reduced pressure, and dried under high vacuum to provide (17) as a solid (73% yield). $^1$H NMR (DMSO-d$_6$, 300 MHz): δ=9.03 (d, J=1.9 Hz, 1H), 8.28 (s, 1H), 8.25 (dd, J=8.4, 2.2 Hz, 1H), 7.68 (d, J=8.3 Hz, 1H), 7.61 (d, J=7.7 Hz, 1H), 4.81-4.99 (m, J=11.8, 7.9, 3.9, 3.9 Hz, 1H), 4.35 (d, J=6.2 Hz, 1H), 3.88 (d, J=6.4 Hz, 1H), 3.25-3.31 (m, 3H), 3.13-3.24 (m, 1H), 2.52-2.67 (m, 2H), 2.13 (d, J=10.4 Hz, 2H), 1.79 (d, J=3.8 Hz, 3H), 1.67 (d, J=10.6 Hz, 2H), 1.36 (d, J=4.0 Hz, 3H), 1.18-1.33 (m, 2H) 0.06-0.18 (m, 9H). Calculated 402.2 (−TMS+1); ES+ (M+2−TMS) 403.2.

A slurry of (17) (1.0 eq), ACN (10.0 vol) and water (2.5 vol) was treated with 1 M HCl (0.185 eq) for 20 h and neutralized to pH 4-6 with 1 M NaOH. The mixture was treated with water (50 vol) and EtOAc (75 vol) and the layers were separated. The aqueous layer was extracted with EtOAc and the combined organic layers were concentrated under reduced pressure. The residue was again treated with water (50 vol) and EtOAc (75 vol) and the layers were separated and the aqueous layer extracted with additional EtOAc. The organic fractions were concentrated under reduced pressure with replacement of EtOAc by ACN addition. The residue was dissolved in ACN (2.5 vol), and a small amount (0.02 eq) of the target product was added followed by additional ACN (0.8 vol). The solids were filtered, washed with ACN, and dried under a N$_2$ stream. The solid was dissolved in EtOAc and silica gel (1.9 wt) was added and the mixture concentrated under reduced pressure. The silica gel containing the crude product was purified by column chromatography on silica gel (eluent: EtOAc) and concentrated under reduced pressure with replacement of EtOAc by ACN addition. The material was dried under high vacuum, slurried in ACN (2.5 vol) for 20 h, and filtered to obtain (18) as a solid (34% yield). $^1$H NMR (DMSO-d$_6$, 300 MHz): δ=9.02 (d, J=1.9 Hz, 1H), 8.28 (s, 1H), 8.23 (dd, J=8.3, 2.1 Hz, 1H), 7.73 (d, J=8.5 Hz, 1H), 7.59 (d, J=7.7 Hz, 1H), 5.24 (d, J=2.3 Hz, 1H), 4.80-5.00 (m, J=11.9, 8.0, 3.9, 3.9 Hz, 1H), 4.36 (d, J=6.2 Hz, 1H), 3.88 (d, J=6.2 Hz, 1H), 3.25-3.31 (m, 3H), 3.14-3.25 (m, 1H), 2.53-2.67 (m, 2H), 2.14 (d, J=10.4 Hz, 2H), 1.68 (d, J=4.0 Hz, 5H), 1.18-1.35 (m, 5H). $^{13}$C NMR (DMSO-d$_6$, 75 MHz): δ=168.7, 168.0, 167.0, 166.6, 166.3, 165.7, 164.9, 162.9, 162.1, 157.4, 156.9, 156.4, 155.9, 154.9, 145.7, 145.7, 145.0, 137.0, 135.6, 133.6, 133.3, 131.3, 119.9, 119.8, 86.4, 85.6, 79.2, 76.5, 75.7, 74.3, 74.0, 73.8, 73.5, 73.2, 73.0, 56.3, 53.3, 47.6, 47.3, 47.0, 41.6, 41.3, 41.0, 40.7, 40.5, 40.2, 39.9, 32.5, 32.1, 31.8, 31.6, 31.0, 27.1. Calculated 402.2, found ES+ (M+1) 403.2.

6.3.3 Synthesis of $^{13}C$ Enriched Metabolite of Compound A $^{13}C_5$-labeled metabolite of Compound A was prepared as follows.

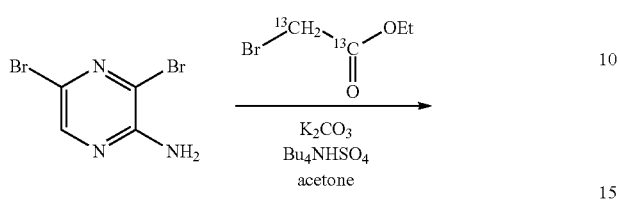

A slurry of 3,5-dibromopyrazin-2-amine (1 eq) in acetone (10 vol) was treated with $K_2CO_3$ (0.8× wt) and ethyl bromoacetate-$^{13}C_2$ (0.87× wt) were added, and the mixture was heated to 30° C. $Bu_4NHSO_4$ (0.1× wt) was added, and the mixture was stirred for 46 h at reflux. Additional ethyl bromoacetate-$^{13}C_2$ was added in portions and the mixture was held at reflux until completion was achieved (~24 h). The reaction mixture was cooled to 20-25° C., filtered, and the filter cake was washed twice with acetone. The filtrate was concentrated under reduced pressure, dissolved in EtOAc, washed twice with water and then with a 5% aqueous NaCl. The combined aqueous washes were extracted with EtOAc, and the combined organic fractions were treated with $MgSO_4$ (0.3× wt) and Ecosorb C-906 (0.1× wt) for 13 h at 30° C. The mixture was cooled to 20° C. and filtered. The collected solids were washed twice with EtOAc, and the filtrate was concentrated to a solid which was dissolved in EtOAc (0.9 vol) and treated with heptane (5.7 volumes) over 40 min at 20-25° C. The suspension was stirred for 4 h and filtered. The isolated solids were washed with heptane and dried under reduced pressure at 35-40° C. to provide 11.8 g of (12) as a solid (46% yield). LC/MS: Calculated [M+1] 342.3; Observed 342, 344.

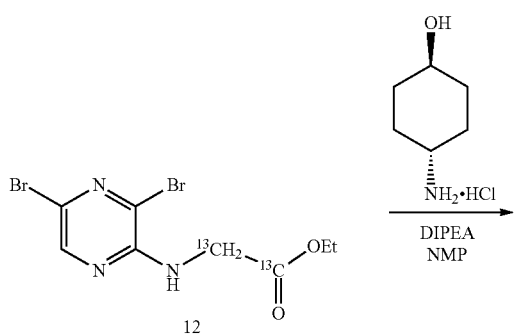

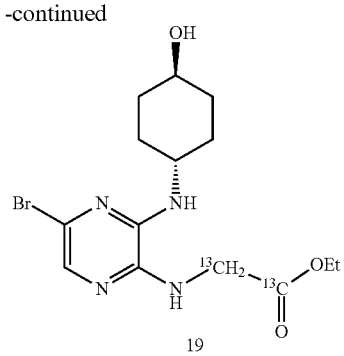

A slurry of compound 12 (1 eq) and trans-4-aminocyclohexanol hydrochloride (1.5 eq) in NMP (5 vol) at ambient temperature was treated with DIPEA (3.5 eq). The mixture was heated to 125-130° C. and held for 18 h. The solution was cooled to 20-25° C., treated with EtOAc (10 vol), and washed three times with 5% aqueous NaCl and once with water. The solution was concentrated under reduced pressure to 2 vol and the slurry was stirred for 18 h at ambient temperature. The solids were collected by filtration and dried to obtain compound (19) (24% yield). The filtrate was concentrated under reduced pressure, stirred for 18 h at ambient temperature, treated with EtOAc (1-2 vol) and filtered. The solids were dried under reduced pressure to obtain compound (19) (14% yield). LC/MS: Calculated [M+1] 375, 377; Observed 375, 377.

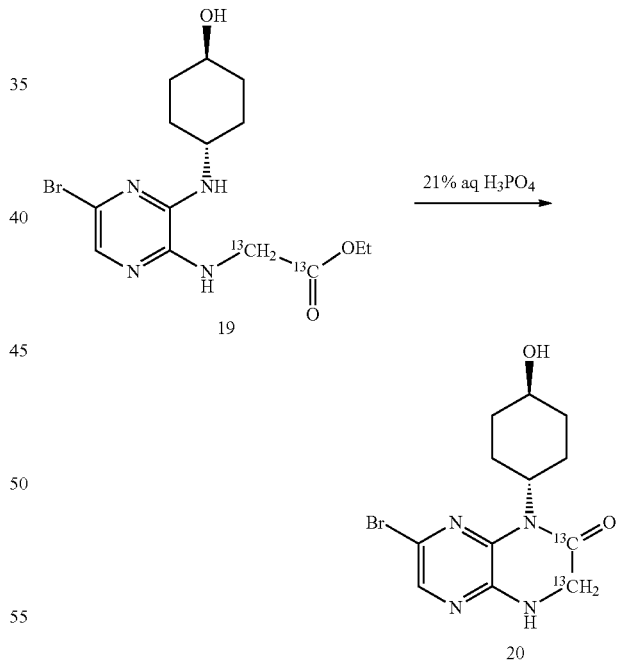

Compound (19) (1× wt) and a 21% $H_3PO_4$ solution (10 vol) were combined at ambient temperature and heated to 75-80° C. and stirred for 16 h. The batch was cooled to 20-25° C. and then filtered, and the filter cake was washed with water. The solid was suspended in water (10 vol) and stirred for 2 h at 20-25° C. The product was filtered, washed twice with water, and dried under reduced pressure at 45-50° C. (20) as a solid (65% yield). LC/MS: Calculated [M+1] 329, 331; Observed 329, 331.

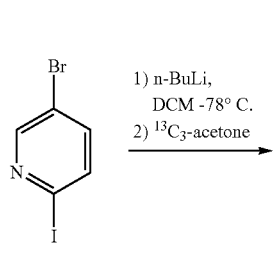

5-bromo-2-iodopyridine (1.0 eq) in DCM (12 vol) was cooled to −78° C. and treated with n-BuLi (1.4 vol of 2.5 M in hexanes) over 45 min. After 40 min, $^{13}C_3$-acetone (2.0 eq) was added over 50 minutes keeping the reaction mixture below −70° C. The mixture was stirred for 2 h below −70° C., warmed to −14° C. over 2 h, quenched with water (10 vol) between −15° and 10° C., and warmed to 10° C. The aqueous layer was extracted with DCM, and the combined organic layers were washed with water and saturated aqueous NaCl, dried over MgSO$_4$, filtered, and washed with DCM. The filtrate was concentrated under reduced pressure to obtain (21) as a liquid (62% yield). LC/MS: Calculated [M+1] 219, 221; Observed 219, 221.

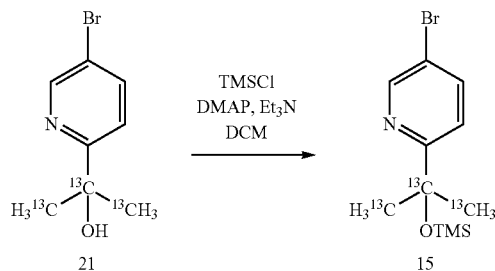

A solution of compound (21) (1 eq) in DCM (395 mL) was treated with DMAP (0.01 eq) and the solution was cooled to 0° C. TEA (1 eq) and TMSCl (1.5 eq) were added and the reaction mixture was stirred at 0-5° C. for 2 h, quenched by addition of saturated aqueous NaHCO3 (2.3 vol) and water (2.3 vol). DCM was added and the layers were separated. The organic layer was washed with water and saturated aqueous NaCl, dried over MgSO4, and filtered. The cake was rinsed with DCM and the filtrate was concentrated under reduced pressure, treated with hexanes, and concentrated under reduce pressure to obtain crude (15). The crude product was purified by column chromatography on silica gel (eluent: 5% EtOAc in hexanes) and concentrated to a residue. The residue was treated with hexanes and concentrated to an oil to provide compound (15) as an oil (61% yield). LC/MS: Calculated [M+1] 291, 293; Observed 291, 293. $^1$H NMR (CDCl$_3$, 300 MHz): δ=8.39 (d, J=2.1 Hz, 1H), 7.61 (dd, J=2.3, 8.5 Hz, 1H), 7.41 (d, J=8.5 Hz, 1H), 1.57-1.73 and 1.17-1.28 (2 m, 6H, 13CH3), 0.00 (s, 9H). $^{13}$C NMR (CDCl$_3$, 75 MHz) δ=164.63 (d, JC-C=6 Hz), 146.57 (d, JC-C=6 Hz), 136.44 (d, JC-C=2 Hz), 118.48 (d, JC-C=4 Hz), 115.94, 74.59 (t, JC-C=39 Hz), 28.80 (d, JC-C=39 Hz), 0.50.

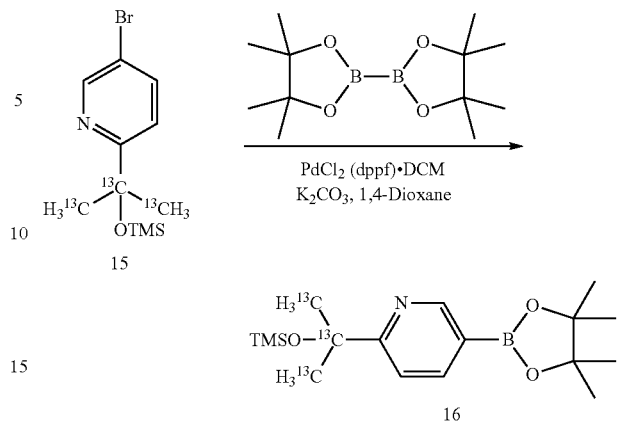

A solution of compound (15) (1 eq) in 1,4-dioxane (8 vol) was treated with KOAc (2.2 eq), bis(pinacolato)diboron (1 eq), and PdCl$_2$(dppf)*DCM complex (0.02 eq). The contents were heated to reflux, held for 4 h, cooled to ambient temperature and treated with MTBE (10 vol). The slurry was filtered and the filter cake was washed with MTBE. The filtrate was passed through a 0.45 mm filter, transferred to a separatory funnel, and washed with water. The aqueous phase was extracted with MTBE and treated with aqueous NaCl. The combined organic extracts were washed with saturated aqueous NaCl, dried over MgSO$_4$, and filtered. The filtrate was concentrated under reduced pressure. The residue was dissolved in ACN (1.1 vol) at 45° C., and transferred with ACN (3.9 vol) to a flask. The crude product was heated to 40-50° C., cooled to ambient temperature, agitated for 14.5 h, cooled to 0-5° C., and stirred for 2 h. The product was filtered, washed with cold ACN, and dried under vacuum at 40-55° C. to provide (16) as a solid (65% yield). $^1$H NMR (DMSO-d$_6$, 300 MHz): δ=9.03 (d, J=1.9 Hz, 1H), 8.28 (s, 1H), 8.25 (dd, J=8.4, 2.2 Hz, 1H), 7.68 (d, J=8.3 Hz, 1H), 7.61 (d, J=7.7 Hz, 1H), 4.81-4.99 (m, J=11.8, 7.9, 3.9, 3.9 Hz, 1H), 4.35 (d, J=6.2 Hz, 1H), 3.88 (d, J=6.4 Hz, 1H), 3.25-3.31 (m, 3H), 3.13-3.24 (m, 1H), 2.52-2.67 (m, 2H), 2.13 (d, J=10.4 Hz, 2H), 1.79 (d, J=3.8 Hz, 3H), 1.67 (d, J=10.6 Hz, 2H), 1.36 (d, J=4.0 Hz, 3H), 1.18-1.33 (m, 2H), 0.06-0.18 (m, 9H). $^1$H NMR (CDCl$_3$, 300 MHz): δ=8.71 (s, 1H), 7.89 (dd, J=0.8, 7.9 Hz, 1H), 7.49 (d, J=7.7 Hz, 1H), 1.61-1.75 and 1.23-1.32 (2 m, 6H, 13CH3), 1.21 (s, 12H), 0.00 (s, 9H). $^{13}$C NMR (CDCl$_3$, 75 MHz) δ=168.76, 151.71 (d, JC-C=6 Hz), 140.21, 115.97 (d, JC-C=4 Hz), 81.55, 74.69 (t, JC-C=39 Hz), 28.60 (d, JC-C=39 Hz), 22.41, 0.087. LC/MS: LC/MS: Calculated [M+1] 339.2; Observed 257.2 (as boric acid).

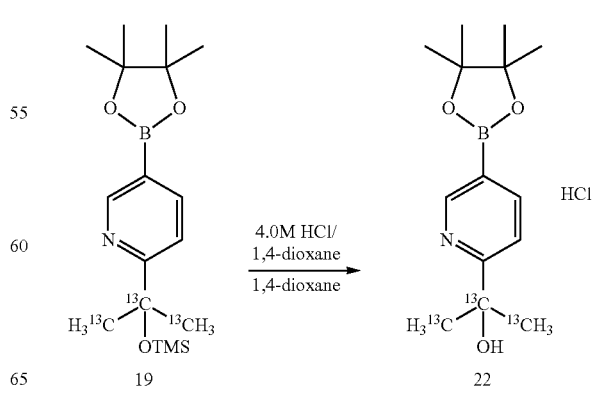

A solution of (16) (1 eq) in 1,4-dioxane (4 vol) was cooled to 15-20° C. and treated with 4 M HCl in 1,4-dioxane (2.1 eq). The slurry was treated with heptane (3.75 vol), cooled to 0-5° C., stirred for 1-2 h, and filtered. The product was washed with heptane and dried under vacuum at 50-60° C. to obtain (22) as a solid (94% yield). $^1$H NMR (CDCl$_3$, 300 MHz): δ=16.56 (br. s., 1H), 9.05 (s, 1H), 8.54 (d, J=7.9 Hz, 1H), 7.78 (dd, J=1.4, 8.0 Hz, 1H), 4.1-6.3 (br. s., 1H), 1.95-1.98 and 1.52-1.56 (2 m, 6H, 13CH3), 1.30 (s, 12H). $^{13}$C NMR (CDCl$_3$, 75 MHz): δ=164.79 (d, JC-C=47 Hz), 150.91 (d, JC-C=2.4 Hz), 146.50, 122.26 (d, JC-C=2.8 Hz), 85.66, 71.92 (t, JC-C=38 Hz), 29.89 (d, JC-C=38 Hz), 24.83. LC/MS: Calculated [M+1] 303; Observed 185 (as boric acid).

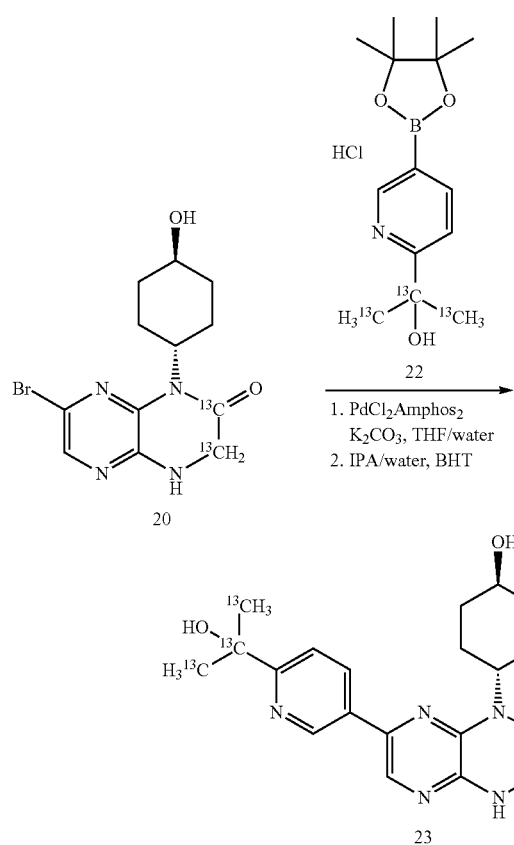

Compound (20) (1 eq), Compound (22) (1.1 eq), PdCl$_2$Amphos$_2$ (0.009 eq), and THF (5 vol) were combined and treated with a solution of K$_2$CO$_3$ (2.1 eq) in water (3.75 vol). The mixture was heated to reflux, held for 6 h, cooled to ambient temperature, stirred for 11 h, and filtered. The filter cake was washed twice with 1 vol of THF/water (5:8) and the filtrate was diluted with THF (6.75 vol). The filtrate was heated to 40-45° C. and treated with toluene (6.75 vol). The organic layer was washed with a solution of KH$_2$PO$_4$ in water (0.04 w/w) and the layers were separated. The organic layer was heated to 40-45° C. and treated with SiliaBond® Thiol for 2 h. The slurry was cooled to ambient temperature, filtered, and the filter cake was washed with THF. The filtrate was treated with activated carbon (decolorizing) for 4 h at ambient temperature, filtered, and the filter cake was washed with THF. The filtrate was concentrated under reduced pressure, dissolved in DCM, and concentrated under reduce pressure. The residue was dried under vacuum, treated with THF, heated to 40-45° C., and treated with silica gel. The slurry was concentrated under reduced pressure and the silica gel containing the crude product was purified by column chromatography on silica gel (eluent 0-41% THF in DCM), concentrated under reduced pressure, and dried under vacuum at 30-40° C. to obtain crude (23). The crude (23) and BHT (0.0005× wt) were treated with IPA/water (1:1.65), heated to 60° C., held for 1 h, cooled to ambient temperature, and held for 16 h. The slurry was heated to 50-60° C., treated with IPA (0.8 vol) and water (23 vol). The slurry was cooled to ambient temperature and filtered. The product was washed with IPA/water (10:90) and dried under vacuum at 50-60° C. to afford (23) as a solid (85% yield). $^1$H NMR (CDCl$_3$, 300 MHz): δ=9.03 (d, J=1.9 Hz, 1H), 8.27 (s, 1H), 8.23 (dd, J=2.1, 8.3 Hz, 1H), 7.72 (d, J=8.3 Hz, 1H), 7.59 (d, J=7.6 Hz, 1H), 5.23 (m, 1H), 4.81-4.92 (m, 1H), 4.65 (d, J=4.3 Hz, 1H), 4.36 (d, J=6.4 Hz, 1H), 3.88 (d, J=6.2 Hz, 1H), 3.41-3.57 (m, 1H), 2.53-2.71 (m, 2H), 1.95 (d, J=10.4 Hz, 2H), 1.66-1.69 and 1.24-1.27 (2 m, 6H, 13CH3), 1.29-1.37 (m, 2H). $^{13}$C NMR (CDCl$_3$, 75 MHz): δ=165.34 (d, JC-C=52 Hz), 144.46 (d, JC-C=5.6 Hz), 143.74 (d, JC-C=2 Hz), 135.78, 134.28, 132.28, 132.01, 130.02, 118.54 (d, JC-C=42 Hz), 72.18 (d, JC-C=38 Hz), 68.54, 52.03, 45.85 (d, JC-C=52 Hz), 35.09, 30.53, (d, JC-C=39 Hz), 26.11. LC/MS: Calculated [M+1] 388; Observed 389.

6.3.4 Synthesis of $^2$H Enriched Compound A

Deuterium-enriched Compound A can be prepared as follows.

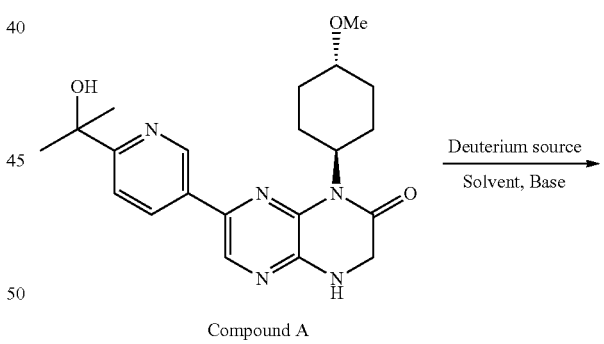

Compound A

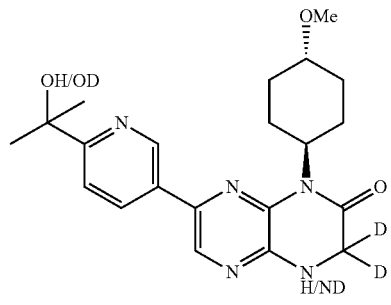

24

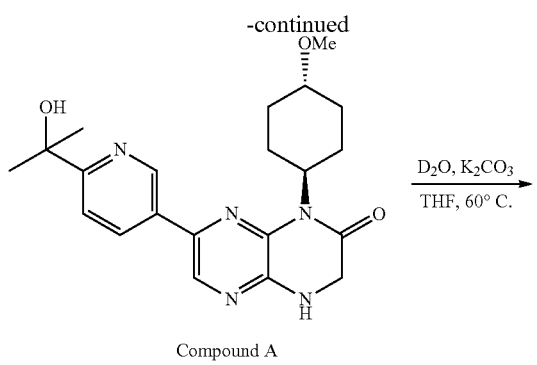

Compound A

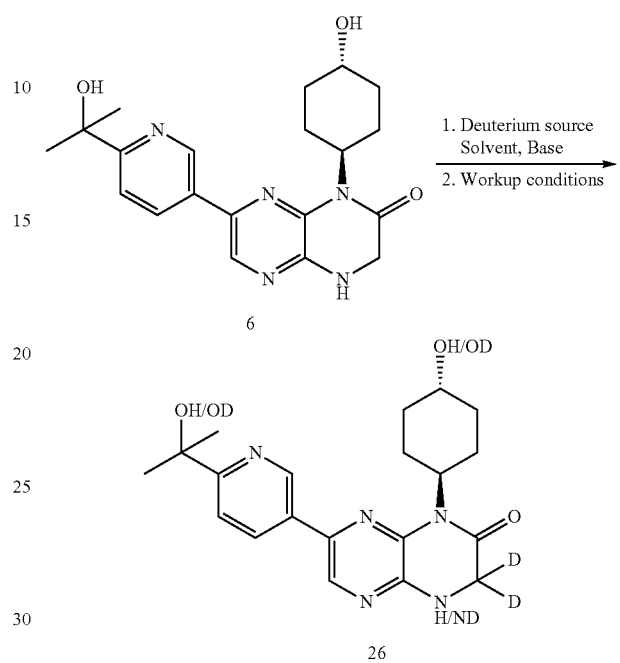

Compound 24 can be made using the route above wherein all of the exchangeable protons are replaced with deuterium. Starting with Compound A, the acidic protons can be exchanged in the presence of base (such as sodium tert-butoxide, potassium carbonate and 1,8-diazabicyclo[5,4,0]undec-7-ene) and a deuterium source (such as tert-BuOD, MeOD, EtOD, iPrOD, AcOD, D₂O) to give Compound 24. A solvent (such as tetrahydrofuran, dimethylformamide, or dimethylsulfoxide) can be used to facilitate the reaction. The hydrogen isotopes on the alcohol and the secondary amine could be either hydrogen or deuterium depending on the workup. A workup solvent with an exchangeable proton (such as H$_2$O, MeOH or EtOH) will provide 25, while a workup solvent with an exchangeable deuterium (e.g., D$_2$O, MeOD, EtOD) will afford 24.

For example, Compound A (10 g, 25.2 mmol) was treated with K$_2$CO$_3$ (3.48 g, 25.2 mmol) in 20% THF/D$_2$O at 50-60° C. for 15 h. After cooling to room temperature, the mixture was extracted with 2-Me-THF, and the organic layer was washed 3 times with water to allow proton exchange of the alcohol and the pyrazine groups. The organic layer was concentrated to a crude oil and crystallization from IPA/water to afford Compound 25 (7.6 g, 76%) as an off-white solid; $^1$H NMR (300 MHz, CDCl$_3$) δ 9.02 (d, J=1.5 Hz, 1H), 8.27-8.05 (m, 2H), 7.49 (d, J=8.3 Hz, 1H), 5.51 (s, 1H), 5.15-4.97 (m, 1H), 4.93 (s, 1H), 3.40 (s, 3H), 3.37-3.23 (m, 1H), 2.79-2.53 (m, 2H), 2.43-2.11 (m, 2H), 1.92-1.70 (m, 2H), 1.60 (s, 6H), 1.52-1.29 (m, 2H); $^{13}$C NMR (300 MHz, CDCl$_3$) δ 165.6, 164.8, 144.6, 143.1, 136.7, 136.5, 133.6, 132.0, 130.8, 118.7, 78.5, 71.9, 55.9, 53.2, 46.4, 31.6, 30.6, 26.4; LCMS (EI) m/z calcd. for C$_{21}$H$_{25}$D$_2$N$_5$O$_3$ [M+H]$^+$, 400.2; found 400.2.

6.3.5 Synthesis of $^2$H Enriched Metabolite of Compound A

A deuterium-enriched metabolite of Compound A can be prepared as follows.

Compound 26 can be made using the route above wherein all of the exchangeable protons are replaced with deuterium. Starting with Compound 6, the acidic protons can be exchanged in the presence of base (such as sodium tert-butoxide, potassium carbonate and 1,8-diazabicyclo[5,4,0]undec-7-ene) and a deuterium source (such as tert-BuOD, MeOD, EtOD, iPrOD, AcOD, D$_2$O) to give Compound 26. A solvent (such as tetrahydrofuran, dimethylformamide, or dimethylsulfoxide) can be used to facilitate the reaction. The hydrogen isotopes on the two alcohols and the secondary amine could be either hydrogen or deuterium depending on the workup. A workup solvent with an exchangeable proton (such as H$_2$O, MeOH or EtOH) will provide 27, while a workup solvent with an exchangeable deuterium (e.g., D$_2$O, MeOD, EtOD) will afford 26.

6.4 Pharmaceutical Compositions

6.4.1 Tablets

Compound A was formulated as tablets containing about 5 mg, 20 mg, and 50 mg of Compound A as an active pharmaceutical ingredient. The excipients and carriers that were used in the tablet formulations are summarized in Table 6, along with their intended functions.

TABLE 6

Pharmaceutical Acceptable Excipients and Carriers

| Ingredients | Function |
| --- | --- |
| Lactose monohydrate, NF (Fast Flo 316) | Diluent |
| Microcrystalline cellulose, NF (Avicel pH 101) | Diluent/binder |
| Microcrystalline cellulose, NF (Avicel pH 102) | Diluent/binder |
| Corn starch, NF | Disintegrant/lubricant |
| Pregelatinized starch, NF (Starch 1500) | Binder/Disintegrant |
| Lactose anhydrous, NF | Diluent |
| Croscarmellose sodium, NF (Ac-Di-Sol) | Disintegrant |
| Stearic acid, NF | Lubricant |
| Magnesium Stearate, NF | Lubricant |

General Method for Tablet Preparation.

Tablets were produced at batch size ranging from 0.5 to 2.2 kg. Form A of compound A was first mixed/blended with binders, diluent(s), and/or disintegrant (e.g., lactose monohydrate (NF), croscarmellose sodium (NF), and/or microcrystalline cellulose (NF)) using a Globepharma 4-8 quart Bin Blender. The mixture was then sieved via 18 mesh screen. The sieved mixture was further mixed/blended with a Globepharma 4-8 quart Bin Blender. After lubricant(s) (e.g., stearic acid (NF) and/or magnesium stearate (NF)) were sieved via 30 mesh screen, the lubricant(s) were then added to the mixture. The resulting mixture was then mixed/blended with a Globepharma 4-8 quart Bin Blender. The mixture was then compressed into tablets with a rotary table press, and then coated in an Ohara 8" pan. The tablets thus produced were evaluated for their powder characteristics, tablet characteristics, drug product photostability/short term stability, and manufacturing process.

Tablet formulations I to VIII of Compound A are summarized in Table 7 to Table 14. The process parameters for tablet preparation (blending/compression) are summarized in Table 15 and Table 16. It was observed that the tablets of Formulations I to VIII showed discoloration. Picking was observed when compressing Formulations I to IV. The addition of stearic acid in Formulations V to VIII improved lubrication without impacting disintegration and compressibility. Compressibility of Formulation II was not acceptable when replacing lactose by pregelatinized starch and tablet hardness could not exceed 4.1 kp (average). Lactose monohydrate, NF (Fast Flo 316) was used as an alternate diluent and was preferred over lactose anhydrous (Formulation III) for its flowability properties. Both Avicel PH 101 and PH 102 were tested for binding properties (Formulations III and IV). Avicel PH 102's larger particle size, and more spherical particle shape provided better flow than Avicel PH 101.

TABLE 7

Tablet Formulation I

| Ingredients | Amounts | |
| --- | --- | --- |
| | mg | % |
| Compound A | 50.0 | 16.7 |
| Lactose monohydrate, NF (Fast Flo 316) | 145.1 | 48.3 |
| Microcrystalline cellulose, NF (Avicel pH 101) | 93.1 | 31.0 |

TABLE 7-continued

Tablet Formulation I

| Ingredients | Amounts | |
| --- | --- | --- |
| | mg | % |
| Croscarmellose sodium, NF (Ac-Di-Sol) | 9.0 | 3.0 |
| Magnesium Stearate, NF | 3.0 | 1.0 |
| Total | 300.0 | 100 |

TABLE 8

Tablet Formulation II

| Ingredients | Amounts | |
| --- | --- | --- |
| | mg | % |
| Compound A | 50.0 | 16.7 |
| Lactose monohydrate, NF (Fast Flo 316) | 168.0 | 56.0 |
| Pregelatinized starch, NF (Starch 1500) | 70.1 | 23.3 |
| Croscarmellose sodium, NF (Ac-Di-Sol) | 9.0 | 3.0 |
| Magnesium Stearate, NF | 3.0 | 1.0 |
| Total | 300.0 | 100 |

TABLE 9

Tablet Formulation III

| Ingredients | Amounts | |
| --- | --- | --- |
| | mg | % |
| Compound A | 50.0 | 16.7 |
| Lactose anhydrous, NF | 145.1 | 48.3 |
| Microcrystalline cellulose, NF (Avicel pH 101) | 93.1 | 31.0 |
| Croscarmellose sodium, NF (Ac-Di-Sol) | 9.0 | 3.0 |
| Magnesium Stearate, NF | 3.0 | 1.0 |
| Total | 300.0 | 100 |

TABLE 10

Tablet Formulation IV

| Ingredients | Amounts | |
| --- | --- | --- |
| | mg | % |
| Compound A | 50.0 | 16.7 |
| Lactose monohydrate, NF (Fast Flo 316) | 145.0 | 48.3 |
| Microcrystalline cellulose, NF (Avicel pH 102) | 93.0 | 31.0 |
| Croscarmellose sodium, NF (Ac-Di-Sol) | 9.0 | 3.0 |
| Magnesium Stearate, NF | 3.0 | 1.0 |
| Total | 300.0 | 100 |

TABLE 11

Tablet Formulation V

| Ingredients | Amounts mg | % |
|---|---|---|
| Compound A | 50.0 | 11.9 |
| Lactose monohydrate, NF (Fast Flo 316) | 220.48 | 52.5 |
| Microcrystalline cellulose, NF (Avicel pH 102) | 130.20 | 31.0 |
| Croscarmellose sodium, NF (Ac-Di-Sol) | 12.6 | 3.0 |
| Stearic acid, NF | 2.52 | 0.6 |
| Magnesium Stearate, NF | 4.20 | 1.0 |
| Total | 420.0 | 100 |

TABLE 12

Tablet Formulation VI

| Ingredients | Amounts mg | % |
|---|---|---|
| Compound A | 50.0 | 11.9 |
| Lactose monohydrate, NF (Fast Flo 316) | 182.20 | 63.1 |
| Microcrystalline cellulose, NF (Avicel pH 102) | 54.0 | 18.0 |
| Croscarmellose sodium, NF (Ac-Di-Sol) | 9.0 | 3.0 |
| Stearic acid, NF | 1.80 | 3.0 |
| Magnesium Stearate, NF | 3.0 | 1.0 |
| Total | 300.0 | 100 |

TABLE 13

Tablet Formulation VII

| Ingredients | Amounts Mg | % |
|---|---|---|
| Compound A | 50.0 | 16.7 |
| Lactose monohydrate, NF (Fast Flo 316) | 265.0 | 88.3 |
| Microcrystalline cellulose, NF (Avicel pH 102) | 75.60 | 25.2 |
| Corn starch, NF | 12.6 | 4.2 |
| Croscarmellose sodium, NF (Ac-Di-Sol) | 12.6 | 4.2 |
| Magnesium Stearate, NF | 4.20 | 1.4 |
| Total | 420.0 | 100 |

TABLE 14

Tablet Formulation VIII

| Ingredients | Amounts Mg | % |
|---|---|---|
| Compound A | 50.0 | 16.7 |
| Lactose monohydrate, NF (Fast Flo 316) | 136.0 | 45.3 |
| Microcrystalline cellulose, NF (Avicel pH 102) | 93.0 | 31.0 |

TABLE 14-continued

Tablet Formulation VIII

| Ingredients | Amounts Mg | % |
|---|---|---|
| Corn starch, NF | 9.0 | 3.0 |
| Croscarmellose sodium, NF (Ac-Di-Sol) | 9.0 | 3.0 |
| Magnesium Stearate, NF | 3.0 | 1.0 |
| Total | 300.0 | 100 |

TABLE 15

Tablet Process Parameters

| Equipment/Process Parameters | I | II | III | IV |
|---|---|---|---|---|
| Batch size (kg) | 0.5 | 0.5 | 0.5 | 0.5 |
| Bin blender (quart) | 4 | 4 | 4 | 4 |
| Pre-blending time (min) | 20/10 | 20/10 | 20/10 | 20/10 |
| Lubrication time (min) | 3 | 3 | 3 | 3 |
| Actual weight (mg) | 299 | 301 | 307 | 297 |
|  | 291-309 | 295-310 | 301-311 | 290-300 |
| Bulk density (g/cc) | 0.4 | 0.53 | 0.37 | 0.42 |
| Tooling (round, SC) | 12/32 | 12/32 | 12/32 | 12/32 |
| Hardness (average in Kp) | 7.9 | 4.1 | 7.9 | 7.4 |
| Thickness (average in mm) | 3.95 | 3.86 | 3.98 | 3.86 |
| Friability (4 min) (%) | 0 | 0.1 | 0 | 0.1 |
| Disintegration time (max) (sec) | 18 | 75 | 55 | 21 |
| Observation | Picking | Picking | Picking | Picking |

TABLE 16

Tablet Process Parameters

| Equipment/Process Parameters | V | VI | VII | VIII |
|---|---|---|---|---|
| Batch size (kg) | 0.5 | 0.5 | 0.5 | 0.5 |
| Bin blender used (quart) | 4 | 4 | 4 | 4 |
| Pre-blending time (min) | 20/10 | 20/10 | 20/10 | 20/10 |
| Lubrication time (min) | 3 | 3 | 3 | 3 |
| Actual weight (mg) | 418 | 299 | 419 | 301 |
|  | 413-421 | 293-307 | 413-426 | 296-305 |
| Bulk density (g/cc) | 0.45 | 0.43 | 0.48 | 0.43 |
| Tooling (round, SC) | 12/32 | 12/32 | 12/32 | 12/32 |
| Hardness (average in Kp) | 9.1 | 8.5 | 9.0 | 8.4 |
| Thickness (average in mm) | 5.20 | 3.8 | 4.12 | 3.86 |
| Friability (4 min) (%) | 0.3 | 0.2 | 0.2 | 0.1 |
| Disintegration time (max) (sec) | 31 | 30 | 29 | 20 |
| Observation | None | None | None | None |

Tablet formulations IX to XI of Compound A are summarized in Table 17 to Table 19. The process parameters for their preparation are summarized in Table 20 and Table 21.

TABLE 17

Tablet Formulation IX

| Ingredients | Amounts mg | % |
|---|---|---|
| Compound A | 50.0 | 15.4 |
| Lactose monohydrate, NF (Fast Flo 316) | 151.5 | 46.6 |

TABLE 17-continued

Tablet Formulation IX

| Ingredients | Amounts mg | % |
|---|---|---|
| Microcrystalline cellulose, NF (Avicel pH 102) | 100.75 | 31.0 |
| Corn starch, NF | 9.75 | 3.0 |
| Croscarmellose sodium, NF (Ac-Di-Sol) | 9.75 | 3.0 |
| Magnesium Stearate, NF | 3.25 | 1.0 |
| Total | 325.0 | 100 |
| Opadry pink 03K140004 | 4% weight gain | |

TABLE 18

Tablet Formulation X

| Ingredients | Amounts mg | % |
|---|---|---|
| Compound A | 50.0 | 15.4 |
| Lactose monohydrate, NF (Fast Flo 316) | 149.55 | 46.0 |
| Microcrystalline cellulose, NF (Avicel pH 102) | 100.75 | 31.0 |
| Corn starch, NF | 9.75 | 3.0 |
| Croscarmellose sodium, NF (Ac-Di-Sol) | 9.75 | 3.0 |
| Stearic acid, NF | 1.95 | 0.6 |
| Magnesium Stearate, NF | 3.25 | 1.0 |
| Total | 325.0 | 100 |
| Opadry pink 03K140004 | 4% weight gain | |

TABLE 19

Tablet Formulation XI

| Ingredients | Amounts mg | % |
|---|---|---|
| Compound A | 5.0 | 3.85 |
| Lactose monohydrate, NF (Fast Flo 316) | 74.82 | 57.55 |
| Microcrystalline cellulose, NF (Avicel pH 102) | 40.30 | 31.00 |
| Corn starch, NF | 3.90 | 3.00 |
| Croscarmellose sodium, NF (Ac-Di-Sol) | 3.90 | 3.00 |
| Stearic acid, NF | 0.78 | 0.60 |
| Magnesium Stearate, NF | 1.30 | 1.00 |
| Total | 130.0 | 100 |
| Opadry beige 03K170001 | 4% weight gain | |

TABLE 20

Tablet Process Parameters

| Equipment/Process Parameters Blending/Compression | IX | X | XI |
|---|---|---|---|
| Batch size (kg) | 0.65 | 0.65 | 0.52 |
| Bin blender used (quart) | 4 | 4 | 4 |
| Pre-blending time (min) | 20/10 | 20/10 | 20/10 |
| Lubrication time (min) | 3 | 3 | 3 |
| Actual weight (mg) | 323 | 326 | 131 |
|  | 318-328 | 316-333 | 130-134 |
| Bulk density (g/cc) | 0.40 | 0.42 | 0.48 |
| Tooling (round, SC) | 12/32 | 12/32 | 1/4 |
| Hardness (average in Kp) | 9.3 | 9.1 | 5.9 |
| Thickness (average in mm) | 4.09 | 4.12 | 3.72 |
| Friability (4 min) (%) | 0.1 | 0.1 | 0.1 |
| Disintegration time (max) (sec) | 39 | 27 | 24 |
| Observations | Picking | None | None |

TABLE 21

Tablet Process Parameters

| Equipment/Process Parameters Coating | IX | X | XI |
|---|---|---|---|
| Batch size (kg) | 0.27 | 0.27 | 0.30 |
| Weight gain (%) | 4 | 4 | 4 |
| Solid in suspension (%) | 12 | 12 | 12 |
| Pan (inch) | 8 | 8 | 8 |
| Nozzle size (mm) | 0.8 | 0.8 | 0.8 |
| Atomizing air pressure (PSI) | 9-10 | 10-12 | 9-10 |
| Pattern (PSI) | 12-13 | 12-13 | 11-12 |
| Distance gun-ben (inch) | 3 | 3 | 3 |
| Airflow (CFM) | 75 | 75 | 75 |
| Pan speed (RPM) | 16-18 | 14-17 | 14-17 |
| Inlet temperature (° C.) | 75 | 75 | 72-73 |
| Exhaust temperature (° C.) | 51-53 | 51-53 | 49-50 |
| Spray rate | 5-7 | 4-6 | 4-6 |
| Observation | Acceptable appearance | | |

The 5 mg and 50 mg tablets (core and coated) were subjected to short term stability and photo-stability evaluations. The short term stability of the 50 mg tablets was tested by storing for 2 weeks at 40° C./75% RH in an open bottle. The results are summarized in Table 22.

TABLE 22

Tablet Formulation X (50 mg) Tablet Short Term Stability

| | Compound A (%) | | Total Impurities (%) | |
|---|---|---|---|---|
| Tablet | Initial | After 2 wks at 40° C./75% RH | Initial | After 2 wks at 40° C./75% RH |
| Core | 99.5 | 98.7 | 0.29 | 0.54 |
| Coated | 100.1 | 99.9 | 0.25 | 0.29 |

The photo-stability of the 50 mg tablets was also tested and the results are summarized in Table 23.

TABLE 23

Tablet Formulation X (50 mg) Tablet Photo-Stability

| | Compound A (%) | | Total Impurities (%) | |
|---|---|---|---|---|
| Tablet | Control | Photo-stability Sample | Control | Photo-stability Sample |
| Core | 99.3 | 99.0 | 0.21 | 1.25 |
| Coated | 99.6 | 97.4 | 0.26 | 0.31 |

The short term stability of the 5 mg tablets was tested by storing them for 2 weeks at 40° C./75% RH in an open bottle. The results are summarized in Table 24. No major increase of impurity was observed for the 50 mg coated tablets after two weeks at 40° C./75% RH and light exposure. The coating appears to offer acceptable protection against moisture and light.

TABLE 24

Tablet Formulation X (5 mg) Tablet Short Term Stability

| Tablet | Compound A (%) | | Total Impurities (%) | |
|---|---|---|---|---|
| | Initial | After 2 wks at 40° C./75% RH | Initial | After 2 wks at 40° C./75% RH |
| Core | 102.3 | 102.3 | 0.24 | 0.92 |
| Coated | 101.1 | 100.7 | 0.21 | 1.11 |

The photo-stability of the 5 mg tablets was also tested and the results are summarized in Table 25.

TABLE 25

Tablet (5 mg) Tablet Photo-Stability

| Tablet | Compound A (%) | | Total Impurities (%) | |
|---|---|---|---|---|
| | Control | Photo-stability Sample | Control | Photo-stability Sample |
| Core | 99.5 | 97.9 | 0.27 | 2.85 |
| Coated | 99.0 | 101.0 | 0.23 | 0.84 |

Tablet formulations XII (50 mg), XIII (20 mg), and XIV (5 mg) are summarized in Table 26, Table 27 and Table 28.

TABLE 26

Tablet Formulation XII (50 mg)

| Ingredients | Amounts | |
|---|---|---|
| | mg | % |
| Compound A | 50.0 | 15.38 |
| Lactose monohydrate, NF (Fast Flo 316) | 159.95 | 49.22 |
| Microcrystalline cellulose, NF (Avicel pH 102) | 100.75 | 31.00 |
| Croscarmellose sodium, NF (Ac-Di-Sol) | 9.75 | 3.00 |
| Stearic acid, NF | 1.30 | 0.40 |
| Magnesium Stearate, NF | 3.25 | 1.00 |
| Total | 325.0 | 100 |
| Opadry pink 03K140004 | 13.0 | 4% weight gain |

TABLE 27

Tablet Formulation XIII (20 mg)

| Ingredients | Amounts | |
|---|---|---|
| | mg | % |
| Compound A | 20.0 | 15.38 |
| Lactose monohydrate, NF (Fast Flo 316) | 63.98 | 49.22 |
| Microcrystalline cellulose, NF (Avicel pH 102) | 40.30 | 31.00 |
| Croscarmellose sodium, NF (Ac-Di-Sol) | 3.90 | 3.00 |
| Stearic acid, NF | 0.52 | 0.40 |
| Magnesium Stearate, NF | 1.30 | 1.00 |
| Total | 130.0 | 100 |
| Opadry yellow 03K12429 | 5.2 | 4% weight gain |

TABLE 28

Tablet Formulation XIV (5 mg)

| Ingredients | Amounts | |
|---|---|---|
| | mg | % |
| Compound A | 5.0 | 3.80 |
| Lactose monohydrate, NF (Fast Flo 316) | 78.98 | 60.70 |
| Microcrystalline cellulose, NF (Avicel pH 102) | 40.30 | 31.00 |
| Croscarmellose sodium, NF (Ac-Di-Sol) | 3.90 | 3.00 |
| Stearic acid, NF | 0.52 | 0.40 |
| Magnesium Stearate, NF | 1.30 | 1.00 |
| Total | 130.0 | 100 |
| Opadry II pink 85F94211 | 5.2 | 4% weight gain |

Figure 5:
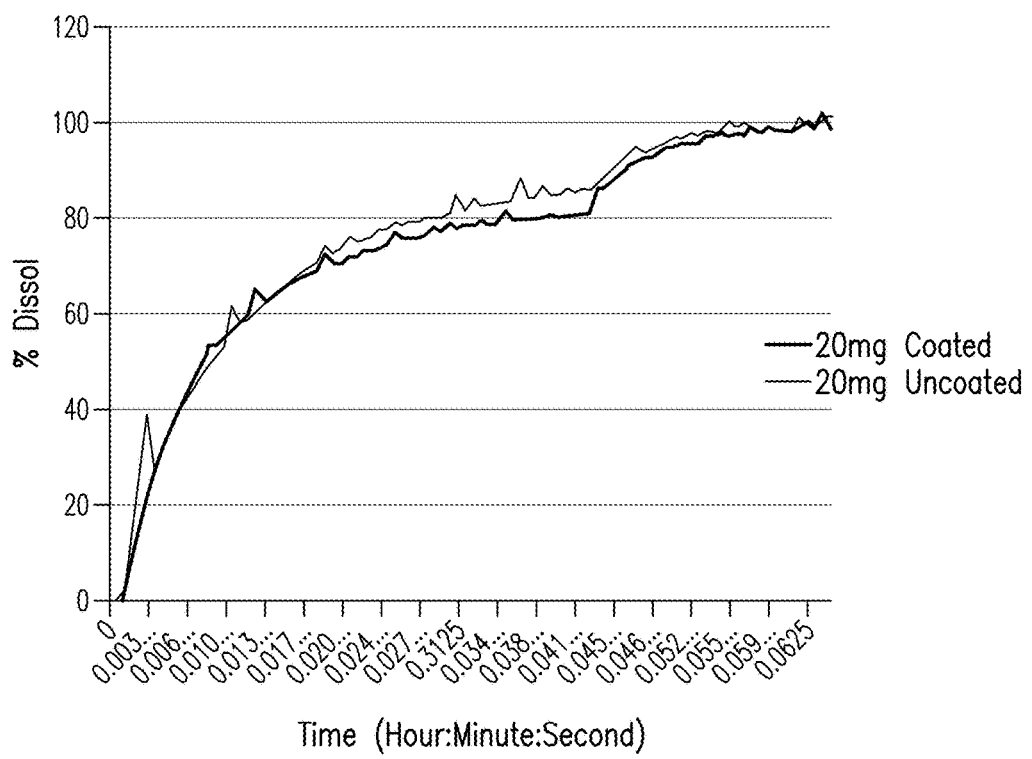
FIG. 5 depicts dissolution profiles of 20 mg tablets of Form A of 7-(6-(2-hydroxypropan-2-yl)pyridin-3-yl)-1-((trans)-4-methoxycyclohexyl)-3,4-dihydropyrazino[2,3-b]pyrazin-2(1H)-one (Core vs Coated).

No event was observed during the preparation of the tablets of Formulations XII, XIII, or XIV. The 20 mg and 50 mg tablets were compressed at various compression forces to assess compressibility and define a hardness range. The parameters for the preparation of the tablets to assess compressibility are summarized in Table 29 (blending/compression) and Table 30 (coating). The 20 mg tablets were coated with Opadry Yellow 03K12429, whereas the 50 mg tablets were not coated. The core and coated tablets (20 mg) were tested for dissolution. It was found that there is no significant difference between the dissolution of the core and coated tablets (FIG. 5).

TABLE 29

Process Parameters for 50 mg and 20 mg Tablet Formulations (Blending/Compression)

| Equipment/Process Parameter | 50 mg | 20 mg |
|---|---|---|
| Batch Size (kg) | 2.21 (Common Blend) | |
| Bin Blende used (quart) | 8 | |
| Pre-blending time (min) | 20/10 | |
| Lubrication time (min) | 3 | 3 |
| | 327 | 129 |
| Actual weight (mg) | 313-339 | 124-135 |
| Bulk density (g/cc) | 0.41 | 0.41 |
| Tooling (round, SC) | 12/32 | 1/4 |
| Hardness (average in Kp) | Hig High-13.6 | High-9.0 |
| | Low-5.9 | Low-3.8 |
| | Target-9.9 | Target-6.1 |
| Thickness (average in mm) | 4.26 | 3.76 |
| Friability (4 min) (%) | 0.09 | 0.04 |
| Disinegration time (max) (sec) | 39 | 22 |
| Observations | None | None |

TABLE 30

Process Parameters for Formulation XIII (Coating)

| Equipment/Process Parameter | 20 mg |
|---|---|
| Batch size (kg) | 0.27 |
| Weight gain (%) | 4 |
| Solid in suspension (%) | 12 |
| Pan (inch) | 8 |
| Nozzle size (mm) | 0.8 |
| Atomizing air pressure (PSI) | 9-10 |
| Pattern (PSI) | 11-12 |
| Distance gun-bed (inch) | 3 |
| Airflow (CFM) | 75 |

TABLE 30-continued

Process Parameters for Formulation XIII (Coating)

| Equipment/Process Parameter | 20 mg |
|---|---|
| Pan speed (RPM) | 14-16 |
| Inlet temperature (° C.) | 65 |
| Exhaust temperature (° C.) | 45-47 |
| Spray rate | 4-5 |
| Observation | Acceptable coating |

Batch formulations of Compound A are summarized in Table 31.

TABLE 31

Batch Tablet Formulations

| Ingredients | 5 mg grams | 20 mg grams |
|---|---|---|
| Compound A | 45.0 | 180.0 |
| Lactose monohydrate | 710.82 | 575.82 |
| Microcrystalline cellulose | 362.70 | 362.70 |
| Croscarmellose sodium | 35.10 | 35.10 |
| Stearic acid | 4.68 | 4.68 |
| Magnesium stearate | 11.70 | 11.70 |
| Total | 1170.0 | 1170.0 |
| Opadry ® II Pink | 65.52 | — |
| Opadry ® Yellow | — | 65.52 |

Tablet formulation XV (45 mg) is summarized in Table 32. Tablet formulation XV can be prepared using methodology provided herein or other methods known to one skilled in the art.

TABLE 32

Tablet Formulation XV (45 mg)

| Ingredients | Amounts | |
|---|---|---|
| | mg | % |
| Compound A | 45.0 | 15.38 |
| Lactose monohydrate, NF (Fast Flo 316) | 143.955 | 49.22 |
| Microcrystalline cellulose, NF (Avicel pH 102) | 90.675 | 31.00 |
| Croscarmellose sodium, NF (Ac-Di-Sol) | 8.775 | 3.00 |
| Stearic acid, NF | 1.170 | 0.40 |
| Magnesium Stearate, NF | 2.925 | 1.00 |
| Total | 292.50 | 100 |
| Opadry pink 03K140004 | 11.7 | 4.0% weight gain |

The batch size of the current 45 mg strength tablet is approx. 10,000 tablets or approximately 3.5 kg (approximately 20% overage is dispensed to allow for losses during manufacturing).

No picking or sticking was visually observed during the preparation of the tablets of Formulations XIII or XIV. As a result, stearic acid was removed from the tablet formulation.

Additionally, Compound A is susceptible to hydrolysis. Accordingly, without being limited by theory, a low-moisture grade microcrystalline cellulose (Avicel pH 112) was used in place of Avicel pH 102 to minimize or prevent hydrolysis.

Tablet formulations XVI (15 mg) and XVII (30 mg) are summarized in Table 33 and Table 34, below. Tablet formulations XVI and XVII can be prepared using blending/sieving via a Comil process. After lubrication, the mixture is then compressed into tablets and film-coated.

TABLE 33

Tablet Formulation XVI (15 mg)

| Ingredients | Amounts | |
|---|---|---|
| | mg | % |
| Compound A | 15.0 | 15.38 |
| Lactose monohydrate, NF (Fast Flo 316) | 48.37 | 49.62 |
| Microcrystalline cellulose, NF (Avicel pH 112) | 30.23 | 31.00 |
| Croscarmellose sodium, NF (Ac-Di-Sol) | 2.925 | 3.00 |
| Magnesium Stearate, NF | 0.975 | 1.00 |
| Total | 97.50 | 100 |
| Opadry II pink 85F94211 | 3.9 | 4% weight gain |

TABLE 34

Tablet Formulation XVII (30 mg)

| Ingredients | Amounts | |
|---|---|---|
| | mg | % |
| Compound A | 30.0 | 15.38 |
| Lactose monohydrate, NF (Fast Flo 316) | 96.75 | 49.62 |
| Microcrystalline cellulose, NF (Avicel pH 112) | 60.45 | 31.00 |
| Croscarmellose sodium, NF (Ac-Di-Sol) | 5.85 | 3.00 |
| Magnesium Stearate, NF | 1.95 | 1.00 |
| Total | 195.0 | 100 |
| Opadry pink 03K140004 | 7.8 | 4% weight gain |

6.4.2 Development of an Oral Dose Vehicle of $^{14}$C Enriched Compound A

A solution was prepared using appropriate amounts of 50:50 (v:v) EtOH:PEG 400, [$^{14}$C]-Compound A, and Compound A to achieve a final concentration of 28.6 mg/mL. An aliquot of the solution was transferred to a white Size 00 Capsugel® V Caps Plus Hypromellose capsule for dose administration. Preliminary stability data indicated that the in-process bulk solution is stable for at least 48 hours when stored at refrigerated conditions and protected from light.

Compound A drug substance was dissolved in five different solvent combinations of EtOH and PEG 400. The solvent combinations selected were 100% EtOH, 80:20 (v:v) EtOH:PEG 400, 50:50 (v:v) EtOH:PEG 400, 20:80 (v:v) EtOH:PEG 400 and 100% PEG 400. Due to solubility and viscosity issues, the 100% EtOH and 100% PEG 400 formulations were not analyzed.

The 80:20 (v:v) EtOH:PEG 400, 50:50 (v:v) EtOH:PEG 400 and 20:80 (v:v) EtOH:PEG 400 solutions were prepared at a concentration of 28.6 mg/mL and diluted to 257 µg/mL for analysis. These samples were analyzed at T=0 and stored at RTmp/PFL and REF/PFL until analysis at T=72 hours post-preparation.

Solution stability was performed on the final [$^{14}$C]-Compound A dosing solution to establish stability for at least 48 hours protected from light at refrigerated and room temperature conditions. Following analysis at T=0, T=24 hours and T=48 hours, it was determined that the [$^{14}$C]-Compound A dosing solution was stable for at least 48 hours protected from light at refrigerated conditions. Degradation was observed at 48 hours for the [$^{14}$C]-Compound A solution that was stored at room temperature and protected from light.

The final formulation for the [$^{14}$C]-Compound A dosing solution was developed to deliver a single capsule containing a solution of 20 mg of Compound A with a microtracer of [$^{14}$C]-Compound A (200 nCi).

The formulation was prepared using 50:50 (v:v) EtOH: PEG 400, [$^{14}$C]-Compound A, and Compound A drug substance to achieve a final concentration of 28.6 mg/mL. Preliminary stability data indicates that this formulation was stable for at least 48 hours when stored at refrigerated conditions and protected from light.

6.5 Biological Examples

6.5.1 A Phase 1, Open-Label, Randomized, Crossover Study to Evaluate the Pharmacokinetics of Compound A after a Single Oral Dose of Tablet and Capsule Formulations in Healthy Male Adult Subjects Certain formulations provided herein were evaluated in a Phase 1, open-label, randomized, crossover study. The study had a Screening phase, three Treatment and Sample Collection periods, and a follow-up visit.

Within no more than 21 days (Day −21) and no less than 2 days (Day −2) prior to the start of Period 1, subjects underwent routine screening procedures including physical examination, 12-lead electrocardiogram (ECG), assessment of vital signs, clinical laboratory safety tests (serum chemistry, hematology, and urinalysis), serology screen, fasting glucose levels and drug/alcohol screen.

Eligible subjects returned to the study center on Day −1 of Period 1 for baseline assessments. During each study period, subjects were domiciled at the study center from Day −1 through Day 5. Subjects were discharged from the study center on the morning of Day 5 upon satisfactory safety review and completion of study-related procedures.

On Day 1 of Period 1, following an overnight fast of at least 8 hours, subjects were randomized to one of the following 3 sequences to receive Treatment A, B or C (Table 35).

TABLE 35

Treatment Sequences

| | Period 1 | Period 2 | Period 3 |
|---|---|---|---|
| Sequence 1 | A | B | C |
| Sequence 2 | B | C | A |
| Sequence 3 | C | A | B |

In Treatment A, one 20-mg reference Compound A API-in-capsule was administered orally after at least 8 hour fast with 240 mL of non-carbonated, room temperature water. In Treatment B, one 20-mg tablet of Compound A (Tablet Formulation XIII) was administered under fasted conditions. In Treatment C, four 5-mg tablets of Compound A (Tablet Formulation XIV) were administered under fasted conditions. The 20-mg tablet and four 5-mg tablets were administered orally after at least 8 hour fast with 240 mL of non-carbonated, room temperature water.

The periods were separated by a washout period of at least 7 days (no more than 10 days) from the prior dose to the next dose. In certain instances, a longer washout is acceptable.

For each period, serial blood samples were collected before dosing (zero hour) and at 0.5, 1, 1.5, 2, 2.5, 3, 4, 6, 8, 12, 24, 48, 72, and 96 hours after dosing. Plasma concentrations of Compound A were determined for determining PK parameters, such as $AUC_{0-t}$, $AUC_{0-\infty}$, $C_{max}$, $T_{max}$, $t_{1/2}$, CL/F, and Vz/F for Compound A. Plasma PK parameters were calculated using non compartmental methods. Analyses of variance (ANOVA) were performed on the natural log-transformed $AUC_{0-t}$, $AUC_{0-\infty}$, and $C_{max}$ for Compound A. The geometric mean ratios (test/reference) and their 90% confidence intervals were also calculated. For $T_{max}$, non parametric analysis was used to produce median differences.

Blood samples to assess PD were collected at Baseline (Day −1) in Period 1 for all subjects. After randomization, serial PD blood samples were collected only in each period in which Treatment B (20 mg tablet formulation) was administered. Samples were collected prior to dosing (zero hour) and at 1.5, 3, 6, 8, 12, 24, and 48 hours after administration of Treatment B. The samples were used for biomarker analysis which involve measuring levels of pAKT (mTORC2), p4EB-P1, and/or pS6RP (mTORC1); and/or and pAKT (mTORC2) by flow cytometry using whole blood samples and/or other exploratory biomarkers in pre- and post-treatment samples at different time points. The biomarker data were used for exploration of PK-PD relationships.

Safety was monitored throughout the study. Safety evaluations included AE reporting, physical examinations, vital sign measurements, ECGs, and clinical laboratory safety tests. Concomitant medications were assessed and recorded throughout the study from the time informed consent was obtained until the follow-up visit.

All subjects returned to the clinic within 7 to 10 days after the last dose in Period 3 for follow-up safety assessments. In the event that a subject discontinued prematurely from the study, every reasonable effort was made (and documented) to ensure that all procedures and evaluations scheduled for the follow-up visit were performed at time of discontinuation or a follow-up visit was scheduled within 7 to 10 days from the discontinuation day.

Figure 8:
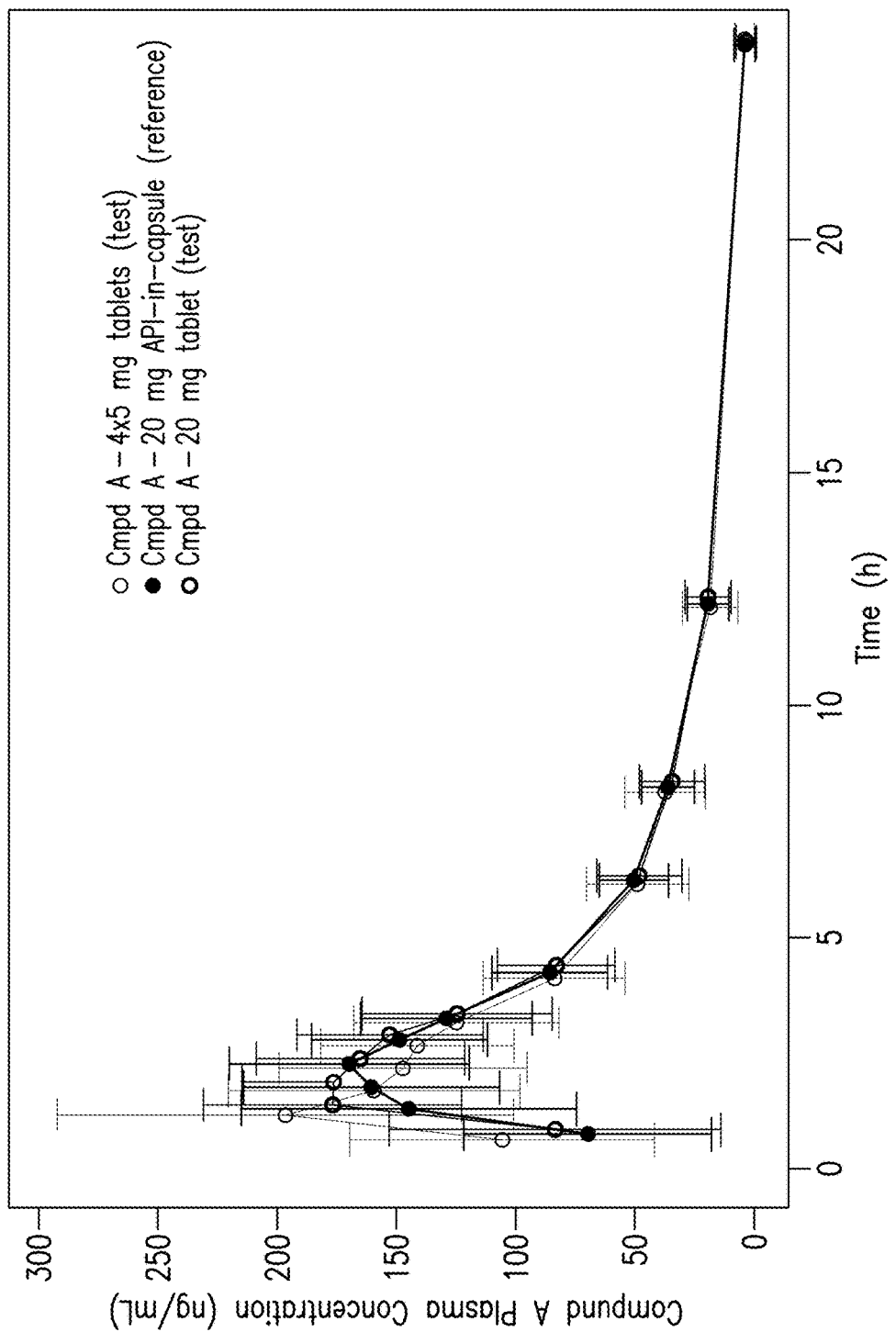
FIG. 8 depicts plasma concentration-time profiles in healthy adult males administered a single 20 mg oral dose of Compound A.

Results: The major PK parameters are summarized in Table 36 and Table 37 (see FIG. 8 for plasma concentration-time profiles).

TABLE 36

Pharmacokinetic Parameters (Geometric Mean (Geometric CV %))

| | Treatment A (n = 18) | | Treatment B (n = 17) | Treatment C (n = 17) |
|---|---|---|---|---|
| Parameter | Cmpd. A | O-Desmethyl metabolite | | |
| $T_{max}$* (h) | 1.5 (13) | 3.0 (2-24) | 1.5 (1-2.5) | 1.00 (1-3) |
| $C_{max}$ (ng/mL) | 190 (20) | 503 (24) | 198 (22) | 212 (29) |
| $AUC_{0-\infty}$ (ng · h/mL) | 985 (26) | 11928 (23) | 988 (27) | 980 (30) |
| $AUC_{0-24}$ (ng · h/mL) | 934 (24) | 7484 (22) | 944 (26) | 938 (29) |
| Vz/F (L) | 167 (28) | ND | 161 (28) | 158 (30) |
| CL/F (L/h) | 20.3 (23) | ND | 20.2 (27) | 20.4 (30) |
| $t_{1/2}$ (h) | 5.7 (24) | 14.3 (20) | 5.6 (22) | 5.4 (23) |

*$T_{max}$ presented as median (range).

TABLE 37

| Parameter | Treatment | N | Geometric Mean | Ratio of Means | 90% CI of Ratio (%) of Means | Intra-Subject CV% |
|---|---|---|---|---|---|---|
| $AUC_{0-t}$ (ng · h/mL) | A | 18 | 941.2 | 99.7 (B vs A) | 94.7-105.0 | 8.9 |
|  | B | 17 | 938.5 |  |  |  |
|  | C | 17 | 934.7 | 99.3 (C vs A) | 94.3-104.6 |  |
| $AUG_\infty$ (ng · h/mL) | A | 18 | 985.4 | 99.3 (B vs A) | 94.8-104.0 | 8.0 |
|  | B | 17 | 978.4 |  |  |  |
|  | C | 17 | 969.8 | 98.4 (C vs A) | 94.0-103.1 |  |
| $C_{max}$ (ng/mL) | A | 18 | 190.2 | 103.8 (B vs A) | 93.6-115.0 | 17.9 |
|  | B | 17 | 197.4 |  |  |  |
|  | C | 17 | 212.3 | 111.6 (C vs A) | 100.7-123.7 |  |

Abbreviations:
$AUC_\infty$ = area under the plasma concentration versus time curve from time zero to infinity;
$AUC_{0-t}$ = area under the plasma concentration versus time curve from time 0 to the last quantifiable concentration;
CI = confidence interval.

Conclusions: Compound A pharmacokinetics are comparable after single dose administration of 20 mg Compound A tablet formulations and API in capsule in healthy adult male subjects.

6.5.2 A Phase 1, Open-Label Study to Evaluate the Metabolism and Excretion of Compound A and the Effect of Food on the Pharmacokinetics of Compound A in Healthy Male Adult Subjects The primary objectives of this study are: to characterize the biotransformation and excretion of Compound A following a single 20 mg oral dose of Compound A capsule containing a microtracer of [$^{14}$C]-Compound A solution in healthy male subjects (Part 1) and to evaluate the effect of a high-fat meal on the pharmacokinetics (PK) of Compound A following a single oral 20-mg dose of Compound A tablet (Part 2).

The secondary objectives of this study are to evaluate the tolerability of Compound A after a single 20-mg oral dose of Compound A capsule containing a microtracer of [$^{14}$C]-Compound A solution in healthy male adult subjects (Part 1), to evaluate the effect of a high-fat meal on the PK of the O-desmethyl metabolite of Compound A following a single 20-mg oral dose of Compound A tablet (Part 2) and to evaluate the tolerability of Compound A after a single 20-mg oral dose of Compound A tablet in healthy male adult subjects (Part 2).

The primary endpoints of Part 1 are: Total [$^{14}$C]-radioactivity in whole blood, plasma, urine and feces; cumulative excretion of Total [$^{14}$C]-radioactivity (as fraction of radioactive dose) in urine and feces; total [$^{14}$C]-radioactivity whole blood-to-plasma ratios; concentration of Compound A and the O-desmethyl metabolite of Compound A in plasma, urine, and feces samples collected up to 14 times from the day prior to dosing to 8 days after dosing; and metabolite characterization and profiling in plasma, urine and fecal samples. Plasma PK parameters for total radioactivity, Compound A and the O-desmethyl metabolite of Compound A (e.g., $C_{max}$, $T_{max}$, $AUC_{0-t}$, $AUC_\infty$, $t_{1/2}$) will be determined provided sufficient data are available.

The primary endpoints of Part 2 are: Plasma PK parameters (e.g., $C_{max}$, $T_{max}$, $AUC_{0-\infty}$, $t_{1/2}$) for Compound A and the O-desmethyl metabolite of Compound A under fed and fasted conditions.

The shared secondary endpoints of Part 1 and Part 2 are: Adverse event (AE) reporting (includes serious AE [SAE] reporting); Complete physical examinations; Clinical laboratory safety tests; Vital sign measurements; 12-lead electrocardiograms (ECGs); and Concomitant medications.

The secondary endpoint of Part 2 is: Plasma PK parameters (e.g., $C_{max}$, $T_{max}$, $AUC_{0-t}$, $AUC_\infty$, $t_{1/2}$) for the O-desmethyl metabolite of Compound A under fed and fasted conditions.

This will be a single-center, 2-part, open-label, randomized (Part 1 only), 2-treatment study in healthy adult males (n=18). Within no more than 28 days (Day −28) prior to the start of Part 1 or Part 2, subjects will undergo routine screening procedures including physical examination, 12-lead electrocardiograms (ECGs), vital signs, clinical laboratory safety tests (plasma or serum chemistry, hematology, and urinalysis), serology screen, fasting glucose levels (including HbA1C) and drug and alcohol screen.

On Day 1 of Part 1, subjects who continue to be qualified for participation in the study will be enrolled following an overnight fast of at least 8 hours. For Part 2 and on Day 1 of Period 1, subjects who continue to be qualified for participation in the study will be randomly assigned to 1 of 2 treatment sequences (Cohort 2 or Cohort 3) and enrolled in Part 2 following an overnight fast of at least 8 hours. Subjects will be enrolled in Part 1) and Part 2) to receive Treatment A or B in one of the following 3 cohorts:

| Study Part | Cohort | Period 1 | Period 2 |
|---|---|---|---|
| Part 1 | Cohort 1 (n = 6) | Treatment A (fasted) | NA |
| Part 2 | Cohort 2 (n = 6) | Treatment B (fasted) | Treatment B (fed) |
|  | Cohort 3 (n = 6) | Treatment B (fed) | Treatment B (fasted) |

Treatment A: A single 20-mg oral dose of Compound A capsule containing a microtracer of [$^{14}$C]-Compound A solution under fasted conditions.
Treatment B: A single 20-mg oral dose of Compound A tablet under fasting or fed conditions.

Part 1 design: After screening, subjects (n=6) eligible for participation in the study will return to the study center on Day −1 for baseline assessments. Subjects who continue to be qualified for participation in the study will be enrolled in the study on the morning of Day 1. Subjects will receive Treatment A after fasting overnight for at least 8 hours and will continue fasting (not consume any food) until 4 hours after dosing on the morning of Day 1. Water will be allowed during the fasting period. Subjects will be domiciled at the study center from Day −1 until the morning of Day 8. Subjects will be discharged from the study center on the morning of Day 8 upon satisfactory safety review and completion of study-related procedures.

Serial blood samples (10 mL) will be collected at predose (0 hour) and at 0.5, 1, 2, 3, 6, 12, 24, 48, 72, 96, 120, 144, and 168 hours post dose. Total [$^{14}$C]-radioactivity will be determined in blood, plasma, urine and feces. Blood-to-plasma ratios will be calculated to determine partitioning for total [14C]-radioactivity. Urine samples will be collected at predose (within 2 hours prior to dose administration) and at the following post dose collection intervals: 0 to 6, 6 to 12, 12 to 24, 24 to 48, 48 to 72, 72 to 96, 96 to 120, 120 to 144, 144 to 168 hours. Total urine volume collected in each interval will be recorded for determination of the fraction of dose excreted in urine. All fecal samples will be collected daily from Day −1 through Day 8 and weight of daily fecal collections will be pooled and recorded.

Part 2 design: Part 2 will be a 2-period crossover study; in Period 1, subjects (n=12) will be randomized to receive either an oral 20 mg dose of Compound A tablet (Treatment B) under fed (n=6) or fasted (n=6) conditions. In Period 2, subjects will receive Treatment B under converse conditions based on treatment assignment in Period 1. After screening, subjects (n=12) eligible for participation in the study will return to the study center on Day −1 for baseline assessments. Subjects who continue to be qualified for participation in the study will be randomized and enrolled in the study on the morning of Day 1. Subjects (n=6) will be enrolled and randomized to receive Treatment B under fed or fasted conditions on the morning of Day 1 after fasting for at least 8 hours. Fed subjects will be served a standard high fat meal breakfast, or its equivalent, that must be consumed within 30 minutes from serving. Dosing must occur 30 minutes (±5 minutes) after serving a subject breakfast. All subjects (fed and fasted) will fast (not to consume any food) until 4 hours post dose. Water will be allowed during the fasting period. Subjects will be domiciled at the study center from Day −1 until the morning of Day 5 of each period. Subjects will be discharged from the study center on the morning of Day 5 upon satisfactory safety review and completion of study-related procedures. Safety and tolerability data will be monitored and collected following each dosing period. Periods 1 and 2 will be separated by a washout period of at least 7 days (no more than 10 days) from prior dose to the next dose. In certain instances, a longer washout may be acceptable if previously agreed to.

Serial blood samples (10 mL) will be collected at predose (0 hour) and at 0.5, 1, 2, 3, 6, 12, 24, 48, 72 and 96 hours post dose for the determination of plasma concentrations of Compound A and the O-desmethyl metabolite of Compound A. Safety will be monitored throughout the study; safety evaluations will include AE reporting, physical examinations, vital sign measurements, ECG, and clinical laboratory safety tests. Concomitant medications will be assessed and recorded throughout the study as well. In addition, during the subjects' stay-in-the clinic (i.e., confinement period), fasting plasma glucose levels will be monitored as part of the clinical laboratory safety tests. For Parts 1 and 2, all subjects will return to the clinic within 7 to 10 days after the last dose for follow up safety assessments. In the event that a subject discontinues prematurely from the study, every reasonable effort should be made (and documented) to ensure that all procedures and evaluations scheduled for the follow-up visit are performed at the time of discontinuation or a follow-up visit should be scheduled within 7 to 10 days from the discontinuation day.

Part 1 dosing: Subjects will fast overnight for at least 8 hours prior to Compound A administration. On the morning of Day 1, each subject will be dosed under fasting conditions with a single 20-mg oral dose of Compound A capsule containing microtracer of [$^{14}$C]-Compound A in an ethanol/polyethylene glycol solution. The exact specific activity, chemical purity and radiochemical purity will be determined prior to dosing. After dosing, subjects will continue to fast until 4 hours after dosing; thereafter, they will be served standard meals and snacks. Dosing time will be recorded in the source documents and CRF. Dosing instruction and calculation for actual dose administered to each subject will be provided at or before study initiation. The actual dose of the [$^{14}$C]-Compound A microtracer administered to each subject will be calculated based on the measured radioactivity concentration (dpm/g) of the solution in the capsule.

Part 2 dosing: In Part 2, subjects will fast overnight for at least 8 hours prior to Compound A administration. On the morning of Day 1, each subject will receive a 20-mg tablet of Compound A orally. Subjects randomized to receive Compound A under fed conditions will be a served a standard high fat meal (breakfast).

The standard high fat meal or its equivalent must be consumed within 30 minutes of serving. Dosing must occur 30 minutes (±5 minutes) after serving the meal. The tablet will be administered with approximately 240 mL of non-carbonated, room temperature water. After dosing, subjects will continue to fast until 4 hours after dosing.

Subjects enrolled in the study will spend a total of approximately 8 weeks on the study.

Subjects must satisfy all of the following inclusion criteria to be eligible for enrollment into the study: 1. Must understand and voluntarily sign a written ICD prior to any study-related procedures being performed and be able to adhere to restrictions and examination schedules; 2. Must be able to communicate with the investigator and clinical staff and to understand and comply with the requirements of the study; 3. Must be a male 18 to 55 years of age (inclusive) at the time of signing, with a BMI (weight (kg)/(height (m$^2$)) between 18 and 33 kg/m$^2$ (inclusive) and weight between 60 and 100 kg (132 to 220 lbs; inclusive); 4. Must be healthy (at Screening and Day −1) as determined by the investigator on the basis of medical history, physical examination, clinical laboratory safety test results, vital signs, and 12 lead ECG (Vital signs (systolic and diastolic blood pressure, pulse rate, and oral body temperature) will be assessed in the supine position after the subject has rested for at least 5 minutes, Subject must be afebrile (febrile is defined as >38.5° C. or 101.3 Fahrenheit), Systolic blood pressure in the range of 90 to 140 mmHg, diastolic blood pressure in the range of 60 to 90 mmHg, and pulse rate in the range of 45 to 100 bpm, Screening fasting plasma glucose value within the normal limits of the institution and HbAlC<6%); 5. Subjects (with or without vasectomy) must agree to use barrier contraception (i.e., latex condom or any non-latex condom not made out of natural (animal) membrane (e.g., polyurethane)) and one other method (e.g., spermicide) when engaging in sexual activity with woman of childbearing potential during study conduct, and for 90 days after the last dose of study medication; and 6. Must agree to refrain from donating blood or plasma (other than for this study) while participating in this study and for at least 28 days after the last dose of study drug.

The presence of any of the following will exclude a subject from enrollment into the study: 1. Recent history (i.e., within 3 years) of any clinically significant neurological, gastrointestinal, hepatic, renal, respiratory, cardiovascular, metabolic, endocrine, hematological, dermatological, psychological, or other major disorders; 2. Any condition, including the presence of laboratory abnormalities, which places the subject at unacceptable risk if he were to participate in the study, or confounds the ability to interpret data from the study; 3. Use of any prescribed systemic or topical medication within 30 days of the first dose; 4. Use of any non-prescribed systemic or topical medication (including herbal medicines) within 7 days of the first dose administration (with the exception of vitamin/mineral supplements); 5. Subject used any metabolic enzyme inhibitors or inducers (i.e., CYP3A inducers and inhibitors or St. John's Wort) within 30 days of the first dose administration; 6. Presence of any surgical or medical conditions possibly affecting drug absorption, distribution, metabolism, and excretion, or plans to have elective or medical procedures during the conduct of the trial; 7. Exposure to an investigational drug (new chemical entity) within 90 days prior to the first dose administration; 8. Donation of blood or plasma within 60 days prior to the first dose administration; 9. History of multiple (i.e., 2 or more) drug allergies; 10. Any clinical significant allergic disease (excluding non-active hay fever), excluding nonactive seasonal allergies and childhood asthma cleared for at least 3 years; 11. History of drug abuse within 2 years prior to first dosing, or positive urine drug screening test due to illicit drugs; 12. History of alcohol abuse within 2 years prior to dosing, or positive alcohol screen; 13. Smokes more than 10 cigarettes, or consumes the equivalent in tobacco, per day; 14. Known to have, or tests positive for, active or chronic hepatitis B or hepatitis C, or HIV antibodies; 15. Received vaccination (excluding seasonal flu vaccination) within 90 days of the study drug administration; or 16. For Part 1 only: Prior exposure to radioactive investigational drugs within 6 months prior to check in, and prior exposure to work-related, diagnostic or therapeutic radiation within 12 months prior to check in.

Inclusion/exclusion criteria will be assessed at screening. Subject eligibility will be confirmed again on the admission day (Day −1) of the first period and/or prior to randomization on Day 1 by physical examination, drug screen, clinical laboratory safety tests vital signs and ECGs.

Preliminary Results: 11/12 enrolled subjects completed Part 2. The results are set forth in Table 38, below.

TABLE 38

Geometric Mean CV %) Pharmacokinetic Parameters After Single 20-mg Oral Dose

| Parameter | Fasted (n = 11) | | Fed (n = 11) | |
|---|---|---|---|---|
| | Cmpd. A | O-Desmethyl metabolite | Cmpd. A | O-Desmethyl metabolite |
| $T_{max}$* (h) | 1.00 (1-2) | 3.00 (1-3) | 3.00 (1-3) | 6.00 (312) |
| $C_{max}$ (ng/mL) | 182 (24) | 425 (23) | 156 (27) | 364 (28) |
| $AUC_{inf}$ (ng*h/mL) | 1005 (38) | 9834 (38) | 1195 (38) | 10131 (35) |
| $AUC_{0-24}$ (ng*h/mL) | 955 (35) | 6401 (30) | 1131 (34) | 6271 (29) |
| Vz/F (L) | 151 (28) | 34.7 (28) | 125 (20) | 42.6 (30) |
| CL/F (L/h) | 19.9 (38) | 2.0 (38) | 16.7 (38) | 2.0 (36) |
| $t_{1/2}$ (h) | 5.3 (33) | 14.8 (25) | 5.2 (27) | 14.9 (29) |

*$T_{max}$ presented as median (range).

CONCLUSIONS

After administration of Compound A with a high fat meal to healthy adult males, there is an approximate 17% decrease in Compound A $C_{max}$ and an approximate 20% increase in overall exposure ($AUC_{inf}$). There is also a 2 hour delay in $T_{max}$. After administration of Compound A with a high fat meal to healthy adult males, there is an approximate 17% decrease in O-desmethyl metabolite $C_{max}$ and an approximate 3% increase in overall exposure ($AUC_{inf}$). There is also a 3 hour delay in $T_{max}$.

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A crystal form of the compound of formula (I), 7-(6-(2-hydroxypropan-2-yl)pyridin-3-yl)-1-((trans)-4-methoxycyclohexyl)-3,4-dihydropyrazino[2,3-b]pyrazin-2(1H)-one, or a salt thereof, which is p-xylene solvated:

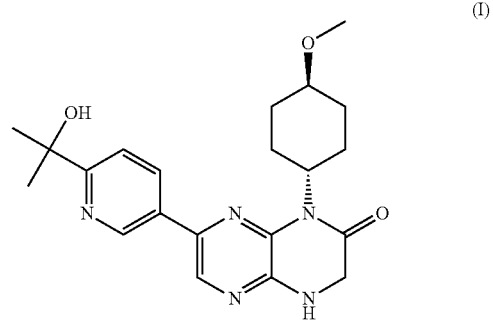 [SMILES: CO[C@H]1CC[C@H](N2C(=O)CNc3ncc(-c4ccc(C(C)(C)O)nc4)nc32)CC1]

which has an X-ray powder diffraction pattern comprising peaks at approximately 7.46, 13.70 and 23.06 °2θ.

2. The crystal form of claim 1, which has an X-ray powder diffraction pattern further comprising peaks at approximately 8.94, 18.22 and 18.78 °2θ.

3. The crystal form of claim 1, which has a thermogravimetric analysis thermogram comprising a total mass loss of approximately 11.0% of the total mass of the crystal form when heated from about 25° C. to about 300° C.

4. The crystal form of claim 1, which has a single differential thermal analysis thermogram comprising an endotherm between about 90° C. and about 125° C. with a maximum at approximately 106-110° C. when heated from about 25° C. to about 300° C.

5. The crystal form of claim 4, wherein the single differential thermal analysis thermogram further comprises an endotherm with a maximum at approximately 193° C.

6. The crystal form of claim 1, which comprises 0.5 molar equivalents of p-xylene.

7. The crystal form of claim 1, which is substantially pure.

* * * * *